US008110199B2

(12) United States Patent
Gilbert et al.

(10) Patent No.: US 8,110,199 B2
(45) Date of Patent: Feb. 7, 2012

(54) STREPTOCOCCUS PNEUMONIAE PROTEINS AND NUCLEIC ACID MOLECULES

(75) Inventors: Christophe François Guy Gilbert, Villeurbanne cedex (FR); Philip Michael Hansbro, Newcastle (AU)

(73) Assignee: Sanofi Pasteur Limited, Toronto, Ontario (CA)

( * ) Notice: Subject to any disclaimer, the term of this patent is extended or adjusted under 35 U.S.C. 154(b) by 17 days.

(21) Appl. No.: 12/411,487

(22) Filed: Mar. 26, 2009

(65) Prior Publication Data

US 2010/0278740 A1      Nov. 4, 2010

Related U.S. Application Data

(60) Division of application No. 11/785,503, filed on Apr. 18, 2007, now Pat. No. 7,632,515, which is a division of application No. 10/873,528, filed on Jun. 23, 2004, now abandoned, which is a division of application No. 09/769,787, filed on Jan. 26, 2001, now Pat. No. 6,936,252, which is a continuation of application No. PCT/GB99/02451, filed on Jul. 27, 1999.

(60) Provisional application No. 60/125,164, filed on Mar. 19, 1999.

(30) Foreign Application Priority Data

Jul. 27, 1998   (GB) .................................. 9816337.1

(51) Int. Cl.
*A61K 39/09* (2006.01)
*C12N 1/20* (2006.01)
*C07K 14/315* (2006.01)

(52) U.S. Cl. ............... 424/244.1; 424/190.1; 435/252.3; 530/350

(58) Field of Classification Search ........................ None
See application file for complete search history.

(56) References Cited

U.S. PATENT DOCUMENTS

| 6,420,135 B1 | 7/2002 | Kunsch et al. |
| 6,573,082 B1 | 6/2003 | Choi et al. |
| 6,699,703 B1 | 3/2004 | Doucette-Stamm et al. |
| 6,800,744 B1 | 10/2004 | Doucette-Stamm et al. |
| 6,936,252 B2 | 8/2005 | Gilbert et al. |
| 2005/0276814 A1 | 12/2005 | Gilbert et al. |
| 2008/0175857 A1 | 7/2008 | Gilbert et al. |

FOREIGN PATENT DOCUMENTS

| EP | 0622081 | 11/1994 |
| EP | 1 785 486 A | 5/2007 |
| WO | WO 95/06732 | 3/1995 |
| WO | WO 97/09994 | 3/1997 |
| WO | WO 97/37026 | 10/1997 |
| WO | WO 97/43303 | 11/1997 |
| WO | WO 98/06734 | 2/1998 |
| WO | WO 98/18930 | 5/1998 |
| WO | WO 98/18931 | 5/1998 |
| WO | WO 98/26072 | 6/1998 |
| WO | WO 98/31786 | 7/1998 |
| WO | WO 99/15675 | 4/1999 |

OTHER PUBLICATIONS

Alonsodevelasco, et al. (Dec. 1995) "*Streptococcus pneumoniae*: Virulence Factors, Pathogenesis, and Vaccines." Microbiological Reviews 59(4): 591-603.
Angel, et al. (1994) "Degradation of C3 by *Streptococcus pneumoniae*." Journal of Infectious Disease 170(3): 600-608.
Nandiwada, et al. (1996) "Genetic Analysis of a C3 degrading proteinase in *Steptococcus pneumoniae*." Abstracts of the General Meeting of the American Society for Microbiology vol. 96 p. 177 (Abstract B-134).
Anderson et al. (1996) "Immune Response in mice following immunization with DNA encoding fragment C of tetanus toxin." Infection and Immunity 64: 3168-3173.
Breiman et al. (1990) Arch. Intern. Med. 150: 1401.
Breiman et al. (1994) J. Am. Med. Assoc. 271: 1831.
Boslego, et al. (1991) Chapter 17 from *Vaccines and Immunotherapy*.
Bowie (1990) Science 257: 1306-1310.
Burgess, et al. (1990) The Journal of Cell Biology 111: 2129-2136.
Donnelly et al. (1997) Ann. Rev. Immunol. 15: 617-648.
Dougall et al. (Sep. 1994) Tibtech 12: 372-379.
Ellis (1988) Vaccines Chapter 29: 568-575.
Greenspan, et al. (1999) Nature Biotechnology 7: 936-937.
Herbert, et al. (1985) The Dictionary of Immunology (Academic Press) 3$^{rd}$ Ed. pp. 58-59.
Houghten, et al. (1986) *Vaccines* (Cold Spring Harbor Laboratory).
Holmes, et al. (2001) Exp. Opin. Invest. Drugs 10(3): 511-519.
Jobling et al. (1991) Mol. Microbiol 5(7): 1755-67.
Kohler & Milstein (1975) Nature 256.
Kolkman et al. (1996) 178: 3736-3741.
Kovacevic et al. (1985) J. Bacteriol. 162: 521-528.
Kurar and Splitter (1997) Vaccine 15: 1851-57.
Lange et al. (Sep. 3, 1999) Gene 237(1): 223-234.
Lazar et al. (1988) Molecular and Cellular Biology 8(3): 1247-1252.
Le Loir et al. (1994) J. Bacteriol. 176: 5135-5139.
LeBlanc et al. (1978) PNAS USA 75: 3484-3487.
Lederman, et al. (1991) Molecular Immonology 28: 1171-1181.
Li, et al. (1980) Proc. Natl. Acad. Sci. USA 77: 3211-3214.
Li et al. (1997) PNAS 94: 13251-13256.
Liebl et al. (1992) J. Bacteriol. 174: 1854-1861.
Marck (1988) Nucleic Acids Research 16: 1829-1836. Miller et al. (1987) J. Bacteriol. 169: 3508-3514.
Morrison et al. (1984) PNAS 81: 6851-6855.
Nanidwada, et al. (1996) "Genetic Analysis of a C3 degrading proteinase in *Steptococcus pneumoniae*." Abstracts of the General Meeting of the American Society for Microbiology vol. 96 p. 177 (Abstract B-134).
Oultram and Klaenhammer (1985) FEMS Microbiological Letters 27: 129-134.
Pearson et al. (1988) "Improved tools for biological sequence comparison," Proc. Natl. Acad. Sci. USA, vol. 85, 2444-2448.
Poquet et al. (1998) J. Bacteriol. 180: 1904-1912.
Roitt, et al. (1993) Immunology p. 7.7-7.8.
Rudinger et al. (Jun. 1976) "Peptide Hormones" p. 6.

(Continued)

*Primary Examiner* — Padma Baskar
(74) *Attorney, Agent, or Firm* — Hunton & Williams LLP

(57) ABSTRACT

Protein antigens from *Streptococcus pneumoniae* are disclosed, together with nucleic acid sequences encoding them. Their use in vaccines and in screening methods is also described.

3 Claims, 4 Drawing Sheets

OTHER PUBLICATIONS

Schappert (1992) Vital and Health Statistics of the Centres for Disease Control/National Centre for Health Statistics 214: 1.
Shortle (1983) Gene 22: 181-189.
Siber (Sep. 1994) "Pneumococcal Disease: Prospects for a New Generation of Vaccines" Science vol. 265, pp. 1385-1387.
Simon and Chopin (1988) Biochimie 70: 559-567.
Stansfield (1987) "Acute respiratory infections in the developing world: strategies for prevention, treatment and control," Pediatric Infect Dis. Journal, vol. 6, 622-629.
Takeda et al. (1985) Nature 314: 452-454.
Taber's Cyclopedic Medical Dictionary (1985) 16$^{th}$ Ed. p. 1354.
van der Vossen, et al. (1985) Applied and Environmental Microbiology 50: 540-542.
Waterfield et al. (1995) Gene 165: 9-15.
Wells and Schoefield (1996) In Current advances in metabolism, genetics, and applications—NATO ASI Series H 98: 37-62.
Wells et al. (1993) J. Appl. Bacteriol. 74: 629-636.
Zhang et al. (1997) Infection and Immunity 176: 1035-1040.
Bowie, et al. (1991) "A Method to Identify Protein Sequences that Fold into a Known Three-Dimensional Structure." Science 253(5016): 164-170.
Chothia & Lesk (1986) "The relation between the divergence of sequence and structure in proteins." The EMBO Journal 5(4): 823-826.
Elgert Immunology (1996) Chapter 3 "Antigens" pp. 46-57.
Ho, et al. (1989) "Site-directed mutagenesis by overlap extension using the polymerase chain reaction." Gene 77(1): 51-59 [Abstract].
Hopp & Woods (1991) "Prediction of protein antigenic determinants from amino acid sequences." Proc. Natl. Acad. Sci. USA 78(6): 3824-3828, 3825-3826.
Kolaskar & Tongaonkar (1990) "A semi-empirical method for prediction of antigenic determinants on protein antigens." FEBS Letters 276(1-2): 172-174.
Landt, et al. (1990) "A general method for rapid site-directed mutagenesis using the polymerase chain reaction." Gene 96(1): 125-128 [Abstract].
Tart, et al. (1996) "Truncated Streptococcus penumoniae PspA Molecules Elicit Cross-Protective Immunity against Pneumococcal Challenge in Mice." The Journal of Infectious Disease 173: 380-386.
Taylor (1988) "Pattern matching methods in protein sequence comparison and structure prediction." Protein Engineering 2(2): 77-86.
Voet & Voet Biochemistry (1990), Chapter 8 "Protein Folding, Dynamics, and Structural Evolution" pp. 193-244.
Welling et al., "Algorithm to predict antigenic determinants,"(1985) "Prediction of sequential antigenic regions in proteins." FEBS Letters 188(2): 215-218.

STREPTOCOCCUS PNEUMONIAE PROTEINS AND NUCLEIC ACID MOLECULES

This application is a divisional of U.S. patent application Ser. No. 11/785,503, filed Apr. 18, 2007, now U.S. Pat. No. 7,632,515, which is a divisional of U.S. patent application Ser. No. 10/873,528, filed Jun. 23, 2004, now abandoned, which is a divisional of U.S. patent application Ser. No. 09/769,787, filed Jan. 26, 2001, now U.S. Pat. No. 6,936,252, which is a continuation of PCT/GB99/02451, filed Jul. 27, 1999, which claims benefit of U.S. Provisional Application No. 60/125,164, filed Mar. 19, 1999, and which also claims benefit of United Kingdom 9816337.1, filed Jul. 27, 1998, the disclosures of which are all hereby incorporated by reference.

The present invention relates to proteins derived from *Streptococcus pneumoniae*, nucleic acid molecules encoding such proteins, the use of the nucleic acid and/or proteins as antigens/immunogens and in detection/diagnosis, as well as methods for screening the proteins/nucleic acid sequences as potential anti-microbial targets.

*Streptococcus pneumoniae*, commonly referred to as the pneumococcus, is an important pathogenic organism. The continuing significance of *Streptococcus pneumoniae* infections in relation to human disease in developing and developed countries has been authoritatively reviewed (Fiber, G. R., *Science*, 265:1385-1387 (1994)). That indicates that on a global scale this organism is believed to be the most common bacterial cause of acute respiratory infections, and is estimated to result in 1 million childhood deaths each year, mostly in developing countries (Stansfield, S. K., *Pediatr. Infect. Dis.*, 6:622 (1987)). In the USA it has been suggested (Breiman, et al., *Arch. Intern. Med.*, 150:1401 (1990)) that the pneumococcus is still the most common cause of bacterial *pneumoniae*, and that disease rates are particularly high in young children, in the elderly, and in patients with predisposing conditions such as asplenia, heart, lung, and kidney disease, diabetes, alcoholism, or with immunosuppressive disorders, especially AIDS. These groups are at higher risk of pneumococcal septicaemia and hence meningitis and therefore have a greater risk of dying from pneumococcul infection. The pneumococcus is also the leading cause of otitis media and sinusitis, which remain prevalent infections in children in developed countries, and which incur substantial costs.

The need for effective preventative strategies against pneumococcal infection is highlighted by the recent emergence of penicillin-resistant pneumococci. It has been reported that 6.6% of pneumoccal isolates in 13 US hospitals in 12 states were found to be resistant to penicillin and some isolates were also resistant to other antibiotics including third generation cyclosporins (Schappert, S. M., *Vital and Health Statistics of the Centres for Disease Control/National Centre for Health Statistics*, 214:1 (1992)). The rates of penicillin resistance can be higher (up to 20%) in some hospitals (Breiman, et al., J. Am. Med. Assoc., 271: 1831 (1994)). Since the development of penicillin resistance among pneumococci is both recent and sudden, coming after decades during which penicillin remained an effective treatment, these findings are regarded as alarming.

For the reasons given above, there are therefore compelling grounds for considering improvements in the means of preventing, controlling, diagnosing or treating pneumococcal diseases.

Various approaches have been taken in order to provide vaccines for the prevention of pneumococcal infections. Difficulties arise for instance in view of the variety of serotypes (at least 90) based on the structure of the polysaccharide capsule surrounding the organism. Vaccines against individual serotypes are not effective against other serotypes and this means that vaccines must include polysaccharide antigens from a whole range of serotypes in order to be effective in a majority of cases. An additional problem arises because it has been found that the capsular polysaccharides (each of which determines the serotype and is the major protective antigen) when purified and used as a vaccine do not reliably induce protective antibody responses in children under two years of age, the age group which suffers the highest incidence of invasive pneumococcal infection and meningitis.

A modification of the approach using capsule antigens relies on conjugating the polysaccharide to a protein in order to derive an enhanced immune response, particularly by giving the response T-cell dependent character. This approach has been used in the development of a vaccine against *Haemophilus influenzae*. There are issues of cost concerning both the multi-polysaccharide vaccines and those based on conjugates.

A third approach is to look for other antigenic components which offer the potential to be vaccine candidates.

BACKGROUND OF THE INVENTION

In the present application we provide a group of proteins antigens which are secreted/exported proteins.

BRIEF SUMMARY OF THE INVENTION

Thus, in a first aspect the present invention provides a *Streptococcus pneumoniae* protein or polypeptide having a sequence selected from those shown in Table 4 herein.

A protein or polypeptide of the present invention may be provided in substantially pure form. For example, it may be provided in a form which is substantially free of other proteins.

In a preferred embodiment, a protein or polypeptide having an amino acid sequence as shown in Table 5 is provided.

The invention encompasses any protein coded for by a nucleic acid sequence as shown in Table 3 herein.

DETAILED DESCRIPTION OF THE INVENTION

As discussed herein, the proteins and polypeptides of the invention are useful as antigenic material. Such material can be "antigenic" and/or "immunogenic". Generally, "antigenic" is taken to mean that the protein or polypeptide is capable of being used to raise antibodies or indeed is capable of inducing an antibody response in a subject. "Immunogenic" is taken to mean that the protein or polypeptide is capable of eliciting a protective immune response in a subject.

Thus, in the latter case, the protein or polypeptide may be capable of not only generating an antibody response and in addition non-antibody based immune responses.

The skilled person will appreciate that homologues or derivatives of the proteins or polypeptides of the invention will also find use in the context of the present invention, ie as antigenic/immunogenic material. Thus, for instance proteins or polypeptides which include one or more additions, deletions, substitutions or the like are encompassed by the present invention.

In addition, it may be possible to replace one amino acid with another of similar "type". For instance replacing one hydrophobic amino acid with another. One can use a program such as the CLUSTAL program to compare amino acid sequences. This program compares amino acid sequences and finds the optimal alignment by inserting spaces in either sequence as appropriate.

It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In the case of homologues and derivatives, the degree of identity with a protein or polypeptide as described herein is less important than that the homologue or derivative should retain its antigenicity or immunogenicity to *Streptococcus pneumoniae*. However, suitably, homologues or derivatives having at least 60% similarity (as discussed above) with the proteins or polypeptides described herein are provided.

Preferably, homologues or derivatives having at least 70% similarity, more preferably at least 80% similarity are provided. Most preferably, homologues or derivatives having at least 90% or even 95% similarity are provided.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

In an additional aspect of the invention there are provided antigenic fragments of the proteins or polypeptides of the invention, or of homologues or derivatives thereof.

For fragments of the proteins or polypeptides described herein, or of homologues or derivatives thereof, the situation is slightly different. It is well known that is possible to screen an antigenic protein or polypeptide to identify epitopic regions, i.e., those regions which are responsible for the protein or polypeptide's antigenicity or immunogenicity. Methods for carrying out such screening are well known in the art. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties.

Thus, what is important for homologues, derivatives and fragments is that they possess at least a degree of the antigenicity/immunogenicity of the protein or polypeptide from which they are derived.

Gene cloning techniques may be used to provide a protein of the invention in substantially pure form, These techniques are disclosed, for example, in J. Sambrook, et al. *Molecular Cloning* 2nd Edition, Cold Spring Harbor Laboratory Press (1989). Thus, in a fourth aspect, the present invention provides a nucleic acid molecule comprising or consisting of a sequence which is:

(i) any of the DNA sequences set out in Table 3 or their RNA equivalents;
(ii) a sequence which is complementary to any of the sequences of (i);
(iii) a sequence which codes for the same protein or polypeptide, as those sequences of (i) or (ii);
(iv) a sequence which is has substantial identity with any of those of (i), (ii) and (iii);
(v) a sequence which codes for a homologue, derivative or fragment of a protein as defined in Table 3.

In a fifth aspect the present invention provides a nucleic acid molecule comprising or consisting of a sequence which is:

(i) any of the DNA sequences set out in Table 6 or their RNA equivalents;
(ii) a sequence which is complementary to any of the sequences of (i);
(iii) a sequence which codes for the same protein or polypeptide, as those sequences of (i) or (ii);
(iv) a sequence which is has substantial identity with any of those of (i), (ii) and (iii);
(v) a sequence which codes for a homologue, derivative or fragment of a protein as defined in Table 6.

The nucleic acid molecules of the invention may include a plurality of such sequences, and/or fragments. The skilled person will appreciate that the present invention can include, novel variants of those particular novel nucleic acid molecules which are exemplified herein. Such variants are encompassed by the present invention. These may occur in nature, for example because of strain variation. For example, additions, substitutions and/or deletions are included. In addition, and particularly when utilising microbial expression systems, one may wish to engineer the nucleic acid sequence by making use of known preferred codon usage in the particular organism being used for expression. Thus, synthetic or non-naturally occurring variants are also included within the scope of the invention.

The term "RNA equivalent" when used above indicates that a given RNA molecule has a sequence which is complementary to that of a given DNA molecule (allowing for the fact that in RNA "U" replaces "T" in the genetic code).

When comparing nucleic acid sequences for the purposes of determining the degree of homology or identity one can use programs such as BESTFIT and GAP (both from the Wisconsin Genetics Computer Group (GCG) software package) BESTFIT, for example, compares two sequences and produces an optimal alignment of the most similar segments. GAP enables sequences to be aligned along their whole length and finds the optimal alignment by inserting spaces in either sequence as appropriate. Suitably, in the context of the present invention compare when discussing identity of nucleic acid sequences, the comparison is made by alignment of the sequences along their whole length.

Preferably, sequences which have substantial identity have at least 50% sequence identity, desirably at least 75% sequence identity and more desirably at least 90 or at least 95% sequence identity with said sequences. In some cases the sequence identity may be 99% or above.

Desirably, the term "substantial identity" indicates that said sequence has a greater degree of identity with any of the sequences described herein than with prior art nucleic acid sequences.

It should however be noted that where a nucleic acid sequence of the present invention codes for at least part of a novel gene product the present invention includes within its scope all possible sequence coding for the gene product or for a novel part thereof.

The nucleic acid molecule may be in isolated or recombinant form. It may be incorporated into a vector and the vector may be incorporated into a host. Such vectors and suitable hosts form yet further aspects of the present invention.

Therefore, for example, by using probes based upon the nucleic acid sequences provided herein, genes in *Streptococcus pneumoniae* can be identified. They can then be excised using restriction enzymes and cloned into a vector. The vector can be introduced into a suitable host for expression.

Nucleic acid molecules of the present invention may be obtained from *S. pneumoniae* by the use of appropriate probes complementary to part of the sequences of the nucleic acid molecules. Restriction enzymes or sonication techniques can be used to obtain appropriately sized fragments for probing.

Alternatively PCR techniques may be used to amplify a desired nucleic acid sequence. Thus the sequence data provided herein can be used to design two primers for use in PCR so that a desired sequence, including whole genes or fragments thereof, can be targeted and then amplified to a high degree. One primer will normally show a high degree of specificity for a first sequence located on one strand of a DNA molecule, and the other primer will normally show a high degree of specificity for a second sequence located on the complementary strand of the DNA sequence and being spaced from the complementary sequence to the first sequence.

Typically primers will be at least 15-25 nucleotides long.

As a further alternative chemical synthesis may be used. This may be automated. Relatively short sequences may be chemically synthesised and ligated together to provide a longer sequence.

In yet a further aspect the present invention provides an immunogenic/antigenic composition comprising one or more proteins or polypeptides selected from those whose sequences are shown in Tables 4-6, or homologues or derivatives thereof, and/or fragments of any of these. In preferred embodiments, the immunogenic/antigenic composition is a vaccine or is for use in a diagnostic assay.

In the case of vaccines suitable additional excipients, diluents, adjuvants or the like may be included. Numerous examples of these are well known in the art.

It is also possible to utilise the nucleic acid sequences shown in Table 3 in the preparation of so-called DNA vaccines. Thus, the invention also provides a vaccine composition comprising one or more nucleic acid sequences as defined herein. The use of such DNA vaccines is described in the art. See for instance, Donnelly, et al., *Ann. Rev. Immunol.*, 15:617-648 (1997).

As already discussed herein the proteins or polypeptides described herein, their homologues or derivatives, and/or fragments of any of these, can be used in methods of detecting/diagnosing *S. pneumoniae*. Such methods can be based on the detection of antibodies against such proteins which may be present in a subject. Therefore the present invention provides a method for the detection/diagnosis of *S. pneumoniae* which comprises the step of bringing into contact a sample to be tested with at least one protein, or homologue, derivative or fragment thereof, as described herein. Suitably, the sample is a biological sample, such as a tissue sample or a sample of blood or saliva obtained from a subject to be tested.

In an alternative approach, the proteins described herein, or homologues, derivatives and/or fragments thereof, can be used to raise antibodies, which in turn can be used to detect the antigens, and hence *S. pneumoniae*. Such antibodies form another aspect of the invention. Antibodies within the scope of the present invention may be monoclonal or polyclonal.

Polyclonal antibodies can be raised by stimulating their production in a suitable animal host (e.g., a mouse, rat, guinea pig, rabbit, sheep, goat or monkey) when a protein as described herein, or a homologue, derivative or fragment thereof, is injected into the animal. If desired, an adjuvant may be administered together with the protein. Well-known adjuvants include Freund's adjuvant (complete and incomplete) and aluminium hydroxide. The antibodies can then be purified by virtue of their binding to a protein as described herein.

Monoclonal antibodies can be produced from hybridomas. These can be formed by fusing myeloma cells and spleen cells which produce the desired antibody in order to form an immortal cell line. Thus the well-known Kohler & Milstein technique (Nature 256 (1975)) or subsequent variations upon this technique can be used.

Techniques for producing monoclonal and polyclonal antibodies that bind to a particular polypeptide/protein are now well developed in the art. They are discussed in standard immunology textbooks, for example in Roitt, et al., *Immunology* second edition (1989), Churchill Livingstone, London.

In addition to whole antibodies, the present invention includes derivatives thereof which are capable of binding to proteins etc as described herein. Thus the present invention includes antibody fragments and synthetic constructs. Examples of antibody fragments and synthetic constructs are given by Dougall, et al. in *Tibtech* 12 372-379 (September 1994).

Antibody fragments include, for example, Fab, F(ab')$_2$ and Fv fragments. Fab fragments (These are discussed in Roitt et al [supra]). Fv fragments can be modified to produce a synthetic construct known as a single chain Fv (scFv) molecule. This includes a peptide linker covalently joining $V_h$ and $V_l$ regions, which contributes to the stability of the molecule. Other synthetic constructs that can be used include CDR peptides. These are synthetic peptides comprising antigen-binding determinants. Peptide mimetics may also be used. These molecules are usually conformationally restricted organic rings that mimic the structure of a CDR loop and that include antigen-interactive side chains.

Synthetic constructs include chimaeric molecules. Thus, for example, humanised (or primatised) antibodies or derivatives thereof are within the scope of the present invention. An example of a humanised antibody is an antibody having human framework regions, but rodent hypervariable regions. Ways of producing chimaeric antibodies are discussed for example by Morrison, et al. in PNAS, 81, 6851-6855 (1984) and by Takeda, et al. in Nature. 314, 452-454 (1985).

Synthetic constructs also include molecules comprising an additional moiety that provides the molecule with some desirable property in addition to antigen binding. For example the moiety may be a label (e.g., a fluorescent or radioactive label). Alternatively, it may be a pharmaceutically active agent.

Antibodies, or derivatives thereof, find use in detection/diagnosis of *S. pneumoniae*. Thus, in another aspect the present invention provides a method for the detection/diagnosis of *S. pneumoniae* which comprises the step of bringing into contact a sample to be tested and antibodies capable of binding to one or more proteins described herein, or to homologues, derivatives and/or fragments thereof.

In addition, so-called AFFIBODIES may be utilised. These are binding proteins selected from combinatorial libraries of an alpha-helical bacterial receptor domain (Nord, et al., Thus, Small protein domains, capable of specific binding to different target proteins can be selected using combinatorial approaches.

It will also be clear that the nucleic acid sequences described herein may be used to detect/diagnose *S. pneumoniae*. Thus, in yet a further aspect, the present invention provides a method for the detection/diagnosis of *S. pneumoniae* which comprises the step of bringing into contact a sample to be tested with at least one nucleic acid sequence as described herein. Suitably, the sample is a biological sample, such as a tissue sample or a sample of blood or saliva obtained from a subject to be tested. Such samples may be pre-treated before being used in the methods of the invention. Thus, for example, a sample may be treated to extract DNA. Then, DNA probes based on the nucleic acid sequences described herein (i.e., usually fragments of such sequences) may be used to detect nucleic acid from *S. pneumoniae*.

In additional aspects, the present invention provides:
(a) a method of vaccinating a subject against *S. pneumoniae* which comprises the step of administering to a subject a protein or polypeptide of the invention, or a derivative, homologue or fragment thereof, or an immunogenic composition of the invention;
(b) a method of vaccinating a subject against *S. pneumoniae* which comprises the step of administering to a subject a nucleic acid molecule as defined herein;
(c) a method for the prophylaxis or treatment of *S. pneumoniae* infection which comprises the step of administering to a subject a protein or polypeptide of the invention, or a derivative, homologue or fragment thereof, or an immunogenic composition of the invention;
(d) a method for the prophylaxis or treatment of *S. pneumoniae* infection which comprises the step of administering to a subject a nucleic acid molecule as defined herein;
(e) a kit for use in detecting/diagnosing *S. pneumoniae* infection comprising one or more proteins or polypeptides of the invention, or homologues, derivatives or fragments thereof, or an antigenic composition of the invention; and
(f) a kit for use in detecting/diagnosing *S. pneumoniae* infection comprising one or more nucleic acid molecules as defined herein.

Given that we have identified a group of important proteins, such proteins are potential targets for anti-microbial therapy. It is necessary, however, to determine whether each individual protein is essential for the organism's viability. Thus, the present invention also provides a method of determining whether a protein or polypeptide as described herein represents a potential anti-microbial target which comprises inactivating said protein and determining whether *S. pneumoniae* is still viable, in vitro or in vivo.

A suitable method for inactivating the protein is to effect selected gene knockouts, ie prevent expression of the protein and determine whether this results in a lethal change. Suitable methods for carrying out such gene knockouts are described in Li, et al., *P.N.A.S.*, 94:13251-13256 (1997).

In a final aspect the present invention provides the use of an agent capable of antagonising, inhibiting or otherwise interfering with the function or expression of a protein or polypeptide of the invention in the manufacture of a medicament for use in the treatment or prophylaxis of *S. pneumoniae* infection.

The invention will now be described with reference to the following examples, which should not be construed as in any way limiting the invention. The examples refer to the figures.

EXAMPLE 1

The Genome sequencing of *Streptococcus pneumoniae* type 4 is in progress at the Institute for Genomic Research (TIGR, Rockville, Md., USA): Up to now, the whole sequence has not been completed or published. On Nov. 21, 1997, the TIGR centre released some DNA sequences as contigs which are not accurate reflections of the finished sequence. These contigs can be downloaded from their website. We downloaded these contigs and created a local database using the application GCGToBLAST (Wisconsin Package Version 9.1, Genetics Computer Group (GCG), Madison, USA). This database can be searched with the FastA and TfastA procedures (using the method of Pearson and Lipman (PNAS USA, 85:2444-2448 (1988)).

Using FastA and TfastA procedures, the local pneumococcus database was searched for putative leader sequence or anchor sequence features. Relevant sequences were used to interrogate for comparative novel sequences. These were:
(i) already described leader sequences of *Streptococcus pneumoniae* (from proteins NanA, NanB, LytA, PapA, pcpA, PsaA and PspA);
(ii) the leader sequence of Usp45, a secreted protein from *Lactococcus lactis;*
(iii) new hypothetical leader sequences derived from the searches in (i) and (ii);
(iv) the anchor motif LPxTG (SEQ ID NO: 364), a feature common to many Gram-positive bacteria surface proteins which are anchored by a mechanism involving the Sortase complex proteins.

Figure 3:
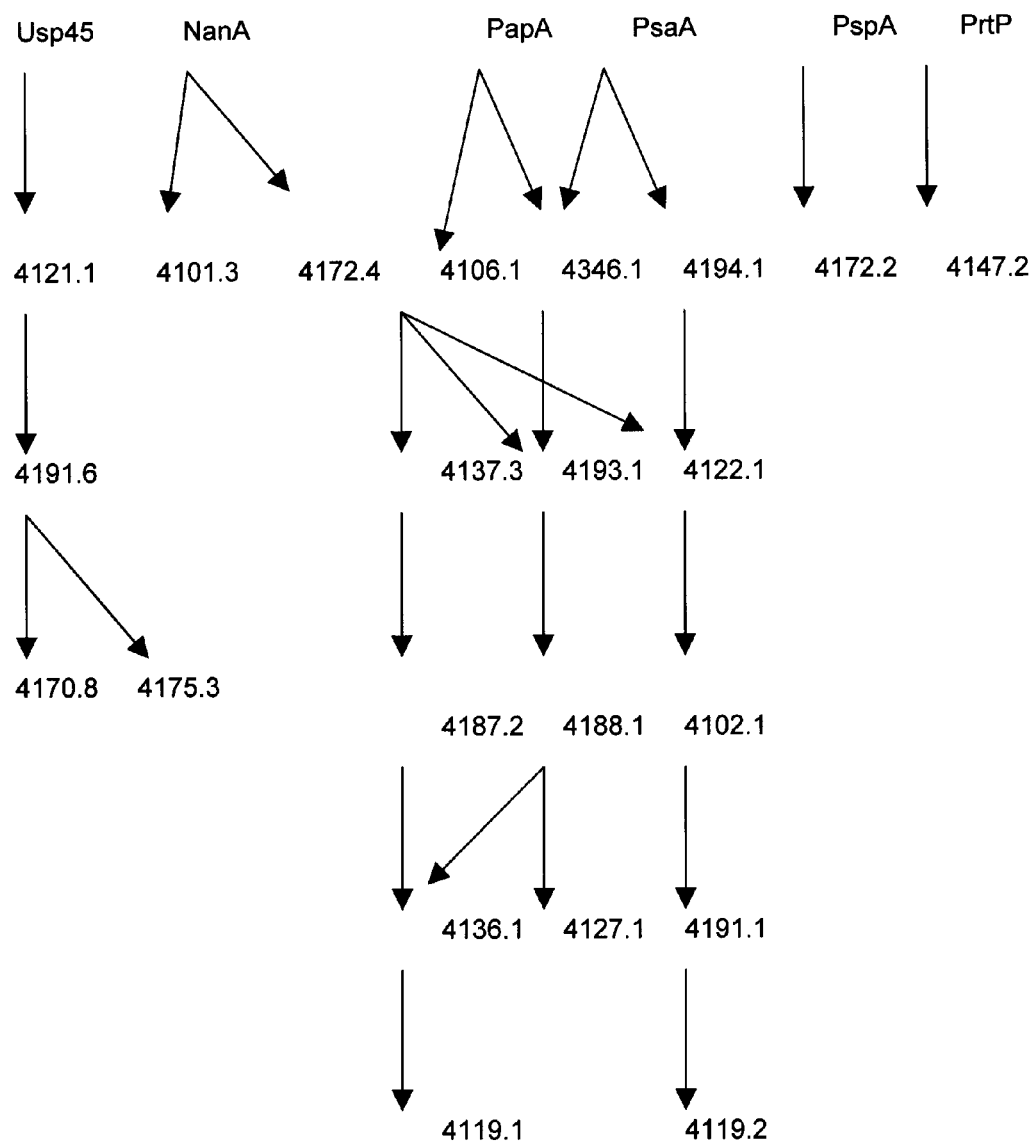
FIG. 3: shows an example of using FastA and TfastA procedures, the local pneumococcus database was searched for putative leader sequence or anchor sequence features. Relevant sequences were used to interrogate for comparative novel sequences.

Provided in FIG. 3 is an example of this approach, with reference to the sequences derived from the database (see table 3).

The protein leader sequences of different known exported proteins were used as a starting point for a search of the local pneumococcus database described above. The hypothetical proteins found with this search were then submitted to a Blast search in general databases such as EMBL, Swissprot etc. Proteins remaining unknown in the pneumococcus are kept and annotated. Then the search is performed again using the new potential protein leader sequence as a probe, using the TfastA procedure.

EXAMPLE 2

DNA Vaccine Trials pcDNA3.1+ as a DNA Vaccine Vector pcDNA3.1+

The vector chosen for use as a DNA vaccine vector was pcDNA3.1 (Invitrogen) (actually pcDNA3.1+, the forward orientation was used in all cases but may be referred to as pcDNA3.1 here on). This vector has been widely and successfully employed as a host vector to test vaccine candidate genes to give protection against pathogens in the literature (Zhang, et al., Kurar and Splitter, Anderson, et al.) The vector was designed for high-level stable and non-replicative transient expression in mammalian cells. pcDNA3.1 contains the ColE1 origin of replication which allows convenient high-copy number replication and growth in *E. coli*. This in turn allows rapid and efficient cloning and testing of many genes. The pcDNA3.1 vector has a large number of cloning sites and also contains the gene encoding ampicillin resistance to aid in cloning selection and the human cytomegalovirus (CMV) immediate-early promoter/enhancer which permits efficient, high-level expression of the recombinant protein. The CMV promoter is a strong viral promoter in a wide range of cell types including both muscle and immune (antigen presenting) cells. This is important for optimal immune response as it remains unknown as to which cells types are most important in generating a protective response in vivo. A T7 promoter upstream of the multiple cloning site affords efficient expression of the modified insert of interest and which allows in vitro transcription of a cloned gene in the sense orientation.

Zhang, D., Yang, X., Berry, J. Shen, C., McClarty, G. and Brunham, R. C. (1997) "DNA vaccination with the major outer-membrane protein genes induces acquired immunity to *Chlamydia trachomatis* (mouse pneumonitis) infection". *Infection and Immunity,* 176, 1035-40.

Kurar, E. and Splitter, G. A. (1997) "Nucleic acid vaccination of *Brucella abortus* ribosomal L7/L12 gene elicits immune response". *Vaccine,* 15, 1851-57.

Anderson, R., Gao, X.-M., Papakonstantinopoulou, A., Roberts, M. and Dougan, G. (1996) "Immune response in mice following immunisation with DNA encoding fragment C of tetanus toxin". *Infection and Immunity,* 64, 3168-3173.

Preparation of DNA Vaccines

Oligonucleotide primers were designed for each individual gene of interest derived using the LEEP system. Each gene was examined thoroughly, and where possible, primers were designed such that they targeted that portion of the gene thought to encode only the mature portion of the gene protein. It was hoped that expressing those sequences that encode only the mature portion of a target gene protein, would facilitate its correct folding when expressed in mammalian cells. For example, in the majority of cases primers were designed such that putative N-terminal signal peptide sequences would not be included in the final amplification product to be cloned into the pcDNA3.1 expression vector. The signal peptide directs the polypeptide precursor to the cell membrane via the protein export pathway where it is normally cleaved off by signal peptidase I (or signal peptidase II if a lipoprotein). Hence the signal peptide does not make up any part of the mature protein whether it be displayed on the surface of the bacteria surface or secreted. Where a N-terminal leader peptide sequence was not immediately obvious, primers were designed to target the whole of the gene sequence for cloning and ultimately, expression in pcDNA3.1.

Having said that, however, other additional features of proteins may also affect the expression and presentation of a soluble protein. DNA sequences encoding such features in the genes encoding the proteins of interest were excluded during the design of oligonucleotides. These features included:

1. LPXTG (SEQ ID NO: 364) cell wall anchoring motifs.
2. LXXC ipoprotein attachment sites.
3. Hydrophobic C-terminal domain.
4. Where no N-terminal signal peptide or LXXC was present the start codon was excluded.
5. Where no hydrophobic C-terminal domain or LPXTG (SEQ ID NO: 364) motif was present the stop codon was removed.

Appropriate PCR primers were designed for each gene of interest and any and all of the regions encoding the above features was removed from the gene when designing these primers. The primers were designed with the appropriate enzyme restriction site followed by a conserved Kozak nucleotide sequence (in all cases) GCCACC was used. The Kozak sequence facilitates the recognition of initiator sequences by eukaryotic ribosomes) and an ATG start codon upstream of the insert of the gene of interest. For example the forward primer using a BamHI site the primer would begin GCGGGATCCGCCACCATG (SEQ ID NO: 365) followed by a small section of the 5' end of the gene of interest. The reverse primer was designed to be compatible with the forward primer and with a NotI restriction site at the 5' end in all cases (this site is TTGCGGCCGC) (SEQ ID NO:366).

PCR Primers

The following PCR primers were designed and used to amplify the truncated genes of interest.

```
ID210
                                                        (SEQ ID NO: 367)
Forward Primer 5' CGGATCCGCCACCATGTCTTCTAATGAATCTGCCGATG 3'
                                                        (SEQ ID NO: 368)
Reverse Primer 5' TTGCGGCCGCCTGTTTAGATTGGATATCTGTAAAGACTT 3'

4172.5
                                                        (SEQ ID NO: 369)
Forward Primer 5' CGCGGATCCGCCACCATGGATTTTCCTTCAAATTTGGAGG 3'
                                                        (SEQ ID NO: 370)
Reverse Primer 5' TTGCGGCCGCACCGTACTGGCTGCTGACT 3'

ID211
                                                        (SEQ ID NO: 371)
Forward Primer 5' CGGATCCGCCACCATGAGTGAGATCAAAATTATTAACGC 3'
                                                        (SEQ ID NO: 372)
Reverse Primer 5' TTGCGGCCGCCGTTCCATGGTTGACTCCT 3'

4197.4
                                                        (SEQ ID NO: 373)
Forward Primer 5' CGCGGATCCGCCACCATGTGGGACATATTGGTGGAAAC 3'
                                                        (SEQ ID NO: 374)
Reverse Primer 5' TTGCGGCCGCTTCACTTGAGCAAACTGAATCC 3'

4122.1
                                                        (SEQ ID NO: 375)
Forward Primer 5' CGCGGATCCGCCACCATGTCACAAGAAAAAACAAAAAATGAA 3'
                                                        (SEQ ID NO: 376)
Reverse Primer 5' TTGCGGCCGCATCGACGTAGTCTCCGCC 3'

4126.7
                                                        (SEQ ID NO: 377)
Forward Primer 5' CGCGGATCCGCCACCATGCTGGTTGGAACTTTCTACTATCAAT 3'
                                                        (SEQ ID NO: 378)
```

-continued
```
Reverse Primer  5'  TTGCGGCCGCAACTTTCGTCCCTTTTTGG 3'

4188.11
                                                    (SEQ ID NO: 379)
Forward Primer  5'  CGCGGATCCGCCACCATGGGCAATTCTGGCGGAA 3'
                                                    (SEQ ID NO: 380)
Reverse Primer  5'  TTGCGGCCGCTTGTTTCATAGCTTTTTTGATTGTT 3'

ID209
                                                    (SEQ ID NO: 381)
Forward Primer  5'  CGCGGATCCGCCACCATGCTATTGATACGAAATGCAGGG 3'
                                                    (SEQ ID NO: 382)
Reverse Primer  5'  TTGCGGCCGCAACATAATCTAGTAAATAAGCGTAGCC 3'

ID215
                                                    (SEQ ID NO: 383)
Forward Primer  5'  CGCGGATCCGCCACCATGACGGCGACGAATTTTC 3'
                                                    (SEQ ID NO: 384)
Reverse Primer  5'  TTGCGGCCGCTTAATTCGTTTTTGAACTAGTTGCT 3'

4170.4
                                                    (SEQ ID NO: 385)
Forward Primer  5'  CGCGGATCCGCCACCATGGCTGTTTTTCTTCGCTATCATG 3'
                                                    (SEQ ID NO: 386)
Reverse Primer  5'  TTGCGGCCGCTTTCTTCAACAAACCTTGTTCTTG 3'

4193.1
                                                    (SEQ ID NO: 387)
Forward Primer  5'  CGCGGATCCGCCACCATGGGTAACCGCTCTTCTCGTAAC 3'
                                                    (SEQ ID NO: 388)
Reverse Primer  5'  TTGCGGCCGCGCTTCCATCAAGGATTTTAGC 3'
```

Cloning

The insert along with the flanking features described above was amplified using PCR against a template of genomic DNA isolated from type 4 S. pneumoniae strain 11886 obtained from the National Collection of Type Cultures. The PCR product was cut with the appropriate restriction enzymes and cloned in to the multiple cloning site of pcDNA3.1 using conventional molecular biological techniques. Suitably mapped clones of the genes of interested were cultured and the plasmids isolated on a large scale (>1.5 mg) using Plasmid Mega Kits (Qiagen). Successful cloning and maintenance of genes was confirmed by restriction mapping and sequencing ~700 base pairs through the 5' cloning junction of each large scale preparation of each construct.

Strain Validation

A strain of type 4 was used in cloning and challenge methods which is the strain from which the S. pneumoniae genome was sequenced. A freeze dried ampoule of a homogeneous laboratory strain of type 4 S. pneumoniae strain NCTC 11886 was obtained from the National Collection of Type Strains. The ampoule was opened and the cultured re suspended with 0.5 ml of tryptic soy broth (0.5% glucose, 5% blood). The suspension was subcultured into 10 ml tryptic soy broth (0.5% glucose, 5% blood) and incubated statically overnight at 37° C. This culture was streaked on to 5% blood agar plates to check for contaminants and confirm viability and on to blood agar slopes and the rest of the culture was used to make 20% glycerol stocks. The slopes were sent to the Public Health Laboratory Service where the type 4 serotype was confirmed.

A glycerol stock of NCTC 11886 was streaked on a 5% blood agar plate and incubated overnight in a $CO_2$ gas jar at 37° C. Fresh streaks were made and optochin sensitivity was confirmed.

Pneumococcal Challenge

Figure 4:
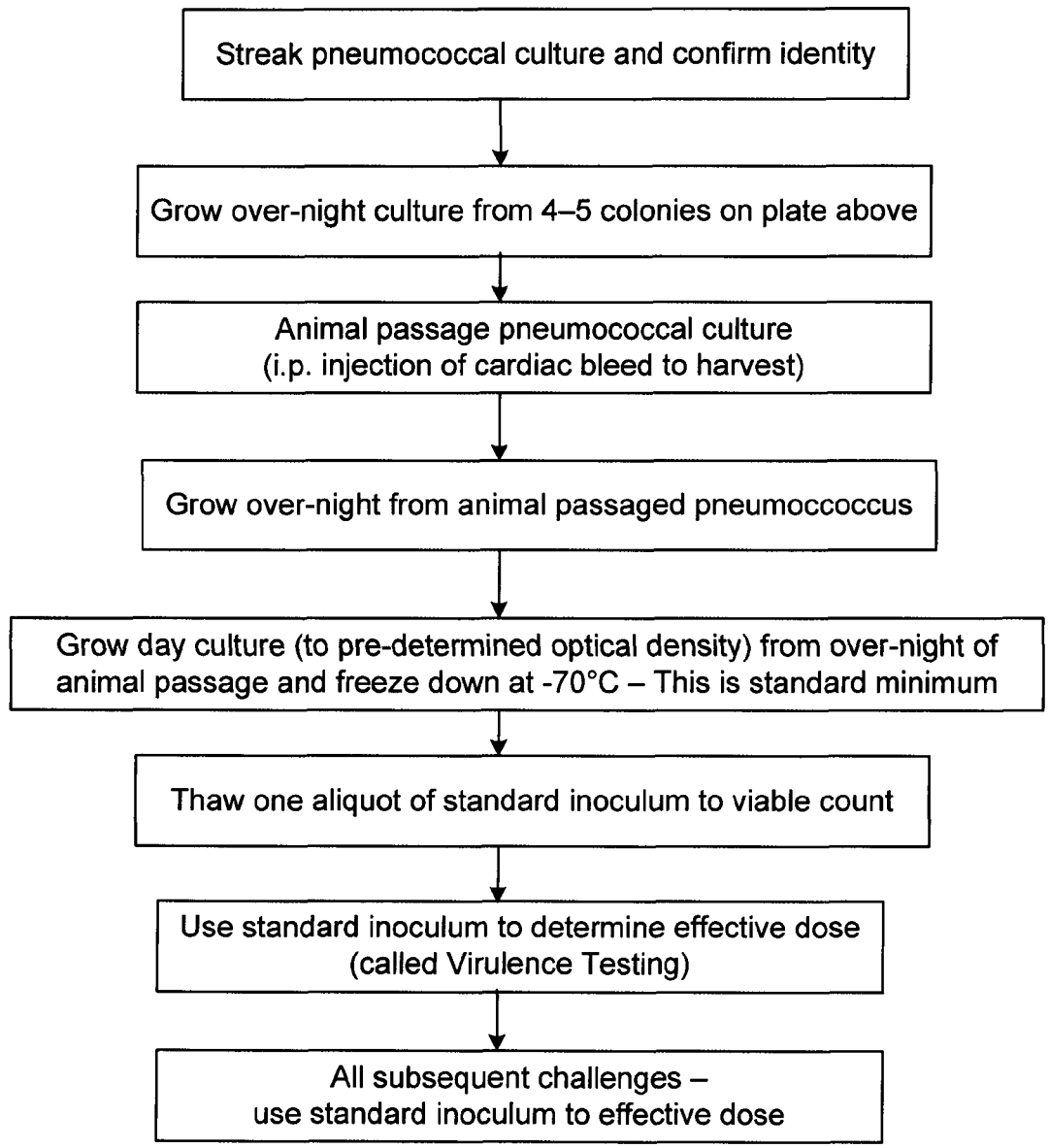
FIG. 4: Flow Chart.

A standard inoculum of type 4 S. pneumoniae was prepared and frozen down by passaging a culture of pneumococcus 1× through mice, harvesting from the blood of infected animals, and grown up to a predetermined viable count of around $10^9$ cfu/ml in broth before freezing down. The preparation is set out below as per the flow chart in FIG. 4.

An aliquot of standard inoculum was diluted 500× in PBS and used to inoculate the mice.

Mice were lightly anaesthetised using halothane and then a dose of $1.4 \times 10^5$ cfu of pneumococcus was applied to the nose of each mouse. The uptake was facilitated by the normal breathing of the mouse, which was left to recover on its back.

S. pneumoniae Vaccine Trials

Vaccine trials in mice were carried out by the administration of DNA to 6 week old CBA/ca mice (Harlan, UK). Mice to be vaccinated were divided into groups of six and each group was immunised with recombinant pcDNA3.1+ plasmid DNA containing a specific target-gene sequence of interest. A total of 100 µg of DNA in Dulbecco's PES (Sigma) was injected intramuscularly into the tibialis anterior muscle of both legs (50 µl in each leg). A boost was carried using the same procedure 4 weeks later. For comparison, control groups were included in all vaccine trials. These control groups were either unvaccinated animals or those administered with non-recombinant pcDNA3.1+DNA (sham vaccinated) only, using the same time course described above. 3 weeks after the second immunisation, all mice groups were challenged intra-nasally with a lethal dose of S. pneumoniae serotype 4 (strain NCTC 11886). The number of bacteria administered was monitored by plating serial dilutions of the inoculum on 5% blood agar plates. A problem with intranasal immunisations is that in some mice the inoculum bubbles out of the nostrils, this has been noted in results table and taken account of in calculations. A less obvious problem is that a certain amount of the inoculum for each mouse may be swallowed. It is assumed that this amount will be the same for each mouse and will average out over the course of innoculations. However, the sample sizes that have been used are small and this problem may have significant effects in some experiments. All mice remaining after the challenge were killed 3 or 4 days after infection. During the infection process, challenged mice were monitored for the development of symptoms associated with the onset of S. pneumoniae induceddisease. Typical symptoms in an appropriate order included piloerection, an increasingly hunched posture, discharge from eyes, increased lethargy and reluctance to move. The latter symptoms usually coincided with the development of a moribund state at which stage the mice were culled to prevent further suffering. These mice were deemed to be very close to death, and the time of culling was used to determine a survival time for statistical analysis. Where mice were found dead, the survival time was taken as the last time point when the mouse was monitored alive.

Interpretation of Results

A positive result was taken as any DNA sequence that was cloned and used in challenge experiments as described above which gave protection against that challenge. Protection was taken as those DNA sequences that gave statistically significant protection (to a 95% confidence level ($p<0.05$)) and also those which were marginal or close to significant using Mann-Whitney or which show some protective features for example there were one or more outlying mice or because the time to the first death was prolonged. It is acceptable to allow marginal or non-significant results to be considered as potential positives when it is considered that the clarity of some of the results may be clouded by the problems associated with the administration of intranasal infections.

TABLE 1

Figure 1:
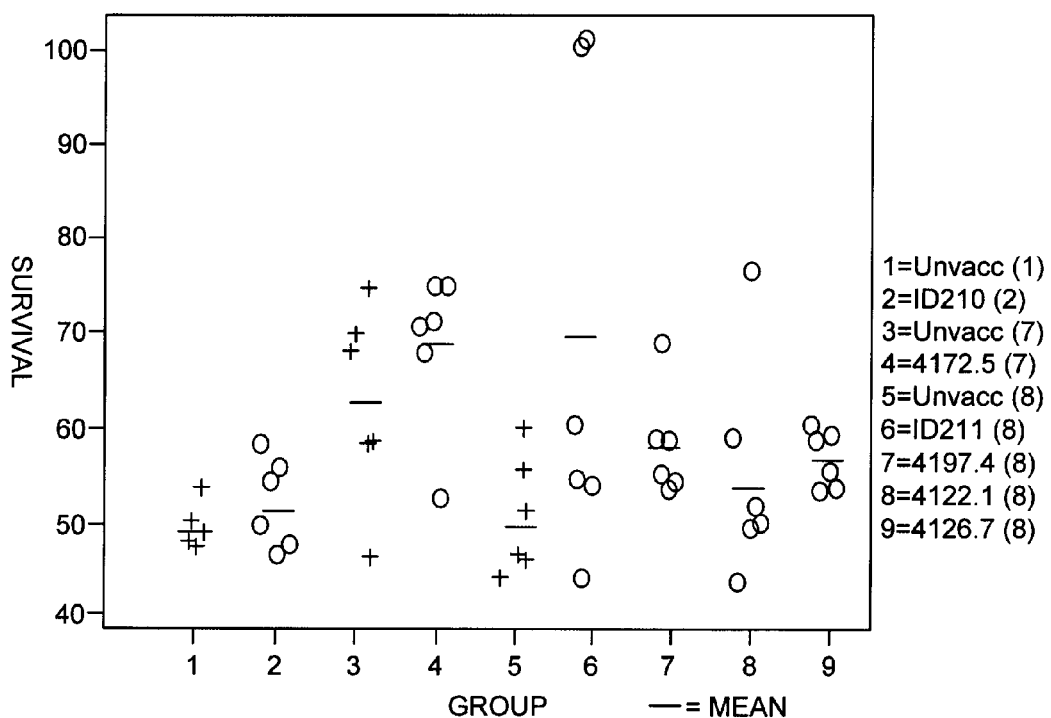
FIG. 1: shows the results of various DNA vaccine trials.

Results for vaccine trials 2, 7, and 8 (See FIG. 1)

| Mouse number | Unvacc control (2) | ID210 (2) | Unvacc control (7) | 4172.5 (7) | Unvacc control (8) | ID211 (8) | 4197.4. (8) | 4122.1 (8) | 4126.7 (8) |
|---|---|---|---|---|---|---|---|---|---|
| | | | | Mean survival times (hours) | | | | | |
| 1 | 49.0 | 55.0 | 59.6 | 72.6 | 45.1 | 102.3T | 60.1 | 50.6 | 60.0 |
| 2 | 51.0 | 46.5 | 47.2 | 67.9 | 50.8 | 55.5 | 54.9 | 77.2 | 60.0 |
| 3 | 49.0 | 49.0 | 59.6 | 54.4 | 60.4 | 60.6* | 68.4 | 60.3 | 54.8 |
| 4 | 55.0 | 59.0 | 70.9 | 75.3 | 55.2 | 45.3 | 60.1 | 50.6 | 52.6 |
| 5 | 49.0 | 55.0 | 68.6* | 70.9 | 45.1 | 55.5 | 54.9 | 50.6* | 54.8 |
| 6 | 49.0 | 49.0 | 76.0 | 75.3 | 45.1 | 102.3T | 52.7 | 44.9 | 60 |
| Mean | 50.3 | 52.3 | 63.6 | 69.4 | 50.2 | 70.2 | 58.5 | 55.7 | 57.0 |
| sd | 2.4 | 4.8 | 10.3 | 7.9 | 6.4 | 25.3 | 5.7 | 11.6 | 3.4 |
| p value 1 | — | 0.3333 | — | 0.2104 | — | 0.0215 | 0.0621 | 0.4038 | 0.0833 |

*bubbled when dosed so may not have received full inoculum.
T - terminated at end of experiment having no symptoms of infection.
Numbers in brackets - survival times disregarded assuming incomplete dosing.
p value 1 refers to significance tests compared to unvaccinated controls.
Statistical Analyses.
Trial 2 - The group vaccinated with ID210 also had a longer mean survival time than the unvaccinated controls but the results are not statistically significant.
Trial 7 - The group vaccinated with 4172.5 showed much greater survival times than unvaccinated controls although the differences were not statistically significant.
Trial 8 - The group vaccinated with ID211 survived significantly longer than unvaccinated controls. 4197.4, 4122.1 and 4126.7 vaccinated groups showed longer mean survival times than the unvaccinated group but the results were not statistically significant. The 4197.4 and 4126.7 groups also showed a prolonged time to the first death and the 4122.1 group showed 1 outlying result.

TABLE 2

Figure 2:
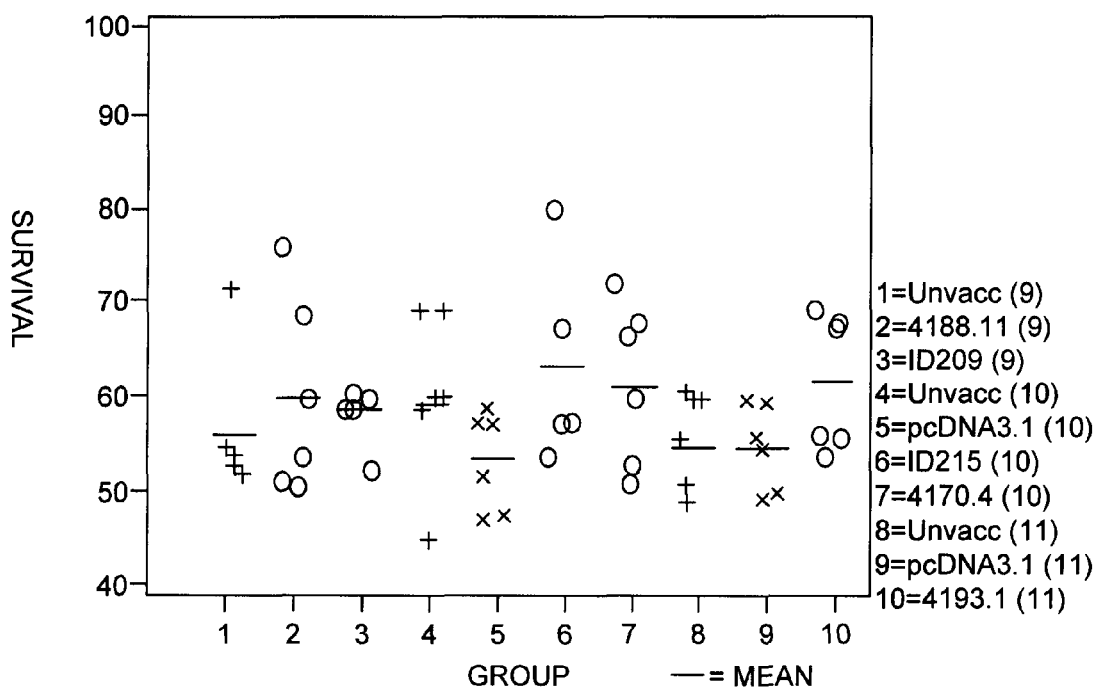
FIG. 2: shows the results of further DNA vaccine trials.

Results of pneumococcal challenge DNA vaccination trials 9-11 (See FIG. 2)

| Mouse number | Unvocc control (9) | 4188.11 (9) | ID209 (9) | Unvacc control (10) | pcDNA3.1+ (10) | ID215 (10) | 4170.4 (10) | Unvacc control (11) | pcDNA3.1+ (11) | 4193.1 (11) |
|---|---|---|---|---|---|---|---|---|---|---|
| | | | | | Mean survival times (hours) | | | | | |
| 1 | (98.5)T | 69.4 | 60.2 | 68.4 | 58.6 | 79.2 | 68.1 | 60.0 | 53.2 | 54.8 |
| 2 | 53.4 | 53.7 | 60.2 | 59.0 | 58.6 | 54.2 | 58.6 | 50.0 | 50.4 | 54.8 |
| 3 | 53.4 | 51.2 | 60.2 | 59.0 | 50.8 | (103.2)*T | 50.9 | 60.0 | 55.4 | 68.7* |
| 4 | 53.4 | 75.0 | (98.0)*T | 45.1* | 58.6 | 58.8 | 72.1 | 55.0 | 60.6 | 54.8 |
| 5 | 70.8 | 51.2 | 60.2 | 68.4 | 46.5 | 68.3 | 68.1 | 60.0 | 50.4 | 68.7 |
| 6 | 53.4 | 61.2 | 52.9 | 59.0 | 48.9 | 58.8 | 54.0 | 50.0 | 60.6 | 68.7* |
| Mean | 56.9 | 60.3 | 58.8 | 59.8 | 53.6 | 63.9 | 62.0 | 55.8 | 55.1 | 61.7 |
| sd | 7.8 | 10.0 | 3.3 | 8.5 | 5.6 | 10.0 | 8.7 | 5.0 | 4.6 | 7.6 |
| p value 1 | — | 0.3894 | 0.2519 | — | 0.0307 | <30.0 | <39.0 | — | — | 0.1837 |
| p value 2 | — | — | — | — | — | 0.0168 | 0.0316 | — | — | 0.0829 |

*bubbled when dosed so may not have received full inoculum.
T - terminated at end of experiment having no symptoms of infection.
Numbers in brackets - survival times disregarded assuming incomplete dosing.
p value 1 refers to significance tests compared to unvaccinated controls.
p value 2 refers to significance tests compared to pcDNA3.1+ vaccinated controls.
Statistical Analyses.
Trial 9 - Although not statistically significant the groups vaccinated with 4188.11 and ID209 did have noticeably higher mean survival times than unvaccinated controls.
Trial 10 - The unvaccinated control group survived for a significantly longer period than the pcDNA3.1+ vaccinated group. The groups vaccinated with ID215 and 4170.4 showed statistically significant longer survival times compared, to the sham vaccinated group (p = 0.0168 and 0.0316) but not compared to the unvaccinated group.
Trial 11 - The group vaccinated with 4193.1 was the most promising and survived an average of 6.5 hours longer than the pcDNA3.1+ vaccinated group and 6 hours longer than the unvaccinated group although the results were not statistically significant.

TABLE 3

4101.1
(SEQ. ID. NO. 208)
ATGGAAGAGTTAGTGACCTTAGATTGTTTGTTTATTGACAGAACTAAGATT
GAAGCCAATGCCAACAAGTATAGTTTTGTGTGGAAGAAAACGACAGAGAAA
TTCTCCGCCAAACTTCAAGAACAGATACAGGTCTATTTTCAAGAAGAAATC
ACTCCCCTTCTGATTAAATATGCCATGTTTGATAAGAAACAAAAGAGAGGG
TATAAAGAGTCAGCTAAAAACTTAGCGAATTGGCACTATAATGACAAGGAG
GATAGCTACACACATCCTGATGGCTGGTATTATCGTTTTCACCATACCAAA
TATCAGAAAACACAGACAGACTTTCAACAAGAAATCAAGGTTTACTACGCC
GACGAACCTGAATCAGCCCCTCAAAAGGGACTGTATATGAACGAACGCTAT
CAAAACTTGAAAGCTAAAGAATGTCAGGCGCTTTTATCTCCCCAAGGTAGA
CAGATTTTCGCTCAACGCAAGATTGATGTGAACCTGTCTTTGGGCAGATA
AAGGCTTCTTTGGGTTACAAGAGATGTAATCTGAGAGGGAAGCGTCAAGTG
AGAATTGACATGGGATTGGTACTTATGGCCAATAACCTCCTAAAATATAGT
AAAATGAAATAA 4101.3
(SEQ. ID. NO. 209)
ATGGGGAAAGGCCATTGGAATCGGAAAAGAGTTTATAGCATTCGTAAGTTT
GCTGTGGGAGCTTGCTCAGTAATGATTGGGACTTGTGCAGTTTTATTAGGA
GGAAATATAGCTGGAGAATCTGTAGTTTATGCGGATGAAACACTTATTACT
CATACTGCTGAGAAACCTAAAGAGGAAAAAATGATAGTAGAAGAAAAGGCT
GATAAAGCTTTGGAAACTAAAAATATAGTTGAAAGGACAGAACAAAGTGAA
CCTAGTTCAACTGAGGCTATTGCATCTGAGAAGAAAGAAGATGAAGCCGTA
ACTCCAAAAGAGGAAAAAGTGTCTGCTAAACCGGAAGAAAAAGCTCCAAGG
ATAGAATCACAAGCTTCAAATCAAGAAAAACCGCTCAAGGAAGATGCTAAA
GCTGTAACAAATGAAGAAGTGAATCAAATGATTGAAGACAGGAAAGTGGAT
TTTAATCAAAATTGGTACTTTAAACTCAATGCAAATTCTAAGGAAGCCATT
AAACCTGATGCAGACGTATCTACGTGAAAAAATTAGATTTACCGTATGAC
TGGAGTATCTTTAACGATTTCGATCATGAATCTCCTGCACAAAATGAAGGT
GGACAGCTCAACGGTGGGGAAGCTTGGTATCGCAAGACTTTCAAACTAGAT
GAAAAAGACCTCAAGAAAAATGTTCGCCTTACTTTTGATGGCGTCTACATG
GATTCTCAAGTTTATGTCAATGGTCAGTTAGTGGGGCATTATCCAAATGGT
TATAACCAGTTCTCATATGATATCACCAAATACCTTCAAAAAGATGGTCGT
GAGAATGTGATTGCTGTCCATGCAGTCAACAAACAGCCAAGTAGCCGTTGG
TATTCAGGAAGTGGTATCTATCGTGATGTGACTTTACAAGTGACAGATAAG
GTGCATGTTGAGAAAAATGGGACAACTATTTTAACACCAAAACTTGAAGAA
CAACAACATGGCAAGGTTGAAACTCATGTGACCAGCAAAATCGTCAATACG
GACGACAAAGACCATGAACTTGTAGCCGAATATCAAATCGTTGAACGAGGT
GGTCATGCTGTAACAGGCTTAGTTCGTACAGCGAGTCGTACCTTAAAAGCA
CATGAATCAACAAGCCTAGATGCGATTTTAGAAGTTGAAAGACCAAAACTC
TGGACTGTTTTAAATGACAAACCTGCCTTGTACGAATTGATTACGCGTGTT
TACCGTGACGGTCAATTGGTTCATGCTAAGAAGGATTTGTTTGGTTACCGT
TACTATCACTGGACTCCAAATGAAGGTTTCTCTTTGAATGGTGAACGTATT
AAATTCCATGGAGTATCCTTGCACCACGACCATGGGGCGCTTGGAGCAGAA
GAAAACTATAAAGCAGAATATCGCCGTCTCAAACAAATGAAGGAGATGGGA
GTTAACTCCATCCGTACAACCCACAACCCTGCTAGTGAGCAAACCTTGCAA
ATCGCAGCAGAACTAGGTTTACTCGTTCAGGAAGAGGCCTTTGATACGTGG
TATGGTGGCAAGAAACCTTATGACTATGGACGTTTCTTTGAAAAAGATGCC
ACTCACCCAGAAGCTCGAAAAGGTGAAAAATGGTCTGATTTTGACCTACGT
ACCATGGTCGAAAGAGGCAAAAACAACCCTGCTATCTTCATGTGGTCAATT
GGTAATGAAATAGGTGAAGCTAATGGTGATGCCCACTCTTTAGCAACTGTT
AAACGTTTGGTTAAGGTTATCAAGGATGTTGATAAGACTCGCTATGTTACC
ATGGGAGCAGATAAATTCCGTTTCGGTAATGGTAGCGGAGGGCATGAGAAA
ATTGCTGATGAACTCGATGCTGTTGGATTTAACTATTCTGAAGATAATTAC
AAAGCCCTTAGAGCTAAGCATCCAAAATGGTTGATTTATGGATCAGAAACA
TCTTCAGCTACCCGTACACGTGGAAGTTACTATCGCCCTGAACGTGAATTG
AAACATAGCAATGGACCTGAGCGTAATTATGAACAGTCAGATTATGGAAAT
GATCGTGTGGGTTGGGGGAAAACAGCAACCGCTTCATGGACTTTTGACCGT
GACAACGCTGGCTATGCTGGACAGTTTATCTGGACAGGTACGGACTATATT
GGTGAACCTACACCATGGCACAACCAAAATCAAACTCCTGTTAAGAGCTCT
TACTTTGGTATCGTAGATACAGCCGGCATTCCAAAACATGACTTCTATCTC
TACCAAAGCCAATGGGTTTCTGTTAAGAAGAAACCGATGGTACACCTTCTT
CCTCACTGGAACTGGGAAAACAAAGAATTAGCATCCAAAGTAGCTGACTCA
GAAGGTAAGATTCCAGTTCGTGCTTATTCGAATGCTTCTAGTGTAGAATTG
TTCTTGAATGGAAAATCTCTTGGTCTTAAGACTTTCAATAAAAAACAAACC
AGCGATGGGCGGACTTACCAAGAAGGTGCAAATGCTAATGAACTTTATCTT
GAATGGAAAGTTGCCTATCAACCAGGTACCTTGGAAGCAATTGCTCGTGAT
GAATCTGGCAAGGAAATTGCTCGAGATAAGATTACGACTGCTGGTAAGCCA
GCGGCAGTTCGTCTTATTAAGGAAGACCATGCGATTGCAGCAGATGGAAAA
GACTTGACTTACATCTACTATGAAATTGTTGACAGCCAGGGGAATGTGGTT
CCAACTGCTAATAATCTGGTTCGCTTCCAATTGCATGGCCAAGGTCAACTG
GTCGGTGTAGATAACGGAGAACAAGCCAGCCGTGAACGCTATAAGGCGCAA
GCAGATGGTCTTGGATTCGTAAAGCATTTAATGGTAAAGGTGTTGCCATT
GTCAAATCAACTGAACAAGCAGGGAAATTCACCCTGACTGCCCACTCTGAT
CTCTTGAAATCGAACCAAGTCACTGTCTTTACTGGTAAGAAAGAAGGACAA
GAGAAGACTGTTTTGGGGACAGAAGTGCCAAAAGTACAGACCATTATTGGA
GAGGCACCTGAAATGCCTACCACTGTTCCGTTTGTATACAGTGATGGTAGC
CGTGCAGAACGTCCTGTAACCTGGTCTTCAGTAGATGTGAGCAAGCCTGGT
ATTGTAACGGTGAAAGGTATGGCTGACGGACGAGAAGTAGAAGCTCGTGTA
GAAGTGATTGCTCTTAAATCAGAGCTACCAGTTGTGAAACGTATTGCTCCA
AATACTGACTTGAATTCTGTAGACAAATCTGTTTCCTATGTTTTGATTGAT
GGAAGTGTTGAAGAGTATGAAGTGGACAAGTGGGAGATTGCCGAAGAAGAT

TABLE 3-continued

```
AAAGCTAAGTTAGCAATTCCAGGTTCTCGTATTCAAGCGACCGGTTATTTA
GAAGGTCAACCAATTCATGCAACCCTTGTGGTAGAAGAAGGCAATCCTGCG
GCACCTGCAGTACCAACTGTAACGGTTGGTGGTGAGGCAGTAACAGGTCTT
ACTAGTCAAAAACCAATGCAATACCGCACTCTTGCTTATGGAGCTAAGTTG
CCAGAAGTCACAGCAAGTGCTAAAAATGCAGCTGTTACAGTTCTTCAAGCA
AGCGCAGCAAACGGCATGCGTGCGAGCATCTTTATTCAGCCTAAAGATGGT
GGCCCTCTTCAAACCTATGCAATTCAATTCCTTGAAGAAGCGCCAAAAATT
GCTCACTTGAGCTTGCAAGTGGAAAAAGCTGACAGTCTCAAAGAAGACCAA
ACTGTCAAATTGTCGGTTCGAGCTCACTATCAAGATGGAACGCAAGCTGTA
TTACCAGCTGATAAAGTAACCTTCTCTACAAGTGGTGAAGGGGAAGTCGCA
ATTCGTAAAGGAATGCTTGAGTTGCATAAGCCAGGAGCAGTCACTCTGAAC
GCTGAATATGAGGGAGCTAAAGACCAAGTTGAACTCACTATCCAAGCCAAT
ACTGAGAAGAAGATTGCGCAATCCATCCGTCCTGTAAATGTAGTGACAGAT
TTGCATCAGGAACCAAGTCTTCCAGCAACAGTAACAGTTGAGTATGACAAA
GGTTTCCCTAAAACTCATAAAGTCACTTGGCAAGCTATTCCGAAAGAAAAA
CTAGACTCCTATCAAACATTTGAAGTACTAGGTAAAGTTGAAGGAATTGAC
CTTGAAGCGCGTGCAAAAGTCTCTGTAGAAGGTATCGTTTCAGTTGAAGAA
GTCAGTGTGACAACTCCAATCGCAGAAGCACCACAATTACCAGAAAGTGTT
CGGACATATGATTCAAATGGTCACGTTTCATCAGCTAAGGTTGCATGGGAT
GCGATTCGTCCAGAGCAATACGCTAAGGAAGGTGTCTTTACAGTTAATGGT
CGCTTAGAAGGTACGCAATTAACAACTAAACTTCATGTTCGCGTATCTGCT
CAAACTGAGCAAGGTGCAAACATTTCTGACCAATGGACCGGTTCAGAATTG
CCACTTGCCTTTGCTTCAGACTCAAATCCAAGCGACCCAGTTTCAAATGTT
AATGACAAGCTCATTTCCTACAATAACCAACCAGCCAATCGTTGGACAAAC
TGGAATCGTACTAATCCAGAAGCTTCAGTCGGTGTTCTGTTTGGAGATTCA
GGTATCTTGAGCAAACGCTCCGTTGATAATCTAAGTGTCGGATTCCATGAA
GACCATGGAGTTGGTGTACCGAAGTCTTATGTGATTGAGTATTATGTTGGT
AAGACTGTCCCAACAGCTCCTAAAAACCCTAGTTTTGTTGGTAATGAGGAC
CATGTCTTTAATGATTCTGCCAACTGGAAACCAGTTACTAATCTAAAAGCC
CCTGCTCAACTCAAGGCTGGAGAAATGAACCACTTTAGCTTTGATAAAGTT
GAAACCTATGCTGTTCGTATTCGCATGGTTAAAGCAGATAACAAGCGTGGA
ACGTCTATCACAGAGGTACAAATCTTTGCGAAACAAGTTGCGGCAGCCAAG
CAAGGACAAACAAGAATCCAAGTTGACGGCAAAGACTTAGCAAACTTCAAC
CCTGATTTGACAGACTACTACCTTGAGTCTGTAGATGGAAAAGTTCCGGCA
GTCACAGCAAGTGTTAGCAACAATGGTCTCGCTACCGTCGTTCCAAGCGTT
CGTGAAGGTGAGCCAGTTCGTGTCATCGCGAAAGCTGAAAATGGCGACATC
TTAGGAGAATACCGTCTGCACTTCACTAAGGATAAGAGCTTACTTTCTCAT
AAACCAGTTGCTGCGGTTAAACAAGCTCGCTTGCTACAAGTAGGTCAAGCA
CTTGAATTGCCGACTAAGGTTCCAGTTTACTTCACAGGTAAAGACGGCTAC
GAAACAAAAGACCTGACAGTTGAATGGGAAGAAGTTCCAGCGGAAAATCTG
ACAAAAGCAGGTCAATTTACTGTTCGAGGCCGTGTCCTTGGTAGTAACCTT
GTTGCTGAGATCACTGTACGAGTGACAGACAAACTTGGTGAGACTCTTTCA
GATAACCCTAACTATGATGAAAACAGTAACCAGGCCTTTGCTTCAGCAACC
AATGATATTGACAAAAACTCTCATGACCGCGTTGACTATCTCAATGACGGA
GATCATTCAGAAAATCGTCGTTGGACAAACTGGTCACCAACACCATCTTCT
AATCCAGAAGTATCAGCGGGTGTGATTTTCCGTGAAAATGGTAAGATTGTA
GAACGGACTGTTACACAAGGAAAAGTTCAGTTCTTTGCAGATAGTGGTACG
GATGCACCATCTAAACTCGTTTTAGAACGCTATGTCGGTCCAGAGTTTGAA
GTGCCAACCTACTATTCAAACTACCAAGCCTACGACGCAGACCATCCATTC
AACAATCCAGAAAATTGGGAAGCTGTTCCTTATCGTGCGGATAAAGACATT
GCAGCTGGTGATGAAATCAACGTAACATTTAAAGCTATCAAAGCCAAAGCT
ATGAGATGGCGTATGGAGCGTAAAGCAGATAAGAGCGGTGTTGCGATGATT
GAGATGACCTTCCTTGCACCAAGTGAATTGCCTCAAGAAAGCACTCAATCA
AAGATTCTTGTAGATGGAAAAGAACTTGCTGATTTCGCTGAAAATCGTCAA
GACTATCAAATTACCTATAAAGGTCAACGGCCAAAAGTCTCAGTTGAAGAA
AACAATCAAGTAGCTTCAACTGTGGTAGATAGTGGAGAAGATAGCTTTCCA
GTACTTGTTCGCCTCGTTTCAGAAAGTGGAAAACAAGTCAAGGAATACCGT
ATCCACTTGACTAAGGAAAAACCAGTTTCTGAGAAGACAGTTGCTGCTGTA
CAAGAAGATCTTCCAAAAATCGAATTTGTTGAAAAAGATTTGGCATACAAG
ACAGTTGAGAAAAAGATTCAACACTGTATCTAGGTGAAACTCGTGTAGAA
CAAGAAGGAAAAGTTGGAAAAGAACGTATCTTTACAGCGATTAATCCTGAT
GGAAGTAAGGAAGAAAAACTCCGTGAAGTGGTAGAAGTTCCGACAGACCGC
ATCGTCTTGGTTGGAACCAAACCAGTAGCTCAAGAAGCTAAAAAACCACAA
GTGTCAGAAAAGCAGATACAAAACCAATTGATTCAAGTGAAGCTAGTCAA
ACTAATAAAGCCCAGTTACCAAGTACAGGTAGTGCGGCAAGCCAAGCAGCA
GTAGCAGCAGGTTTAACTCTTCTAGGTTTGAGTGCAGGATTAGTAGTTACT
AAAGGTAAAAAAGAAGACTAG
```

4101.5

(SEQ. ID. NO. 210)
```
ATGGATGCAATCTTTGACCTAATCGGAAAGGTTTTCAATCCCATCTTAGAA
ATGGGTGGACCTGTCATCATGTTAATCATTTTGACAGTATTGGCTTTACTT
TTTGGAGTGAAATTCTCCAAAGCGCTTGAAGGTGGTATCAAACTTGCCATC
GCTCTTACAGGTATCGGTGCTATCATCGGTATGCTAAACACTGCTTTCTCA
GCATCACTAGCAAAATTCGTTGAAAACACTGGTATCCAATTGAGTATTACC
GACGTTGGTTGGGCACCACTTGCTACAATCACTTGGGGTTCTGCTTGGACA
CTATACTTCTTGCTCATCATGTTGATTGTCAACATAGTGATGCTAGCTATG
AAGAAAACAGATACACTTGATGTCGATATCTTTGATATCTGGCACTTGTCT
ATCACAGGTCTCTTGATTAAATGGTATGCTGATAACAATGGTGTGAGTCAA
GGGGGTTTCACTCTTTATTGCTACAGCAGCTATCGTCCTTGTCGGTGTGTTG
AAAATTATCAACTCTGACTTGATGAAACCTACATTTGATGACCTTCTTAAC
GCCCCAAGTTCATCACCAATGACATCAACTCACATGAACTACATGATGAAC
```

TABLE 3-continued

CCAGTTATCATGGTTTTGGATAAGATTTTTGAAAAATTCTTCCCAGGCCTT
GATAAATATGACTTTGATGCTGCTAAATTGAACAAGAAAATCGGTTTCTGG
GGATCTAAATTCTTCATCGGTTTCATCCTTGGTATCGTTATCGGTATTATG
GGAACTCCACATCCAATTGCAGGTGTTGCAGATGCAGATAAATGGCGTCTT
GTTATCAAAGGATGGTTGTCTCTTGGTTTGACTGCCGGTGTATCTTTGGAA
CTCTTCTCACTTATCGGTTCATGGTTCATCGCAGCCTAGAACCACTATCA
CAAGGTATTACAAACGTTGCTACTAAACGTCTTCAAGGACGTAAATTCAAT
ATCGGTCTTGACTGGCCATTCATCGCTGGTCGTGCTGAAATCTGGGCTTGT
GCCAACGTACTTGCACCAATCATGTTGATTGAAGCAGTGCTTCTTTCAAAA
GTTGGAAATGGTATCTTGCCACTTGCAGGTATCATCGCTATGGGTGTTACT
CCAGCTCTCTTGGTTGTAACTCGTGGTAAATTGCTCCGTATGATTATCTTC
GGAACACTCTTGTTGCCACTCTTCCTTCTTTCAGGTACACTTATTGCACCA
TTTGCAACAGAACTTGCTAAAGGTGTAGGTGCCTTCCCAGAAGGTGTGAGC
CAAACTCAATTGATTACTCACTCTACTCTTGAAGGACCAATCGAAAAACTT
CTTGGTTGGACAATTGGTAACACTACAACTGGTGATATCAAAGCAATCCTT
GGTGCAGTAGTCTTCCTTGTATTCTATATCGGTATCTTTGCTTGGTACAGA
AAACAAATGATCAAACGTAACGAAGAGTACGCAGCAAAAGCAAAATAA 4102.1
(SEQ. ID. NO. 211)
ATGAAGATTATGAAAAAAAAATATTGGACTTTAGCGATATTATTCTTTTGT
TTGTTCAATAATTCTGTTACTGCTCAAGAAATACCTAAAAATCTTGATGGC
AATATAACTCACACTCAGACTAGCGAAAGTTTTTCTGAATCTGATGAAAAA
CAGGTTGACTATTCTAATAAAAATCAAGAAGAAGTAGACCAAAATAAATTT
CGTATTCAAATCGATAAGACAGAATTATTTGTAACAACAGATAAACATTTA
GAAAAAAACTGTTGTAAATTGGAACTTGAACCACAAATAAATAACGATATT
GTTAACTCTGAAAGTAATAATTTACTAGGCGAAGATAATTTAGATAATAAA
ATTAAGGAAAATGTTTCTCATCTAGATAATAGAGGAGGAAATATAGAGCAT
GACAAAGATAACTTAGAATCGTCGATTGTAAGAAAATATGAATGGGATATA
GATAAAGTTACTGGTGGAGGCGAAAGTTATAAATTATATTCTAAAGTAAT
TCTAAAGTTTCAATTGCTATTTTAGATTCAGGAGTCGATTTACAAAATACT
GGATTACTGAAAAATCTTTCAAATCACTCAAAAAACTATGTCCCCAATAAA
GGATATTTAGGAAAAGAGGAGGGAGAGGAAGGAATAATATCAGATATTCAA
GATAGATTAGGTCATGGTACGGCTGTTGTAGCTCAAATTGTAGGGGATGAC
AATATTAATGGAGTAAATCCTCACGTTAATATTAACGTCTATAGAATATTT
GGTAAGTCGTCAGCTAGTCCAGATTGGATTGTAAAAGCAATTTTTGATGCT
GTAGATGATGGCAATGATATTATCAATCTTAGTACTGGACAATATTTAATG
ATTGATGGAGAATATGAGGACGGAACAAATGATTTTGAAACATTTTTGAAG
TATAAAAAGGCTATTGATTACGCGAATCAAAAAGGAGTAATTATAGTAGCT
GCATTAGGGAATGACTCCCTAAATGTATCAAATCAGTCAGATTTATTGAAA
CTTATTAGTTCACGCAAAAAAGTAAGAAAACCAGGATTAGTAGTTGATGTT
CCAAGTTATTTCTCATCTACAATTTCGGTCGGAGGCATAGATCGCTTAGGT

AATTTATCAGATTTTAGCAATAAAGGGGATTCTGATGCAATATATGCGCCT
GCAGGCTCAACATTATCTCTTTCAGAATTAGGACTTAATAACTTTATTAAT
GCAGAAAAATATAAAGAAGATTGGATTTTTTCGGCAACACTAGGAGGATAT
ACGTATCTTTATGGAAACTCATTTGCTGCTCCTAAAGTTTCTGGTGCGATT
GCAATGATTATTGATAAATACAAATTAAAAGATCAGCCCTATAATTATATG
TTTGTAAAAAAATTCTGGAAGAAACATTACCAGTAA 4106.1
(SEQ. ID. NO. 212)
ATGAAGAAAACATGGAAAGTGTTTTTAACGCTTGTAACAGCTCTTGTAGCT
GTTGTGCTTGTGGCCTGTGGTCAAGGAACTGCTTCTAAAGACAACAAAGAG
GCAGAACTTAAGAAGGTTGACTTTATCCTAGACTGGACACCAAATACCAAC
CACACAGGGCTTTATGTTGCCAAGGAAAAAGGTTATTTCAAAGAAGCTGGA
GTGGATGTTGATTTGAAATTGCCACCAGAAGAAAGTTCTTCTGACTTGGTT
ATCAACGGAAAGGCACCATTTGCAGTGTATTTCCAAGACTACATGGCTAAG
AAATTGGAAAAGGAGCAGGAATCACTGCCGTTGCAGCTATTGTTGAACAC
AATACATCAGGAATCATCTCTCGTAAATCTGATAATGTAAGCAGTCCAAAA
GACTTGGTTGGTAAGAAATATGGGACATGGAATGACCCAACTGAACTTGCT
ATGTTGAAAACCTTGGTAGAATCTCAAGGTGGAGACTTTGAGAAGGTTGAA
AAAGTACCAAATAACGACTCAAACTCAATCACACCGATTGCCAATGGCGTC
TTTGATACTGCTTGGATTTACTACGGTTGGGATGGTATCCTTGCTAAATCT
CAAGGTGAGATGCTAACTTCATGTACTTGAAAGACTATGTCAAGGAGTTTG
ACTACTATTCACCAGTTATCATCGCAAACAACGACTATCTGAAAGATAACA
AAGAAGAAGCTCGCAAAGTCATCCAAGCCATCAAAAAAGGCTACCAATATG
CCATGGAACATCCAGAAGAAGCTGCAGATATTCTCATCAAGAATGCACCTG
AACTCAAGGAAAAACGTGACTTTGTCATCGAATCTCAAAAATACTTGTCAA
AAGAATACGCAAGCGACAAGGAAAATGGGGTCAATTTGACGCAGCTCGCT
GGAATGCTTTCTACAAATGGGATAAAGAAATGGTATCCTTAAAGAAGACT
TGACAGACAAAGGCTTCACCAACGAATTTGTGAAATAA 4106.4
(SEQ. ID. NO. 213)
ATGATAAAAAATCCTAAATTATTAACCAAGTCTTTTTTAAGAAGTTTTGCA
ATTCTAGGTGGTGTTGGTCTAGTCATTCATATAGCTATTTATTTGACCTTT
CCTTTTTATTATATTCAACTGGAGGGGAAAAGTTTAATGAGAGCGCAAGA
GTGTTTACGGAGTATTTAAAGACTAAGACATCTGATGAAATTCCAAGCTTA
CTCCAGTCTTATTCAAAGTCCTTGACCATATCTGCTCACCTTAAAAGAGAT
ATTGTAGATAAGCGGCTCCCTCTTGTGCATGACTTGGATATTAAAGATGGA
AAGCTATCAAATTATATCGTGATGTTAGATATGTCTGTTAGTACAGCAGAT
GGTAAACAGGTAACCGTGCAATTTGTTCACGGGGTGGATGTCTACAAAGAA
GCAAAGAATATTTGCTTTTGTATCTCCCATATACATTTTTGGTTACAATT
GCTTTTTCCTTTGTTTTTTCTTATTTTTATACTAAACGCTTGCTCAATCCT
CTTTTTTACATTTCAGAAGTGACTAGTAAAATGCAAGATTTGGATGACAAT
ATTCGTTTTCATCAAACTAGGAAAGATGAAGTTGGTGAAGTTGGAAAACAG

TABLE 3-continued

```
ATTAATGGTATGTATGAGCACTTGTTGAAGGTTATTTATGAGTTGGAAAGT
CTGTAATGAGCAAATTGTAAAATTGCAAATCAAAAGGTTTCCTTTGTCCG
CGGAGCATCACATGAGTTGAAAACCCCTTTAGCCAGTCTTAGAATTATCCT
AGAGAATATGCAGCATAATATTGGAGATTACAAAGATCATCCAAATATAT
TGCAAAGAGTATAAATAAGATTGACCAGATGAGCCACTTATTAGAAGAAGT
ACTGGAGTCTTCTAAATTCCAAGAGTGGACAGAGTGTCGTGAGACCTTGAC
TGTTAAGCCAGTTTTAGTAGATATTTTATCACGTTATCAAGAATTAGCTCA
TTCAATAGGTGTTACAATTGAAAATCAATTGACAGATGCTACCAGGGTCGT
CATGAGTCTTAGGGCATTGGATAAGGTTTTGACAAACCTGATTAGTAATGC
AATTAAATATTCAGATAAAAATGGGCGTGTAATCATATCCGAGCAAGATGG
CTATCTCTCTATCAAAATACATGTGCGCCTCTAAGTGACCAAGAACTAGA
ACATTTATTTGATATATTCTATCATTCTCAAATCGTGACAGATAAGGATGA
AAGTTCCGGTTTGGGTCTTTACATTGTGAATAATATTTTAGAAAGCTATCA
AATGGATTATAGTTTTCTCCCTTATGAACACGGTATGGAATTTAAGATTAG
CTTGTAG 4106.6
                                        (SEQ. ID. NO. 214)
ATGTATTTAGGAGATTTGATGGAGAAAGCCGAGTGTGGTCAATTTTCAATA
CTTTCCTTTCTATTACAAGAGTCTCAGACGACCGTCAAGGCTGTAATGGAA
GAAACAGGATTTTCAAAAGCAACCCTAACCAAATATGTCACCCTGCTCAAT
GACAAGGCTTTGGATAGTGGCTTAGAGCTGGCTATTCACTCAGAAGATGAA
AATCTGCGTCTGTCTATCGGTGCAGCTACCAAGGGGAGAGATATTCGGAGC
TTGTTTTTGGAGAGTGCTGTTAAATACCAGATTTTGGTTTATCTTCTCTAC
CACCAACAGTTTTTAGCCCATCAGCTGGCTCAAGAATTGGTGATTAGCGAG
GCTACGCTTGGTCGTCACTTGGCTGGTTTAAATCAGATTTTGTCAGAATTT
GATTTATCCATCCAAAATGGCCGTTGGCGAGGTCCAGAGCATCAGATTCAC
TATTTCTATTTCTGTCTTTTCCGAAAGGTCTGGTCGAGTCAGGAATGGGAA
GGTCACATGCAGAAACCAGAGAGAAAACAGGAGATTGCCAATTTAGAGGAA
ATCTGCGGTGCAAGTTTGTCTGCGGGGCAGAAATTGGACTTGGTTCTCTGG
GCTCACATCAGTCAACAACGTCTTCGGGTCAATGCTTGTCAGTTTCAAGTC
ATAGAAGAGAAAATGCGAGGGTATTTTGACAATATCTTTTATCTTCGTTTG
CTGAGAAAGGTTCCGTCCTTTTTTGCTGGGCAACATATTCCACTAGGAGTT
GAGGATGGTGAGATGATGATATTCTTCTCTTTTCTCCTATCTCATCGCATT
CTTCCTCTTCATACTATGGAGTATATTCTTGGTTTTGGAGGGCAGTTGGCA
GATTTACTGACGCAATTGATTCAAGAAATGAAGAAGGAGGAACTATTGGGG
GATTATACAGAGGACCATGTCACCTATGAACTCAGTCAGCTTTGTGCTCAA
GTCTATCTCTATAAGGGCTATATTTTACAGGATCGCTACAAGTACCAGTTA
GAGAATCGTCATCCATATTTACTGATGGAACATGATTTTAAAGAGACAGCA
GAGGAGATTTTTCATGCTCTACCTGCTTTTCAACAGGGGACAGATTTAGAT
AAGAAGATTCTCTGGGAATGGCTCCAGTTAATCGAATATATGGCTGAAAAC
GGTGGCCAGCATATGCGGATTGGTCTGGATTTGACATCTGGTTTTCTTGTC
```

```
TTTTCAAGGATGGCAGCCATTTTGAAACGGTATTTGGAATACAATCGTTTT
ATTACCATTGAAGCTTATGACCCTAGTCGGCATTATGATTTGCTGGTTACC
AATAACCCGATTCATAAGAAGGAACAGACACCAGTCTATTATTTAAAAAAT
GACTTGGATATGGAGGATTTGGTAGCGATTCGCCAGTTATTATTCACTTAA 4106.7
                                        (SEQ. ID. NO. 215)
ATGGAATTTTCAAAAGAAAACACGTGAATTGTCAATTAAAAAAATGCAGGA
ACGTACCCTGGACCTCTTGATTATCGGTGGAGGAATCACAGGAGCTGGTGT
AGCCTTGCAGGCGGCAGCTAGCGGTCTTGAGACTGGTTTGATTGAAATGCA
AGACTTTGCAGAAGGAACATCTAGTCGTTCAACAAAATTGGTTCACGGAGG
ACTTCGTTACCTCAAACAATTTGACGTAGAAGTGGTCTCAGATACGGTTTC
TGAACGTGCAGTGGTTCAACAAATCGCTCCACACATTCCAAATCAGATCC
AATGCTCTTACCAGTTTACGATGAAGATGGAGCAACCTTTAGCCTCTTCCG
TCTTAAAGTAGCCATGGACTTGTACGACCTCTTGGCAGGTGTTAGCAACAC
ACCAGCTGCGAACAAGGTTTTGAGCAAGGATCAAGTCTTGGAACGCCAGCC
AAACTTGAAGAAGGAAGGCTTGGTAGGAGGTGGAGTGTATCTTGACTTCCG
TAACAACGATGCGCGTCTCGTGATTGAAAACATCAAACGTGCCAACCAAGA
CGGTGCCCTCATTGCCAACCACGTGAAGGCAGAAGGCTTCCTCTTTGACGA
AAGTGGCAAGATTACAGGTGTTGTAGCTCGTGATCTCTTGACAGACCAAGT
GTTTGAAATCAAGGCCCGTCTGGTTATTAATACAACAGGTCCTTGGAGTGA
TAAAGTACGTAATTTGTCTAATAAGGGAACGCAATTCTCACAAATGCGCCC
AACTAAGGGAGTTCACTTGGTAGTAGATTCAAGCAAAATCAAGGTTTCACA
GCCAGTTTACTTCGACACAGGTTTGGGTGACGGTCGTATGGTCTTTGTTCT
CCCACGTGAAAACAAGACTTACTTTGGTACAACTGATACAGACTACACAGG
TGATTTGGAGCATCCAAAAGTAACTCAAGAAGATGTAGATTATCTACTTGG
CATTGTCAACAACCGCTTCCCAGAATCCAACATCACCATTGATGATATCGA
AAGCAGCTGGGCAGGTCTTCGTCCATTGATTGCAGGGAACAGTGCCTCTGA
CTATAATGGTGGAAATAACGGTACCATCAGTGATGAAAGCTTTGACAACTT
GATTGCGACTGTTGAATCTTATCTCTCCAAAGAAAAAACACGTGAAGATGT
TGAGTCTGCTGTCAGCAAGCTTGAAAGTAGCACATCTGAGAAACATTTGGA
TCCATCTGCAGTTTCTCGTGGGTCTAGCTTGGACCGTGATGACAATGGTCT
CTTGACTCTTGCTGGTGGTAAAATCACAGACTACCGTAAGATGGCTGAAGG
AGCTATGGAGCGCGTGGTTGACATCCTCAAAGCAGAATTTGACCGTAGCTT
TAAATTGATCAATTCTAAAACTTACCCTGTTTCAGGTGGAGAATTGAACCC
AGCAAATGTGGATTCAGAAATCGAAGCCTTTGCGCAACTTGGAGTATCACG
TGGTTTGGATAGCAAGGAAGCTCACTATCTGGCAAATCTTTACGGTTCAAA
TGCACCGAAAGTCTTTGCACTTGCTCACAGCTTGGAACAAGCGCCAGGACT
CAGCTTGGCAGATACTTTGTCCCTTCACTATGCAATGCGCAATGAGTTGAC
TCTTAGCCCAGTTGACTTCCTTCTTCGTCGTACCAATCACATGCTCTTTAT
GCGTGATAGCTTGGATAGTATCGTTGAGCCAATTTTGGATGAAATGGGACG
ATTCTATGACTGGACAGAAGAAGAAAAAGCAACTTACCGTGCTGATGTCGA
```

TABLE 3-continued

AGCAGCTCTCGCTAACAACGATTTAGCAGAATTAAAAAATTAA 4106.8
(SEQ. ID. NO. 216)
ATGATGAATGAATTATTTGGAGAATTTCTAGGGACTTTAATCCTGATTCTT

CTAGGAAATGGTGTTGTTGCAGGTGTGGTTCTTCCTAAAACCAAGAGCAAT

AGCTCAGGTTGGATTGTGATTACTATGGGTTGGGGGATTGCAGTTGCGGTT

GCAGTCTTTGTATCTGGCAAGCTCAGTCCAGCTTATTTAAACCCAGCTGTG

ACCATCGGTGTGGCCTTAAAAGGTGGTTTGCCTTGGGCTTCCGTTTTGCCT

TATATCTTAGCCCAGTTCGCAGGGGCCATGCTGGGTCAGATTTTGGTTTGG

TTGCAATTCAAACCTCACTATGAGGCAGAAGAAAATGCAGGCAATATCCTG

GCAACCTTCAGTACTGGACCAGCCATCAAGGATACTGTATCAAACTTGATT

AGCGAAATCCTTGGAACTTTTGTTTTGGTGTTGACAATCTTTGCTTTGGGT

CTTTACGACTTTCAGGCAGGTATCGGAACCTTTGCAGTGGGAACTTTGATT

GTCGGTATCGGTCTATCACTAGGTGGGACAACAGGTTATGCCTTGAACCCA

GCTCGTGACCTTGGACCTCGTATCATGCACAGCATCTTGCCAATTCCAAAC

AAGGGAGACGGAGACTGGTCTTACGCTTGGATTCCTGTTGTAGGCCCTGTT

ATCGGAGCAGCCTTGGCAGTGCTTGTATTCTCACTTTTCTAG 4106.10
(SEQ. ID. NO. 217)
ATGAAAAGGACCTGGAGGAACTCATTCGTGACAAATCTTAATACACCTTTT

ATGATTGGCAATATTGAGATTCCCAATCGTACCGTTTTAGCGCCTATGGCT

GGCGTGACCAACTCAGCCTTTCGTACTATCGCAAAGGAGCTCGGAGCTGGA

CTCGTTGTAATGGAAATGGTCTCTGACAAGGGAATCCAATACAACAACGAA

AAAACCCTGCACATGCTTCATATCGATGAGGGCGAAAACCCTGTCTCTATC

CAACTTTTTGGTAGCGATGAAGACAGCCTAGCACGCGCAGCAGAATTCATC

CAAGAAAACACCAAGACCGATATCGTCGATATCAACATGGGCTGCCCTGTC

AACAAAATCGTGAAGAACGAAGCTGGTGCTATGTGGCTCAAGGATCCAGAC

AAGATTTACTCCATCATCAACAAGGTCCAGTCTGTCCTTGATATCCCACTT

ACTGTCAAAATGCGTACCGGCTGGGCGGACCCATCTCTTGCAGTAGAAAAT

GCTCTCGCTGCTGAAGCTGCAGGTGTTTCTGCCCTCGCCATGCATGGCCGT

ACCCGTGAACAAATGTATACTGGCCACGCAGACCTTGAGACCCTTTACAAG

GTTGCCCAAGCTCTAACCAAGATTCCATTCATCGCCAACGGTGATATCCGT

ACTGTCCAAGAAGCCAAGCAACGCATCGAAGAAGTTGGTGCTGACGCAGTC

ATGATTGGCCGAGCTGCCATGGGAAATCCTTACCTCTTCAACCAAATCAAC

CATTACTTTGAAACAGGAGAAATCCTACCTGATTTGACCTTTGAAGACAAG

ATGAAGATCGCCTAGGAACACTTGAAACGATTGATTAACCTCAAAGGAGAA

AACGTCGCAGTTCGTGAATTCCGCGGTCTCGCTCCTCACTATCTCCGTGGA

ACATCTGGCGCTGCCAAACTCCGTGGAGCCATTTCGCAAGCCAGCACCCTG

GCAGAGATTGAAACCCTCTTGCAATTGGAGAAGGCTTAA 4107.1
(SEQ. ID. NO. 218)
ATGACAAAGAAGAAAATTGAGCGTATTTCTGTAATACACCGAGAAAAGATT

TTATGGCTCAAGTGGTATTTCATGCGAGATAAAGAACAACCTAAGTATAGT

GTCCTTGAGCGTAAAATGTTTGATGCTGCTAAAAATCAAGATATGCTAGCT

TATCAAAAATACGCAACTATCAAGCAGATAACAGATATTAGGGTACAAACA

AGTGAGGCTGACATTTTAGAGGCTGTAAAAGAGGTTTATGTGTACAATCAC

ATGAATGTTATCGGAGCTTGTCAGCGGATATTATTTATCAGTCAATCACCA

GCTTATGATAAGTTAAATAAGTGGTTTAATATCTATTCTGATTTGTATTTT

AGCGTTGTACCCTTGCCCAAAATGGGGGTATATCATGAGATGGTAGGTATC

TAG 4107.2
(SEQ. ID. NO. 219)
ATGAAAAATTCCAACGAGGCTGAGATGAAATTACTTTATACTGATATTCGG

ACTTCTTTGACAGAAATTCTAACAAGAGAGGCAGAAGAGCTAGTTGCAGCT

GGCAAGCGGGTCTTCTACATTGCCCCCAACTCTCTTTCTTTTGAAAAGGAA

CGCGCCGTGCTGGAATACTTGTCCCAGCAGGCTTCTTTTTCGATTACCGTC

ACGCGCTTTGCTCAAATGGCTCGCTATCTGGTCTTGAATGATTTACCAGCT

AAAACTACTCTTGATGATATCGGTCTTGGGTTGGCCTTTTACAAATGCCTT

GCCGAACTCGATCCCAAGGACTTGCGTGTTTATGGCGCTATTAAGCAGGAT

CCTCAATTGATCCAGCAGTTAATTGAGCTTTACCATGAGATGACCAAATCT

CAGATGAGTTTTTTGGACTTGGAGAATTTAACAGATGAGGATAAGAGGGCG

GATTTACTCTTGATTTTTGAGAAAGTAACAGCCTATCTTAATCAAGGTCAG

TTAGCCCAGGAAAGTCAGTTGTCCCATTTGATTGAGGCTATTGAGAATGAC

AAGGTAAGTAGTGATTTTAATCAAATCGCCTTGGTCATTGACGGCTTTACT

CGTTTTTCTGCTGAGGAAGAGCGGGTTGTGGACTTACTTCACGGCAAAGGT

GTTGAGATTGTTATCGGGGCTTATGCTAGTAAGAAAGCCTATACCAGTCCT

TTTAGCGAGGGCAATCTCTACCAAGCCAGCGTAAAATTTCTCCATCATCTG

GCTTCTAAATACCAAACGCCTGCTCAGGACTGTTCTCAAACTCATGAGAAG

ATGGATAGTTTTGACAAGGCCTCTCGTTTGTTGGAGTCTTCTTATGACTTT

TCAGAACTCGCTTTGGATGTCGATGAGAAAGACCGTGAAAATTTACAAATC

TGGTCTTGTTTGACGCAAAAGGAGGAGTTGGAGCTAGTAGCCCGTAGTATT

CGTCAGAAATTACATGAGAACTCAGACCTGAGCTACAAGCATTTTCGTATT

CTCTTGGGGATGTAGCTTCTTACCAGTTATCTCTCAAAACCATTTTTGAC

CAGTATCAGATTCCTTTTTATCTTGGTAGAAGCGAAGCCATGGCTCATCAT

CCCTTGACTCAGTTTGTCGAGTCTATTTTAGCTTTAAAACGTTACCGTTTT

CGTCAGGAGGATTTGATTAATCTTCTTAGAACTGATTTGTATACTGACCTC

AGTCAGTCTGATATTGATGCTTTTGAGCAATATATCCGCTATCTTGGTATC

AATGGCTTGCCAGCCTTTCAGCAAACCTTCACCAAATCCCACCATGGAAAA

TTTAATCTTGAGCGTTTGAATGTCCTCCGCCTGAGAATTTTAGCACCTCTT

GAAACCCTCTTTGCCAGCCGAAAACAAAAGGCTGAAAAACTCCTACAAAAA

TGGAGTGTCTTTCAAAAGAAGGAGCTGTGACCAAGCAGTTACAAGATTTG

ACAACCACTTTGGAAGCTGTAGAACAGGAAAGACAAGCCGAAGTTTGGAAG

GCTTTCTGCCATGTTTTAGAACAATTTGCGACTGTTTTTGCTGGTTCACAG

GTTAGTCTGGAAGACTTCCTAGCCTGCTCCATTCTGGAATGAGTTTGTCCC

TABLE 3-continued

AATACCGTACCATTCCAGCAACAGTGGACACTGTTCTGGTGCAGCGTTACG
ATTTGATTGCACCATTGACTGCTGACTTTGTCTATGCTATTGGACTAACTC
AGGACCATTTACCAAAAATTTCTCAAAACACCAGTCTTCTGACAGATGAAG
AAAGGCAAAACCTAAACCAAGCGACCGAAGAAGGCGTTCAATTACTGATTG
CCAGCAGTGAAAATCTCAAGAAAAATCGCTACACTATGCTTTCCTTGGTCA
ATTCTGCTCGTAAGCAGTTGTTCTTGTCGGCTCCAAGCCTTTTTAACGAAA
GTGAAAGTAAGGAATCTGCCTATCTTCAAGAGTTGATCCATTTTGGATTTA
GGCGGAGAGAGAAGAGGATGAATCACAAAGGACTGTCTAAGGAGGATATGG
GGTCCTATCACAGTCTTTTGTCTAGTCTGGTTGCCTATCACCAGCAGGGTG
AGATGAGCGATACTGAGCAAGATTTGACTTTTGTCAAGGTTCTGTCGCGTG
TCATAGGTAAAAAACTAGATCAGCAAGGTCTGGAAAATCCAGCTATCCCAA
CCAGTCCAAGCAGCAAGACCTTAGCCAAGGACACCTTGCAAGCTCTCTATC
CTGCCAAACAGGAGTTTTACCTGTCTACGTCGGGTTTGACAGAGTTTTATC
GCAATGAATACAGTTATTTCCTACGCTACGTTTTAGGCTTGCAGGAGGAAT
TACGTTTGCATCCTGATGCCCGTAGTCACGGGAATTTCTTGCATCGTATCT
TTGAACGCGCCTTACAGTTGCCTAATGAAGATTCCTTTGACCAACGTCTAG
AACAAGCTATTCAAGAAACCAGTCAAGAACGCGAATTTGAAGCTATTTATC
AAGAAACTTTGGAAGCCCAGTTTACCAAGGAAGTTTTGCTTGATGTTGCAC
GGACAACTGGACATATTCTCCGACACAATCCAGCCATCGAAACCATCAAAG
AAGAAGCAAATTTTGGTGGAAAAGACCAAGCCTTTATTCAATTAGACAATG
GACGCAGTGTCTTTGTACGAGGCAAGGTGGACCGGATTGACCGTTTGAAAG
CTAATGGAGCGATAGGAGTAGTAGACTACAAATCCAGTCTGACTCAGTTCC
AGTTTCCTCATTTCTTTAATGGGCTCAATTCTCAGTTACCAACCTATCTTG
CTGCCCTAAAAAGAGAAGGGGAGCAGAACTTTTTCGGCGCCATGTACTTGG
AAATGGCTGAACCTGTCCAATCTCTGATGGCGGTAAAAAGTCTGGCAGGAG
CAGTGGTAGAAGCCAGCAAATCTATGAAATACCAAGGGCTCTTCTTGGAAA
AAGAAAGCAGTTATTTAGGCGAATTTTATAACAAAAACAAGGCTAATCAAC
TGACAGATGAGGAATTTCAGCTCCTACTGGACTACAATGCCTATCTTTACA
AGAAAGCTGCTGAGAAGATTTTAGCAGGCCGGTTCGCCATCAATCCTTATA
CTGAAAATGGCAGAAGCATTGCCCCATACGTCCAGCAACATCAGGCTATTA
CAGGCTTTGAAGCCAATTACCATCTGGGCAAGCCCGTTTCCTAGAAAAGT
TGGACCTAGCTGATGGCAAGCGTCTGGTCGGAGAAAAACTCAAGCAAGCTT
GGCTTGAAAAAATAAGAGAGGAGTTGAATCGATGA 4107.3
(SEQ. ID. NO. 220)
ATGAAGCTTATTCCCTTTTTAAGTGAGGAGGAGATTCAAAAACTGCAAGAA
GCAGAAGCAAATTCGAGCAAGGAACAGAAGAAAACTGCCGAGCAAATCGAA
GCTATCTACACTTCTGCCCAGAATATCCTGGTCTCAGCATCGGCTGGTTCT
GGAAAGACCTTTGTCATGGCAGAGCGCATTCTGGACCAATTGGCGCGTGGT
GTCGAAATTTCTCAACTCTTTATCTCAACCTTTACCGTCAAGGCTGCAACT
GAACTTAAAGAACGTTTAGAGAAAAAAATCAGCAAGAAAATCCAAGAAACA

TABLE 3-continued

GATGATGTCGACCTCAAACAACACTTGGGTCGCCAGTTGGCAGACCTACCC
AACGCTGCCATTGGAACCATGGATTCTTTCACACAAAAATTCCTTGGCAAA
CATGGTTATCTGCTTGATATTGCACCTAATTTCCGTATTTTACAAAACCAA
AGCGAGCAACTTATTCTCGAAAACGAAGTCTTTCATGAGGTCTTTGAAGCG
CATTACCAAGGTAAACAGAAAGAGACCTTTAGTCATTTGCTGAAAAACTTT
GCTGGGCGTGGCAAGGACGAACGGGGTCTGCGCCAGCAGGTCTATAAAATC
TATGACTTCCTCCAATCCACCAGTAATCCTCAAAAGTGGCTGAGTGAATCT
TTCCTCAAAGGATTTGAGAAAGCTGATTTTACCAGTGAAAAAGAAAAACTG
ACCGAGCAAATCAAACAAGCCCTTTGGGATTTGGAAAGCTTTTTCCGTTAC
CATCTGGATAACGATGCCAAGGAGTTTGCAAAGGCTGCCTATTTAGAAAAT
GTTCAGTTAATTCTGGATGAAATTGGCTCCCTAAATCAGGAGTCCGATAGT
CAGGCTTATCAGGCAGTGCTTGCGCGTGTTGTCGCCATCTCTAAGGAGAAA
AACGGTCGAGCTCTGACTAATGCCAGCCGTAAGGCTGATTTGAAGCCCCTG
GCTGATGCCTACAACGAAGAGAGAAAGACCCAGTTTGCTAAACTAGGACAA
TTATCAGACCAGATAGCGATTCTCGACTATCAAGAACGTTATCATGGAGAC
ACTTGGAAACTAGCTAAAACCTTCCAATCTTTCATGAGCGATTTTGTAGAG
GCTTATCGTCAGAGAAAACGACAGGAAATGCCTTCGAATTCGCTGATATC
AGCCATTACACCATTGAGATTTTAGAGAATTTCCCACAAGTTCGTGAGTCT
TATCAGGAGCGCTTCCATGAAGTCATGGTCGATGAGTATCAGGATACCAAC
CATATTCAAGAACGGATGCTGGAATTGTTGTCTAATGGCCACAATCGCTTT
ATGGTGGGAGATATCAAGCAATCCATCTATCGTTTCCGTCAGGCAGACCCG
CAGATTTTCAATGAGAAATTCCAACGCTATGCGCAAAATCCCCAAGAAGGC
AGGCTCATTATCCTCAAGGAAAATTTCCGTAGTAGTTCAGAAGTGCTGTCA
GCAACCAATGATGTCTTTGAACGTCTCATGGACCAAGAGGTCGGCGAAATC
AACTATGATAACAAGCACCAGCTTGTTTTTGCCAATACCAAACTGACTCCC
AATCCAGACAACAAGGCAGCATTTCTCCTCTACGACAAGGACGATACAGGT
GAGGAAGAAGAGAGTCAAACAGAAACGAAACTAACAGGCGAAATGCGCTTA
GTTATCAAGGAGATTCTGAAACTTCATCAAGAAAAAGGTGTTGCCTTTAAG
GAAATTGCCCTTCTGACCTCCAGCCGCAGTCGTAATGACCAGATTCTCCTC
GCCCTGTCTGAGTACGGAATTCCTGTCAAAACTGACGGAGAGCAAAACAAT
TATCTCCAATCCCTAGAAGTGCAAGTCATGCTAGACACTCTTCGTGTCATT
CACAATCCCCTGCAAGACTACGCCTTGGTTGCCCTTATGAAGTCTCCAATG
TTTGGTTTTGATGAGGATGAGCTAGCACGTTTGTCCCTTCAGAAAGCAGAG
GATAAAGTCCACGAAAATCTCTATGAGAAACTGGTCAATGCACAAAAAATG
GCAAGTAGTCAAAAAGGCTTGATTCACACAGCTCTAGCTGAAAAACTAAAG
CAATTCATGGATATCCTAGCTTCTTGGCGCTTGTATGCCAAAACCCACTCT
CTCTATGACTTGATTTGGAAGATTTACAACGACCGTTTTTATTATGACTAT
GTTGGGCTTTGCCGAATGGTCCTGCTAGGCAGGCCAATCTCTATGCCCTA
GCACTGCGTGCTGATCAATTTGAAAAGAGCAATTTCAAAGGTTTGTCGCGT
TTTATTCGTATGATTGACCAAGTCTTAGAAGCCCAGCACGATTTGGCAAGC

TABLE 3-continued

GTGGCCGTCGCACCGCCAAAAGATGCAGTAGAGCTCATGACCATCCACAAG
AGTAAAGGGCTGGAGTTTCCTTACGTCTTTATCCTCAATATGGATCAAGAT
TTCAACAAGCAAGACTCTATGTCAGAAGTCATTCTCAGTCGTCAGAATGGT
CTTGGTGTCAAATATATTGCCAAGATGGAGACAGGGGCAGTAGAAGACCAC
TATCCTAAAACCATCAAACTCTCCATTCCTAGTCTGACCTATAGGCAGAAC
GAAGAGGAATTACAGCTAGCAAGCTATTCTGAGCAGATGCGTTTGCTGTAT
GTTGCTATGACGCGGGCTGAGAAAAAGCTCTATCTTGTCGGCAAGGGTTCT
CGTGAAAAGCTGGAATCCAAGGAATACCCAGCAGCCAAAAATGGGAAACTA
AATAGCAATACTAGACTGCAAGCACGGAATTTCCAAGATTGGCTTTGGGCT
ATCAGTAAAGTGTTTACTAAGGACAAGCTCAACTTTAGTTATCGTTTTATT
GGCGAAGATCAGTTGACCAGAGAAGCTATCGGAGAGTTGGAAACCAAGAGT
CCTCTCCAAGATAGCTCCCAAGCAGACAATCGTCAGTCAGATACCATCAAA
GAAGCTCTGGAAATGCTGAAGGAGGTGGAAGTTTATAATACTCTTCACCGC
GCAGCTATTGAACTTCCTAGTGTTCAAACCCCAAGTCAAATCAAGAAATTC
TACGAACCAGTTATGGATATGGAAGGTGTCGAGATTGCTGGTCAAGGTCAG
TCAGTAGGCAAGAAAATCAGCTTCGATTTGCCAGATTTTTCAACCAAAGAA
AAGGTAACTGGAGCTGAGATTGGTAGTGCTACTCACGAACTCATGCAGAGA
ATTGACCTCAGCCAGCAACTAACCCTTGCTAGCCTAACAGAAACACTCAAA
CAAGTTCAAACTAGCCAAGCTGTCAGAGACAAGATCAATCTTGATAAAATT
CTTGCTTTCTTTGACACAGTACTCGGTCAGGAAATTCTTGCTAATACCGAC
CATCTTTATCGCGAGCAACCTTTCTCCATGCTCAAACGAGACCAAAAGAGT
CAGGAAGACTTTGTTGTCCGTGGTATCCTTGATGGCTATCTGCTTTACGAA
AACAAAATTGTTCTGTTCGACTACAAGACAGACCGCTATGATGAACCAAGT
CAACTCGTAGACCGCTATCGTGGTCAGTTAGCTCTATACGAAGAGGCTTTA
TCACGAGCCTATTCGATTGAAAATATTGAAAAATACTTGATTTTACTCGGT
AAAGACGAGGTTCAAGTTGTAAAAGTATAA 4109.1
(SEQ. ID. NO. 221)
ATGGAACTTGCTCGCCATGCTGAAACGTTGGGAGTAGATGCTATTGCAACG
ATTCCACCAATTTATTTCCGCTTGCCAGAATACTCAGTTGCCAAATACTGG
AACGATATCAGTTCTGCAGCTCCAAACACAGACTACGTGATTTACAACATT
CCTCAATTGGCAGGGGTTGCTTTGACTCCAAGCCTTTACACAGAAATGTTG
AAAAATCCTCGTGTTATCGGTGTGAAGAACTCTTCTATGCCAGTTCAAGAT
ATCCAAACCTTTGTCAGCCTTGGTGGAGAAGACCATATCGTCTTTAATGGT
CCTGATGAGCAGTTCCTAGGAGGACGCCTCATGGGGGCTAGGGCTGGTATC
GGTGGTACTTATGGTGCTATGCCAGAACTCTTCTTGAAACTCAATCAGTTG
ATTGCGGATAAGGACCTAGAAACAGCGCGTGAATTGCAGTATGCTATCAAC
GCAATCATTGGTAAACTCACTTCTGCTCATGGAAATATGTACGGTGTCATC
AAAGAAGTCTTGAAAATCAATGAAGGCTTGAATATTGGATCTGTTCGTTCA
CCATTGACACCAGTGACTGAAGAAGATCGTCCAGTTGTAGAAGCGGCTGCT
GCCTTGATTCGTGAAACCAAGGAGCGCTTCCTCTAA 4110.2
(SEQ. ID. NO. 222)
ATGTATAAGACAAAGTGTTTACGAGAGAAGTTAGTATTATTTTTAAAAATT
TTCTTCCCAATCCTGATCTACCAATTTGCCAATTATTCTGCCTCTTTTGTT
GATACTGCAATGACAGGTCAATACAACACTATGGACTTGGCTGGTGTATCT
ATGGCAACCAGTATCTGGAATCCTTTCTTTACATTTCTAACAGGGATTGTG
TCAGCCTTGGTGCCTATCATTGGTCACCATCTTGGTCGAGGCAAAAAGGAA
TGAAGTTGCGTCTGATTTTTACCAATTTATTTATTGGCCTTGGGCCTATCT
GTGGTCTTGCTGGGGATGGTACTTTTCTTGGCACCAATAATCTTGAATCAT
ATTGGGTTAGAAGCAGCAGTAGCGGCAGTAGCGGTTCGCTATCTTTGGTTT
TTATCTATCGGATTATCCCCTTGTTGCTCTTTAGCGTCATTCGTTCCTTG
CTGGATTCGCTGGGCTTGACCAAACTGTCCATGTACCTCATGCTTTTCTTA
CTCCCTCTCAATAGCGGATTTAACTATCTCTTGATTTACGGTGCCTTTGGT
GTTCCACAACTGGGAGGGGCTGGTGCTGGTTTAGGAACATCCTTGGCCTAC
TGGGTCTTGCTTGGGATTTCTGTTCTGGTTTTATTTAAACAGGAGAAGCTC
AAAGCCTTACACCTTGAGAAACGAATTCCACTTAATATGGATAAAATTAAG
GAAGGAGTTCGTTTAGGTCTGCCTATTGGGGAACTGTCTTCGCGGAAGTG
GCTATCTTTTCAGTGGTTGGCTTGATTATGGCTAAGTTTTCGCCCTTGATT
ATAGCTAGTCACCAGTCAGCTATGAACTTTTCAAGTCTTATGTACGCCTTT
CCTATGAGTATCTCATCGGCTATGGCTATTGTCGTTTCCTATGAAGTGGGA
GCCAAGCGATTTGATGATGCGAAAACCTATATTGGTCTAGGAAGATGGACT
GCCCTCATTTTTGCGGCCTTCACCTTAACCTTCCTTTACATTTTTAGGGGA
AATGTGGCCAGTCTTTATGGTAACGACCCAAAATTTATCGATTTGACAGTG
CGTTTTTTAACTTATAGTCTTTTCTTCCAGTTAGCAGATACCTTTGCGGCG
CCGCTTCAGGGAATTTTGCGGGGGTATAAGGATACAGTTATTCCTTTTTAC
CTTGGTTTGCTTGGTTATTGGGCGTAGCAATCCCTGTGTACGCTATTTGA 4112.2
(SEQ. ID. NO. 223)
ATGAGTACTTTAGCAAAAATAGAAGCGCTCTTGTTTGTAGCGGGTGAAGAT
GGGATTCGGGTCCGCCAGTTAGCTGAACTCCTCTCTCTGCCACCGACAGGC
ATCCAGCAAAGTTTAGGAAAATTAGCCCAGAAGTATGAAAAGGACCCAGAT
TCCAGTTTGGCTTTGATTGAGACAAGTGGTGCTTATAGATTGGTGACCAAG
CCTCAATTTGCAGAGATTTTGAAGGAATACTCTAAGGCGCCTATCAACCAG
AGCTTGTCTCGGGCTGCCCTTGAGACCTTGTCCATTATTGCCTACAAACAG
CCGATTACGCGGATAGAAATTGATGCCATCCGTGGAGTTAACTCGAGTGGA
GCCTTGGCAAAGTTGCAGGCTTTTGACCTGATAAAGGAAGACGGGAAAAAG
GAAGTATTGGGCGCCCCAACCTCTATGTGACTACGGATTATTTCCTAGAT
TACATGGGATAAACCATTTAGAAGAATTACCAGTGATTGATGAGCTTGAG
ATTCAAGCCCAAGAAAGCCAATTATTTGGTGAAAGGATAGAAGAAGATGAG
AATCAATAA

TABLE 3-continued 4113.1
(SEQ. ID. NO. 224)
ATGGATACGATGATTAGTAGATTTTTTCGCCATTTATTTGAAGCCTTAAAA
AGTTTGAAACGAAATGGTTGGATGACAGTAGCTGCTGTCAGTTCAGTCATG
ATTACTTTGACCTTGGTGGCAATATTTGCATCTGTTATTTTCAATACAGCG
AAACTAGCTACAGATATTGAAAATAATGTCCGTGTAGTAGTTTATATCCGA
AAGGATGTGGAAGATAATAGTCAGACAATTGAAAAGAAGGTCAAACTGTT
ACAAATAATGACTACCACAAGGTATATGATTCTTTGAAGAACATGTCTACG
GTTAAAAGTGTTACCTTTTCAAGTAAAGAAGAACAATATGAAAAATTAACC
GAGATAATGGGAGATAACTGGAAAATCTTTGAAGGAGATGCCAATCCTCTC
TATGATGCCTATATTGTAGAGGCAAACACTCCAAATGATGTAAAAACTATA
GCCGAAGATGCTAAAAAAATTGAAGGTGTCTCTGAGGTTCAAGATGGCGGT
GCCAATACAGAAAGACTCTTCAAGTTAGCTTCATTTATCCGTGTTTGGGA
CTAGGGATTGCTGCTTTGTTAATTTTTATCGCAGTTTTCTTGATTTCAAAT
ACCATTCGTATTACCATTATTTCCCGCAGTCGCGAAATTCAAATCATGCGC
TTGGTCGGAGCTAAAAACAGTTATATCCGTGGACCGTTCTTGTTAGAAGGA
GCCTTTATCGGTTTATTGGGAGCTATCGCACCATCTGTTTTGGTCTTTATT
GTTTATCAAATTGTTTACCAATCTGTCAACAAATCGTTGGTAGGGCAAAAT
CTATCCATGATTAGTCCAGATTTATTTAGTCCGTTGATGATTGCCCTACTA
TTTGTGATTGGGGTTTTCATTGGTTCATTGGGATCAGGAATATCCATGCGC
CGATTCTTGAAGATTTAG 4117.1
(SEQ. ID. NO. 225)
ATGAAGAAAGTAAGATTTATTTTTTAGCTCTGCTATTTTTCTTAGCTAGT
CCAGAGGGTGCAATGGCTAGTGATGGTACTTGGCAAGGAAAACAGTATCTG
AAAGAAGATGGCAGTCAAGCAGCAAATGAGTGGGTTTTTGATACTCATTAT
CAATCTTGGTTCTATATAAAAGCAGATGCTAACTATGCTGAAAATGAATGG
CTAAAGCAAGGTGACGACTATTTTTACCTCAAATCTGGTGGCTATATGGCC
AAATCAGAATGGGTAGAAGACAAGGGAGCCTTTTATTATCTTGACCAAGAT
GGAAAGATGAAAAGAAATGCTTGGGTAGGAACTTCCTATGTTGGTGCAACA
GGTGCCAAAGTAATAGAAGACTGGGTCTATGATTCTCAATACGATGCTTGG
TTTTATATCAAAGCAGATGGACAGCACGCAGAGAAAGAATGGCTCCAAATT
AAAGGGAAGGACTATTATTTCAAATCCGGTGGTTATCTACTGACAAGTCAG
TGGATTAATCAAGCTTATGTGAATGCTAGTGGTGCCAAAGTACAGCAAGGT
TGGCTTTTTGACAAACAATACCAATCTTGGTTTTACATCAAAGAAAATGGA
AACTATGCTGATAAAGAATGGATTTTCGAGAATGGTCACTATTATTATCTA
AAATCCGGTGGCTACATGGCAGCCAATGAATGGATTTGGGATAAGGAATCT
TGGTTTTATCTCAAATTTGATGGGAAAATGGCTGAAAAGAATGGGTCTAC
GATTCTCATAGTCAAGCTTGGTACTACTTCAAATCCGGTGGTTACATGACA
GCCAATGAATGGATTTGGGATAAGGAATCTTGGTTTTATCTCAAATCTGAT
CGGGAAAATAGCTGAAAAGAATGGGTCTACGATTCTCATAGTAAGCTTGG
TACTACTTCAAATCCGGTGGTTACATGACAGCCAATGAATGGATTTGGGAT AAGGAATCTTGGTTTTACCTCAAATCTGATGGGAAAATAGCTGAAAAGAA
TGGGTCTACGATTCTCATAGTCAAGCTTGGTACTACTTCAAATCTGGTGGC
TACATGGCGAAAAATGAGACAGTAGATGGTTATCAGCTTGGAAGCGATGGT
AAATGGCTTGGAGGAAAAACTACAAATGAAAATGCTGCTTACTATCAAGTA
GTGCCTGTTACAGCCAATGTTTATGATTCAGATGGTGAAAAGCTTTCCTAT
ATATCGCAAGGTAGTGTCGTATGGCTAGATAAGGATAGAAAAAGTGATGAC
AAGCGCTTGGCTATTACTATTTCTGGTTTGTCAGGCTATATGAAAACAGAA
GATTTACAAGCGCTAGATGCTAGTAAGGACTTTATCCCTTATTATGAGAGT
GATGGCCACCGTTTTTATCACTATGTGGCTCAGAATGCTAGTATCCCAGTA
GCTTCTCATCTTTCTGATATGGAAGTAGGCAAGAAATATTATTCGGCAGAT
GGCCTGCATTTTGATGGTTTTAAGCTTGAGAATCCCTTCCTTTTCAAAGAT
TTAACAGAGGCTACAAACTACAGTGCTGAAGAATTGGATAAGGTATTTAGT
TTGCTAAACATTAACAATAGCCTTTTGGGAGAACAAGGGCGCTACTTTTAAG
GAAGCCGAAGAACATTACCATATCAATGCTCTTTATCTCCTTGCCCATAGT
GCCCTAGAAAGTAACTGGGGAAGAAGTAAAATTGCCAAAGATAAGAATAAT
GTTCTTTGGCATTACAGCCTATGATACACCCCTTACCTTTCTGCTAAGACA
ATTTGATGATGTGGATAAGGGAATTTTAGGTGCACCAAGTGGATTAAGGAA
AAATTATATCGATAGGGGAAGAACTTTCCTTGGAAACAGGCTTCTGGTATG
AATGTGGAATATGCTTCAGACCCTTATTGGGGCGAAAAAATTGCTAGTGTG
ATGATGAAAATCAATGAGAAGCTAGGTGGCAAAGATTAG 4119.2
(SEQ. ID. NO. 226)
ATGAAAAAAGTATTACAAAAATATTGGGCATGGGCTTTTGTGGTCATCCCC
CTCTTGTTACAAGCAATTTTCTTCTATGTGCCGATGTTTCAAGGAGCCTTT
TACAGTTTTACCAACTGGACAGGATTGACTTATAACTACAAATTTGTTGGC
TTAAACAACTTTAAGCTCCTCTTCATGGATCCAAAATTCATGAATGCGATT
GGCTTTACCGCAATCATTGCGATTGCCATGGTGGTTGGTGAGATTGCACTC
GGGATCTTCATTGCGCGTGTCTTGAATTCTAAAATCAAAGGCCAAACCTTC
TTCCGTGCTTGGTTCTTCTTCCCAGCTGTTTTATCTGGTTTGACAGTGGCT
TTGATCTTCAAGCAAGTCTTCAACTACGGTCTTCCAGCGATTGGAAATGCC
CTTCATATTGAATTTTCCAAACCAGTCTTTTAGGGACTAAGTGGGGAGCA
ATCTTTGCGGCTGTCTTTGTCCTTCTTTGGCAAGGGGTGGCTATGCCCATC
ATCATCTTCCTAGCTGGTTTGCAATCTATTCCAACTGAGATTACAGAGGCA
GCAAGGATTGATGGTGCGACTAGCAAGCAAGTTTTCTGGAACATTGAATTG
CCTTACTTGCTACCAAGTGTCTCTATGGTCTTTATCCTAGCCTAAAAGGTG
GGCTGACTGCCTTTGACCAAGTCTTTGCCATGACCGGTGGTGGTCCAAACA
ATGCCACAACCTCACTTGGGCTCTTGGTTTATAACTATGCCTTTAAAAACA
ACCAATTCGGTTATGCCAATGCCATTGCCGTAATCTTGTTCTTCTTAATTG
TAGTGATTTCGATCATCCAATTGAGAGTATCTAAGAAATTTGAAATTTAA TABLE 3-continued 4119.3
(SEQ. ID. NO. 227)
ATGATGAAACAAGATGAAAGAAAAGCCCTGATTGGCAAATACATTCTATTG
ATTCTAGGATCGGTTCTGATTTTAGTGCCGCTCCTTGCTACCCTCTTTAGT
TCCTTCAAACCCACTAAGGATATTGTAGATAATTTCTTTGGCTTTCCAACC
AACTTCACATGGGACAACTTTAGCCGTCTCTTAGCTGATGGGATTGGAGGC
TATTATTGGAACTCTGTCGTCATCACTGTCTTGTCTTTACTTGCAGTAATG
ATCTTTATCCCTATGGCAGCGTACTCCATCGCTCGCAATATGAGTAAAAGA
AAAGCCTTTACCATCATGTATACCCTCTTAATCCTCGGAATCTTCGTACCT
TTCCAAGTCATCATGATTCCGATTACGGTTATGATGAGTAAACTCGGTTTG
GCTAATACCTTTGGTTTGATCTTGCTCTACTTGACCTATGCGATTCCACAG
ACCCTCTTTCTCTATGTTGGCTATATCAAAATCTCGATTCCAGAAAGTCTG
GATGAAGCAGCAGAGATCGATGGGGCTAATCAATTTACAACCTATTTCCGC
ATCATCTTCCCAATGATGAAACCGATGCATGCGACAACCATGATCATCAAT
GCCCTTTGGTTCTGGAATGACTTCATGTTGCCACTCCTTGTCTTGAACCGG
GATTCCAAAATGTGGACTCTGCCTTTGTTCCAATACAACTACGCAGGCCAA
TATTTCAACGACTACGGACCAAGCTTTGCCTCTTACGTGGTCGGCATTATC
AGTATCACCATTGTCTATCTCTTCTTCCAACGCCATATCATTTCAGGAATG
AGCAACGGGGCAGTGAAGTAA 4119.4
(SEQ. ID. NO. 228)
ATGAAAAGTATTCTTCAGAAAATGGGGGAGCATCCGATGCTGCTTCTTTTT
CTTAGCTATAGTACTGTTATATCCATTCTTGCACAAAATTGGATGGGTCTT
GTGGCTTCAGTAGGAATGTTTCTATTTACTATTTTCTTTTTGCACTATCAG
TCGATTTTATCCCATAAATTCTTTCGATTGATTTTGCAGTTTGTCTTGTTT
GGTAGTGTCTTGTCAGCTGCTTTTGCCAGTTTAGAACATTTCCAAATTGTG
AAGAAATTTAACTATGCTTTTCTTTCACCCAATATGCAGGTGTGGCATCAG
AACCGGGCAGAAGTGACCTTCTTTAATCCTAATTATTATGGAATTATTTGT
TGTTTCTGTATTATGATTGCTTTCTATCTGTTTACAACGACCAAGTTGAAT
TGGTTGAAAGTATTCTGTGTGATTGCAGGCTTTGTTAATCTCTTTGGTTTG
AACTTTACTCAAAATCGAACTGCCTTTCCTGCTATTATCGCTGGAGCAATT
ATCTATCTCTTTACGACTATTAAAAACTGGAAGGCCTTTTGGCTTAGTATT
GGGGTCTTCGCGATTGGTTTGAGTTTCCTCTTTTCTAGTGATTTGGGAGTT
CGAATGGGTACTTTAGACTCTTCTATGGAAGAACGCATTTCTATCTGGGAT
GCTGGGATGGCCTTGTTTAAGCAAAATCCTTTTTGGGGTGAAGGGCCATTG
ACCTATATGAACTCTTATCCTCGGATACATGCTCCTTATCATGAACATGCC
CACAGTCTTTATATTGATACGATTCTGAGTTACGGAATTGTGGGACTATT
TTATTAGTTTTGTCTTCTGTTGCTCCTGTTCGCTTGATGATGGATATGAGT
CAGGAGTCGGGGAAACGTCCGATTATCGGCCTTTATCTATCTTTCCTTACA
GTGGTTGCTGTGCACGGAATTTTTGACTTGGCTCTCTTCTGGATTCAGTCA
GGCTTTATTTTCTTGCTAGTTATGTGCAGTATTCCATTGGAGCATCGAATG
TTGGTATCGGACATGACGGATTAA 4120.1
(SEQ. ID. NO. 229)
ATGTCAAAGATGGATGTTCAGAAAATCATTGCACCGATGATGAAGTTTGTG
AATATGCGTGGCATTATAGCTCTAAAAGATGGGATGTTAGCAATTTTGCCA
TTGACAGTAGTTGGTAGTTTGTTCTTGATTATGGGACAATTGCCGTTCGAA
GGATTAAATAAGAGCATTGCTAGTGTTTTTGGAGCTAATTGGACAGAGCCG
TTTATGCAAGTATATTCAGGAACTTTTGCTATTATGGGTCTAATTTCTTGT
TTTTCAATTGCCTATTCTTATGCTAAGAATAGCGGCGTAGAGGCTTTACCA
GCTGGACTTCTATCTGTATCTGCATTCTTTATTTTGCTAAGATCATCTTAT
ATCCCTAAACAAGGTGAGGCGATTGGGGACGCTATTAGTAAAGTTTGGTTT
GGAGGCCAAGGAATTATCGGTGCTATCATTATAGGTTTGGTAGTAGGAAGT
ATTTATACCTTCTTTATAAAGAGAAAAATTGTTATTAAGATGCCAGAACAA
GTTCCACAAGCTATTGCCAAACAGTTTGAAGCAATGATTCCAGCATTTGTA
ATTTTCTTATCTTCTATGATTGTATATATTTTAGCGAAGTCATTGACTAAT
GGCGGAACATTCATAGAAATGATTTATTCTGCTATTCAAGTTCCGTTGCAA
GGTTTAACTGGATCTTTGTATGGTGCTATTGGAATTGCATTCTTTATATCA
TTTTTGTGGTGGTTTGGTGTTCATGGGCAATCGGTAGTAAATGGAGTAGTG
ACAGCTCTGCTTTTATCTAATCTTGATGCTAATAAAGCTATGTTAGCCTCT
GCTAATCTATCATTAGAAAATGGTGCACATATTGTTACTCAACAATTTTTA
GATTCATTTTAATTCTATCAGGTTCAGGGATTACGTTTGGTCTTGTAGTT
GCCATGCTTTTGCAGCAAAATCAAAACAATACCAAGCCTTAGGAAAAGTT
GCAGCTTTTCCAGCAATATTTAACGTAAATGAGCCAGTTGTATTTGGATTT
CCGATTGTCATGAATCCAGTTATGTTTGTACCTTTCATTCTTGTTCCTGTA
CTTGCAGCTGTGATAGTATATGGAGCTATTGCAACAGGTTTCATGCAGCCA
TTCTCAGGGGTAACATTGCCTTGGAGTACACCAGCTATTTTATCAGGATTT
TTGGTGGGTGGATGGCAAGGAGTTATTACTCAGCTGGTGATATTAGCGATG
TCTACATTGGTTTATTTTCCATTCTTTAAAGTACAGGATCGTTTAGCTTAC
CAAAATGAAATCAAACAATCTTAG 4121.2
(SEQ. ID. NO. 230)
ATGAAGAAAAAGGACTTAGTAGACCAACTAGTCTCAGAGATCGAGACGGGG
AAAGTCAGGACACTGGGAATATACGGTCATGGAGCTTCAGGTAAATCAACC
TTTGCACAGGAATTGTACCAAGCTTTAGATTCTACTACAGTAAATTTGCTA
GAGACAGATCCTTATATCACCTCAGGACGCCATCTGGTACTACCCAAGGAC
GCGCCGAATCAAAAGGTGACAGCCAGTCTGCCAGTGGCGCATGAACTGGAG
AGTTTGCAGAGAGATATCCTTgCTTGCAGGCGGGTATGGATGTCTTGA 4122.1
(SEQ. ID. NO. 231)
ATGAAGAAAAGATACCTAGTCTTGACAGCTTTGCTAGCCTTGAGTCTAGCA
GCTTGTTCACAAGAAAAAACAAAAAATGAAGATGGAGAAACTAAGACAGAA
CAGACAGCCAAAGCTGATGGAACAGTCGGTAGTAAGTCTCAAGGAGCTGCC
CAGAAGAAAGCAGAAGTGGTCAATAAAGGTGATTACTACAGCATTCAAGGG
AAATACGATGAAATCATCGTAGCCAACAAACACTATCCATTGTCTAAAGAC TABLE 3-continued TATAATCCAGGGGAAAATCCAACAGCCAAGGCAGAGTTGGTCAAACTCATC
AAAGCGATGCAAGAGGCAGGTTTCCCTATTAGTGATCATTACAGTGGTTTT
AGAAGTTATGAAAACTCAGACCAAGCTCTATCAAGATTATGTCAACCAAGA
TGGAAAGGCAGCAGCTGACCGTTACTCTGCCCGTCCTGGCTATAGCGAACA
CCAGACAGGCTTGGCCTTTGATGTGATTGGGACTGATGGTGATTTGGTGAC
AGAAGAAAAAGCAGCCCAATGGCTCTTGGATCATGCAGCTGATTATGGCTT
TGTTGTCCGTTATCTCAAAGGCAAGGAAAAGGAAACAGGCTATATGGCTGA
AGAATGGCACCTGCGTTATGTAGGAAAAGAAGCTAAAGAAATTGCTGCAAG
TGGTCTCAGTTTGGAAGAATACTATGGCTTTGAAGGCGGAGACTACGTCGA
TTAA 4125.6
(SEQ. ID. NO. 232)
ATGCGTAAATTCTTAATTATTTTGTTGCTACCAAGTTTTTTGACCATTTCA
AAAGTCGTTAGCACAGAAAAAGAAGTCGTCTATACTTCGAAAGAAATTTAT
TACCTTTCACAATCTGACTTTGGTATTTATTTTAGAGAAAAATTAAGTTCT
CCCATGGTTTATGGAGAGGTTCCTGTTTATGCGAATGAAGATTTAGTAGTG
GAATCTGGGAAATTGACTCCCAAAACAAGTTTTCAAATAACCGAGTGGCGC
TTAAATAAACAAGGAATTCCAGTATTTAAGCTATCAAATCATCAATTTATA
GCTGCGGACAAACGATTTTTATATGATCAATCAGAGGTAACTCCAACAATA
AAAAAAGTATGGTTAGAATCTGACTTTAAACTGTACAATAGTCCTTATGAT
TTAAAAGAAGTGAAATCATCCTTATCAGCTTATTCGCAAGTATCAATCGAC
AAGACCATGTTTGTAGAAGGAAGAGAATTTCTACATATTGATCAGGCTGGA
TGGGTAGCTAAAGAATCAACTTCTGAAGAAGATAATCGGATGAGTAAAGTT
CAAGAAATGTTATCTGAAAAATATCAGAAAGATTCTTTCTCTATTTATGTT
AAGCAACTGACTACTGGAAAAGAAGCTGGTATCAATCAAGATGAAAAGATG
TATGCAGCCAGCGTTTTGAAACTCTCTTATCTCTATTATACGCAAGAAAAA
ATAAATGAGGGTCTTTATCAGTTAGATACGACTGTAAAATACGTATCTGCA
GTCAATGATTTTCCAGGTTCTTATAAACCAGAGGGAAGTGGTAGTCTTCCT
AAAAAAGAAGATAATAAAGAATATTCTTTAAAGGATTTAATTACGAAAGTA
TCAAAAGAATCTGATAATGTAGCTCATAATCTATTGGGATATTACATTTCA
AACCAATCTGATGCCACATTCAAATCCAAGATGTCTGCCATTATGGGAGAT
GATTGGGATCCAAAAGAAAAATTGATTTCTTCTAAGATGGCCGGGAAGTTT
ATGGAAGCTATTTATAATCAAAATGGATTTGTGCTAGAGTCTTTGACTAAA
ACAGATTTTGATAGTCAGCGAATTGCCAAAGGTGTTTCTGTTAAAGTAGCT
CATAAAATTGGAGATGCGGATGAATTTAAGCATGATACGGGTGTTGTCTAT
GCAGATTCTCCATTTATTCTTTCTATTTTCACTAAGAATTCTGATTATGAT
ACGATTTCTAAGATAGCCAAGGATGTTTATGAGGTTCTAAAATGA 4125.7
(SEQ. ID. NO. 233)
ATGAAAAAACAAATAATGGTTTAATTAAAAATCCTTTTCTATGGTTATTA
TTTATCTTTTTCCTTGTGACAGGATTCCAGTATTTCTATTCTGGGAATAAC
TCAGGAGGAAGTCAGCAAATCAACTATACTGAGTTGGTACAAGAAATTACC GATGGTAATGTAAAAGAATTAACTTACCAACCAAATGGTAGTGTTATCGAA
GTTTCTGGTGTCTATAAAAATCCTAAAACAAGTAAAGAAGAAACAGGTATT
CAGTTTTTCACGCCATCTGTTACTAAGGTAGAGAAATTTACCAGCACTATT
CTTCCTGCAGATACTACCGTATCAGAATTGCAAAAACTTGCTACTGACCAT
AAAGCAGAAGTAACTGTTAAGCATGAAAGTTCAAGTGGTATATGGATTAAT
CTACTCGTATCCATTGTGCCATTTGGAATTCTATTCTTCTTCCTATTCTCT
ATGATGGGAAATATGGGAGGAGGCAATGGCCGTAATCCAATGAGTTTTGGA
CGTAGTAAGGCTAAAGCAGCAAATAAAGAAGATATTAAAGTAAGATTTTCA
GATGTTGCTGGAGCTGAGGAAGAAAAACAAGAACTAGTTGAAGTTGTTGAG
TTCTTAAAAGATCCAAAACGATTCACAAAACTTGGAGCCCGTATTCCAGCA
GGTGTTCTTTTGGAGGGACCTCCGGGGACAGGTAAAACTTTGCTTGCTAAG
GCAGTCGCTGGAGAAGCAGGTGTTCCATTCTTTAGTATCTCAGGTTCTGAC
TTTGTAGAAATGTTTGTCGGAGTTGGAGCTAGTCGTGTTCGCTCTCTTTTT
GAGGATGCCAAAAAAGCAGCACCAGCTATCATCTTTATCGATGAAATTGAT
GCTGTTGGACGTCAACGTGGAGTCGGTCTCGGCGGAGGTAATGACGAACGT
GAACAAACCTTGAACCAACTTTTGATTGAGATGGATGGTTTTGAGGGAAAT
GAAGGGATTATCGTCATCGCTGCGACAAACCGTTCAGATGTACTTGACCCT
GCCCTTTTGCGTCCAGGACGTTTTGATAGAAAAGTATTGGTTGGTCGTCCT
GATGTTAAAGGTCGTGAAGCAATCTTGAAAGTTCACGCTAAGAATAAGCCT
TTAGCAGAAGATGTTGATTTGAAATTAGTGGCTCAACAAACTCCAGGCTTT
GTTGGTGCTGATTTAGAGAATGTCTTGAATGAAGCAGCTTTAGTTGCTGCT
CGTCGCAATAAATCGATAATTGATGCTTCAGATATTGATGAAGCAGAAGAT
AGAGTTATTGCTGGACCTTCTAAGAAAGATAAGACAGTTTCACAAAAAGAA
CGAGAATTGGTTGCTTACCATGAGGCAGGACATACCATTGTTGGTCTAGTC
TTGTCGAATGCTCGCGTTGTCCATAAGGTTACAATTGTACCACGCGGCCGT
GCAGGCGGATACATGATTGCACTTCCTAAAGAGGATCAAATGCTTCTATCT
AAAGAAGATATGAAAGAGCAATTGGCTGGCTTAATGGGTGGACGTGTAGCT
GAAGAAATTATCTTTAATGTCCAAACCACAGGAGCTTCAAACGACTTTGAA
CAAGCGACACAAATGGCACGTGCAATGGTTACAGAGTACGGTATGAGTGAA
AAACTTGGCCCAGTACAATATGAAGGAAACCATGCTATGCTTGGTGCACAG
AGTCCTCAAAAATCAATTTCAGAACAAACAGCTTATGAAATTGATGAAGAG
GTTCGTTCATTATTAAATGAGGCACGAAATAAAGCTGCTGAAATTATTCAG
TCAAATCGTGAAACTCACAAGTTAATTGCAGAAGCATTATTGAAATACGAA
ACATTGGATAGTACACAAATTAAAGCTCTTTACGAAACAGGAAAGATGCCT
GAAGCAGTAGAAGAGGAATCTCATGCACTATCCTATGATGAAGTAAAGTCA
AAAATGAATGACGAAAAATAA 4125.10
(SEQ. ID. NO. 234)
ATGAGGGAACCAGATTTTTTAAATCATTTTCTCAAGAAGGGATATTTCAAA
AAGCATGCTAAGGCGGTTCTAGCTCTTTCTGGTGGATTAGATTCCATGTTT
CTATTTAAGGTATTGTCTACTTATCAAAAAGAGTTAGAGATTGAATTGATT TABLE 3-continued CTAGCTCATGTGAATCATAAGCAGAGAATTGAATCAGATTGGGAAGAAAG
GAATTAAGGAAGTTGGCTGCTGAAGCAGAGCTTCCTATTTATATCAGCAAT
TTTTCAGGAGAATTTTCAGAAGCGCGTGCACGAAATTTTCGTTATGATTTT
TTTCAAGAGGTCATGAAAAAGACAGGTGCGACAGCTTTAGTCACTGCCCAC
CATGCTGATGATCAGGTGGAAACGATTTTTATGCGCTTGATTCGAGGAACT
CGCTTGCGCTATCTATCAGGAATTAAGGAGAAGCAAGTAGTCGGAGAGATA
GAAATCATTCGTCCCTTCTTGCATTTTCAGAAAAAGACTTTCCATCAATT
TTTCACTTTGAAGATACATCAAATCAGGAGAATCATTATTTTCGAAATCGT
ATTCGAAATTCTTACTTACCAGAATTGGAAAAAGAAAATCCTCGATTTAGG
GATGCAATCTTAGGCATTGGCAATGAAATTTTAGATTATGATTTGGCAATA
GCTGAATTATCTAACAATATTAATGTGGAAGATTTACAGCAGTTATTTTCT
TACTCTGAGTCTACACAAGAGTTTTACTTCAAACTTATCTGAATCGTTTT
CCAGATTTGAATCTTACAAAAGCTCAGTTTGCTGAAGTTCAGCAGATTTTA
AAATCTAAAAGCCAGTATCGTCATCCGATTAAAAATGGCTATGAATTGATA
AAAGAGTACCAACAGTTTCAGATTTGTAAAATCAGTCCGCAGGCTGATGAA
AAGGAAGATGAACTTGTGTTACACTATCAAAATCAGGTAGCTTATCAAGGA
TATTTATTTTCTTTTGGACTTCCATTAGAAGGTGAATTAATTCAACAAATA
CCTGTTTCACGTGAAACATCCATACACATTCGTCATCGAAAACAGGAGAT
GTTTTGATTAAAAATGGGCATAGAAAAAAACTCAGACGTTTATTTATTGAT
TTGAAAATCCCTATGGAAAAGAGAAACTCTGCTCTTATTATTGAGCAATTT
GGTGAAATTGTCTCAATTTTGGGAATTGCGACCAATAATTTGAGTAAAAAA
ACGAAAAATGATATAATGAACACTGTACTTTATATAGAAAAAATAGATAGG
TAA 4126.1
(SEQ. ID. NO. 235)
ATGAAGCGTTCTTCTCTTTTAGTTAGAATGGTTATTTCCATCTTTCTGGTC
TTTCTCATTCTCCTAGCTCTGGTTGGAACTTTCTACTATCAATCAAGTTCT
TCAGCCATTGAGGCCACCATTGAGGGCAACAGCCAAACGACCATCAGCCAG
ACTAGCCACTTTATTCAGTCTTATATCAAAAAACTAGAAACCACCTCGACT
GGTTTGACCCAGCAGACGGATGTTCTGGCCTATGCTGAGAATCCCAGTCAA
GACAAGGTCGAGGGAATCCGAGATTTGTTTTTGACCATCTTGAAGTCAGAT
AAGGACTTGAAAACTGTTGTGCTGGTGACCAAATCTGGTCAGGTCATTTCT
ACAGATGACAGTGTGCAGATGAAAACTTCCTCTGATATGATGGCTGAGGAT
TGGTACCAAAAGGCCATTCATCAGGGAGCTATGCCTGTTTTGACTCCAGCT
CGTAAATCAGATAGTCAGTGGGTCATTTCTGTCACTCAAGAACTTGTTGAT
GCAAAGGGAGCCAATCTTGGTGTGCTTCGTTTGGATATTTCTTATGAAACT
CTGGAAGCCTATCTCAATCAACTCCAGTTGGGGCAGCAGGGCTTTGCCTTC
ATTATCAATGAAAACCATGAATTTGTCTACCATCCTCAACACACAGTTTAT
AGTTCGTCTAGCAAAATGGAGGCTATGAAACCCTACATCGATACAGGTCAG
GGTTATACTCCTGGTCACAAATCCTACGTCAGTCAAGAGAAGATTGCAGGA
ACTGATTGGACGGTGCTTGGCGTGTCATCATTGGAAAAGTTAGACCAGGTT
CGGAGTCAGCTCTTGTGGACCTTGCTTGGGGCCAGTGTCACATCTCTTCTT
GTCTGTCTCTGCTTAGTGTGGTTCAGTCTTAAACGCTGGATTGCTCCTTTG
AAGGATTTGAGAGAAACCATGTTGGAAATTGCTTCTGGTGCTCAAAATCTT
CGTGCCAAGGAAGTTGGTGCCTATGAACTGAGAGAAGTAACTCGCCAATTT
AATGCTATGTTGGATCAGATTGATCAGTTGATGGTAGCTATTCGTAGCCAG
GAAGAAACGACCCGTCAGTACCAACTTCAAGCCCTTTCGAGCCAGATTAAT
CCACATTTCCTCTATAACACTTTGGACACCATCATCTGGATGGCTGAATTT
CATGATAGTCAGCGAGTGGTGCAGGTGACCAAGTCCTTGGCAACCTATTTC
CGCTTGGCGCTCAATCAAGGCAAGGACTTGATTTGTCTCTCTGACGAAATC
AATCATGTCCGCCAGTATCTCTTTATCCAGAAACAACGCTATGGAGATAAG
CTTGGAATACGAAATTAATGAAAATGTTGCCTTTGATAATTTAGTCTTACC
CAAGCTGGTCCTACAACCCCTTGTAGAAAATGCTCTTTACCATGGCATTAA
GGAAAAGGAAGGTCAGGGCCATATTAAACTTTCTGTCCAGAAACAGGATTC
GGGATTGGTCATCCGTATTGAGGATGATGGCGTTGGCTTCCAAGATGCTGG
TGATAGTAGTCAAAGTCAACTCAAACGTGGGGGAGTTGGTCTTCAAAATGC
GATCAACGGCTCAAACTTCATTTTGGAGCCAATTACCATATGAAGATTGAT
TCTAGACCCCAAAAAGGGACGAAAGTTGAAATATATATAAATAGAATAGAA
ACTAGCTAA 4126.7
(SEQ. ID. NO. 236)
ATGAAGCGTTCTTCTCTTTTAGTTAGAATGGTTATTTCCATCTTTCTGGTC
TTTCTCATTCTCCTAGCTCTGGTTGGAACTTTCTACTATCAATCAAGTTCT
TCAGCCATTGAGGCCACCATTGAGGGCAACAGCCAAACGACCATCAGCCAG
ACTAGCCACTTTATTCAGTCTTATATCAAAAAACTAGAAACCACCTCGACT
GGTTTGACCCAGCAGACGGATGTTCTGGCCTATGCTGAGAATCCCAGTCAA
GACAAGGTCGAGGGAATCCGAGATTTGTTTTTGACCATCTTGAAGTCAGAT
AAGGACTTGAAAACTGTTGTGCTGGTGACCAAATCTGGTCAGGTCATTTCT
ACAGATGACAGTGTGCAGATGAAAACTTCCTCTGATATGATGGCTGAGGAT
TGGTACCAAAAGGCCATTCATCAGGGAGCTATGCCTGTTTTGACTCCAGCT
CGTAAATCAGATAGTCAGTGGGTCATTTCTGTCACTCAAGAACTTGTTGAT
GCAAAGGGAGCCAATCTTGGTGTGCTTCGTTTGGATATTTCTTATGAAACT
CTGGAAGCCTATCTCAATCAACTCCAGTTGGGGCAGCAGGGCTTTGCCTTC
ATTATCAATGAAAACCATGAATTTGTCTACCATCCTCAACACACAGTTTAT
AGTTCGTCTAGCAAAATGGAGGCTATGAAACCCTACATCGATACAGGTCAG
GGTTATACTCCTGGTCACAAATCCTACGTCAGTCAAGAGAAGATTGCAGGA
ACTGATTGGACGGTGCTTGGCGTGTCATCATTGGAAAAGTTAGACCAGGTT
CGGAGTCAGCTCTTGTGGACCTTGCTTGGGGCCAGTGTCACATCTCTTCTT
GTCTGTCTCTGCTTAGTGTGGTTCAGTCTTAAACGCTGGATTGCTCCTTTG
AAGGATTTGAGAGAAACCATGTTGGAAATTGCTTCTGGTGCTCAAAATCTT
CGTGCCAAGGAAGTTGGTGCCTATGAACTGAGAGAAGTAACTCGCCAATTT
AATGCTATGTTGGATCAGATTGATCAGTTGATGGTAGCTATTCGTAGCCAG TABLE 3-continued GAAGAAACGACCCGTCAGTACCAACTTCAAGCCCTTTCGAGCCAGATTAAT
CCACATTTCCTCTATAACACTTTGGACACCATCATCTGGATGGCTGAATTT
CATGATAGTCAGCGAGTGGTGCAGGTGACCAAGTCCTTGGCAACCTATTTC
CGCTTGGCGCTCAATCAAGGCAAGGACTTGATTTGTCTCTCTGACGAAATC
AATCATGTCCGCCAGTATCTCTTTATCCAGAAAACAACGCTATGGAGATAA
GCTGGAATACGAAATTAATGAAAATGTTGCCTTTGATAATTTAGTCTTACC
CAAGCTGGTCCTACAACCCCTTGTAGAAAATGCTCTTTACCATGGCATTAA
GGAAAAGGAAGGTCAGGGCCATATTAAACTTTCTGTCCAGAAACAGGATTC
GGGATTGGTCATCCGTATTGAGGATGATGGCGTTGGCTTCCAAGATGCTGG
TGATAGTAGTCAAAGTCAACTCAAACGTGGGGGAGTTGGTCTTCAAAATGT
CGATCAACGGCTCAAACTTCATTTTGGAGCCAATTACCATATGAAGATTGA
TTCTAGACCCCAAAAAGGGACGAAAGTTGAAATATATATAAATAGAATAGA
AACTAGCTAA 4127.4
(SEQ. ID. NO. 237)
ATGTTTTTTAAATTATTAAGAGAAGCTCTTAAAGTCAAGCAGGTTCGATCA
AAAATTTTATTTACAATTTTTATCGTTTTGGTCTTTCGTATCGGAACTAGC
ATTACAGTTCCTGGTGTGAATGCCAATAGCTTGAATGCTTTAAGTGGATTA
TCCTTCTTAAACATGTTGAGCTTGGTGTCGGGGAATGCCCTAAAAAACTTT
TCGATTTTTGCCCTAGGAGTTAGTCCCTATATCACCGCTTCTATTGTTGTC
CAACTCTTGCAAATGGATATTTTACCCAAGTTTGTAGAGTGGGGTAAACAA
GGGGAAGTAGGTCGAAGAAAATTGAATCAAGCTACTCGTTATATTGCTCTA
GTTCTCGCTTTTGTGCAATCTATCGGGATTACAGCTGGTTTTAATACCTTG
GCTGGAGCTCAATTGATTAAAACTGCTTTAACTCCACAAGTTTTTCTGACG
ATTGGTATCATCTTAACAGCTGGTAGTATGATTGTCACTTGGTTGGGTGAG
CAAATTACAGATAAGGGATACGGAAACGGTGTTTCCATGATTATCTTTGCC
GGGATTGTTTCCTCAATTCCAGAGATGATTCAGGGCATCTATGTGGACTAC
TTTGTGAACGTCCCAAGTAGCCGTATCACTTCATCTATCATTTTCGTAATC
ATTTTGATTATTACTGTATTGTTGATTATTTACTTTACAACTTATGTTCAA
CAAGCAGAATACAAAATTCCAATCCAATATACTAAGGTTGCACAAGGTGCT
CCATCTAGCTCTTACCTTCCGTTAAAAGTAAACCCTGCTGGAGTTATCCCT
GTTATCTTTGCCAGTTCGATTACTGCAGCGCCTGCGGCTATTCTTCAGTTT
TTGAGTGCCACAGGTCATGATTGGGCTTGGGTAAGGGTAGCACAAGAGATG
TTGGCAACTACTTCTCCAACTGGTATTGCCATGTATGCTTTGTTGATTATT
CTCTTTACATTCTTCTATACGTTTGTACAGATTAATCCTGAAAAAGCAGCA
GAGACCTACAAAAGAGTGGTGCCTATATCCATGGAGTTCGTCCTGGTAAAG
GTACAGAAGAATATATGTCTAAACTTCTTCGTCGTCTTGCAACTGTTGGTT
CCCTCTTCCTTGGTGTGA 4127.5
(SEQ. ID. NO. 238)
ATGGATATTAGACAAGTTACTGAAACCATCGCCATGATTGAGGAGCAAAAC
TTCGATATTAGAACCATTACCATGGGGATTTCTCTTTTGGACTGTATCGAT
CCAGATATCAATCGTGCTGCGGAGAAAATCTATCAAAAAATTACGACAAAG
GCGGCTAATTTAGTAGCTGTTGGTGATGAAATTGCGGCTGAGTTGGGAATT
CCTATCGTTAATAAGCGTGTATCGGTGACACCTATTTCTCTGATTGGGGCA
GCGACAGATGCGACGGACTACGTGGTTCTGGCAAAAGCGCTTGATAAGGCT
GCGAAAGAGATTGGTGTGGACTTTATTGGTGGTTTTTCTGCCTTAGTACAA
AAAGGTTATCAAAAGGGAGATGAGATTCTCATCAATTCCATTCCTCGCGCT
TTGGCTGAGACGGATAAGGTCTGCTCGTCAGTCAATATCGGCTCAACCAAG
TCTGGTATTAATATGACGGCTGTGGCAGATATGGGACGAATTATCAAGGAA
ACAGCAAATCTTTCAGATATGGGAGTGGCCAAGTTGGTTGTATTCGCTAAT
GCTGTTGAGGACAATCCATTTATGGCGGGTGCCTTTCATGGTGTTGGGGAA
GCAGATGTTATCATCAATGTCGGAGTTTCTGGTCCTGGTGTTGTGAAACGT
GCTTTGGAAAAGTTCGTGGACAGAGCTTTGATCTAGTAGCCGAAACAGTT
AAGAAAACTGCCTTTAAAATCACTCGTATCGGTCAATTGGTTGGTCAAATG
GCCAGTGAGAGACTGGGTGTGGAGTTTGGTATTGTGGACTTGAGTTTGGCA
CCAACCCCTGCGGTTGGAGACTCTGTGGCACGTGTCCTTGAGGAAATGGGG
CTAGAAACAGTTGGCACGCATGGAACGACGGCTGCCTTGGCCCTCTTGAAC
GACCAAGTTAAAAAGGGTGGAGTGATGGCCTGCAACCAAGTCGGTGGTTTA
TCTGGTGCCTTTATCCCTGTTTCTGAGGATGAAGGAATGATTGCTGCAGTG
CAAAATGGCTCTCTTAATTTAGAAAAACTAGAAGCTATGACGGCTATCTGT
TCTGTTGGATTGGATATGATTGCCATCCCAGAAGATACGCCTGCTGAAACT
ATTGCGGCTATGATTGCGGATGAAGCAGCAATCGGTGTTATCAACATGAAA
ACAACAGCTGTTCGTATCATTCCCAAAGGAAAAGAAGGCGATATGATTGAG
TTTGGTGGTCTATTAGGAACTGCACCCGTTATGAAGGTTAATGGGGCTTCG
TCTGTCGACTTCATCTCTCGCGGTGGACAAATCCCAGCACCAATTCATAGT
TTTAAAAATTAA 4128.1
(SEQ. ID. NO. 239)
ATGACACAGATTATTGATGGGAAAGCTTTAGCGGCCAAATTGCAGGGGCAG
TTGGCTGAAAAGACTGCAAAATTAAAGGAAGAAACAGGTCTAGTGCCTGGT
TTGGTAGTGATTTTGGTTGGGGACAATCCAGCCAGCCAAGTCTACGTTCGC
AACAAGGAGAGGTCAGCCCTTGCGGCTGGTTTCCGTAGCGAAGTAGTACGG
GTTCCAGAGACCATTACTCAAGAGGAATTCTTAGACCTGATTGCTAAATAC
AATCAGGATCCAGCTTGGCATGGGATTTTGGTTCAGTTGCCATTACCAAAA
CACATTGATGAAGAGGCGGTTCTATTGGCTATTGACCCAGCAAAAGGATGT
GGATGGTTTCCATCCTCTAAACATGGGGCGTCTTTGGTCTGGTCATCCAGT
CATGATTCCTTCGACACCGGCAGGAATTATGAAATGTTCCATGAATATGG
GATTGACT6GGAAGGTAAAAATGCAGTCGTCATCGGTCGATCCAATATTG
TCGGAAAACCTATGGCCCAGCTTCTTTTGGCAAAGAATGCAACAGTAACCT
TGACTCACTCACGTACTCATAATCTTTCCAAGGTGGCTGCAAAAGCAGATA
TTCTGGTTGTTGCAATCGGTCGTGCCAAGTTTGTGACTGCTGACTTTGTCA
AACCAGGTGCGGTAGTCATTGACGTTGGGATGAACCGCGATGAAAATGGTA TABLE 3-continued

AGCTCTGTGGGGATGTTGATTATGAGGCGGTTGCCCCACTTGCTAGCCACA

TTACGCCAGTCCCTGGAGGTGTCGGTCCTATGACCATTACTATGCTGATGG

AGCAAACCTATCAGGCAGCACTTAGGACATTGGATAGAAAATAA 4128.2

(SEQ. ID. NO. 240)
ATGTCTAAATTTAATCGTATTCATTTGGTGGTACTGGATTCTGTAGGAATC

GGTGCAGCACCAGATGCTAATAACTTTGTCAATGCAGGGGTTCCAGATGGA

GCTTCTGACACACTGGGACACATTTCAAAAACAGTTGGTTTGAATGTCCCA

AACATGGCTAAAATAGGTCTTGGAAATATTCCTCGTGAAACTCCTCTTAAG

ACTGTAGCAGCTGAAAGCAATCCAACTGGATATGCAACAAAATTAGAGGAA

GTATCTCTTGGTAAGGATACTATGACTGGACACTGGGAAATCATGGGACTC

AACATTACTGAGCCTTTCGATACTTTCTGGAACGGATTCCCAGAAGAAATC

CTGACAAAAATCGAAGAATTCTCAGGACGCAAGGTTATTCGTGAAGCCAAC

AAACCTTATTCAGGAACGGCTGTTATCTATGATTTTGGACCACGTCAGATG

GAAACTGGAGAGTTGATTATCTATACTTCAGCTGACCCTGTTTTGCAGATT

GCTGCCCACGAAGACATTATTCCTTTGGATGAATTGTACCGTATCTGTGAA

TACGCTCGTTCGATTACCCTTGAGCGTCCTGCCCTTCTTGGTCGCATCATT

GCTCGCCCTTATGTAGGTGAACCAGGTAACTTCACTCGTACGGCAAACCGT

CGTGACTTGGCTGTATCTCCATTTTTCCCAACTGTTTTGGATAAATTGAAT

GAGGCTGGTATCGATACTTATGCTGTGGGTAAAATCAACGATATCTTTAAC

GGTGCTGGTATCAACCATGACATGGGTCACAACAAGTCAAATAGTCATGGA

ATTGATACACTATTGAAGACTATGGGACTTGCTGAGTTTGAAAAAGGATTC

TCATTCACAAACCTAGTTGACTTTGATGCCCTTTACGGCCATCGTCGTAAT

GCTCACGGTTACCGTGATTGCTTGCATGAGTTTGATGAACGCTTACCTGAA

ATTATCGCAGCTATGAGAGAGAATGACCTTCTCTTGATTACTGCGGACCAT

GGAAATGACCCAACGTATGCAGGAACGGATCACACTCGGGAATATATTCCA

TTGTTGGCCTATAGCCCTGCCTTTAAAGGAAATGGTCTCATTCCAGTAGGA

CATTTTGCAGATATTTCAGCGACTGTTGCCGATAACTTTGGTGTGGAAACT

GCTATGATTGGGGAAAGTTTCTTAGATAAATTGGTATAA 4129.2

(SEQ. ID. NO. 241)
ATGTTTATTTCCATCAGTGCTGGAATTGTGACATTTTTACTAACTTTAGTA

GAAATTCCGGCCTTTATCCAATTTTATAGAAAGGCGCAAATTACAGGCCAG

CAGATGCATGAGGATGTCAAACAGCATCAGGCAAAAGCTGGGACTCCTACA

ATGGGAGGTTTGGTTTTCTTGATTACTTCTGTTTTGGTTGCTTTCTTTTTC

GCCCTATTTAGTAGCCAATTCAGCAATAATGTGGGAATGATTTTGTTCATC

TTGGTCTTGTATGGCTTGGTCGGATTTTAGATGACTTTCTCAAGGTCTTT

CGTAAAATCAATGAGGGGCTTAATCCTAAGCAAAAATTAGCTCTTCAGCTT

CTAGGTGGAGTTATCTTCTATCTTTTCTATGAGCGCGGTGGCGATATCCTG

TCTGTCTTTGGTTATCCAGTTCATTTGGGATTTTTCTATATTTTCTTGCGCT

CTTTTCTGGCTAGTCGGTTTTTCAAACGCAGTAAACTTGACAGACGGTGTT

GACGGTTTAGCTAGTATTTCCGTTGTGATTAGTTTGTCTGCCTATGGAGTT

ATTGCCTATGTGCCAGGTCAGATGGATATTCTTCTAGTAATTCTTGCCATG

ATTGGTGGTTTGCTCGGTTTCTTCATCTTTAACCATAAGCCTGCCAAGGTC

TTTATGGGTGATGTGGGAAGTTTGGCCCTAGGTGGGATGCTGGCAGCTATC

TCTATGGCTCTCCACCAAGAATGGACTCTCTTGATTATCGGAATTGTGTAT

GTTTTTGAAACAACTTCTGTTATGATGCAAGTCAGTTATTTCAAACTGACA

GGTGGTAAACGTATTTTCCGTATGACGCCTGTACATCACCATTTTGAGCTT

GGGGGGATTGTCTGGTAAAGGAAATCCTTGGAGCGAGTGGAAGGTTGACTT

CTTCTTTTGGGGAGTGGGACTTCTAGCAAGTCTCCTGACCCTAGCAATTTT

ATATTTGATGTAA 4133.1

(SEQ. ID. NO. 242)
TTGTTTAAGAAAAATAAAGACATTCTTAATATTGCATTGCCAGCTATGGGT

GAAAACTTTTTGCAGATGCTAATGGGAATGGTGGACAGTTATTTGGTTGCT

CATTTAGGATTGATAGCTATTTCAGGGGTTTCAGTAGCTGGTAATATTATC

ACCATTTATCAGGCGATTTTCATCGCTCTGGGAGCTGCTATTTCCAGTGTT

ATTTCAAAAAGCATAGGGCAGAAAGACCAGTCGAAGTTGGCCTATCATGTG

ACTGAGGCGTTGAAGATTACCTTACTATTAAGTTTCCTTTTAGGATTTTTG

TCCATCTTCGCTGGGAAAGAGATGATAGGACTTTTGGGGACGGAGAGGGAT

GTAGCTGAGAGTGGTGGACTGTATCTATCTTTGGTAGGCGGATCGATTGTT

CTCTTAGGTTTAATGACTAGTCTAGGAGCCTTGATTCGTGCAACGCATAAT

CCACGTCTGCCCTCTCTATGTTAGTTTTTTATCCAATGCCTTGAATATTCTT

TTTTCAAGTCTAGCTATTTTTGTTCTGGATATGGGGATAGCTGGTGTTGCT

TGGGGGACAATTGTGTCTCGTTTGGTTGGTCTTGTGATTTTGTGGTCACAA

TTAAAACTGCCTTATGGGAAGCCAACTTTTGGTTTAGATAAGGAACTGTTG

ACCTTGGCTTTACCAGCAGCTGGAGAGCGACTTATGATGAGGGCTGGAGAT

GTAGTGATCATTGCCTTGGTCGTTTCTTTTGGGACGGAGGCAGTTGCTGGG

AATGCAATCGGAGAAGTCTTGACCCAGTTTAACTATATGCCTGCCTTTGGC

GTCGCTACGGCAACGGTCATGCTGTTGGCCCGAGCAGTTGGAGAGGATGAT

TGGAAAAGAGTTGCTAGTTTGAGTAAACAAACCTTTTGGCTTTCTCTGTTC

CTCATGTTGCCCCTGTCCTTTAGTATATATGTCTTGGGTGTACCATTAACT

CATCTCTATACGACTGATTCTCTAGCGGTGGAGGCTAGTGTTCTAGTGACA

CTGTTTTCACTACTTGGGACCCCTATGACGACAGGAACAGTCATCTATACG

GCAGTCTGGCAGGGATTAGGAAATGCACGCCTCCCTTTTTATGCGACAAGT

ATAGGAATGTGGTGTATCCGCATTGGGACAGGATATCTGATGGGATTGTG

CTTGGTTGGGCTTGCCTGGTATTTGGGCAGGGTCTCTCTTGGATAATGGT

TTTCGCTGGTTATTTCTACGCTATCGTTACCAGCGCTATATGAGCTTGAAA

GGATAG 4135.2

(SEQ. ID. NO. 243)
ATGCAAACCAAGAAAAACACTCGCAAGCAGCCGTTCTTGGCTTGCAGCACT

TACTAGCCATGTACTCAGGATCTATCCTGGTTCCCATCATGATTGCGACAG

CCCTTGGCTATTCAGCTGAGCAGTTGACCTACCTGATTTCTACAGATATCT

TABLE 3-continued

TCATGTGTGGGGTGGCAACCTTCCTCCAACTCCAACTCAACAAATACTTTG
GGATTGGACTCCCAGTCGTTCTTGGAGTTGCATTCCAGTCGGTCGCTCCCT
TGATTATGATTGGGCAAAGCCATGGTAGTGGCGCTATGTTTGGTGCCCTTA
TCGCATCTGGGATTTACGTGGTTCTTGTTTCAGGCATCTTCTCAAAAGTAG
CCAATCTCTTCCCATCTATCGTAACAGGATCTGTTATTACCACGATTGGTT
TAACCTTGATCCCTGTCGCTATTGGAAATATGGGAATAACGTTCCAGAGC
CAACTGGTCAAAGTCTCTTGCTTCAGCTATTACTGTTCTGATTATCCTCT
TGATCAACATCTTTACCAAAGGATTTATCAAGTCTATCTCTATTTTGATTG
GTCTGGTTGTTGGAACTGCCATTGCTGCTACTATGGGCTTGGTGGACTTCT
CTCCTGTTGCGGTAGCTCCACTTGTCCATGTCCCAACTCCACTCTACTTTG
GGATGCCAACCTTTGAAATCTCATCTATTGTCATGATGTGTATCATCGCAA
CGGTGTCTATGGTTGAGTCAACTGGTGTTTATCTGGCCTTGTCTGATATCA
CAAAGGAATCCAATCGACAGCACGCGCCTTCGCAACGGATACCGCGCAGAA
GGTTTGGCCGTACTTCTCGGAGGAATCTTTAACACCTTCCCTTACACCGGA
TTTTCACAAAACGTTGGTTTGGTTAAATTGTCAGGCATCAAAAAACGCCTG
CCAATCTACTACGCAGCTGGTTTCCTGGTTCTCCTTGGACTGCTTCCTAAG
TTTGGCGCCCTTGCCCAAATCATTCCAAGCTCCGTCCTCGGTGGTGCCATG
CTGGTAATGTTTGGTTTTGTATCAATTCAAGGGATGCAAATCCTCGCCCGT
GTTGACTTTGCTAACAATGAACACAACTTCCTTATCGCAGCTGTTTCAATC
GCTGCAGGTGTCGGTCTCAACAACAGTAATCTCTTTGTCAGCATGCCGACA
GCCTTCCAAATGTTCTTCTCAAACGGAATCGTCGTAGCCAGCCTACTCGCT
ATTGTCCTCAATGCCGTATTAAATCATAAAAAGAAATAA 4136.2

(SEQ. ID. NO. 244)
ATGAAAGATAGAATAAAAGAATATTTACAAGACAAGGGAAAGGTGACTGTT
AATGATTTGGCTCAGGCTTGGGAAAAGACAGTTCCAAGGATTTTCGTGAGT
TGATTAAAACCTTGTCCTTAATGGAAAGAAAGCACCAAATTCGTTTTGAAG
AAGATGGTAGTCTGACATTAGAAATTAAGAAAAAACATGAGATTACCCTCA
AGGGGATTTTTCATGCCCATAAAAATGGCTTTGGCTTTGTTAGTCTGGAAG
GCGAGGAGGACGACCTTTTTGTAGGGAAAAATGATGTCAACTATGCTATTG
ATGGTGATACCGTCGAGGTAGTGATTAAGAAAGTCGCTGACCGCAATAAGG
GAACAGCAGCAGAAGCCAAAATTATTGATATCCTAGAACACAGTTTGACAA
CAGTTGTCGGGCAAATCGTTCTGGATCAGGAAAAACCTAAGTATGCTGGCT
ATATTCGTTCAAAAAATCAGAAAATCAGTCAACCGATTTATGTTAAGAAAC
CAGCCCTAAAATTAGAAGGAACAGAAGTTCTCAAAGTCTTTATCGATAAAT
ACCCAAGCAAGAAACATGATTTCTTTGTCGCGAGTGTTCTCGATGTAGTGG
GACACTCAACGGATGTCGGAATTGATGTTCTTGAGGTCTTGGAATCAATGG
ACATTGTATCCGAGTTTCCAGAAGCTGTTGTTAAGGAAGCAGAAAGTGTGC
CTGATGCTCCGTCTCAAAAGGATATGGAAGGTCGTCTGGATCTAAGAGATG
AAATTACCTTTACCATTGACGGTGCGGATGCCAAGGACTTGGACGATGCAG
TGCATATCAAGGCTCTGAAAAATGGCAATCTGGAGTTTGGGGTTCACATCG

CAGATGTTTCTTATTATGTGACCGAGGGGTCTGCCCTTGACAAGGAAGCCC
TTAACCGTGCGACTTCTGTTTACGTGACAGACCGAGTGGTGCCAATGCTTC
CAGAACGACTATCAAATGGCATCTGCTCTCTCAATCCCCAAGTTGACCGCC
TGACCCAGTCTGCTATTATGGAGATTGATAAACATGGTCGTGTGGTCAACT
ATACCATTACACAAACAGTTATCAAGACCAGTTTTCGTATGACCTATAGCG
ATGTCAATGATATCCTAGCTGGCGATGAAGAAAAGAGAAAAGAATATCATA
AAATTGTATCAAGTATCGAACTCATGGCCAAGCTTCATGAAACTTTAGAAA
ACATGCGTGTGAAACGTGGAGCTCTCAATTTTGATACCAATGAAGCGAAGA
TTTTAGTGGATAAACAAGGTAAGCCTGTTGATATCGTTCTTCGGCAGCGTG
GTATTGCCGAGCGGATGATTGAGTCTTTTATGTTGATGGCTAATGAAACAG
TTGCCGAACATTTCAGCAAGTTGGATTTGCCTTTTATCTATCGAATTCACG
AGGAGCCTAAGGCTGAAAAGGTTCAGAAGTTTATTGATTATGCTTCGAGTT
TTGGCTTGCGCATTTATGGAACTGCCAGTGAGATTAGTCAGGAGGCACTTC
AAGACATCATGCGTGCTGTTGAGGGAGAACCTTATGCAGATGTATTGTCCA
TGATGCTTCTTCGCTCTATGCAGCAGGCTCGTTATTCGGAGCACAATCACG
GCCACTATGGACTAGCTGCTGACTATTATACTCACTTTACCAGTCCAATTC
GTCGTTATCCAGACCTTCTTGTTCACCGTATGATTCGGGATTACGGCCGTT
CTAAGGAAATAGCAGAGCATTTTGAACAAGTGATTCCAGAGATTGCGACCC
AGTCTTCCAACCGTGAACGTCGTGCCATAGAAGCTGAGCGTGAAGTCGAAG
CCATGAAAAAGGCTGAGTATATGGAAGAATACGTGGGTGAAGAGTATGATG
CAGTTGTATCAAGTATTGTCAAATTCGGTCTCTTTGTCGAATTGCCAAACA
CAGTTGAAGGCTTGATTCACATCACTAATCTGCCTGAATTTATCATTTCA
ATGAGCGTGATTTGACTCTTCGTGGAGAAAAATCAGGTATCACTTTCCGAG
TGGGTCAGCAGATCCGTATCCGTGTTGAAAGAGCGGATAAAATGACTGGAG
AGATTGATTTTTCATTCGTACCTAGTGAGTTTGATGTGATTGAAAAAGGCT
TGAAACAGTCTAGTCGTAGTGGCAGAGGGCGTGATTCAAATCGTCGTTCGG
ATAAGAAGGAAGACAAGAGAAAATCAGGACGCTCAAATGATAAGCGTAAGC
ATTCACAAAAAGACAAGAAGAAAAAAGGAAAGAAACCTTTTTCACCGGAAG
TAGCTAAGAAAGGAGCCAAGCATGGCAAAGGGCGAGGGAAAGGTCGTCGCA
CAAAATAA 4137.2

(SEQ. ID. NO. 245)
ATGGGCACAACAGGATTTACAATAATTGACTTAATTATCTTGATTGTTTAT
TTACTTGCGGTGTTGGTTGCAGGTATCTATTTCTCTAAAAAAGAGATGAAA
GGAAAAGAGTTCTTTAAAGGAGATGGTTCGGTTCCTTGGTATGTTACTTCG
GTATCCATTTTTGCCACAATGCTCAGTCCGATTTCCTTCTTGGGACTCGCT
GGTAGCTCTTATGCAGGTAGCTGGATTTATGGTTTGCTCAATTAGGGATG
GTAGTAGCTATTCCACTGACAATTCGTTTTATCTTACCTATCTTTGCACGG
ATAGACATCGATACGGCATATGATTACTTGGATAAACGTTTTAATTCTAAA
AGCACTTCGTATTTTTCAGCACTCTTGTTTATTATTTATCAATTGGGACG
TATGTCTATCATTATGTACCTCCCATCAGCTGGTTTATCAGTATTGACAGG

TABLE 3-continued

AATTGACATCAATATTTTGATTATTTTGATGGGTGTAGTTGCAATTGTTTA

TTCTTATACTGGTGGTCTAAAATCCGTATTATGGACAGACTTTATTCAAGG

TGTGATTCTGATTAGTGGTGTCGTTTTAGCTTTATTTGTACTGATTGCTAA

TATTAAAGGTGGCTTTGGTGCAGTAGCAGAAACATTAGCAAACGGGAAATT

CCTTGCTGCAAATGAAAAACTTTTCGATCCTAACTTGCTTTCAAACTCCAT

CTTTTTAATTGTGATGGGTTCAGGCTTTACAATCTTGTCTTCCTATGCTTC

ATCTCAAGATTTGGTTCAACGTTTTACTACAACACAAAATATTAAGAAACT

TAATAAGATGTTGTTCACAAACGGTGTTTTGTCACTTGCAACTGCAACAGT

CTTTTACTTGATTGGTACAGGCTTGTACGTATTCTATCAAGTACAAAATGC

AGATAGTGCAGCTAGCAATATCCCTCAAGACCAAATCTTTATGTACTTTAT

TGCATACCAGTTACCAGTAGGTATCACAGGTTTGATCTTGGCAGCGATTTA

TGCAGCATCTCAATCAACTATTTCAACAGGTTTGAACTCTGTTGCAACTTC

ATGGACATTGGATATTCAAGATGTCATTTCTAAAAATATGTCAGACAATCG

TCGTACGAAAATTGCACAATTCGTATCTCTAGCAGTAGGTTTATTCTCAAT

TGGTGTTTCCATTGTCATGGCTCACTCAGATATTAAATCTGCATACGAATG

GTTCAATAGTTTCATGGGACTTGTACTTGGTCTACTTGGTGGTGTATTTAT

TCTTGGATTTGTTTCTAAAAAAGCAAATAAACAAGGTGCTTATGCAGCGCT

GATTGTATCAACCATCGTCATGGTATTTATTAAATACTTCCTTCCTCCAAC

AGCTGTTAGCTACTGGGCATATTCATTGATTTCAATCTCTGTATCAGTAGT

TTCAGGTTATATTGTATCTGTTCTTACTGAAATAAAGTATCTGCACCTAA

ATATACAACGATTCATGATATTACAGAAATTAAAGCGGATTCAAGTTGGGA

AGTTCGTCACTAA 4138.1

(SEQ. ID. NO. 246)
ATGAAATTTAGTAAAAAATATATAGCAGCTGGATCAGCTGTTATCGTATCC

TTGAGTCTATGTGCCTATGCACTAAACCAGCATCGTTCGCAGGAAAATAAG

GACAATAATCGTGTCTCTTATGTGGATGGCAGCCAGTCAAGTCAGAAAAGT

GAAAACTTGACACCAGACCAGGTTAGCCAGAAAGAAGGAATTCAGGCTGAG

CAAATTGTAATCAAAATTACAGATCAGGGCTATGTAACGTCACACGGTGAC

CACTATCATTACTATAATGGGAAAGTTCCTTATGATGCCCTCTTTAGTGAA

GAACTCTTGATGAAGGATCCAAACTATCAACTTAAAGACGCTGATATTGTC

AATGAAGTCAAGGGTGGTTATATCATCAAGGTCGATGGAAAATATTATGTC

TACCTGAAAGATGCAGCTCATGCTGATAATGTTCGAACTAAAGATGAAATC

AATCGTCAAAAACAAGAACATGTCAAAGATAATGAGAAGGTTAACTCTAAT

GTTGCTGTAGCAAGGTCTCAGGGACGATATACGACAAATGATGGTTATGTC

TTTAATCCAGCTGATATTATCGAAGATACGGGTAATGCTTATATCGTTCCT

CATGGAGGTCACTATCACTACATTCCCAAAAGCGATTTATCTGCTAGTGAA

TTAGCAGCAGCTAAAGCACATCTGGCTGGAAAAAATATGCAACCGAGTCAG

TTAAGCTATTCTTCAACAGCTAGTGACAATAACACGCAATCTGTAGCAAAA

GGATCAACTAGCAAGCCAGCAAATAAATCTGAAAATCTCCAGAGTCTTTTG

AAGGAACTCTATGATTCACCTAGCGCCCAACGTTACAGTGAATCAGATGGC

CTGGTCTTTGACCCTGCTAAGATTATCAGTCGTACACCAAATGGAGTTGCG

ATTCCGCATGGCGACCATTACCACTTTATTCCTTACAGCAAGCTTTCTGCC

TTAGAAGAAAGATTGCCAGAATGGTGCCTATCAGTGGAACTGGTTCTACA

GTTTCTACAAATGCAAAACCTAATGAAGTAGTGTCTAGTCTAGGCAGTCTT

TCAAGCAATCCTTCTTCTTTAACGACAAGTAAGGAGCTCTCTTCAGCATCT

GATGGTTATATTTTAATCCAAAAGATATCGTTGAAGAAACGGCTACAGCT

TATATTGTAAGACATGGTGATCATTTCCATTACATTCCAAAATCAAATCAA

ATTGGGCAACCGACTCTTCCAAACAATAGTCTAGCAACACCTTCTCCATCT

CTTCCAATCAATCCAGGAACTTCACATGAGAAACATGAAGAAGATGGATAC

GGATTTGATGCTAATCGTATTATCGCTGAAGATGAATCAGGTTTTGTCATG

AGTCACGGAGACCACAATCATTATTTCTTCAAGAAGGACTTGACAGAAGAG

CAAATTAAGGTGCGCAAAAACATTTAG 4139.1

(SEQ. ID. NO. 247)
ATGAAAAAAAGAGCAATAGTGGCAGTCATTGTACTGCTTTTGATTGGGCTG

GATCAGTTGGTCAAATCCTATATCGTCCAGCAGATTCCACTGGGTGAAGTG

CGCTCCTGGATCCCCAATTTCGTTAGCTTGACCTACCTGCAAAATCGAGGT

GCAGCCTTTTCTATCTTACAAGATCAGCAGCTGTTATTCGCTGTCATTACT

CTGGTTGTCGTGATAGGTGCCATTTGGTATTTACATAAAACACATGGAGGA

CTCATTCTGGATGGTCTTGGGTTTGACTCTAATAATCGCGGGTGGTCTTGG

AAACTTTATTGACAGGGTCAGTCAGGGCTTTGTTGTGGATATGTTCCACCT

TGACTTTATCAACTTTGCAATTTTCAATGTGGCAGATAGCTATCTGACGGT

TGGAGTGATTATTTTATTGATTGCAATGCTAAAAGAGGAAATAAATGGAAA

TTAA 4139.5

(SEQ. ID. NO. 248)
ATGAATACAAATCTTGCAAGTTTTATCGTTGGACTGATCATCGATGAAAAC

GACCGTTTTTACTTTGTGCAAAAGGATGGTCAAACCTATGCTCTTGCTAAG

GAAGAAGGCCAACATACAGTAGGGGATACGGTCAAAGGTTTTGCATACACG

GATATGAAGCAAAAACTCCGCCTGACAACCTTAGAAGTGACTGCCACTCAG

GACCAATTTGGTTGGGACGTGTCACAGAGGTTCGTAAGGACTTGGGTGTC

TTTGTGGATACAGGCCTTCCTGACAAGGAAATCGTTGTGTCACTCGATATT

CTCCCTGAGCTCAAGGAACTCTGGCCTAAGAAGGGCGACCAACTCTACATC

CGTCTTGAAGTGGATAAGAAAGACCGTATCTGGGGCCTCTTGGCTTATCAA

GAAGACTTCCAACGTCTTGCTCGTCCTGCCTACAACAACATGCAGAACCAA

AACTGGCCAGCCATTGTTTACCGTCTCAAGCTGTCAGGAACTTTTGTTTAC

CTACCAGAAAATAATATGCTTGGTTTTATTCATCCTAGCGAGCGTTACGCA

GAGCCACGTTTGGGGCAAGTATTAGATGCGCGCGTTATTGGTTTCCGTAAG

TGGACCGCACTCTGAACCTCTCCCTCAAACCACGCTCCTTTGAAATGTTGG

AAAACGATGCTCAGATGATTTTGACTTATTTGGAAAGCAATGGCGGTTTCA

TGACCTTAAATGACAAGTCATCTCCAGACGACATCAAGGCAACCTTTGCA

TTTCTAAAGGTCAGTTCAAGAAAGCTTTAGGTGGTCTTATGAAGGCTGGTA

TABLE 3-continued

AAATCAAGCAGGACCAGTTTGGGACAGAGTTGATTTAG 4139.8
(SEQ. ID. NO. 249)
ATGAAAGATGTTAGTCTATTTTTATTGAAAAAAGTTTTCAAAAGCCGCTTA

AACTGGATTGTCTTAGCTTTATTTGTATCTGTACTCGGTGTTACCTTTTAT

TTAAATAGTCAGACTGCAAACTCACACAGCTTGGAGAGCAGGTTGGAAAGT

CGCATTGCAGCCAACGAGAGGGCTATCAATGAAAATGAAGAGAAACTCTCC

CAAATGTCTGATACCAGCTCGGAGGAATACCAGTTTGCTAAAAATAATTTA

GACGTGCAAAAAATCTTTTGACGCGAAAGACAGAAATTCTGACTTTATTA

AAAGAAGGGCGCTGGAAAGAAGCCTACTATTTGCAGTGGCAAGATGAAGAG

AAGAATTATGAATTTGTATCAAATGACCCGACTGCTAGCCCTGGCTTAAAA

ATGGGGGTTGACCGCGAACGGAAGATTTACCAAGCCCTGTATCCCTTGAAC

ATAAAAGCACATACTTTGGAGTTTCCGACCCACGGGATTGATCAGATTGTC

TGGATTTTAGAGGTTATCATCCCAAGTTTGTTTGTGGTTGCTATTATTTTT

ATGCTAACACAACTATTTGCAGAAAGATATCAAAATCATCTGGACACAGCT

CACTTATATCCTGTTTCAAAAGTGACATTTGCAATATCCTCTCTTGGAGTT

GGAGTGGGATATGTAACTGTGCTGTTTATCGGAATCTGTGGCTTTTCTTTT

CTAGTGGGAAGTCTGATAAGTGGTTTTGGACAGTTAGATTATCCCTACCCA

ATTTATAGCTTAGTGAATCAAGAAGTAACTATTGGGAAAATACAAGATGTA

TTATTTCCTGGCTTGCTCTTAGCTTTCTTAGCCTTTATCGTCATTGTGGAA

GTTGTGTACTTGATTGCTTACTTTTTCAAGCAAAAAATGCCTGTCCTCTTT

CTTTCACTCATTGGGATTGTTGGCTTATTGTTTGGTATCCAAACCATTCAG

CCTCTTCAAAGGATTGCACATCTGATTCCCTTTACTTACTTGCGTTCAGTG

GAGATTTTATCTGGAAGATTACCTAAGCAGATTGATAATGTCGATCTAAAT

TGGAGCATGGGAATGGTCTTACTTCCTTGCCTGATTATCTTTTTGCTATTG

GGAATTCTATTTATTGAAAGATGGGGAAGTTCACAGAAAAAGAATTTTTT

AATAGATTCTAG 4141.1
(SEQ. ID. NO. 250)
ATGATGAAGTTCATATTGGATATTGTTAGTACACCAGCTATTTTAGTAGCT

TTAATTGCAATCTTAGGATTAGTTCTTCAGAAGAAGAAATTACCTGATATT

ATTAAAGGTGGAATTAAGACCTTTGTTGGTTTCTTAGTTGTATCTGGTGGT

GCAGGAATTGTACAAAATTCTTTAAATCCATTTGGTACCATGTTTGAGCAT

GCTTTTCATTTATCTGGCGTTGTGCCGAATAATGAAGCAATTGTAGCTGTA

GCTTTAACAACATATGGCTCAGCTACTGCAATGATTATGTTTGCAGGCATG

GTGTTCAATATCTTAATCGCTCGTTTTACTCGATTTAAATATATTTTTTA

ACAGGGCACCACACTCTATATATGGCATGTATGATTGCGGTCATTTTATCA

GTTGCTGGCTTTACTAGCTTGCCTCTCATCTTACTAGGAGGATTAGCACTC

GGTATTATTATGAGTATTTCCCCAGCATTTGTGCAAAAATATATGGTTCAA

TTAACTGGAAATGACAAGGTAGCTTTAGGTCATTTCAGTTCTTTGGGATAT

TGGTTGAGTGGTTTTACTGGTAGCCTTATCGGTGACAAATCAAAATCAACA

GAGGACATTAAATTTCCAAAGAGTTTAGCTTTTTTACGTGATAGTACTGTT

AGTATTACTTTATCCATGGCAGTTATTTACATTATTGTAGCTATCTTTGCA

GGGTCAGAATATATAGAAAAAGAAATCAGTAGTGGTACAAGTGGTCTAGTT

TATGCTTTACAATTAGCAGGTCAATTTGCAGCAGGGGTATTTGTTATTTTA

GCAGGTGTTCGCCTTATTTTGGGCGAAATTGTTCCAGCCTTTAAAGGTATT

TCAGAGCGTCTTGTACCTAATTCAAAACCTGCTTTGGATTGTCCGATTGTT

TATACTTATGCACCCAATGCAGTTCTAATTGGATTTATCTCTAGTTTTGTT

GGTGGTTTAGTAAGTATGGTAATTATGATTGCTTCAGGAACGGTTGTTATC

TTACCAGGTGTTGTGCCTCATTTCTTCTGTGGAGCGACTGCAGGTGTCATT

GGGAATGCATCTGGTGGTGTTCGTGGAGCCACTATTGGAGCATTTTTACAA

GGTATTTTAATCAGTTTTCTTCCAGTCTTTTTAATGCCAGTTTTGGGAGGA

CTTGGTTTCCAAGGATCAACTTTCTCAGATGCAGATTTTGGTCTATCAGGA

ATTATTTTAGGAATGTTAAATCAATTTGGCTCACAAGCAGGCATTGTGATT

GGTCTTGTTCTTATTCTAGCAGTTATGTTTGGAGTATCCTTTATTAAAAAG

CCATCTGCAACGGAGGAATAA 4142.3
(SEQ. ID. NO. 251)
ATGATTAAAACATTTCTCTCTGCCCTTTCGGTCATTCTCTTTTCTATCCCT

ATCATAACTTATTCTTTTTTCCCATCTTCTAATCTTAACATTTGGCTATCT

ACCCAACCTATCTTGGCACAGATTTATGCCTTCCCCTTAGCTACTGCAACT

ATGGCTGCTATTTTAAGTTTCTTATTTTTTTTCCTATCTTTTTACAAGAAA

AATAAACAAATACGGTTTTACTCTGGCATTTTGCTCTTACTATCGCTCATA

TTACTATTATTCGGAACAGATAAAACCCTTTCTTCTGCATCAAATAAGACT

AAAAACTTAAAATTAGTAACTTGGAACGTCGCTAATCAAATAGAAGCACAA

CATATTGAGCGAATTTTTAGCCATTTTGACGCCGATATGGCTATATTCCCT

GAACTAGCTACCAATATCAGAGGTGAGCAAGAAAACCAGAGAATCAAACTA

TTGTTTCATCAAGTTGGACTTTCTATGGCCAACTATGATATTTTCACTTCT

CCACCTACCAATAGTGGAATAGCTCCTGTGACTGTGATTGTCAAGAAAGT

TATGGTTTCTATACAGAAGCTAAAACTTTTCATACAACACGGTTCGGGACA

ATTGTATTACATTCGAGAAACAAAATATACCAGATATCATTGCCTTGCAT

ACTGCGCCTCCTCTGCCAGGTTTAATGGAAATCTGGAAGCAAGACTTAAAC

ATCATTCATAATCAATTGGCTTCAAAATATCCAAAGGCTATTATTGCAGGT

GATTTTAATGCAACTATGCGTCATGGAGCACTTGCAAAAATAAGCTCTCAT

AGGGACGCATTAAATGCACTGCCACCTTTTGAAAGAGGAACTTGGAATAGC

CAAAGTCCAAAACTTTTTAATGCAACAATAGATCATATTTTATTGCCTAAA

AACCACTACTATGTTAAAGATTTAGACATTGTAAGTTTTCAAAACTCTGAT

CATAGATGTATTTTTACAGAAATCACATTTTAA 4142.4
(SEQ. ID. NO. 252)
ATGAATCCAATCCAAAGATCTTGGGCTTATGTCAGCAGAAAGCGACTGAGA

AGTTTTATTTTATTTCTGATTTTATTGGTCTTATTGGCCGGAATTTCAGCC

TGTTTGACTCTGATGAAGTCCAACAAAACAGTAGAAAGCAATCTTTATAAA

TCACTCAATACATCTTTTTCTATTAAGAAGATAGAGAATGGTCAGACATTC

TABLE 3-continued

AAGTTGTCAGACCTAGCATCTGTAAGCAAGATTAAGGGGCTGGAAAATGTC
TCTCCTGAACTTGAGACGGTCGCAAAACTAAAAGACAAGGAAGCAGTGACT
GGCGAGCAGAGCGTGGAGCGTGATGATTTATCAGCTGCAGACAATAACTTG
GTTAGCTTAACGGCTCTTGAGGATTCATCCAAGGATGTAACCTTTACCAGT
TCGGCTTTCAATCTAAAAGAAGGGCGACACCTTCAAAAAGGGGATTCCAAG
AAAATCCTTATCCACGAAGAATTGGCTAAGAAGAACGGTCTTTCGCTTCAT
GACAAGATTGGCTTGGATGCTGGTCAGTCTGAATCTGGAAAAGGACAAACA
GTAGAGTTTGAGATTATCGGCATCTTTTCTGGTAAAAAACAAGAGAAATTC
ACAGGCTTGTCTTCTGACTTCAGTGAAAATCAAGTCTTTACAGACTATGAA
AGTAGCCAAACCCTTTTGGGCAATAGTGAAGCTCAAGTCAGTGCAGCACGC
TTCTATGTAGAAATCCTAAGGAAATGGACGGACTCATGAAGCAGGTAGAA
AACTTGGCCTTGGAAAATCAAGGCTACCAAGTCGAAAAGGAAACAAGGCT
TTTGAACAAATCAAAGACTCAGTTGCAACTTTCCAAACCTTCCTGACCATC
TTCCTTTATGGGATGTTGATAGCAGGAGCTGGAGCCTTAATTCTGGTTTTG
TCTCTCTGGTTGAGAGAACGGGTCTATGAAGTGGGGATTTTACTTGCACTT
GGAAAAGGCAAGAGCTCGATCTTCCTACAATTCTGTTTAGAGGTAGTTTTG
GTATCTCTTGGAGCTTTGCTTCCAGCATTTGTTGCAGGAAACGCAATCACA
ACTTACCTACTCCAAACTCTACTAGCAAGTGGAGATCAGGCAAGCTTACAA
GATACACTAGCCAAAGCAAGCAGTTTATCAACTAGCATCTTATCTTTTGCA
GAATCCTATGTTTTCTAGTTCTGCTTAGTTGCTTATCTGTAGCCCTTTGT
TTCCTATTCTTATTTAGAAAATCACCGAAAGAAATTTTATCATCTATTAGT
TAA 4142.5

(SEQ. ID. NO. 253)
ATGTTACACAACGCATTTGCCTATGTTACAAGGAAGTTTTTCAAATCGATT
GTCATCTTCCTGATTATTCTCCTCATGGCGAGCTTGAGTTTGGTCGGCTTG
TCAATCAAGGGAGCTACTGCCAAGGCTTCTCAGGAGACCTTTAAAAATATC
ACCAATAGCTTCTCCATGCAAATCAATCGTCGCGTCAACCAAGGAACGCCT
CGTGGTGCTGGGAATATCAAGGGTGAAGACATCAAAAAAATCACCGAAAAC
AAGGCCATTGAGTCTTATGTCAAACGTATCAACGCTATCGGAGATTTGACT
GGATATGACCTGATTGAAACGCCAGAAACCAAGAAGAATCTCACTGCTGAT
CGTGCCAAGCGTTTTGGAAGTAGCTTGATGATTACAGGTGTCAATGACTCC
TCTAAAGAAGACAAGTTTGTCTCTGGTTCTTATAAACTAGTCGAAGGAGAG
CACTTAACCAACGACGACAAGGATAAAATCCTCTTGCACAAGGACTTGGCA
GCCAAACACGGCTGGAAAGTAGGGGACAAGGTTAAACTGGACTCTAATATC
TACGATGCAGATAATGAAAAGGAGCCAAGGAAACAGTTGAAGTGACAATC
AAGGGACTCTTTGATGGTCATAATAAGTCAGCAGTAACCTACTCACAAGAA
CTTTACGAAAACACAGCTATTACAGACATTCACACTGCTGCAAAACTTTAT
GGATACACAGAAGACACAGCCATTTATGGGACGCAACCTTCTTTGTAACA
GCAGACAAGAACTTGGATGATGTTATGAAAGAGTTGAATGGCATCAGTGGT
ATCAACTGGAAGAGCTACACACTCGTCAAGAGCTCCTCTAACTACCCAGCT
CTTGAGCAATCTATCTCTGGTATGTACAAGATGGCCAACCTCCTCTTCTGG
GGTAGCTTGAGCTTCTCAGTTCTCCTCCTTGCCCTCTTGCTCAGCCTTTGG
ATCAACGCCCGTCGCAAGGAAGTGGGAATTCTCCTCTCTATCGGCCTCAAG
CAGGCAAGTATCTTGGGTCAATTCATCACCGAATCTATCTTGATTGCTATC
CCTGCTCTAGTTTCTGCTTACTTCCTAGCTAATTACACTGCCCGTGCAATT
GGAAACACTGTCCTTGCCAATGTGACTTCAGGTGTTGCCAAACAGGCTAGT
AAGGCGGCTCAAGCCTCTAACCTTGGTGGTGGTGCAGAAGTAGATGGCTTT
AGCAAGACCTTGTCGAGCCTAGACATTTCCATTCAGACATCAGACTTTATC
ATCATTTTGTCCTTGCCTTGGTTCTAGTGGTTCTCGTTATGGCGCTTGCT
TCAAGCAATCTCCTTAGAAAACAACCAAAAGAGCTCTTGCTGGATGGTGAA
TAA 4144.1

(SEQ. ID. NO. 254)
ATGTCACAGGATAAACAAATGAAAGCTGTTTCTCCCCTTCTGCAGCGAGTT
ATCAATATCTCATCGATTGTCGGTGGGGTTGGGAGTTTGATTTTCTGTATT
TGGGCTTATCAGGCTGGGATTTTACAATCCAAGGAAACCCTCTCTGCCTTT
ATCCAGCAGGCAGGCATCTGGGGTCCACCTCTCTTTATCTTTTTACAGATT
TTACAGACTGTCGTCCCTATCATTCCAGGGGCCTTGACCTCGGTGGCTGGG
GTCTTTATCTACGGGCACATCATCGGGACTATCTACAACTATATCGGCATC
GTGATTGGCTGTGCCATTATCTTTTATCTAGTGCGCCTATACGGAGCTGCC
TTTGTCCAGTCTGTCGTCAGCAAGCGCACCTACGACAAGTACATCGACTGG
CTAGATAAGGGCAATCGTTTTGACCGCTTCTTTATTTTTATGATGATTTGG
CCCATTAGCCCAGCTGACTTTCTCTGTATGCTGGCTGCCCTGACCAAGATG
AGCTTCAAGCGCTACATGACCATCATCATTCTGACCAAACCCTTTACCCTC
GTGGTTTATACCTACGGTCTGACCTATATTATTGACTTTTTCTGGCAAATG
CTTTGA 4144.2

(SEQ. ID. NO. 255)
ATGAGAAATATGTGGGTTGTAATCAAGGAAACCTATCTTCGACATGTCGAG
TCATGGAGTTTCTTCTTTATGGTGATTTCGCCGTTCCTCTTTTTAGGAATC
TCTGTAGGAATTGGGCATCTCCAAGGTTCTTCTATGGCTAAAAATAATAAA
GTGGCAGTAGTGACAACAGTGCCATCTGTAGCAGAAGGACTGAAGAATGTA
AATGGTGTTAACTTCGACTATAAAGACGAAGCAAGTGCCAAAGAAGCAATT
AAAGAAGAAAATTAAAAGGTTATTTGACCATTGATCAAGAAGATAGTGTT
CTAAAGGCAGTTTATCATGGCGAAACATCGCTTGAAAATGGAATTAAATTT
GAGGTTACAGGTACACTCAATGAACTGCAAAATCAGCTTAATCGTTCAACT
GCTTCCTTGTCTCAAGAGCAGGAAAACGCTTAGCGCAGACAATTCAATTC
ACAGAAAAGATTGATGAAGCCAAGGAAAATAAAAAGTTTATTCAAACAATT
GCAGCAGGTGCCTTAGGATTCTTTCTTTATATGATTCTGATTACCTATGCG
GGTGTAACAGCTCAGGAAGTTGCCAGTGAAAAAGGCACCAAAATTATGGAA
GTCGTTTTTTCTAGCATAAGGGCAAGTCACTATTTCTATGCGCGGATGATG
GCTCTGTTTCTAGTGATTTTAACGCATATTGGGATCTATGTTGTAGGTGGT

TABLE 3-continued

CTGGCTGCCGTTTTGCTCTTTAAAGATTTGCCATTCTTGGCTCAGTCTGGT
ATTTTGGATCACTTGGGAGATGCTATCTCACTGAATACCTTGCTCTTTATT
TTGATCAGTCTTTTCATGTACGTAGTCTTGGCAGCCTTCCTAGGATCTATG
GTTTCTCGTCCTGAGGACTCAGGGAAAGCCTTGTCGCCTTTGATGATTTTG
ATTATGGGTGGTTTTTTGGAGTGACAGCTCTAGGTGCAGCTGGTGACAAT
CTCCTCTTGAAGATTGGTTCTTATATTCCCTTTATTTCGACCTTCTTTATG
CCGTTTCGAACGATTAATGACTATGCGGGGGGAGCAGAAGCATGGATTTCA
CTTGCTATTACAGTGATTTTTGCGGTGGTAGCAACAGGATTTATCGGACGC
ATGTATGCTAGTCTCGTTCTTCAAACGGATGATTTAGGGATTTGGAAAACC
TTTAAACGTGCCTTATCTTATAAATAG 4144.3
(SEQ. ID. NO. 256)
ATGACAGAAACCATTAAATTGATGAAGGCTCATACTTCAGTGCGCAGGTTT
AAAGAGCAAGAAATTCCCCAAGTAGACTTAAATGAGATTTTGACAGCAGCC
CAGATGGCATCATCTTGGAAGAATTTCCAATCCTACTCTGTGATTGTGGTA
CGAAGTCAAGAGAAGAAAGATGCCTTGTATGAATTGGTACCTCAAGAAGCC
ATTCGCCAGTCTGCTGTTTTCCTTCTCTTTGTCGGAGATTTGAACCGAGCA
GAAAAGGGAGCCCGACTTCATACCGACACCTTCCAACCCCAAGGTGTGGAA
GGTCTCTTGATTAGTTCGGTCGATGCAGCTCTTGCTGGACAAAACGCCTTG
TTGGCAGCTGAAAGCTTGGGCTATGGTGGTGTGATTATCGGTTTGGTTCGA
TACAAGTCTGAAGAAGTGGCAGAGCTCTTTAACCTACCTGACTACACCTAT
TCTGTCTTTGGGATGGCACTGGGTGTGCCAAATCAACATCATGATATGAAA
CCGAGACTGCCACTAGAGAATGTTGTCTTTGAGGAAGAATACCAAGAACAG
TCAACTGAGGCAATCCAAGCTTATGACCGTGTTCAGGCTGACTATGCTGGG
GCGCGTGCGACCACAAGCTGGAGTCAGCGCCTAGCAGAACAGTTTGGTCAA
GCTGAACCAAGCTCAACTAGAAAAAATCTTGAACAGAAGAAATTATTGTAG 4146.1
(SEQ. ID. NO. 257)
ATGTTAAAACTTATTGCTATTGTTGGAACAAATTCAAAACGTTCTACAAAC
CGTCAATTGCTTCAATACATGCAAAAACACTTTACTGACAAAGCTGAAATT
GAACTTGTTGAAATCAAGGCCATTCCTGTCTTCAACAAACCAGCTGACAAG
CAAGTACCTGCTGAAATATTGGAAATTGCTGCTAAAATCGAAGAGGCAGAT
GGCGTTATTATCGGTACTCCTGAGTATGATCACTCTATTCCAGCTGTTTTG
ATGAGCGCTCTTGCTTGGTTGTCTTATGGTATTTACCCACTTTTGAACAAA
CCAATCATGATTACAGGTGCTTCTTACGGTACGCTTGGTTCATCTCGTGCC
CAATTGCAACTTCGTCAAATCTTGAATGCTCCTGAAATCAAGGCAAATGTT
CTTCCAGATGAATTCTTGCTCTCACACTCTCTTCAAGCATTTAACCCAAGT
GGCGACTTGGTTGACCTTGATGTTATCAAGAAATTGGATGCCATCTTTGAT
GACTTCCGTATCTTTGTAAAAATCACAGAAAAATTACGTAATGCACAAGAA
TTACTTCGCAAAGATGCTGAAGACTTTGACTGGGAAATTTGTAA 4146.2
(SEQ. ID. NO. 258)
ATGAATACCTATCAATTAAATAATGGAGTAGAAATTCCAGTATTGGGATTT
GGAACTTTTAAGGCTAAGGATGGAGAAGAAGCCTATCGTGCAGTGTTAGAA
GCCTTGAAGGCTGGTTATCGTCATATTGATACGGCGGCGATTTATCAGAAT
GAAGAAAGTGTTGGTCAAGCAATCAAAGATAGCGGAGTTCCACGTGAAGAA
ATGTTCGTAACTACCAAGCTTTGGAATAGTCAGCAAACCTATGAGCAAACT
CGTCAAGCTTTGGAAAAATCTATAGAAAAACTGGGCTTGGATTATTTGGAT
TTGTATTTGATTCATTGGCCGAACCCAAAACCGCTCAGAGAAAATGACGCA
TGGAAAACTCGCAATGCGGAAGTTTGGAGAGCGATGGAAGACCTCTATCAA
GAAGGGAAATCCGTGCTATCGGCGTTAGCAATTTTCTTCCCCATCATTTG
GATGCCTTGCTTGAAACTGCAACTATCGTTCCTGCGGTCAATCAAGTTCGC
TTGGCGCCAGGTGTGTATCAAGATCAAGTCGTAGCTTACTGTCGTGAAAAG
GGAATTTTATTGGAAGCTTGGGGGCCTTTTGGACAAGGAGAACTGTTTGAT
AGCAAGCAAGTCCAAGAAATAGCAGCAAATCACGGAAAATCGGTTGCTCAG
ATAGCCTTGGCCTGGAGCTTGGCAGAAGGATTTTTACCACTTCCAAAATCT
GTCACAACCTCTCGTATTCAAGCTAATCTTGATTGCTTTGGAATTGAACTG
AGTCATGAGGAGAGAGAAACCTTAAAAACGATTGCTGTTCAATCGGGTGCT
CCACGAGTTGATGATGTGGATTTCTAG 4147.1
(SEQ. ID. NO. 259)
ATGAGGTGCAAAATGCTTGATCCAATTGCTATTCAACTAGGACCCCTAGCC
ATTCGTTGGTATGCCTTATGTATTGTGACAGGCTTGATTCTTGCGGTTTAT
TTGACCATGAAAGAAGCACCTAGAAAGAAGATCATACCAGACGATATTTTA
GATTTTATCTTAGTAGCCTTTCCCTTGGCTATTTTAGGAGCTCGTCTCTAC
TATGTTATTTTCCGATTTGATTACTATAGTCAGAATTTAGGAGAGATTTTT
GCCATTTGGAATGGTGGTTTGGCCATTTACGGTGGTTTGATAACTGGGGCT
CTTGTGCTCTATATCTTTGCTGACCGTAAACTCATCAATACTTGGGATTTT
CTAGATATTGCGGCGCCTAGCGTTATGATTGCTCAAAGTTTGGGGCGTTGG
GGTAATTTCTTTAACCAAGAAGCTTATGGTGCAACAGTGGATAATCTGGAT
TATCTACCTGGCTTTATCCGTGACCAGATGTATATTGAGGGGAGCTACCGT
CAACCGACTTTCCTTTATGAGTCTCTATGGAATCTGCTTGGCTTTGCCTTG
ATTCTGATTTTAGACGGAAATGGAAGAGTCTCAGACGAGGTCATATCACG
GCCTTTTACTTGATTTGCTATGGTTTCGGTCGTATGGTTATCGAAGGTATG
CGAACAGATAGTCTCATGTTCTTCGGCTTTCGAGTGTCCCAATGGCTGTCA
GTTGTCCTTATCGGTCTCGGTATAATGATCGTTATTTATCAAAATCGAAAG
AAGGCCCCTTACTATATTACAGAGGAGGAAAACTAA 4147.2
(SEQ. ID. NO. 260)
ATGGGTAAATTATCCTCAATCCTTTTAGGAACCGTTTCAGGTGCAGCTCTT
GCCTTGTTTTTAACAAGTGATAAGGGCAAACAAGTTTGCAGTCAGGCTCAA

TABLE 3-continued

GATTTTCTAGATGATTTGAGAGAAGATCCGGAGTATGCCAAGGAGCAAGTC

TGTGAAAAACTGACAGAAGTTAAGGAGCAGGCTACAGATTTTGTTCTGAAA

ACAAAAGAACAGGTTGAGTCAGGTGAAATCACTGTGGACAGTATACTTGCT

CAAACTAAATCCTATGCTTTTCAAGCGACAGAAGCATCAAAAAATCAATTA

AATAATCTCAAGGAGCAATGGCAAGAAAAAGCCGAAGCTCTTGATGACTCA

GAAGAGATTGTGATTGATATAACAGAAGAATAA 4147.3
(SEQ. ID. NO. 261)
ATGAAAACTAAATTGATCTTTTGGGGCTCTATGCTCTTTCTCCTCTCCCTC

TCCATCCTTCTGACCATTTATCTGGCTTGATTTTCTATCCTATGGAGATTC

AGTGGCTAAACTTAACGAATCGAGTCTATCTAAAACCAGAAACCATTCAAT

ACAATTTTCATATCTTGATGAATTATCTGACCAATCCTTTTAGTCAGGTCT

TACAGATGCCTGATTTTCGTTCGTCAGCAGCTGGTCTGCACCATTTCGCAG

TGGTCAAGAATCTCTTTCATTTGGTTCAGCTAGTAGCTCTAGTGACACTGC

CAAGTTTCTATGTCTTTGTCAATAGGATTGTGAAAAAGGACTTTTTGTCTC

TTTATCGAAAAGTCTCCTGGCTCTAGTAGTCTTACCTGTGATGATTGGAC

TTGGGGGAGTTTTCATTGGTTTTGACCAATTCTTTACTCTTTTCCATCAAA

TTCTCTTTGTGGGAGATGATACCTGGCTTTTTGATCCAGCCAAGGATCCTG

TTATTATGATTTTGCCAGAGACCTTCTTTCTTCATGCCTTCCTCCTCTTTT

TTGCCCTCTATGAAAACTTCTTTGGCTATCTGTATCTGAAAAGTCGTAGGA

AGTGA 4149.1
(SEQ. ID. NO. 262)
ATGACTTATCATTTTACTGAAGAATACGATATTATTGTAATTGGTGCGGGA

CACGCTGGGGTTGAGGCTTCCTTGGCCGCTAGCCGTATGGGCTGTAAGGTC

CTGCTTGCGACCATCAATATTGAAATGCTGGCTTTCATGCCTTGTAATCCC

TCTATCGGTGGTTCTGCCAAGGGGATTGTCGTGCGTGAAGTCGATGCCCTC

GGTGGCGAGATGGCCAAAACCATTGACAAGACTTACATCCAGATGAAGATG

CTAAACACAGGGAAGGGGCCAGCTGTCCGTGCCCTTCGTGCGCAGGCTGAC

AAGGAACTTTACTCTAAGGAGATGCGCAAGACGGTTGAAAACCAAGAAAAT

CTGACCCTTCGTCAAACCATGATTGATGAGATTTTGGTGGAAGATGGCAAG

GTTGTCGGTGTGCGCTACAGCCACCCATCAAGAATATGCTGCTAAGGCTGTT

ATTGTGACGACAGGGACTGCTCTCCGTGGGGAAATTATCATCGGAGACCTC

AAGTACTCATCAGGTCCTAACCACAGCTTGGCTTCTATTAACCTAGCTGAC

AATCTCAAGGAACTGGGTCTCGAAATCGGTCGTTTCAAGACAGGACCCCTC

CACGTGTCAAGGCTTCTTCTATCAATTACGATGTGACAGAAATTCAGCCAG

GAGACGAAGTGCCTAATCATTTCTCATACACTTCACGTGATGAGGATTATG

TCAAGGACCAAGTACCATGCTGGTTGACCTATACCAATGGTACCAGTCATG

AGATTATCCAAAACAACCTCCACCGTGCGCCTATGTTTACAGGTGTGGTCA

AGGGAGTGGGGCCTCGTTACTGTCCGTCGATTGAAGACAAGATTGTGCGCT

TGCGGACAAGGAACGTCACCAACTCTTCCTTGAGCCAGAAGGGCGCATTA

CTGAGGAAGTCTATGTGCAAGGACTTTCAACCAGTCTGCCTGAGGATGTCC

AGCGTGACTTGGTGCATTCCATCAAAGGTTTGGAAAATGCAGAGATGATGC

GGACAGGTTATGCTATTGAGTATGATATGGTCTTGCCTCATCAGTTGCGTG

CGACTTTGGAAACCAAGAAAATCTCAGGTCTCTTCACTGCTGGTCAGACAA

ATGGAACATCAGGTTACGAAGAGGCAGCAGGCCAAGGGATTATCGCGGGTA

TCAATGCGGCTCTGAAAATCCAAGGCAAGCCTGAATTGATTTTGAAGCGCA

GTGATGGTTATATCGGGGTGATGATCGACGACTTGGTGACCAAGGGAACCA

TTGAACCCTACCGTCTCTTGACCAGTCGTGCTGAATACCGTCTCATTCTTC

GTCATGACAATGCTGATATGCGCTTGACTGAGATGGGACGCGAGATTGGCC

TTGTGGACGATGAACGCTGGGCTCGTTTTGAAATCAAGAAAAATCAATTTG

ATAATGAGATGAAGCGCCTAGACAGTATCAAACTCAAGCCAGTCAAGGAAA

CCAATGCCAAGGTTGAGGAGATGGGCTTCAAACCCTTGACCGATGCAGTGA

CAGCCAAGGAATTCCTTCGCCGTCCAGAAGTTTCTTACCAAGATGTGGTGG

CCTTCATCGGACCAGCTGCAGAAGACTTGGATGACAAGATTATCGAATTGA

TTGAAACAGAAATCAAGTATGAAGGCTATATTTCCAAAGCCATGGACCAGG

TTGCCAAGATGAAACGCATGGAAGAAAAACGCATTCCGGCCAATATCGACT

GGGATGACATTGATTCTATCGCAACCGAAGCCCGTCAGAAGTTCAAACTCA

TCAATCCAGAAACCATCGGCCAAGCCAGCCGTATTTCGGGAGTAAACCCAG

CAGATATTTCTATTTTGATGGTGTATCTGGAAGGTAAAAATCGTAGTATTT

CTAAAACTCTTCAAAAATCAAATGA 4149.2
(SEQ. ID. NO. 263)
ATGAAAGTATTAGCTTTTGATACGTCCAGCAAGGCTCTTTCTCTGGCTATT

TTAGAGGATAAGCAGGTTCTTGCCGAGACGACGATTAATATTAAGAAAAAT

CACAGTATTACTCTTATGCCTGCCATCGATTTTTTGATGGCAAGTTTGGAT

TGGACACCCAAGGATTTGGACCGAATCGTGGTAGCTGAAGGGCCGGGTAGC

TATACAGGCTTGCGAATTGCGGTAGCAACTGCTAAGACCTTAGCTCACACC

CTGAACATCGAGTTGGTTGGTATGTCGAGTCTCTTGGCTCTGGTGCCCCAT

CAACAAGAAGGTTTGTTTGTCCCCTTGATGGATGCGCGTCGCAATAATGTT

CTATGCAGGATTTTATGAAAATGCCAAACCTGTCATGGCAGAAGGCACCTA

TCTTTTGAAGAGGTGCTAGAAAAAGTCAAGGGTACTAGTCAGGTAACCTTT

GTCGGAGAAGTTGGCCCCTTTGTTGAGCAGATTCAAAAACACTTGCCAAGG

ACTGATTACAAAGAAACATTGCCCAATGCAGCTAATCTAGCTCTTTTGGCC

TGGGACAAGGAAGCAGACTCCTTGCATGATTTTGTGCCGAATTACCTCAAA

CGAGTCGAGGCTGAGGAAAACTGGCTCAAGAACCATACCGAGTCTGGCGAG

TCTTACATTAAACGCCTATGA 4149.3
(SEQ. ID. NO. 264)
ATGATAGAAATCAAGCGAATTCAACAACAGCCTGACCTAGCTCAAGCCATC

TACGCTGTTATGGCAGCTGTTTACCTAGTCAGTCCTTGGACTCTGGAGCAA

ATCCAAGCAGATCTGTCCCAAGACCAGACTTGGTATGCATTGGCTTATGAT

GGGGCAGAAGTGATTGATTTCTAGCTGTGCAGGAGAATCTTTTTGAAGCA

GAAGTCCTGCAAATCGCTGTCAAAGGAGCTTATCAGGGTCAGGGGATTGCG

TCagCCTTGTTTGCTCAATTGCCGACAGACAAGGAAATTTTCCTCGAAGTC
AGACAGTCAAATCAACGAGCGCAAGCATTTTACAAGAAAGAAAGATGACA
GTTATCGCTGAGCGAAAGGCCTACTACCATGACCCAGTCGAGGACGCCATT
ATCATGAAGAGAGAAATAGATGAAGGATAG 4152.2
(SEQ. ID. NO. 265)
ATGACAAAACAAGTCTTATTAGTGGATGATGAAGAACACATTCTGAAATTG
CTTGACTACCATTTAAGTAAGGAAGGCTTTTCTACTCAATTGGTGACAAAT
GGACGGAAGGCCTTAGCTTTGGCAGAAACAGAACCCTTTGATTTTATCTTG
CTTGATATCATGTTACCACAATTAGATGGCATGGAAGTTTGTAAGCGGCTG
AGAGCCAAAGGCGTCAAAACTCCAATTATGATGGTTTCTGCGAAAAGTGAT
GAATTTGATAAGGTTTTGGCCTTGGAATTAGGGGCTGATGACTACCTGACC
AAGCCTTTTAGCCCTAGAGAATTGCTGGCGGCGTGCAAGGCTGTCCTCAGG
CGAACTAAAGGAGAACAAGAAGGAGATGATTCAGATAATATCGCTGACGAT
TCTTGGCTATTTGGGACCTTGAAAGTATACCCTGAGCGTCATGAAGTCTAC
AAGGCGAATAAGTTACTGAGTTTGACCCCAAAAGAATTTGAAAGCGATAAA
AATCCGTTTTTTGAAGTTTTCAAAGTTTCGAAAGTAACCGCCCAATAA 4154.1
(SEQ. ID. NO. 266)
ATGACTACTTTTAAAGATGGATTTTTATGGGGTGGTGCTGTTGCTGCTCAT
CAACTTGAAGGTGGATGGCAAGAAGGTGGCAAGGGAATTAGTGTTGCTGAT
GTTATGACTGCTGGTCGTCATGGAGTAGCTCGTGAAATACTTTGGGAGTTT
TAGAGGGTAAATATTATCCAAATCATGAGGCGATAGATTTTTATCACCGTT
ATAAAGAAGATATAGCACTTTTTGCTGAAATGGGATTCAAGTGCTTCCGTA
CCTCTATTGCATGGACACGTATCTTTCCAAAAGGTGATGAGTTAGAGCCGA
ATGAAGAAGGATTACAGTTTTATGATAATCTTTTTGATGAATGCTTAAAGA
CATGGTATTGAACCTGTCATCACTCTATCTCATTTTGAAATGCTTATCACT
TAGTGACCGAATATGGTGGTTGGAAAAATAGGAAATTGATTGATTTCTTTG
CTCGTTTTGCAGAAGTCGTATTTAAACGTTACAAAGATAAGGTTAAATATT
GGATGACTTTCAATGAAATCAATAATCAAGCGAATTATCAGGAAGATTTTG
CACCATTTACTAACTCAGGTATTGTATATGAGGAAGGTGATAATAGAGAAG
CAATTATGTATCAAGCAGCACATTACGAATTAGTTGCTTCTGCACGAGCTG
TAAAAATTGGTCATGAGATTAATCCAGATTTTCAAATAGGTTGTATGATTG
CGATGTGTCCAATTTATCCAGTTACTTGCAATCCTAAGGATATCTTAATGG
CAATGAAAGCTATGCAGAAGCGTTATTATTTTGCTGATGTGCATGTTTTAG
GTAAATATCCTGAGCATATTTTCAAGTATTGGGAACGAAAAGGTATTTCAG
TTGATTTTACTGCCCAGGATAAAGAAGATTTACTTGGTGGGACTGTAGATT
ACATTGGTTTCAGTTACTATATGTCCTTTGCTATCGACTCTCATCGTGAAA
ATAATCCTTATTTTGATTATCTTGAAACAGAAGATTTAGTGAAAATAATT
ATGTTAAGGCTTCTGAATGGGAGTGGCAAATTGATCCAGAAGGTTTGCGTT
ATGCGTTAAATTGGTTTACAGACCACTATCACTTACCACTCTTTATTGTTG
AAATGGTTTTGGAGCTATAGATCAAGTTGCAGCAGATGGTATGGTACATG

ATGATTATAGAATTGAATATCTAGGTGCCCATATTCGTGAAATGAAAAAGG
CTGTAGTTGAAGATGGTGTTGATTTAATGGGTTATACTCCATGGGGATGTA
TTGATTTGGTTTCAGCTGGTACCGGTGAAATGCGGAAACGTTATGGCTTTA
TTTATGTAGATAAAGATGATAATGGGAAGGGAAGTTATAATCGTTCCCCGA
AAAAATCTTTTGGCTGGTATAAGGAAGTTATTTCATCTAACGGTGAATCAG
TAGAATAG 4154.2
(SEQ. ID. NO. 267)
ATGGATCAACAAAACGGGTTGTTTGGTTTTCTTGAAAACCATGTTATGGGA
CCAATGGGCAAACTTGCTCAGTTTAAAGTAGTACGTGCTATCACGGCTGCA
GGTATGGCTGCTGTACCATTTACTATTGTAGGATCAATGTTTTTGGTATTC
AGTATTTTGCCACAAGCTTTCTCATTTTGGCCAATTGTGGCAGATATTTTC
TCTGCTTCATTTGATAAATTCACATCACTTTACATGGTTGCAAACTATGCG
ACTATGGGTTCTCTATCTCTTTATTTCGTTCTATCACTTGCATATGAATTG
ACAAAAATTTATGCAGAGGAAGAAGAACTCAATATGAATCCTCTTAATGGT
GCCTTGCTTGCCTTGATGGCTTTTGTCATGACAGTACCGCAAATCATTTTT
GATGGTGGAATGATGAAGACTGTGACAAGTCTAAAAGAAGGTGCAGTAATT
GCAGATGGATGGGCAATGGGAAATGTCGTCGCACGTTTTGGGACAACAGGG
ATTTTTACCGCAATCATTATGGCAATTGTGACTGTTCTTATTTATCGTATG
TGTGTTAAACATAATTGGGTTATTAAAATGCCTGAAGCTGTTCCAGAAGGA
GTTTCTCGTGGATTTACCGCTTTGGTTCCGGGATTTGTTGTTGCATTTGTT
GTTATCTTTATCAACGGTCTTCTTGTAGCAATGGGAACAGATATTTTTAAA
GTCATTGCAATTCCATTTGGTTTTGTATCCAATCTGACTAATTCGTGGATT
GGTTTAATGATTATTTATCTATTGACTCAACTACTTTGGATTGTAGGTATC
CACGGTGCGAACATTGTTTTTGCATTTGTTAGTCCAATTGCTCTTGCTAAC
ATGGCTGAAAATGCTGCTGGCGGGCACTTCGCTGTTGCAGGTGAATTTTCT
AATATGTTTGTAATTGCAGGTGGTTCTGGTCAACTTTAGGACTATGTTTA
TATATTGCTTTTGCCTCTAAATCTGAACAGCTTAAAGCAATAGGACGAGCA
TCTGTAGTTCCAGCCTTATTTAATATTAATGAACCATTAATTTTTGGATTA
CCTATTATCTATAATCCAGCCTTGGCTATACCATTTATTTTAGCACCAATG
GTTACTGCTACTATTTATTACGTAGCGAATTCTCTAAACTTTATTAAGCCA
ATTATCGCACAGGTTCCATGGCCAACTCCAGTAGGGATTGGAGCTTTCTTA
GGGACAGCAGATCTTCGAGCTGTATTAGTTGCTCTAGTATGTGCATTTGCA
GCATTCCTAGTCTATCTTCCATTCATCCGTGTATATGATCAAAAATTGGTG
AAAGAAGAGCAAGGTATCTAA 4155.1
(SEQ. ID. NO. 268)
ATGAAAAAATTTTATGTAAGTCCAATTTTTCCTATTCTAGTAGGATTGATT
GCGTTTGGAGTCTTATCCACTTTCATTATTTTTGTTAATAATAATCTGTTG
ACGGTTTTAATTTTGTTTCTTTTTGTAGGAGGCTATGTTTTTTTATTTAAG
AAACTGAGAGTGCATTATACAAGGAGTGATGTAGAACAGATACAGTATGTA
AACCACCAAGCGGAAGAAAGTTTGACAGCTCTATTGGAACAGATGCCTGTA

GGTGTTATGAAATTGAATTTATCTTCTGGAGAGGTTGAGTGGTTTAATCCC
TATGCTGAATTGATTTTGACCAAGGAAGATGGTGATTTTGATTTAGAAGCT
GTTCAAACGATTATCAAGGCTTCAGTAGGAAATCCGTCTACTTATGCCAAG
CTTGGTGAGAAGCGTTATGCTGTTCATATGGATGCTTCTTCCGGTGTTTTG
TATTTTGTAGATGTATCCAGGGAACAAGCCATAACAGATGAATTGGTAACA
AGTAGACCAGTGATTGGGATTGTCTCTGTGGATAATTATGATGATTTGGAG
GATGAAACTTCTGAGTCAGATATTAGTCAAATCAATAGTTTTGTAGCTAAT
TTTATATCAGAGTTTTCAGAAAAACACATGATGTTTTCTCGTCGGGTAAGT
ATGGATCGATTTTATCTATTTACTGACTACACGGTGCTTGAGGGCTTGATG
AATGATAAATTTTCTGTTATTGATGCTTTCAGAGAAGAGTCGAAACAGAGA
CAGTTGCCCTTGACCTAAGTATGGGATTTTCTTATGGCGATGGAAATCAT
GATGAGATAGGGAAAGTTGCTTTGCTCAATTTGAACTTGGCTGAAGTACGT
GGTGGCGACCAGGTGGTTGTTAAGGAAAACGACGAAACGAAAAATCCAGTT
TATTTTGGTGGTGGGTCTGCTGCTTCAATCAAGCGTACACGGACTCGTACG
CGCGCTATGATGACAGCTATTTCAGATAAGATTCGGAGTGTAGATCAGGTT
TTTGTAGTCGGTCACAAAAATTTAGACATGGATGCTTTGGGCTCTGCTGTA
GGTATGCAGTTGTTCGCCAGCAATGTGATTGAAAATAGCTATGCTCTTTAT
GATGAAGAACAAATGTCTCCAGATATTGAACGAGCTGTTTCATTCATAGAA
AAAGAAGGAGTTACGAAGTTGTTGTCTGTTAAGGATGCAATGGGGATGGTG
ACCAATCGTTCTTTGTTGATTCTTGTAGACCATTCAAAGACAGCCTTAACA
TTATCAAAAGAATTTTATGATTTATTTACCCAAACCATTGTTATTGACCAC
CATAGAAGGGATCAGGATTTTCCAGATAATGCGGTTATTACTTATATCGAA
AGTGGTGCAAGTAGTGCCAGTGAGTTGGTAACGGAATTGATTCAGTTCCAG
AATTCTAAGAAAAATCGTTTGAGTCGTATGCAAGCAAGTGTCTTGATGGCT
GGTATGATGTTGGATACTAAAAATTTCACCTCGCGAGTAACTAGTCGGACA
TTTGATGTTGCTAGCTATCTCAGAACGCGCGAAGTGATAGTATTGCTATC
CAGGAAATCGCTGCGACAGATTTTGAAGAATATCGTGAGGTCAATGAACTT
ATTTTCAGGGGCGTAAATTAGGTTCAGATGTACTAATAGCAGAGGCTAAG
GACATGAAATGCTATGATACAGTTGTTATTAGTAAGGCAGCAGATGCCATG
TTAGCCATGTCAGGTATTGAAGCGAGTTTTGTTCTTGCGAAGAATACACAA
GGATTTATCTCTATCTCAGCTCGAAGTCGTAGTAAACTGAATGTACAACGG
ATTATGGAAGAGTTAGGCGGTGGAGGCCACTTTAATTTGGCAGCAGCTCAA
ATTAAAGATGTAACCTTGTCAGAAGCAGGTGAAAAACTGACAGAAATTGTA
TTAAATGAAATGAAGGAAAAGGAGAAAGAAGAATGA 4156.1

(SEQ. ID. NO. 269)
ATGAAAGAGAAAAATATGTGGAAAGAATTGTTGAATCGTGCAGGCTGGATT
TTGGTCTTTTTACTTGCCGTCCTTTTATATCAGGTTCCCCTAGTGGTTACC
TTCTATTTTGACTTAAAAGAAGTAGCCCTGCTACAGTCAGGGCTGATAGTT
GCTGGCCTTTCAATTGTGGTTCTGGCTCTATTTATTATGGGAGCTCGTAAA
ACCAAGTTAGCTAGTTTTAATTTTTCTTTTTTTAGAGCTAAAGATTTGGCA

CGTTTGGGCTTGAGTTATCTAGTTATTGTCGGGTCAAATATACTTGGTTCC
ATTTTATTGCAACTGTCAAATGAGACGACAACAGCTAACCAGTCTCAGATT
AATGATATGGTTCAAAATAGTTCGTTGATTTCCAGTTTCTTCTTGCTAGCC
TTGCTTGCTCCGATTTGTGAGGAAATCTTGTGTCGTGGGATTGTTCCTAAA
AAGATTTTCCGAGGCAAGGAGAACTTGGGATTTGTAGTCGGTACGATTGTG
TTTGCTTTATTGCATCAACCAAGTAATTTACCTTCTTTATTGATTTATGGA
GGTATGTCGACAGTTCTATCTTGGACAGCCTACAAGACCCAACGTTTGGAA
ATGTCGATCTTGCTTCACATGATTGTTAATGGGATTGCTTTCTGTTTGTTG
GCTCTTGTGGTGATTATGAGTCGGACATTAGGAATTTCTGTTTAAATGAAA
GAGAAAATATGTGGAAAGAATTGTTGAATCGTGCAGGCTGGATTTTGGTC
TTTTTACTTGCCGTCCTTTTATATCAGGTTCCCCTAGTGGTTACCTCTATT
TTGACTTTAAAAGAAGTAGCCCTGCTACAGTCAGGGCTGATAGTTGCTGGC
CTTTCAATTGTGGTTCTGGCTCTATTTATTATGGGAGCTCGTAAAACCAAG
TTAGCTAGTTTTAATTTTTCTTTTTTTAGAGCTAAAGATTTGGCACGTTTG
GGCTTGAGTTATCTAGTTATTGTCGGGTCAAATATACTTGGTTCCATTTTA
TTGCAACTGTCAAATGAGACGACAACAGCTAACCAGTCTCAGATTAATGAT
ATGGTTCAAAATAGTTCGTTGATTTCCAGTTTCTTCTTGCTAGCCTTGCTT
GCTCCGATTTGTGAGGAAATCTTGTGTCGTGGGATTGTTCCTAAAAAGATT
TTCCGAGGCAAGGAGAACTTGGGATTTGTAGTCGGTACGATTGTGTTTGCT
TTATTGCATCAACCAAGTAATTTACCTTCTTTATTGATTTATGGAGGTATG
TCGACAGTTCTATCTTGGACAGCCTACAAGACCCAACGTTTGGAAATGTCG
ATCTTGCTTCACATGATTGTTAATGGGATTGCTTTCTGTTTGTTGGCTCTT
GTGGTGATTATGAGTCGGACATTAGGAATTTCTGTTTAA 4156.4

(SEQ. ID. NO. 270)
ATGGATACACAAAAGATTGAAGCGGCTGTAAAAATGATTATCGAGGCTGTA
GGAGAGGACGCTAATCGCGAGGGCTTGCAGGAAACACCTGCTCGTGTAGCC
CGTATGTATCAAGAGATTTTTTCAGGTCTTGGTCAAACAGCAGAGGAACAT
TTGTCAAAATCCTTTGAAATTATTGACGATAATATGGTGGTAGAAAAGGAT
ATCTTTTTCCATACCATGTGTGAACACCACTTCTTGCCATTTTATGGTAGA
GCGCACATTGCCTACATTCCAGATGGTCGTGTGGCAGGCTTGTCTAAGCTA
GCCCGTACGGTTGAAGTTTATTCGAAAAAACCACAAATTCAAGAACGTTTG
AATATCGAAGTGGCCGATGCCTTGATGGACTATCTAGGTGCTAAAGGAGCC
TTTGTTGTCATTGAGGCGGAACATATGTGTATGAGTATGCGTGGTGTTAGA
AAACCAGGCACTGCAACCTTGACGACAGTAGCTCGTGGTCTATTTGAAACA
GATAAGGATCTCCGTGACCAAGCTTATCGTTTAATGGGGCTATAA 4157.2

(SEQ. ID. NO. 271)
ATGAAAGACTTGTTTTAAAGAGAAAGCAGGCCTTTCGTAAGGAGTGTCTT
GGTTATCTGCGCTATGTGCTCAATGACCACTTTGTCTTGTTCCTGCTTGTC
CTGTTGGGCTTTCTAGCCTACCAGTACAGTCAACTCTTACAACATTTTCCT
GAAAATCATTGGCCTATCCTTTTGTTTGTAGGAATTACGTCTGTTTTACTT

TABLE 3-continued

TTACTTTGGGGAGGAACTGCCACCTATATGGAGGCTCCAGACAAGCTCTTT
CTCTTAGTTGGAGAAGAGGAAATTAAGCTCCATCTCAAGCGTCAAACTGGC
ATTTCCCTAGTCTTTTGGCTCTTTGTACAGACCCTTTTCTTGCTGTTATTT
GCGCCTTTATTTTTAGCAATGGGTTATGGCTTGCCAGTTTTTCTGCTCTAT
GTGCTTTTATTGGGGGTAGGAAAATATTTCCACTTTTGTCAAAAGGCCAGC
AAATTTTTCACTGAAACTGGACTGGACTGGGACTATGTTATTTCTCAAGAA
AGCAAGCGTAAGCAAGTCTTGCTTCGTTTCTTTGCCCTCTTTACGCAGGTC
AAGGGAATTTCAAACAGCGTTAAGCGTCGTGCCTATCTGGACTTTATTTTA
AAGGCTGTTCAGAAGGTGCCTGGGAAGATTTGGCAAAATCTCTATCTGCGT
TCTTATCTGCGAAATGGCGACCTCTTTGCTCTCAGTCTTCGTCTTCTCTTG
CTTTGCCTTGCTGGCGCAGGTTTTTATCGAGCAAGCTTGGATTGCGACAGC
AGTGGTAGTTCTCTTTAACTACCTCTTGCTCTTCCAGTTGCTGGCCCTCTA
TCATGCCTTTGACTACCAGTATTTGACCCAACTCTTTCCGCTGGACAAGGG
GCAAAAGGAAAAAGGCTTACAGGAGGTAGTTCGAGGATTGACCAGTTTTGT
TTTACTTGTGGAATTAGTTGTTGGGTTGATTACCTTCCAAGAAAAACTAGC
CCTTCTAGCCTTACTAGGAGCTGGTTTGGTTTTACTAGTCTTGTATTTGCC
TTATCAGGTAAAACGTCAGATGCAGGACTAA 4258.2

(SEQ. ID. NO. 272)
ATGAGAAAATCAATAGTATTAGCGGCAGATAATGCCTATCTTATTCCTTTA
GAGACGACTATAAAGTCTGTATTGTATCACAATAGAGATGTTGATTTTTAT
ATTCTCAACAGTGATATAGCTCCTGAATGGTTTAAATTATTGGGGAGAAAA
ATGGAAGTTGTGAATTCTACAATTCGCAGTGTACACATTGATAAAGAACTT
TTTGAAAGCTATAAAACAGGACCTCATATAAATTATGCTTCTTACTTTAGA
TTTTTTTGCGACAGAAGTGGTTGAATCTGATAGGGTATTGTATCTGGATTCC
AGATATCATTGTAACTGGGGAACTAGCTACTTTGTTTGAGTAGATCTCAAA
GGATATTCAATTGGTGCTGTTGATGATGTCTATGCCTATGAAGGACGAAAA
TCTGGATTTAATACTGGTATGTTACTAATGGATGTTGCAAAGTGGAAAGAA
CATTCTATTGTCAATAGTTTATTGGAATTAGCGGCCGAGCAGAATCAAGTT
GTTCATCTTGGGGATCAGAGTATTTTAAATATTTATTTTGAGGATAATTGG
CTAGCCTTAGATAAAACATATAATTTATATGGTGGGTATTGATATTTATCAC
CTTGCTCAAGAATGTGAACGTCTAGATGACAATCCACCTACAATTGTTCAC
TATGCTAGTCATGATAAACCTTGGAATACATATAGTATATCTAGACTACGT
GAATTATGGTGGGTTTATAGAGATTTGGATTGGTCAGAGATTGCTTTTCAA
CGTTCCGATTTAAATTATTTTGAAAGAAGCAATCAGTCTAAAAAACAAGTG
ATGCTTGTGACATGGAGTGCAGATATAAAACATTTAGAGTATTTAGTACAA
CGGTTACCTGATTGGCATTTTCATTTGGCTGCACCGTGTGATTGTTCTGAG
GAGCTGACCTCTCTATCACAGTATACGAATGTAACAGTATATCAAAATGTA
TTACATAGTAGAATTGATTGGCTATTGGACGATTCTATAGTTTATTTAGAT
ATTAATACAGGTGGAGAGGTTTTTAATGTAGTTACAAGGGCACAAGAAAGT
GGCAAGAAAATCTTCGCTTTTGATATCACACGTAAAAGTATGGATGATGGA

CTCTATGACGGTATTTTTTCTGTGGAGAGACCAGATGATTTAGTGGATAGA
ATGAAGAATATAGAGATAGAGTAA 4158.2

(SEQ. ID. NO. 273)
ATGACTAAGATTTATTCGTCAATAGCAGTAAAAAAAGGACTATTTACCTCA
TTTCTACTGTTTATCTATGTATTGGGAAGTCGTATTATTCTCCCTTTTGTT
GACCTAAATACTAAAGATTTTTTAGGAGGTTCAACAGCCTATCTAGCCTTC
TCAGCCGCCCTAACAGGTGGGAATCTAAGAAGTTTATCAATTTTTTCTGTT
GGATTATCCCCTTGGATGTCCGCCATGATTTTATGGCAGATGTTTTCTTTT
TCTAAACGGTTGGGTTTAACATCTACGTCTATAGAAATACAAGATCGCCGT
AAAATGTACCTGACCTTGCTAATTGCTGTGATTCAATCCTTGGCAGTTAGC
TTGAGACTGCCAGTACAATCCTCCTATTCTGCAATATTGGTTGTTCTAATG
AATACAATATTGCTGATAGCAGGAACATTTTTTCTTGTTTGGTTGTCAGAT
TTAAATGCGAGTATGGGGATTGGAGGTTCTATTGTAATCCTCCTATCCAGT
ATGGTTTTAAATATTCCTCAGGATGTTTTGGAAACATTTCAGACAGTACAC
ATTCCAACAGGGATTATTGTGTTACTTGCTTTATTAACCCTTGTCTTTTCT
TATTTACTTGCCCTTATGTATCGAGCTCGCTATTTGGTTCCTGTTAATAAA
ATTGGCTTACACAATCGATTTAAACGCTATTCTTATCTCGAAATCATGTTG
AATCCTGCAGGTGGGATGCCTTATATGTATGTGATGAGTTTTCTTAGTGTA
CCAGCTTATTTGTTCATCTTGTTGGGATTTATTTTCCCTAATCATTCAGGG
TTAGCGGCTTTATCAAAGGAATTTATGGTTGGAAAGCCTTTGTGGGTCTAT
GTTTATATTTCGGTCTTATTTTTATTTAGTATCATTTTTGCTTTTGTTACG
ATGAATGGAGAAGAGATTGCAGACCGTATGAAAAAATCTGGAGAATACATT
TATGGTATTTATCCAGGTGCGGATACTAGTCGATTTATTAATCGATTGGTC
CTTCGTTTCTCAGTCATAGGTGGTCTCTTTAATGTGATTATGGCAGGTGGT
CCCATGCTTTTTGTTTTGTTTGATGAAAAGTTATTACGATTGGCAATGATT
CCAGGCTTATTTATGATGTTCGGGGCATGATTTTTACGATTAGAGACGAG
GTCAAGGCTTTAAGGCTAAATGAGACCTATAGACCTTTGATTTAG 4158.3

(SEQ. ID. NO. 274)
ATGTCCTCTCTTTCGGATCAAGAATTAGTAGCTAAAACAGTAGAGTTTCGT
CAGCGTCTTTCCGAGGGAGAAAGTCTAGACGATATTTTGGTTGAAGCTTTT
GCTGTGGTGCGTGAAGCAGATAAGCGGATTTTAGGGATGTTTCCTTATGAT
GTTCAAGTCATGGGAGCTATTGTCATGCACTATGGAAATGTTGCTGAGATG
AATACGGGGAAGGTAAGACCTTGACAGCTACCATGCCTGTCTATTTGAAC
GCTTTTTCAGGAGAAGGAGTGATGGTTGTGACTCCTAATGAGTATTTATCA
AAGCGTGATGCCGAGGAAATGGGTCAAGTTTATCGTTTTCTAGGATTGACC
ATTGGTGTACCATTTACGGAAGATCCAAAGAAGGAGATGAAAGCTGAAGAA
AAGAAGCTTATCTATGCTTCGGATATCATCTACACAACCAATAGTAATTTA
GGTTTTGATTATCTAAATGATAACCTAGCCTCGAATGAAGAGGTAAGTTT
TTACGACCGTTTAACTATGTGATTATTGATGAAATTGATGATATCTTGCTT
GATAGTGCACAAACTCCTCTGATTATTGCGGGTTCTCCTCGTGTTCAGTCT

TABLE 3-continued

AATTACTATGCGATCATTGATACACTTGTAACAACCTTGGTCGAAGGAGAG
GATTATATCTTTAAAGAGGAGAAAGAGGAGGTTTGGCTCACTACTAAGGGG
GCCAAGTCTGCTGAGAATTTCCTAGGGATTGATAATTTATACAAGGAAGAG
CATGCGTCTTTTGCTCGTCATTTGGTTTATGCGATTCGAGCTCATAAGCTC
TTTACTAAAGATAAGGACTATATCATTCGTGGAAATGAGATGGTACTGGTT
AGATAAGGGAACAGGGCGTCTAATGGAAATGACTAAACTTCAAGGGGTCTC
CATCAGGCTATTGAAGCCAAGGAACATGTCAAATTATCTCCTGAGACGCGG
GCTATGGCCTCGATCACCTATCAGAGTCTTTTTAAGATGTTTAATAAGATA
TCTGGTATGACAGGGACAGGTAAGGTCGCGGAAAAAGAGTTTATTGAAACT
TACAATATGTCTGTAGTACGCATTCCAACCAATCGTCCGAGACAACGGATT
GACTATCCAGATAATCTATATATCACTTTACCTGAAAAAGTGTATGCATCC
TTGGAGTACATCAAGCAATACCATGCTAAGGGAAATCCTTTACTCGTTTTT
GTAGGCTCAGTTGAAATGTCTCAACTCTATTCGTCTCTCTTGTTTCGTGAA
GGGATTGCCCATAATGTCCTAAATGCTAATAATGCGGCGCGTGAGGCTCAG
ATTATCTCCGAGTCAGGTCAGATGGGGCTGTGACAGTGGCTACCTCTATG
GCAGGACGTGGTACGGATATCAAGCTTGGTAAAGGAGTCGCAGAGCTTGGG
GGCTTGATTGTTATTGGGACTGAGCGGATGGAAAGTCAGCGGATCGACCTA
CAAATTCGTGGCCGTTCTGGTCGTCAGGGAGATCCTGGTATGAGTAAATTT
TTTGTATCCTTAGAGGATGATGTTATCAAGAAATTTGGTCCATCTTGGGTG
CATAAAAAGTACAAAGACTATCAGGTTCAAGATATGACTCAACCGGAAGTA
TTGAAAGGTCGTAAATACCGGAAACTAGTCGAAAAGGCTCAGCATGCCAGT
GATAGTGCTGGACGTTCAGCACGTCGTCAGACTCTGGAGTATGCTGAAAGT
ATGAATATACAACGGGATATAGTCTATAAAGAGAGAAATCGTCTAATAGAT
GGTTCTCGTGACTTAGAGGATGTTGTTGTGGATATCATTGAGAGATATACA
GAAGAGGTAGCGGCTGATCACTATGCTAGTCGTGAATTATTGTTTCACTTT
ATTGTGACCAATATTAGTTTTCATGTTAAAGAGGTTCCAGATTATATAGAT
GTAACTGACAAAACTGCAGTTCGTAGCTTTATGAAGCAGGTGATTGATAAA
GAACTTTCTGAAAAGAAAGAATTACGTTAATCAACATGACTTATATGAACA
GTTTTTACGACTTTCACTGCTTAAAGCCATTGATGACAACTGGGTAGAGCA
GGTAGACTATCTACAACAGCTATCCATGGCTATCGGTGGTCAATCTGCTAG
TCAGAAAAATCCAATCGTAGAGTACTATCAAGAAGCCTACGCGGGCTTTGA
AGCTATGAAAGAACAGATTCATGCGGATATGGTGCGTAATCTCCTGATGGG
GCTGGTTGAGGTCACTCCAAAAGGTGAAATCGTGACTCATTTTCCATAA 4158.4
(SEQ. ID. NO. 275)
ATGATAGGGACTTTCGCCGCTGCTCTTGTAGCTGTACTAGCAAATTTCATC
GTCCCTATTGAAATTACCCCAAATAGTGCCAATACTGAAATTGCACCACCA
GATGGGATTGGGCAGGTTCTCAGCAACCTCTTGCTCAAACTGGTTGACAAC
CCAGTCAACGCCCTGCTTACTGCTAACTATATTAGAATCTTATCTTGGGCA
GTCATTTTTGGAATCGCTATGAGAGAAGCCAGTAAAAATAGTCAAGAATTG
CTAAAAACTATCGCTGACGTGACTTCTAAAATTGTCGAATGGATCATCAAT

CTGGCTCCATTTGGAATCCTTGGTCTTGTTTTTAAAACCATTTCTGACAAG
GGAGTCGGAAGCCTTGCCAACTACGGTATTTTATTGGTTCTATTAGTAACG
ACTATGCTTTTTGTTGCCCCTGTGGTCAACCCTTTGATTGCCTTCTTCTTT
ATGAGACGCAATCCTTACCCTCTAGTTTGGAACTGCCTCCGTGTCAGCGGT
GTGACAGCCTTTTTCACTCGTAGTTCTGCGACTAACATTCCTGTCAACATG
AAACTCTGCCATGACCTTGGACTCAACCCAGATACCTATTCTGTTTCTATC
CCACTCGGTTCTACTATCAATATGGCTGGAGTAGCGATTACCATTAACCTT
TTGACCCTTGCTGCAGTTAACACTCTTGGAATTCCTGTTGACTTTGCCACA
GCCTTTGTCCTCAGTGTGGTAGCAGCTATCTCATCCTGTGATGCTTCAGGT
ATTGCCGGAGGTTCCCTCCTTCTTATCCCAGTTGCTTGTAGCCTTTTCGGT
ATTTCTAACGATATTGCCATACAAATTGTTGGGGTTGGTTTTGTGATTGGT
GTCATCCAAGACTCATGTGAAACAGCCCTTAACTCTTCTACAGATGTCCTC
TTTACCGCCGTTGCCGAATACGCAGCAACCCGTAAAAAATAA 4158.5
(SEQ. ID. NO. 276)
ATGTCTATTAGCCAACGTACGACCAAGCTCATCTTAGCTACCTGTCTTGCC
TGCCTGCTTGCTTATTTTCTCAATCTTTCGTCAGCAGTTTCGGCTGGAATT
ATCGCTCTCTTGAGCCTATCTGATACGCGTAGAAGTACTTTAAAACTGGCT
CGCAATCGTCTTTTTTCTATGCTTCTAGCTCTGGCTATCGGTGTTCTAGCT
TTTCACTTGAGCGGATTTCATATCTGGAGTCTCGGCCTCTATCTGGCCTTC
TACGTTCCTTTAGCCTACAAGATGGGCTGGGAAATTGGCATCACACCAAGC
ACTGTTTTGGTTAGCCATCTCTTGGTTCAAGAGTCAACCTCTCCAGACCTT
CTAGTCAATGAATTCCTTCTCTTTGCTATTGGTACAGGATTTGCCTTGCTT
GTTAATCTCTATATGCCTTCACGAGAAGAGGAAATCCAGCACTACCACACG
CTGGTGGAAGAAAAGTTAAAAGATATCCTCCAGCGCTTCAAATACTATTTA
TCCAGAGGAGACGGACGCAACCGAGCACAGCTGGTAGCAGAATTAGACACG
CTTTTGAAAGAAGCCCTCAGACTGGTCTATTTGGATCACTCTGACCACCTC
TTTCACCAGACAGACTACCATATCCACTACTTTGAGATGAGACAGCGACAA
AGTCGTATCCTGAGAAACATGGCCCAACAGATTAACACTTGTCACCTTGCC
GCCAGTGAAAGCCTGATCTTAGCGCAACTCTTTTCAAAAATTGCAGGTCAA
CTGAGCCAGACCAATCCTGCTTCTGATTTGCTAGATGAAATTGAACGTTAT
CTGGAAGTCTTCCGGAACCGCAGTCTGCCCAAGACAAGAGAAGAATTTGAA
ACCCGCGCCACCCTTCTTCAACTCCTACGTGAAGCCAAAACCTTCATCCAA
GTAAAAGTTGATTTTTACCAAAAATATAGACAGTAA 4158.6
(SEQ. ID. NO. 277)
ATGGAAATCATGTCGCTTGCGATTGCTGTTTTTGCCGTCATCATTGGTTTA
GTCATTGGATATGTCAGCATCTCAGCTAAGATGAAATCATCTCAGGAAGCT
GCAGAGTTGATGCTTTTAAATGCTGAACAAGAAGCAACTAATTTACGTGGA
CAAGCTGAGCGTGAAGCGGATTTACTTGTTAATGAAGCCAAACGTGAAAGC
AAGTCTCTTAAAAAAGAAGCACTATTGGAGGCCAAAGAAGAAGCCAGAAAA
TACCGTGAAGAAGTGGACGCTGAATTCAAATCAGAACGTCAAGAACTCAAA

TABLE 3-continued

CAAATCGAAAGTCGTTTGACAGAGAGAGCTACTAGCCTTGACCGTAAGGAC

GACAATTTGACGAGTAAAGAACAAACACTTGAACAAAAAGAACAAAGTATT

TCTGATAGAGCGAAAAACCTTGATGCGCGTGAAGAGCAATTAGAGGAAGTC

GAAAGACAAAAAGAAGCAGAACTAGAGCGTATTGGTGCGCTGTCTCAGGCA

GAAGCACGAGATATTATCTTGGCTCAGACAGAGGAAAACTTGACCAGGGAG

ATTGCCAGTCGCATTCGCGAAGCTGAGCAAGAGGTCAAGGAACGTTCTGAC

AAAATGGCCAAGGACATCTTGGTTCAAGCTATGCAACGTATCGCTGGTGAA

TATGTAGCGGAGTCAACAAACTCAACAGTTCATCTGCCAGACGATACTATG

AAGGGACGCATTATTGGTCGTGAAGGTCGTAACATTCGTACCTTTGAAAGT

TTGACAGGGGTCGATGTGATTATCGACGATACACCAGAAGTGGTGACCTTG

TCAGGATTTGATCCGATTCGTCGTGAGATTGCCCGTATGACTATGGAAATG

TTGCTCAAAGATGGTCGTATACATCCAGCTCGTATCGAAGAGTTGGTTGAG

AAAAACCGTCAAGAGATTGACAATAAGATTCGTGAATACGGTGAGGCTGCT

GCCTATGAAATTGGTGCGCCAAACCTTCATCCAGACTTGATGAAGATTATG

GGACGTTTGCAGTTCCGTACTTCATATGGACAAAATGTTTTGCGCCATTCG

ATTGAGGTTGCTAAGTTGGCTGGTATCATGGCGAGCGAACTTGGTGAAAAT

GCGGCTCTTGCCCGTCGTGCTGGATTCCTTCACGATATCGGGAAAGCCATT

GACCATGAGGTTGAAGGTAGCCACGTTGAAATCGGTATGGAATTGGCCCGT

AAGTACAAGGAACCCCCAGTTGTGGTGAATACGATTGCTAGTCACCACGGA

GATGTTGAAGCTGAGAGCGTGATAGCAGTTATCGTCGCTGCAGCAGATGCC

TTGAGCGCAGCCCGTCCAGGTGCTCGTAGTGAGTCTCTTGAAAGCTACATC

TAAGCGTCTCCATGATTTGGAAGAAATTGCTAACGGCTTGAAGGAGTGCAA

ACTAGCTTTGCCCTTCAAGCAGGACGTGAAATTCGTATCATGGTCAATCCA

GGAAAAATCAAGGACGACAAAGTCACAATCTTGGCTCACAAAGTTCGTAAG

AAAATTGAAAACAATCTCGATTATCCAGGAAATATCAAGGTAACCGTGATT

CGCGAGCTTCGTGCAGTAGATTATGCTAAATAA 4158.7

(SEQ. ID. NO. 278)
ATGATGTTAAAACCCTCTATTGATACCTTGCTCGACAAGGTTCCTTCAAAA

TATTCACTCGTAATCTTGGAAGCAAACGTGCCCACGAATTGGAAGCAGGT

GCCCCAGCAACTCAAGGTTTCAAGTCTGAAAAATCAACTCTTCGCGCTTTA

GAAGAAATCGAATCAGGAAACGTTACAATTCACCCAGATCCAGAAGGAAAA

CGTGAAGCAGTGCGTCGCCGTATCGAAGAAGAAACGCCGCAAAGAAGAAG

AAGAAAAGAAAATCAAAGAGCAAATTGCTAAAGAAAAAGAAGATGGTGAAA

AAATTTAA 4161.1

(SEQ. ID. NO. 279)
ATGTCAGCATATCAATTACCGACCGTATGGCAGGATGAAGCTAGTAATCAA

GGAGCTTTTACGGGGCTAAACAGACCAACAGCAGGTGCCCGTTTCGAACAA

AACTTGCCAAAAGGAGAACAAGCTTTTCAGCTTTATTCACTGGGAACACCA

AATGGTGTGAAGGTTACTATCTTATTGGAAGAATTACTAGAAGCTGGTTTT

AAGGAAGCGGCTTACGACTTGTATAAGATTGCTATCATGGATGGGGATCAA

TTCGGATCAGACTTTGTGAAGCTCAATCCAAATTCCAAGATTCCAGCCTTA

TTGGACCAGTCAGGTACTGAAAACGTAAGAGTCTTTGAGTCTGCTCATATT

CTTCTTTACCTTGCTGAGAAATTTGGAGCCTTTTTACCAAGTAATCCTGTG

GAAAAGGTAGAAGTTTTGAATTGGCTATTCTGGCAAGCAGGTGCAGCACCT

TTTCTAGGTGGGGGATTTGGACATTTCTTCAATTATGCTCCTGAAAAATTG

GAATATCCTATTAACCGTTTTACGATGGAAGTGAAACGCCAGTTGGATTTA

TTGGATAAGGAATTGGCTCAGAAACCTTATATTGCAGGCAATGACTATACG

ATTGCAGATATTGCTATCTGGTCTTGGTATGGACAGTTAGTTCAAGGAAAT

CTTTACCAAGGTTCTGCAAAATTCTTGGATGCCTCAAGTTATCAAAATCTA

GTAAATGGGCAGAAAAAATTGCCAATCGTCCAGCTGTTAAGCGTGGCTTG

GAAGTAACTTATACAGAAATTAAATAG 4161.2

(SEQ. ID. NO. 280)
TTGGCAAGCTTGATCACTTCTATCATCATGTTCTATGTCGGTTTCGATGTT

CTAAGAGATACCATTCAAAAGATTCTCAGTCGGGAAGAAACGGTCATTGAT

CCTCTTGGTGCAACTCTAGGAATCATTTCTGCAGCGATTATGTTTGTGGTC

TATCTCTACAATACTCGCCTCAGTAAGAAATCCAACTCCAATGCGCTGAAG

GCAGCTGCTAAGGACAATCTTTCTGACGCTGTTACCTCACTTGGAACCGCC

ATTGCCATCCTAGCTAGTAGTTTCAATTATCCGATTGTGGATAAACTGGTT

GCTATCATCATCACTTTCTTTATCTTGAAGACTGCCTATGATATCTTCATC

GAGTCTTCCTTTAGTCTTTCAGATGGCTTTGACGACCGCCTGCTCGAGGAC

TACCAAAAGGCTATCATGGAAATTCCCAAAATCAGCAAGGTCAAATCGCAA

AGAGGTCGCACCTACGGTAGCAACATCTACCTGGATATTACACTAGAGATG

AATCCTGACTTGTCTGTTTTTGAAAGCCATGAAATCGCGGATCAGGTCGAG

TCTATGCTGGAGGAGCGTTTTGGCGTCTTTGATACCGATGTCCATATCGAA

CCAGCACCTATCCCTGAGGATGAAATTTTAGACAATGTCTATAAAAAATTG

CTTATGCGTGAACAATTGATTGACCAAGGAAACCAACTAGAAGAACTCTTG

ACTGATGATTTTGTCTATATTCGCCAAGATGGAGAGCAGATGGATAAAGAG

GCTTATAAGACCAAAAAGAGTTAAATTCTGCTATCAAGGACATTCAAATT

ACTTCCATCAGTCAAAAAACCAAACTCATCTGCTATGAGTTAGATGGTATC

ATCCATACCAGTATCTGGCGTCGCCACGAAACCTGGCAAAATATCTTTCAT

CAAGAAACCAAAAAAGAATAG 4162.1

(SEQ. ID. NO. 281)
ATGACAATTAAACTAGTAGCAACGGATATGGACGGAACCTTCCTAGATGGG

AATGGACGCTTTGATATGGATCGTCTCAAGTCTCTCTTGGTTTCCTACAAG

GAAAAAGGGATTTACTTTGCGGTAGCTTCGGGTCGGGGATTTCTGTCTCTA

GAAAAATTATTTGCTGGTGTTCGTGATGACATTATTTTCATCGCGGAAAAT

GGCAGTTTGGTAGAGTATCAAGGTCAGGACTTGTATGAAGCGACTATGTCT

CGTGACTTTTATCTGCAACTTTTGAAAGCTGAAAACTTCACCTTATGTA

GATATCAATAAACTGCTCTTGACGGGTAAGAAGGGTTCATATGTTCTAGAT

ACGGTTGATGAGACCTATTTGAAAGTGAGTCAGCACTATAATGAAAATATC

TABLE 3-continued

CAAAAAGTAGCGAGTTTGGAAGATATCACAGATGACATTTTCAAATTTACA
ACCAACTTCACAGAAGAAACGCTGGAAGATGGGGAGGCTTGGGTAAACGAA
AACGTTCCTGGTGTTAAGGCCATGACAACTGGCTTTGAATCCATTGATATT
GTTCTGGACTATGTCGATAAGGGAGTGGCCATTGTTGAATTAGTTAAAAAA
CTTGGTATCACAATGGATCAGGTCATGGCTTTTGGAGACAATCTTAATGAC
TTACATATGATGCAGGTTGTGGGACATCCTGTAGCTCCTGAAAATGCACGA
CCTGAAATTTAGAATTAGCAAAGACTGTGATTGGTCACCATAAGGAACGGT
CGGTTATAGCTTATATGGAGGGCTTATAA 4162.2 (SEQ. ID. NO. 282)
ATGGCAGATATAAAATTGATTGCATTGGACTTGGACGGGACCTTGCTGACT
ACTGATAAAAGGCTGACGGATCGTACCAAGGAAACCTTGCAAGCTGCGCGT
GATCGTGGTATCAAGGTCGTATTGACAACTGGTCGTCCCTTAAAAGCCATG
GATTTCTTTCTCCATGAGTTAGGGACTGACGGTCAGGAAGATGAGTATACC
ATTACTTTTAATGGTGGATTAGTTCAGAAAAATACAGGAGAAATCCTTGAT
AAAACAGTCTTTTCATATGATGATGTGGCACGTTTGTATGAAGAAACAGAG
AAATTATCACTGCCTCTTGATGCCATCTCAGAAGGAACAGTTTATCAAATC
CAATCGGACCAAGAAAGTCTTTATGCCAAATTCAATCCAGCTTTGACCTTT
GTTCCAGTGGACTTTGAAGACTTATCTAGTCAAATGACCTACAACAAATGC
GTGACTGCCTTTGCTCAAGAACCCTTGGATGCAGCCATTCAGAAGATTTCT
CCAGAATTGTTTGACCAATATGAAATCTTTAAATCACGTGAAATGTTGCTA
GAATGGTCACCAAAGAATGTTCATAAAGCAACAGGTTTGGCAAAACTAATC
AGCCATCTTGGAATCGACCAAAGTCAAGTGATGGCTTGTGGTGACGAGGCC
AATGACCTCTCTATGATTGAATGGGCAGGTCTTGGTGTTGCTATGCAAAAC
GCTGTTCCTGAAGTAAAGGCAGCCGCAAATGTAGTGACGCCGATGACCAAC
GATGAGGAAGCTGTCGCCTGGGCTATCGAAGAATATGTGCTAAAGGAGAAC
TAA 4164.2 (SEQ. ID. NO. 283)
ATGGAAAGTTTACTTATTCTATTATTAATTGCCAATCTAGCTGGTCTCTTT
CTGATTTGGCAAAGGCAGGATAGGCAGGAGAAACACTTAAGTAAGAGCTTG
GAGGATCAGGCAGATCATTTGTCAGACCAGTTGGATTACCGCTTTGACCAA
GCCAGACAAGCCAGCCAGTTAGACCAAAAAGATTTGGAAGTGGTTGTCAGC
GACCGTTTGCAAGAAGTGCGGATTGAATTGCACCAAGGTCTGACCCAAGTC
CGTCAAGAAATGACAGATAATCTCCTCCAAACTAGAGACAAGACAGACCAA
CGTCTCCAAGCCTTGCAGGAATCAAATGAGCAACGTTTGGAACAAATGCGC
CAGACGGTCGAGGAAAAACTAGAAAAGACCTTGCAGACACGCTTACAGGCT
TCCTTTGAGACAGTTTCTAAACAACTGGAGTCTGTCAATCGTGGCCTTGGA
GAAATGCAGACAGTTGCCCGTGATGTCGGAGCTCTTAACAAGGTTCTCTCT
GGAACCAAGACGCGAGGGATTCTGGGAGAATTGCAACTGGGGCAAATTATT
GAAGACATCATGACACCTGCCCAGTACGAACGAGAATACGCAACGGTTGAA
AACTCTAGTGAACGAGTGGAGTATGCCATCAAGTTACCCGGACAAGGCGAC

CAAGAATACGTCTATCTGCCAATTGACTCTAAGTTTCCACTGGCAGATTAT
TACCGCTTGGAAGAAGCCTATGAGACAGGTGACAAGGATGAGATTGAACGC
TGTCGTAAGTCACTCCTAGCAAGCGTCAAGCGCTTTGCTAGGGATATTAGG
AACAAGTACATAGCACCACCTCGGACGACCAATTTTGGAGTTTTGTTTGTT
CCGACAGAAGGTCTCTACTCAGAAATCGTCCGCAATCCGGTCTTCTTTGAT
GATTTGAGACGGGAAGAACAGATTATTGTTGCAGGACCAAGTACCCTATCA
GCCCTTCTTAACTCCCTATCAGTTGGTTTCAAGACCCTTAATATCCAAAAG
AGTGCCGACCATATCAGCAAGACTCTTGCCAGTGTCAAGACCGAGTTTGGC
AAGTTTGGTGGTATTCTGGTCAAGGCACAAAAACATCTCCAACATGCCTCT
GGCAATATTGATGAATTATTAAACCGTCGTACCATAGCTATCGAGCGGACG
ATCCGTCACATTGAGTTGTCAGAAGGTGAGCCTGCGCTTGATCTACTCCAT
TTTCAAGAAAATGAGGAAGAATATGAAGATTAG 4164.3 (SEQ. ID. NO. 284)
ATGAAGATTAGTCACATGAAAAAAGATGAGTTATTTGAAGGCTTTTACCTA
ATCAAATCAGCTGACCTGAGGCAAACTCGAGCTGGGAAAAACTACCTAGCC
TTTACCTTCCAAGATGATAGTGGCGAGATTGATGGGAAGCTCTGGGATGCC
CAACCTCATAACATTGAGGCCTTTACCGCAGGTAAGGTTGTCCACATGAAA
GGACGCCGAGAAGTTTATAACAATACCCCTCAAGTCAATCAAATTACTCTC
CGCCTGCCTCAAGCTGGTGAACCCAATGACCCAGCTGATTTCAAGGTCAAG
TCACCAGTTGATGTCAAGGAAATTCGTGACTACATGTCGCAAATGATTTTC
AAAATTGAAAATCCTGTCTGGCAACGGATTGTCCGAAATCTCTACACCAAG
TATGATAAGGAATTCTACTCCTATCCAGCTGCCAAGACCAACCACCATGCC
TTTGAAACGGGCTTGGCCTATCATACGGCGACCATGGTGCGTTTGGCAGAC
GCTATTAGCGAAGTTTATCCTCAGCTCAATAAGAGCCTGCTCTATGCGGGG
ATTATGTTGCATGACTTAGCTAAGGTCATCGAGTTGACGGGCCAGACCAG
ACAGAGTACACAGTGCGAGGTAATCTTCTTGGACATATCGCTCTCATTGAT
AGCGAAATTACCAAGACAGTTATGGAACTCGGCATCGATGATACCAAGGAA
GAAGTCGTTTTGCTTCGTCATGTCATCCTCAGTCACCACGGCTTGCTTGAG
TATGGAAGCCCAGTCCGTCCACGCATTATGGAAGCAGAGATTATCCATATG
ATTGACAATCTGGATGCAAGCATGATGATGATGTCAACAGCTCTTGCTTTG
GTGGATAAAGGAGAGATGACCAATAAAATCTTCGCTATGGATAATCGTTCC
TTCTATAAACCAGATTTAGATTAA 4166.2 (SEQ. ID. NO. 285)
ATGAGTGAAAAAGCTAAAAAAGGGTTTAAGATGCCTTCATCTTACACCGTA
TTATTGATAATCATTGCTATTATGGCAGTGCTAACTTGGTTTATCCCTGCG
GGGGCTTTATAGAAGGTATTTACGAGACTCAGCCTCAAAATCCACAAGGG
ATTTGGGATGTCCTGATGGCACCGATTCGGGCTATGCTAGGTACTCATCCA
GAGGAAGGTTCGCTCATTAAAGAAACGAGCGCAGCGATTGATGTAGCCTTC
TTCATCCTTATGGTTGGTGGTTTCCTTGGCATTGTCAACAAAACTGGTGCT
CTTGACGTAGGGATTGCCTCTATCGTGAAGAAGTATAAGGGCCGCGAAAAA

TABLE 3-continued

ATGTTAATTTTGGTACTGATGCCTTTGTTGCCCTCGGTGGTACAACTTAT
GGTATGGGTGAAGAAACAATGGCCTTCTATCCACTCCTTGTGCCAGTTATG
ATGGCCGTTGGTTTTGATAGCCTGACTGGTGTTGCAATTATTTTGCTCGGT
TCTCAAATCGGCTGTTTGGCATCTACTCTGAATCCATTTGCGACAGGTATT
GCTTCAGCGACTGCGGGAGTTGGTACAGGGGACGGTATCGTACTTCGTCTG
ATCTTCTGGGTTACCTTGACTGCTCTTAGTACTTGGTTTGTTTACCGTTAT
GCGGATAAGATTCAAAAAGATCCGACTAAGTCACTGGTTTATAGTACTCGC
AAAGAAGATTTGAAACACTTTAACGTAGAAGAATCTTCATCTGTAGAATCT
ACACTTAGCAGCAAACAAAATCAGTTCTCTTCTTATTTGTGTTGACATTC
ATCTTGATGGTATTGAGCTTCATTCCATGGACAGACCTTGGCGTTACCATT
TTTGATGACTTTAATACTTGGTTGACTGGTCTTCCAGTTATTGGTAATATT
GTCGGTTCATCTACTTCTGCACTAGGTACTTGGTACTTCCCAGAAGGCGCA
ATGCTCTTTGCCTTTATGGGTATCCTGATTGGTGTTATTTATGGTCTTAAA
GAAGATAAGATTATCTCTTCCTTCATGAATGGTGCTGCTGACTTGCTCAGT
GTTGCCTTGATCGTAGCGATTGCTCGTGGTATTCAAGTTATCATGAACGAC
GGTATGATTACCGATACAATCCTCAACTGGGGTAAAGAAGGCTTGAGCGGT
CTATCTTCACAAGTCTTTATCGTTGTAACTTATATCTTCTATCTACCTATG
TCATTCTTGATCCCATCTTCATCTGGTCTTGCCAGCGCAACTATGGGTATC
ATGGCTCCACTTGGAGAATTTGTAAATGTCCGTCCTAGCTTGATTATCACT
GCTTACCAATCTGCTTCAGGTGTCTTGAACTTGATTGCACCAACATCTGGT
ATTGTGATGGGAGCTCTTGCACTTGGACGTATCAACATTGGTACTTGGTGG
AAATTCATGGGCAAACTCGTAGTCGCTATTATTGTAGTGACCATCGCCCTT
CTTCTCCTTGGAACCTTCCTTCCATTCCTATAA 4166.3
                    (SEQ. ID. NO. 286)
ATGAAAATAGATATAACAAATCAAGTTAAAGATGAATTTCTTATATCATTA
AAAACCTTGATTTCCTATCCTTCAGTACTCAATGAAGGAGAAAATGGAACA
CCTTTTGGACAAGCAATCCAAGATGTCCTAGAAAAAACTTTAGAGATTTGT
CGAGACATAGGTTTCACTACCTATCTTGACCCTAAAGGTTATTACGGATAT
GCAGAAATCGGTCAGGGAGCAGAGCTTCTGGCCATTCTCTGTCATTTGGAT
GTTGTTCCATCAGGTGATGAAGCAGATTGGCAGACACCGCCATTTGAAGCA
ACTATCAAAGACGGCTGGGTATTCGGACGTGGTGTCCAAGATGATAAAGGC
CCTTCGCTCGCAGCTCTCTATGCAGTAAAAAGCTTGCTGGACCAAGGTATT
CAGTTCAAAAAGCGCGTACGCTTTATCTTTGGTACCGATGAGGAAACCCTC
TGGCGCTGCATGGCACGCTACAATACCATCGAAGAACAGGCCAGTATGGGC
TTTGCACCTGACTCATCTTTTCCTCTGACCTATGCTGAAAAAGGGCTTCTA
CAGGTCAAACTTCATGGCCCTGGATCGGATCAACTAGAGCTTGAAGTAGGA
GGCGCCTTTAACGTTGTACCAGACAAGGCCAACTACCAAGGTCTCCTCTAT
GAACAGGTTTGTAACGGTCTCAAAGAAGCTGGTTATGATTACCAAACCACT
GAACAAACCGTAACGGTTCTCGGAGTGCCAAAGCATGCTAAGGATGCTAGT
CAAGGTATCAATGCTGTCATCCGACTAGCTACCATTCTTGCTCCTCTCCAA

GAACACCCTGCTCTCAGTTTTCTTGCAACACAAGCAGGTCAAGACGGCACA
GGAAGACAAATCTTTGGTGATATAGCAGATGAACCTTCTGGTCACCTATCC
TTTAATGTCGCAGGTCTCATGATCAATCATGAACGTTCTGAAATCCGTATT
GACATTCGGACTCCTGTCTTAGCTGACAAGGAAGAACTAGTAGAGTTGCTT
ACAAGATGTGCACAAAACTACCAACTCCGCTACGAAGAGTTTGACTATCTA
GCGCCTCTATACGTCGCAGAAGACAGTAAACTCGTTAGCACACTGATGCAA
ATCTACCAAGAAAAGACTGGCGATAACAGTCCTGCTATTTCATCCGGTGGT
GCCACTTTTGCTCGCACCATGCCAAATTGTGTAGCCTTCGGCGCCTTATTC
CCAGGAGCGAAGCAGACAGAACATCAGGCAAATGAATGTGCCGTTCTAGAA
GATTTGTACCGTGCTATGGATATTTATGCCGAAGCCGTCTATCGACTTGCA
ACTTAA 4169.1
                    (SEQ. ID. NO. 287)
ATGTCTAATTCATTTGTCAAGTTGTTAGTCTCTCAATTATTTGCAAATTTA
GCAGATATTTTCTTTAGAGTAACAATCATTGCTAACATATACATTATTTCA
AAATCAGTAATTGCCACATCACTAGTTCCTATCTTAATAGGAATATCCTCT
TTTGTTGCGAGTCTTTTAGTTCCGTTGGTTACTAAAAGGTTAGCGCTAAAT
AGGGTTTTATCTTTATCTCAATTTGGAAAGACTATATTATTGGCGATACTG
GTAGGAATGTTTACCGTAATGCAATCCGTAGCGCCTTTGGTGACCTATCTA
TTTGTTGTTGCAATTTCCATACTAGATGGTTTTGCAGCACCCGTTTCCTAT
GCTATTGTGCCACGCTATGCGACCGATTTGGGTAAGGCTAATTCAGCCTTA
TCAATGACTGGTGAAGCTGTTCAATTGATAGGTTGGGGATTAGGTGGACTC
TTGTTTGCAACAATTGGTCTGTTACCTACCACGTGTATCAATTTAGTCTTG
TATATCATTTCTAGCTTTCTGATGTTATTCTTCCTAACGCTGAAGTGGAG
GTGTTAGAGTCAGAAACTAATCTTGAAATTTGCTCAAAGGTTGGAAGTTA
GTTGCTAGAAATCCTAGATTAAGACTTTTTGTATCAGCAAATTTATTGGAA
ATTTTTTCAAATACGATTTGGGTTTCTTCCATTATACTTGTTTTTGTAACG
GAGTTATTAAATAAAACGGAAAGTTACTGGGGATATTCTAATACAGCATAC
TCTATTGGTATTATAATTAGTGGCTTAATTGCTTTTAGGCTATCTGAAAAG
TTCCTTGCTGCTAAATGGGAAGGGGAATTATTCACCCCAAATCTAAAAACC
ATCCAGAATCCTTGCCTTAGCTTAGATCCTGGATGGTTTCTTTTTTCACCC
AATGGGTGTTTTTACTAGACAAAAAGAGTTTCCCCTTTATGGTATAAGT
GTAGAAAAAACACAAAAAGAAAGGAAACTCACATGAACAGTTTACCAAAT
CATCACTTCCAAAACAAGTCTTTTTACCAACTATCTTTCGATGGAGGTCAT
TTAACCCAGTATGGTGGTCTTATCTTTTTTCAGGAACTTTTTTCCCAGTTG
AAACTAAAAGAGCGGATTTCTAAGTATTTAGTAACGAATGACCAACGCCGC
TACTGTCGTTATTCGGATTCAGATATCCTTGTCCAGTTCCTCTTTCAACTG
TTAACAGGTTATGGAACGGACTATGCTTGTAAAGAATTGTCAGCTGATGCC
TACTTTCCAAAATTGTTGGAAGGAGGGCAGCTTGCTTCACAGCCAACCTTA
TCCCGTTTTCTTTCCAGAACTGACGAGGAAACAGTCCATAGTTTGCGATGC
CTCAACCTTGAATTGGTCGAATTCTTTTTACAGTTTCACCAGCTAAACCAA

TABLE 3-continued

CTCATTGTAGATATCGATTCTACCCATTTCACAACTTATGGCAAGCAAGAA
GGTGTTGCTTATAACGCCCACTATCGTGCTCATGGCTATCATCCTCTTTAT
GCTTTCGAGGGAAGACAGGTTATTGTTTCAATGCCCAGCTTCGTCCTGGT
AATCGTTATTGTTCTGAAGAGGCAGACAGCTTTATCACACCTGTTTTAGAA
CGGTTTAATCAACTTCTCTTTCGAATGGATAGTGGCTTTGCGACCCCAAAA
TTATACGATTTAATTGAAAAAACAGGGCAATACTACCTCATAAAACTCAAG
AAAAATACTGTTCTGAGCCGTCTTGGAGACCTTTCCCTCCCTTGCCCACAG
GATGAGGACTTAACCATCTTGCCCCACTCCGCCTACTCAGAAACTCTCTAT
CAAGCAGGATCTTGGTCGCACAAGCGTCGTGTCTGCCAGTTCTCTGAACGA
AAAGAAGGAAACTTGTTCTACGATGTTATTTCTCTCGTTACAAATATGACG
AGTGGAACAAGCCAAGACCAGTTTCAGCTTTATCGTGGACGTGGTCAAGCC
GAGAATTTCATCAAGGAGATGAAGGAGGGATTTTTTGGCGATAAAACGGAT
GAGTTCAACCTTAATCAAAAACGAATTCGTATGATGATGAGCTGTATCGCC
TACAATCTCTATCTTTTTCTCAAACATCTAGCTGGAGGTGACTTCCAAACT
TTAACAATCAAACGCTTCCGCCATCTTTTTCTTCACGTGGTGGGAAAATGT
GTTCGAACAGGACGCAAGCAGCTCCTCAAATTGTCTAGTCTCTATGCCTAT
TCCGAATTGTTTTCAGCACTTTATTCTAGGATTAGAAAAGTCAACCTGAAT
CTTCCTGTTCCTTATGAACCACCTAGAAGAAAAGCGTCGTTAATGATGCAT
TAA 4169.3
(SEQ. ID. NO. 288)
ATGATGGAGTTTTTTCAACAGCTTCCTCATTTAGAGCCATATGGCAATCCT
CAGTATTTTGTTTATGTGATTGCTGCAACCTTGCCCATCTTTATAGGTCTC
TTTTTCAAGAAACGCTTTGCCTGGTATGAAGTGTTGGTAAGTCTCTTCTTT
ATTGTCACCATGTTGGTGGGTGGAAAGACCAATCAACTAGCTGCCTTGGGT
ATTTACCTTTGCTGGGAAATATTGCTCCTGCTTTTCTACAAGCATTATCGA
AAAAGCAAGGATGGCAAGTGGGTCTTCTACTTAGTTAGTTTTCTGTCCCTA
CTTCCGATTATCTTTGTCAAGGTGCAACCAGCTATCAATGGAACGCAGTCT
TTGCTTGGGTTCTTGGGAATTTCTTACCTGACCTTTCGTTCGGTTGGAATT
GTCATCGAGCTGAGAGATGGAGTGATTAAGGATTTTACCCTCTGGGAATTC
CTCCGTTTCCTTCTCTTCATGCCAACTTTCTCGAGTGGTCCAATCGATCGC
TTTAAGCGATTTAATGAAAATTATCAGGCTATTCCTGAGCGAGATGAGTTG
ATGGATATGCTGGATGAATCTGTCCGCTATATCATGTGGGGCTTTTGTAT
AAGTTTATCCTAGCTCATGTTTTAGGAGAGACCTTACTACCTCCTCTGAAG
AATTTAGCCTTGCAGTCAGGTGGCTTCTTTAATCTCTATGCCTTGGCAGTT
ATGTATACTTTTGGTCTGGAACTCTTCTTTGACTTTGCAGGTTATTCTATG
TTTGCTTTGGCCATCTCAAACTTGATGGGAATCCGTAGCCCTATCAACTTT
AACAAGCCCTTTTTATCAAGGGATTTAAAGGAGTTTTGGAATCGCTGGCAT
ATGAGTCTGTCCTTCTGGTTCCGTGACTTTGTCTTTATGCGAATGGTGATG
GTGTTAACCAGAAAGAAAGTCTTTAAAAATCGTAATGTAACCTCAAGCATG
GCCTACATTGTAAATATGCTGATTATGGGATTTTGGCATGGTGTGACCTGG

TACTATATCGCCTATGGACTCTTTCATGGACTAGGCTTGGTCATCAATGAT
GCCTGGGTTCGCAAGAAAAAACGCTCAATAAGGAACGGAAAAAAGCAGGG
AAGGCTGCCCTACCTGAGAATCGCTGGATTCAGTTGCTTGGCATGGTTGTC
ACTTTCCATGTTGTCATGTTGTCATTCTTAATCTTTTCTGGATTCTTGAAT
AATCTATGGTTTAAAAAATAA 4169.4
(SEQ. ID. NO. 289)
ATGCTTAAACGCTTATGGATGATCTTCGGACCGGTCTTGATCGCTGGTTTG
TTGGTTTTTCTGCTCATTTTCTTTTATCCTACTGAGATGCATCATAATCTA
GGAGCTGAAAAGCGTTCAGCAGTGGCTACTACTATCGATAGTTTTAAGGAG
CGAAGTCAAAAAGTCAGAGCACTATCTGATCCAAATGTGCGTTTTGTTCCC
TTCTTTGGCTCTAGTGAATGGCTTCGTTTTGACGGTGCTCATCCTGCGGTA
TTAGCTGAGAAATACAATCGTTCCTACCGTCCTTATCTTTTAGGACAGGGG
GGAGCTGCATCGCTTAACCAATATTTTGGAATGCAACAGATGTTACCACAG
CTGGAGAATAAACAAGTTGTGTATGTTATCTCACCTCAGTGGTTCAGTAAA
AATGGCTATGATCCAGCAGCCTTCCAGCAGTATTTTAATGGAGACCAGTTG
ACTAGTTTTCTGAAACATCAATCTGGGGATCAGGCTAGTCAATATGCAGCG
ACTCGCTTACTGCAACAGTTCCCAAACGTAGCTATGAAGGACCTGGTTCAG
AAGTTGGCAAGTAAAGAAGAATTGTCGACAGCAGACAATGAAATGATTGAA
TTATTGGCTCGTTTTAATGAACGCCAAGCTTCCTTTTTTGGTCAGTTTTCG
GTTAGAGGCTATGTTAACTACGATAAGCATGTAGCTAAGTATTTAAAAATC
TTGCCAGACCAGTTTTCTTATCAGGCAATAGAAGATGTTGTCAAAGCAGAT
GCTGAAAAAAATACTTCCAATAATGAGATGGGAATGGAAAATTATTTCTAT
AATGAGCAGATCAAGAAGGATTTGAAGAAATTAAAGGATTCTCAGAAAAGC
TTTACCTATCTCAAGTCGCCAGAGTATAATGACTTGCAGTTGGTTTTAACA
CAGTTTTCTAAATCTAAGGTAAACCCGATTTTTATCATTCCACCTGTTAAT
AAAAAATGGATGAACTATGCTGGTCTACGAGAGGATATGTACCAACAAACG
GTGCAGAAGATTCGCTACCAGTTAGAAAGTCAAGGTTTTACCAATATAGCA
GATTTTTCTAAGGACGGCGGGGAGCCTTTCTTTATGAAGGACACCATTCAC
CTTGGTTGGTTGGGTTGGTTGGCTTTTGACAAGGCAGTTGATCCTTTCCTA
TCCAATCCCACACCAGCTCCGACTTACCATCTGAATGAGCGCTTTTTCAGC
AAAGATTGGGCGACTTATGATGGAGATGTCAAAGAATTTCAATAG 4169.6
(SEQ. ID. NO. 290)
ATGGAGAAAAACCTCAAGGCTTTGAAACAAACAACAGACCAAGAAGGCCCA
GCAATTGAACCTGAAAAGGCAGAGGATACCAAGACAGTCCAAAATGGTTAC
TTCGAGGATGCAGCTGTCAAGGACCGCACCTTGAGTGACTATGCAGGTAAC
TGGCAATCAGTTTATCCTTTCCTTGAAGACGGCACGTTTGACCAAGTCTTT
GACTACAAGGCTAAGTTGACTGGTAAGATGACCCAGGCTGAGTACAAGGCT
TACTATACAAAAGGCTATCATACAGATGTGACTAAGATTAACATTACTGAT
AATACTATGGAATTTGTTCAAGGTGGACAAAGCAAGAAATACACTTACAAG
TATGTCGGTAAGAAAATTTTGACTTACAAGAAAGGCAATCGTGGCGTGCGT

TABLE 3-continued

TTCCTCTTTGAAGCCACAGATGCTGACGCTGGACAATTCAAGTATGTTCAG

TTTAGTGACCACAATGTTGCCCCAGTTAAGGCAGAACATTTCCATATCTTC

TTTGGAGGCACAAGCCAAGAAGCCCTCTTTGAAGAAATGGACAACTGGCCA

ACCTACTACCCAGATAACCTATCTGGCCAAGAAATCGCCCAAGAAATGTTG

GCGCATTGA 4170.3

(SEQ. ID. NO. 291)
ATGAAAGATGGTCATTTGCTAGCCCATCATATTCGTTTGTTGAATGGGCGG

ATTTTTCAAAAGTTACTGAGTCAAGATCCTGAGGCTCTTTATAGGGGTGAA

CAGGGCAAGATTTTAGCGGTTTTATGGAATAGTGAAACTGGCTGCGCAACT

GCGACAGATATCGCGCTTGCGACTGGACTTGCGAATAATACGCTGACGACT

ATGATAAAAAAGCTAGAGGAACAAAAGCTTGTAATTGTTAGTCCGTGTGGA

AAAGACAAGCGTAAGAAGTATTTAGTTTTAACGGAGTTAGGCAAGTCCCAG

AAAGAAGTGGGGCATCGTGTCAGTCAGAAATTGGATACTATCTTTTACAAA

GGATTTTCAGAGGAAGAAATTCACCAATTTGAAGGTTTTCAAGAAAGAATT

TTGGCGAATCTGAAAGAGAAGGGAAATGAGGTTTAG 4170.4

(SEQ. ID. NO. 292)
ATGACTAATTTAATTGCAACTTTTCAGGATCGTTTTAGTGATTGGTTGACA

GCTCTATCTCAACATTTGCAGTTGTCGCTTTTGACCTTGTTACTAGCTATT

TTGCTTGCGATTCCCTTGGCTGTTTTTCTTCGCTATCATGAGAAGCTGGCC

GACTGGGTCTTGCAGATTCAGGTATTTTCCAGACCATCCCGTCTCTGGCC

TTGTTGGGGCTCTTTATCCCTTTGATGGGAATTGGGACCTTGCCGGCTTTG

ACAGCTCTAGTGATTTATGCGATTTTCCCTATTTTGCAAAATACTATCACT

GGGCTGAAGGGAATTGATCCGAACCTGCAAGAGGCTGGGATTGCCTTTGGG

ATGACCAGATGGGAACGTCTCAAGAAATTTGAAATTCCACTCGCCATGCCT

GTTATCATGTCTGGGATTCGGACGGCAGCTGTTTTGATTATCGGTACGGCA

ACCTTGGCGGCCTTGATTGGTGCAGGGGGACTAGGTTCCTTTATTCTTTTG

GGAATTGACCGTAATAATGCCAGTTTGATTTTGATTGGGGCACTTTCTTCT

GCAGTGCTAGCCATTGCCTTTAACTTCCTACTAAAAGTGATGGAAAAAGCA

AAATTACGGACGATTTTCTCAGGTTTTGCCTTGGTGGCTTTATTACTGGGT

ACTGTCTTATAGTCCAGCTCTTTTGGTTCAAAAGAGAAGGAAAACTTGGTT

ATTGCTGGGAAAATAGGTCCAGAACCAGAAATTTTGGCCAATATGTATAAG

TTGCTGATTGAAGAAATACCAGCATGACTGCGACTGTTAAACCGAATTTT

GGGAAGACAAGCTTCCTTTATGAAGCTCTGAAAAAGGCGATATTGACATC

TATCCTGAATTTACTGGTACGGTGACTGAAAGTTTGCTTCAACCATCACCC

AAGGTGAGTCATGAACCAGAACAGGTTTATCAGGTGGCGCGTGATGGCATT

GCTAAGCAGGATCATCTAGCCTATCTCAAACCCATGTCTTATCAAAACACC

TATGCTGTAGCTGTTCCGAAAAAGATTGCTCAAGAATATGGCTTGAAGACC

ATTTCAGACTTGAAAAAGTGGAAGGGCAGTTGAAGGCAGGTTTTACACTC

GAGTTTAACGACCGTGAAGATGGAAATAAGGGCTTGCAATCAATGTATGGT

CTCAATCTCAATGTAGCGACCATTGAGCCAGCCCTTCGCTATCAGGCTATT

CAGTCAGGGGATATTCAAATCACGGATGCCTATTCGACTGATGCGGAATTG

GAGCGTTATGATTTACAGGTCTTGGAAGATGACAAGCAACTCTTCCCACCT

TATCAAGGGGCTCCACTCATGAAAGAAGCTCTTCTCAAGAAACACCCAGAG

TTGGAAAGAGTTCTTAATACATTGGCTGGTAAGATTACAGAAAGCCAGATG

AGCCAGCTCAACTACCAAGTCGGTGTTGAAGGCAAGTCAGCAAAGCAAGTA

GCCAAGGAGTTTCTCCAAGAACAAGGTTTGTTGAAGAAATGA 4170.5

(SEQ. ID. NO. 293)
ATGATGCATACTTATTTGCAAAAGAAATTGAAAATATCAAAACAACCCTA

GGTGAAATGTCAGGTGGTTACCGTCGTATGGTTGCGGCTATGGCTGATTTA

GGATTTTCAGGAACTATGAAGGCTATCTGGGATGACCTCTTTGCCCATCGT

AGTTTTGCCCAGTGGATTTATTTGCTGGTTTTAGGAAGTTTTCCTCTCTGG

CTGGAGTTGGTTTACGAACATCGTATTGTTGACTGGATTGGGATGATTTGT

AGCTTGACAGGGATTATCTGTGTAATCTTTGTATCGGAAGGTCGAGCAAGT

AATTATCTTTTTGGCTTGATTAACTCTGTTATTTACCTTATTTTGGCCCTA

CAGAAAGGCTTTTATGGTGAGGTGCTGACGACACTTTACTTCACAGTCATG

CAGCCAATTGGACTTCTAGTTTGGATTTATCAGGCACAGTTTAAGAAGGAA

AAGCAGGAGTTTGTCGCGCGTAAACTGGACGGCAAGGGCTGGACAAAGTAT

CTTTTCCATTAGTGTGCTTTGGTGGTTGGCCTTTGGCTTCATTTATCAGTCT

ATTGGTGCCAATCGTCCCTATCGTGATTCAATCACAGATGCAACCAATGGG

GTAGGGCAAATCCTCATGACAGCTGTTTACCGTGAACAGTGGATATTCTGG

GCGGCTACCAATGTCTTTTCAATCTATCTCTGGTGGGAGAAAGCCTGCAA

ATTCAAGGGAAATATCTAATTTATCTCATTAACAGTCTAGTTGGTTGGTAT

CAATGGAGCAAGGCAGCTAAGCAGAATACTGATTTACTTAACTAG 4170.6

(SEQ. ID. NO. 294)
ATGAGAAATATGAAGGCAAAATATGCTGTTTGGGTGGCTTTTTTCTTAAAT

TTGACTTATGCCATTGTTGAGTTTATGCAGGTGGAGTATTTGGTTCTAGCG

CTGTTCTTGCTGACTCTGTGCATGACTTGGGAGATGCGATTGCAATTGGAA

TATCAGCTTTTCTAGAAACAATCTCCAATCGTGAAGAAGACAATCAGTACA

CCTTGGGCTATAAGCGGTTTAGCCTGCTAGGAGCCTTGGTAACAGCTGTGA

TTCTCGTAACGGGCTCTGTTCTAGTCATTTTGGAAAATGTCACGAAGATTT

GCATCCGCAACCAGTCAATGATGAGGGGATTCTCTGGTTAGGAATTATTGC

GATTACTATCAATCTGTTAGCGAGTCGGTGGTTGGTAAGGGAAAGACAAA

GAATGAGTCTATTCTGAGTCTGCATTTTCTGGAAGATACGCTAGGGTGGGT

AGCTGTTATCCTGATGGCGATTGTTCTTCGATTTACGGACTGGTATATCCT

AGATCCTCTTTTGTCCCTTGTCATTTCTTTCTTTATTCTTTCAAAAGCCCT

TCCACGTTTTGGTCTACACTCAAGATTTTCTTGGATGCTGTGCCAGAAGG

TCTTGATATCAAGCAAGTAAAGAGTGGCCTGGAGCGATTGGACAATGTGGC

CAGCCTTAATCAGCTTAATCTCTGGACTATGGATGCTTTGGAAAAAAATGC

CATTGTCCATGTTTGTCTAAAAGAAATGGAACATATGGAAACTTGTAAAGA

GTCTATTCGAATTTTCCTAAAAGATTGTGGTTTTCAAAATATTACCATTGA

TABLE 3-continued

AATTGATGCTGACCTAGAAACTCACCAAACCCATAAGCGAAAGGTGTGTGA
CTTGGAACGGAGTTATGAGCATCAACATTAG 4170.8
(SEQ. ID. NO. 295)
ATGATTGAATACAAAAATGTAGCACTGCGCTACACAGAAAAGGATGTCTTG
AGAGATGTCAACTTACAGATTGAGGATGGGGAATTTATGGTTTTAGTAGGG
CCTTCTGGGTCAGGTAAGACGACCATGCTCAAGATGATTAACCGTCTTTTG
GAACCAACTGATGGAAATATTTATATGGATGGGAAGCGCATCAAAGACTAT
GATGAGCGTGAACTTCGTCTTTCTACTGGTTATGTTTTACAGGCTATTGCT
CTTTTTCCAAATCTAACAGTTGCGGAAAATATTGCTCTCATTCCTGAAATG
AAGGGGTGGAGCAAGGAAGAAATTACGAAGAAAACAGAAGAGCTTTTGGCT
AAGGTTGGTTTACCAGTAGCCGAGTATGGGCATCGCTTACCTAGTGAATTA
TCTGGTGGAGAACAGCAACGGGTCGGTATTGTCCGAGCTATGATTGGTCAG
CCCAAGATTTTCCTCATGGATGAACCCTTTTCGGCCTTGGATGCTATTTCG
AGAAAACAGTTGCAGGTTCTGACAAAAGAATTGCATAAAGAGTTTGGGATG
ACAACGATTTTTGTAACCCATGATACGGATGAAGCCTTGAAGTTGGCGGAC
CGTATTGCTGTCTTGCAGGATGGAGAAATTCGCCAGGTAGCGAATCCCGAG
ACAATTTTAAAAGCGCCTGCAACAGACTTTGTAGCAGACTTGTTTGGAGGT
AGTGTTCATGACTAA 4171.1
(SEQ. ID. NO. 296)
ATGTCAGCAGTTGCTATTTCAGCTATGACCAAGGTTATGCAAGAAACCCAC
GGAAATCCTTCTAGTATTCATGGTCATGGTCGTCAAGCTGGCAAACTCTTG
CGAGAAGCCCGTCAGGAACTAGCCCAGTTACTAAGGACAAAACCTCAACAT
ATCTTTTTCACTTCTGGTGGGACTGAAGGCAATAATACTACCATCATTGGC
TACTGTCTTCGTCACCAAGAACAAGGAAAACATATCATCACAACTGCCATC
GAGCACCATGCTGTCCTTGAAACAATTGATTACTTGGTTCAACACTTTGGG
TTTGAAGCAACCATTATCCAGCCAGAAAATCAAGAAATCACAGCCCAGCAA
ATTCAAAAGGCTTTACGTGACGATACGATTTTGGTTTCTACCATGTTTGTC
AATAATGAGACAGGAAACCTACTGCCCATCGCTGAAATTGGCCAAATACTC
AAGCAACACCCTGCTGCCTATCATGTTGATGCAGTTCAGGCTATTGGTAAA
ATCCCAATTCATTCAGAAGAATTGGGCATTGATTTTCTCACTGCTTCTGCC
CACAAATTCCATGGTCCTAAGGGAATCGGTTTTCTCTACGCATCTAGCATG
GACTTTGATTCCTATCTACATGGCGGAGACCAGGAACAGAAAAAACGTGCA
GGAACTGAAAATCTGCCTGCCATTGTAGGCATGGTTGCAGCCCTAAAAGAA
GACCTAGAAAACAAGAAGAACATTTTCAACATGTACAAAATCTAGAAACT
GCCTTTCTGGCAGAGCTGGAGGGCATTCAGTATTACCTGAATAGAGGAAAA
CATCATCTCCCTTATGTTCTCAATATTGGATTTCCTGGTCAGAAAAATGAC
CTCTTACTCCTTCGGCTAGATTTAGCTGGAATTTCAATCTCTACTGGCTCA
GCCTGTACTGCAGGCGTTGTCCAATCCAGCCATGTTCTTGAAGCCATGTAT
GGCGCAAATTCAGAACGCTTGAAGGAATCCCTTCGCATCAGTTTGTCGCCA

CAAATACCGTTGAAGACCTACAAACCCTCGCAAAAACCTTAAAAGAAATT
ATCGGAGGTTAG 4172.1
(SEQ. ID. NO. 297)
ATGTTATTCAAATTATCTAAGGAAAAAATAGAGCTAGGCTTATCTCGTTTA
TCGCCAGCCCGTCGTATTTTTTTGAGTTTTGCCTTGGTCATTTTACTAGGC
TCTCTTCTTTTGAGCTTGCCCTTTGTCCAAGTTGAAAGCTCACGAGCGACT
TATTTTGATCATCTTTTCACTGCTGTCTCTGCAGTCTGTGTGACGGGTCTC
TCAACCCTTCCAGTAGCTCACACCTATAATATCTGGGGTCAAATAATCTGT
TTGCTCTTGATTCAGATCGGTGGTCTAGGGCTCATGACCTTTATTGGGGTT
TTCTATATCCAGAGCAAGCAAAAGCTTAGTCTTCGTAGCCGTGCAACTATT
CAGGATAGTTTTAGTTATGGAGAAACTCGATCTTTGAGAAAGTTTGTCTAT
TCTATTTTTCTCACGACCTTTTTGGTTGAGAGCTTGGGAGCTATTTTGCTT
AGTTTTCGCCTTATTCCTCAACTTGGCTGGGGACGTGGTCTTTTTAGTTCC
ATTTTTCTAGCGATCTCAGCCTTCTGTAATGCCGGTTTTGATAATTTAGGG
AGCACCAGTTTATTTGCTTTTCAGACCGATTTACTGGTCAATCTGGTGATT
GCAGGCTTGATTATTACAGGCGGCCTTGGTTTTATGGTCTGGTTTGATTTG
GCTGGTCATGTAGGAAGAAAGAAAAAAGGACGTCTGCACTTTCATACGAAG
CTTGTACTATTATTGACTATAGGTTTGTTGTTATTTGGAACAGCAACTACT
CTCTTTCTTGAGTGGAACAATGCTGGAACGATTGGCAATCTCCCTGTTGCC
GATAAGGTTTTAGTTAGCTTTTTTCAAACAGTGACGATGCGAACAGCTGGC
TTTTCTACGATAGATTATACTCAGGCTCATCCTGTGACTCTTTTGATTTAT
ATCTTACAGATGTTTCTAGGTGGGCACCTGGAGGAACAGCTGGGGGACTC
AAGATTACGACATTTTTTGTCCTCTTGGTCTTTGCACGAAGTGAGCTTCTA
GGCTTGCCTCATGCCAATGTTGCGAGACGAACGATCGCGCCGCGAACGGTT
CAAAAATCCTTTAGTGTCTTTATTATCTTTTTGATGAGCTTCTTGATAGGA
TTGATTCTGCTAGGGATAACAGCCAAAGGCAATCCTCCCTTTATCCACCTC
GTATTTGAAACCATTTCAGCTCTTAGTACAGTTGGTGTAACGGCAAATCTG
ACTCCTGACCTTGGGAAATTGGCTCTCAGTGTTATCATGCCACTTATGTTT
ATGGGACGAATTGGTCCCTTGACCTTGTTTGTTAGCTTGGCAGATTACCAT
CCAGAAAAGAAAGATATGATTCACTATATGAAAGCAGATATTAGTATTGGT
TAA 4172.2
(SEQ. ID. NO. 298)
ATGTCAGATCGTACGATTGGAATTTTGGGCTTGGGAATTTTTGGGAGCAGT
GTCCTAGCTGCCCTAGCCAAGCAGGATATGAATATTATCGCTATTGATGAC
CACGCAGAGCGCATCAATCAGTTTGAGCCAGTTTTGGCGCGTGGAGTGATT
GGTGACATCACAGATGAAGAATTATTGAGATCAGCAGGGATTGATACCTGC
GATACCGTTGTAGTCGCGACAGGTGAAAATCTGGAGTCGAGTGTGCTTGCG
GTTATGCACTGTAAGAGTTTGGGGGTACCGACTGTTATTGCTAAGGTCAAA
AGTCAGACCGCTAAGAAAAGTGCTAGAAAAGATTGGAGCTGACTCGGTTAT
CTCGCCAGAGTATGAAATGGGGCAGTCTCTAGCACAGACCATTCTTTTCCA

TAATAGTGTTGATGTCTTTCAGTTGGATAAAAATGTGTCTATCGTGGAGAT

GAAAATTCCTCAGTCTTGGGCAGGTCAAAGTCTGAGTAAATTAGACCTCCG

TGGCAAATACAATCTGAATATTTTGGGTTTCCGAGAGCAGGAAAATTCCCC

ATTGGATGTTGAATTTGGACCAGATGACCTCTTGAAAGCAGATACCTATAT

TTTGGCAGTCATCAACAACCAGTATTTGGATACCCTAGTAGCATTGAATTC

GTAA 4172.3

(SEQ. ID. NO. 299)
ATGAAGTTATTGTCTATCGCAATTTCTAGCTATAATGCAGCAGCCTATCTT

CATTACTGTGTGGAGTCGCTAGTGATTGGTGGTGAGCAAGTTGGGATTTTG

ATTATCAATGACGGGTCTCAGGATCAGACTCAGGAAATCGCTGAGTGTTTA

GCTAGCAAGTATCCTAATATCGTTAGAGCCATCTATCAGGAAAATAAATGC

CATGGCGGTGCGGTCAATCGTGGCTTGGTAGAGGCTTCTGGGCGCTATTTT

AAAGTAGTTGACAGTGATGACTGGGTGGATCCTCGTGCCTACTTGAAAATT

CTTGAAACCTTGCAGGAACTTGAGAGCAAAGGTCAAGAGGTGGATGTCTTT

GTGACCAATTTTGTCTATGAAAAGGAAGGGCAGTCTCGTAAGAAGAGTATG

AGTTACGATTCAGTCTTGCCTGTTCGGCAGATTTTTGGCTGGGACCAGGTC

GGAAATTTCTCCAAAGGCCAGTATACCATGATGCACTCGCTGATTTATCGG

ACAGATTTGTTGCGTGCTAGCCAGTTCTAA 4172.4

(SEQ. ID. NO. 300)
ATGAAATTCAATCCAAATCAAAGATATACTCGTTGGTCTATTCGCCGTCTC

AGTGTCGGTGTTGCCTCAGTTGTTGTGGCTAGTGGCTTCTTTGTCCTAGTT

GGTCAGCCAAGTTCTGTACGTGCCGATGGGCTCAATCCAACCCCAGGTCAA

GTCTTACCTGAAGAGACATCGGGAACGAAAGAGGGTGACTTATCAGAAAAA

CCAGGAGACACCGTTCTCACTCAAGCGAAACCTGAGGGCGTTACTGGAAAT

ACGAATTCACTTCCGACACCTACAGAAAGAACTGAAGTGAGCGAGGAAACA

AGCCCTTCTAGTCTGGATACACTTTTTGAAAAAGATGAAGAAGCTCAAAAA

AATCCAGAGCTAACAGATGTCTTAAAAGAAACTGTAGATACAGCTGATGTG

GATGGGACACAAGCAAGTCCAGCAGAAACTACTCCTGAACAAGTAAAAGGT

GGAGTGAAAGAAAATACAAAAGACAGCATCGATGTTCCTGCTGCTTATCTT

GAAAAAGCTGAAGGGAAAGGTCCTTTCACTGCCGGTGTAAACCAAGTAATT

CCTTATGAACTATTCGCTGGTGATGGTATGTTAACTCGTCTATTACTAAAA

GCTTCGGATAATGCTCCTTGGTCTGACAATGGTACTGCTAAAAATCCTGCT

TTACCTCCTCTTGAAGGATTAACAAAAGGGAAATACTTCTATGAAGTAGAC

TTAAATGGCAATACTGTTGGTAAACAAGGTCAAGCTTTAATTGATCAACTT

CGCGCTAATGGTACTCAAACTTATAAAGCTACTGTTAAAGTTTACGGAAAT

AAAGACGGTAAAGCTGACTTGACTAATCTAGTTGCTACTAAAAATGTAGAC

ATCAACATCAATGGATTAGTTGCTAAAGAAACAGTTCAAAAAGCCGTTGCA

GACAACGTTAAAGACAGTATCGATGTTCCAGCAGCCTACCTAGAAAAGCC

AAGGGTGAAGGTCCATTCACAGCAGGTGTCAACCATGTGATTCCATACGAA

CTCTTCGCAGGTGATGGCATGTTGACTCGTCTCTTGCTCAAGGCATCTGAC

AAGGCACCATGGTCAGATAACGGCGACGCTAAAAACCCAGCCCTATCTCCA

CTAGGCGAAAACGTGAAGACCAAAGGTCAATACTTCTATCAAGTAGCCTTG

GACGGAAATGTAGCTGGCAAAGAAAAACAAGCGCTCATTGACCAGTTCCGA

GCAAATGGTACTCAAACTTACAGCGCTACAGTCAATGTCTATGGTAACAAA

GACGGTAAACCAGACTTGGACAACATCGTAGCAACTAAAAAAGTCACTATT

AACATAAACGGTTTAATTTCTAAAGAAACAGTTCAAAAAGCCGTTGCAGAC

AACGTTAAAGACAGTATCGATGTTCCAGCAGCCTACCTAGAAAAAGCCAAG

GGTGAAGGTCCATTCACAGCAGGTGTCAACCATGTGATTCCATACGAACTC

TTCGCAGGTGATGGTATGTTGACTCGTCTCTTGCTCAAGGCATCTGACAAG

GCACCATGGTCAGATAACGGTGACGCTAAAAACCCAGCCCTATCTCCACTA

GGTGAAAACGTGAAGACCAAAGGTCAATACTTCTATCAATTAGCCTTGGAC

GGAAATGTAGCTGGCAAAGAAAAACAAGCGCTCATTGACCAGTTCCGAGCA

AACGGTACTCAAACTTACAGCGCTACAGTCAATGTCTATGGTAACAAAGAC

GGTAAACCAGACTTGGACAACATCGTAGCAACTAAAAAAGTCACTATTAAC

ATAAACGGTTTAATTTCTAAAGAAACAGTTCAAAAAGCCGTTGCAGACAAC

GTTAAGACAGTATCGATGTTCCAGCAGCCTACCTAG 4172.5

(SEQ. ID. NO. 301)
ATGAAACTAAAAGTTATATTTTGGTTGGATATATTATTTCAACCCTCTTA

ACCATTTTGGTTGTTTTTTGGGCTGTTCAAAAAATGCTGATTGCGAAAGGC

GAGATTTACTTTTTGCTTGGGATGACCATCGTTGCCAGCCTTGTCGGTGCT

GGGATTAGTCTCTTTCTCCTATTGCCAGTCTTTACGTCGTTGGGCAAACTC

AAGGAGCATGCCAAGCGGGTAGCGGCCAAGGATTTTCCTTCAAATTTGGAG

GTTCAAGGTCCTGTAGAATTTCAGCAATTAGGGCAAACTTTTAATGAGATG

TCCCATGATTTGCAGGTAAGCTTTGATTCCTTGGAAGAAAGCGAACGAGAA

AAGGGCTTGATGATTGCCCAGTTGTCGCATGATATTAAGACTCCTATCACT

TCGATCCAAGCGACGTAGAAGGGATTTTGGATGGGATTATCAAGGAGTCG

GAGCAAGCTCATTATCTAGCAACCATTGGACGCCAGACGGAGAGGCTCAAT

AAACTGGTTGAGGAGTTGAATTTTTTGACCCTAAACACAGCTAGAAATCAG

GTGGAAACTACCAGTAAAGACAGTATTTTTCTGGACAAGCTCTTAATTGAG

TGCATGAGTGAATTTCAGTTTTTGATTGAGCAGGAGAAGAGATGTCCAC

TTGCAGGTAATCCCAGAGTCTGCCCGGATTGAGGGAGATTATGCTAAGCTT

TCTCGTATCTTGGTGAATCTGGTCGATAACGCTTTTAAATATTCTGCTCCA

GGAACCAAGCTGGAAGTGGTGGCTAAGCTGGAGAAGGACCAGCTTTCAATC

AGTGTGACCGATGAAGGGCAGGGTATTGCCCCAGAGGATTTGGAAAATATT

TTCAAACGCCTTTATCGTGTCGAAACTTCGCGTAACATGAAGACAGGTGGT

CATGGATTAGGACTTGCGATTGCGCGTGAATTGGCCCATCAATTGGGTGGG

GAAATCACAGTCAGCAGCCAGTACGGTCTAGGAAGTACCTTTACCCTCGTT

CTCAACCTCTCTGGTAGTGAAAATAAAGCCTAA

TABLE 3-continued 4172.6
(SEQ. ID. NO. 302)
ATGTTTGGTCAAACGGCTCAACATGGTCTTACGAATAGCCTGAAAGACTTC
TGGATTTTTCTGCTGAATATAGGTCCACAATTGGCGTTTTTTTGCCAGATG
CTCCGCTGTTCCAGATCGGTTGAGCAGGGTACTGGAAATCACCGTCGTGAG
TTCAATATGATTCAGCAGATATTCTCGCATTTTGGGATGACTCACTTGGGA
CAAATCAAGTTGGTCTATCAAGAGTCGATTGACCTTGAGTTGCTGGTCAAT
GCACTTAATCATCACTTGCTCATTGACAGACTGGTCCTCACGCCCAATCAA
ATAACGATAGAAATCGACAGGCAGATAGTACATGGTCTTGACCTGCTGAAG
GGGCGTAAAGACAAAGAGATTATCGACATAAAAAGTATGTTCAGGCAGTTA
GAACTGGCTAGCACGCAACAAATCTGTCCGATAAATCAGCGAGTGCATCAT
GGTATACTGGCCTTTGGAGAAATTTCCGACCTGGTCCCAGCCAAAAATCTG
CCGAACAGGCAAGACTGA 4174.1
(SEQ. ID. NO. 303)
ATGGAACATTTAGCAACTTATTTTTCAACCTATGGAGGAGCTTTCTTCGCT
GCATTGGGAATTGTATTGGCGGTTGGATTAAGCGGTATGGGGTCTGCTTAT
GGAGTTGGTAAGGCTGGGCAATCTGCCGCAGCTTTACTGAAAGAACAGCCT
GAAAAGTTTGCCTCAGCTTTGATATTGCAATTATTGCCCGGAACACAAGGA
TTATATGGTTTTGTTATTGGAATTTTAATTTGGTTGCAATTAACTCCAGAA
CTTCCTTTAGAAAAAGGCGTTGCTTATTTCTTTGTAGCTCTTCCAATTGCT
ATTGTAGGATACTTTTCAGCTAAGCATCAAGGAAATGTAGCAGTAGCGGA
ATGCAAATCTTGGCTAAAAGACCAAAAGAATTCATGAAGGGAGCAATTTTA
GCTGCCATGGTAGAAACCTATGCAATTCTTGCTTTTGTCGTATCATTCATT
TTGACCCTTCGTGTATTA 4175.2
(SEQ. ID. NO. 304)
ATGTTAAAATCAGAAAAACAATCACGTTATCAAATGTTAAATGAAGAATTG
TCCTTCCTATTGGAAGGCGAAACCAATGTTTTGGCTAATCTTTCCAACGCC
AGTGCTCTCATAAAATCACGTTTTCCTAATACCGTATTTGCAGGCTTTTAT
TTGTTCGATGGAAAGGAATTGGTTTTAGGCCCCTTCCAAGGAGGTGTTTCC
TGCATCCGTATTGCACTAGGCAAGGGTGTTTGTGGTGAGGCAGCTCACTTT
CAGGAAACTGTTATTGTTGGAGATGTGACGACCTATCTCAACTATATTTCT
TGTGATAGTCTAGCTAAAAGTGAAATTGTGGTGCCGATGATGAAGAATGGT
TTACGATGCTATGGATCGAGATTATTTGGAACAATTTGTCGCTATTTTGCT
CAGTTACTTGGAGTTCTGGATCTGGATTCTTCAGAGATTGAGGATGAAAAG
ACAGCATGGGACTTTACGATGTTTGAGGAAAAATCTTAA 4175.3
(SEQ. ID. NO. 305)
ATGTCAGTATTAGAGATCAAAGATCTTCACGTTGAGATTGAAGGAAAAGAA
ATTTTAAAAGGGGTTAACCTGACCCTGAAAACAGGAGAAATTGCCGCTATC
ATGGGACCAAATGGTACAGGTAAATCGACTCTTTCTGCCGCTATCATGGGA
AATCCAAACTATGAAGTAACTAAAGGTGAAGTTTTGTTTGATGGCGTAAAC
ATCCTTGAGTTGGAAGTGGATGAGCGTGCGCGTATGGGACTTTTCCTTGCT 4172.6 continued
ATGCAATACCCATCAGAAATCCCTGGAATTACCAATGCTGAGTTTCTTCGT
GCCGCTATGAATGCGGGTAAAGAAGATGATGAGAAGATTTCAGTTCGTGAG
TTTATTACTAAGCTAGATGAAAAAATGGAATTGCTCAACATGAAAGAAGAA
ATGGCAGAGCGTTACCTCAACGAAGGCTTCTCTGGTGGTGAGAAAAAACGC
AATGAAATTCTTCAACTTTTGATGTTGGAGCCAACATTTGCTCTTTTGGAC
GAGATTGACTCAGGTCTTGATATTGACGCTCTTAAAGTTGTGTCTAAAGGT
GTCAATGCCATGCGTGGTGAAGGTTTTGGTGCTATGATCATCACTCACTAC
CAACGTCTTTTGAACTATATCACACCTGATGTGGTACACGTGATGATGGAA
GGTCGTGTTGTCCTTTCTGGTGGTCCAGAATTGGCTGCGCGTTTGGAACGT
GAAGGATACGCAAAATTAGCTGAAGAACTTGGCTACGACTACAAGGAAGAA
TTGTAA 4174.4
(SEQ. ID. NO. 306)
ATGCCCTACAAAAGACAAAGGAGTTTTTCAATGGCACTTTCTAAACTAGAT
AGCCTTTATATGGCAGTGGTAGCAGACCATTCGAAAAATCCACATCACCAA
GGGAAGTTAGAAGATGCTGAGCAAATCAGTCTCAACAATCCGACTTGTGGG
GATGTCATCAACCTCTCTGTCAAGTTTGATGCAGAGGACCGTTTGGAAGAT
ATTGCTTTTCTAAATTCAGGATGCACGATTTCAACTGCTTCTGCTAGTATG
ATGACAGATGCCGTTTTAGGAAAAACCAAACAAGAAATTTTAGAACTGGCG
ACTATTTTTCTGAAATGGTTCAAGGGCAAAAAGATGAGCGTCAAGACCAA
CTTGGGAGACGCGGCATTCTTGTCAGGTGTTGCCAAATTCCCTCAAAGAATC
AAGTGTGCAACCCTAGCTTGGAATGCCCTTAAGAAAACAATTGAAAATCAA
GAAAAACAGTAA 4175.5
(SEQ. ID. NO. 307)
ATGAAAATTCAAGACCTATTGAGAAAAGATGTCATGTTGCTAGATTTGCAG
GCAACTGAAAAAACAGCTGTCATCGACGAGATGATTAAAAATTTGACAGAC
CACGGTTATGTAACAGATTTTGAAACATTTAAAGAAGGAATTTTGGCGCGT
GAAGCTTTGACTTCTACTGGTTTGGGTGATGGAATCGCAATGCCTCACAGC
AAAAACGCTGCTGTCAAAGAAGCGACAGTTCTATTTGCTAAGTCAAATAAG
GGTGTTGACTACGAGAGCTTGGATGGACAAGCAACTGACCTCTTCTTCATG
ATTGCAGCTCCAGAAGGTGCCAATGATACTCACTTGGCAGCCTTGGCAGAA
TTGTCTCAATACTTGATGAAAGACGGTTTTGCAGACAAACTTCGTCAAGCA
ACATCTGCAGACCAAGTTATCGAACTTTTTGACCAAGCTTCAGAAAAAACT
GAGGAACTTGTTCAAGCACCTGCTAATGACTCTGGTGACTTTATCGTAGCT
GTTACAGCTTGTACAACAGGTATTGCCCACACTTACATGGCCCAAGAAGCC
CTTCAAAAAGTAGCTGCTGAAATGGGGGTTGGTATCAAGGTCGAAACCAAC
GGTGCTAGCGGTGTTGGAAATCAACTAACTGCAGAAGATATCCGTAAGGCT
AAAGCTATTATCATTGCAGCAGACAAGGCCGTTGAAATGGATCGATTTGAT
GGAAAACCATTGATCCATCGTCCAGTTGCTGACGGTATCCGTAAGACAGAA
GAGCTAATTAACTTGGCTCTTTCAGGAGATACTGAAGTCTACCGTGCCGCT
AATGGTGCCAAAGCTGCAACAGCCTCTAACGAAAAACAAAGCCTTGGTGGT TABLE 3-continued GCCTTGTACAAACACTTGATGAGTGGTGTATCTCAAATGTTACCATTCGTT
ATCGGTGGTGGTATCATGATTGCCCTTGCCTTCTTGATTGACGGTGCTTTG
GGTGTTCCAAATGAAAACCTTGGCAATCTTGGTTCTTACCATGAGTTAGCT
TCTATGTTCATGAAAATTGGTGGAGCTGCCTTTGGTTTGATGCTTCCAGTC
TTTGCGGGTTATGTTGCCTACTCTATTGCTGAAAAACCGGGTTTGGTAGCA
GGTTTCGTGGCTGGTGCTATTGCCAAAGAAGGTTTTGCCTTTGGTAAAATT
CCTTATGCCGCAGGTGGTGAAGCAACTTCAACTCTTGCAGGTGTCTCATCT
GGTTTCCTAGGTGCCCTTGTTGGTGGATTTATCGCAGGTGCCTTGGTTCTT
GCCATCAGAAATACGTTAAAGTTCCTCGTTCACTCGAAGGTGCTAAATCAA
TCCTTCTATTGCCACTTCTTGGAACAATCTTGACAGGATTTGTTATGCTAG
CTGTGAATATCCCAATGGCTGCAATCAACACTGCTATGAATGACTTCCTAG
GCGGTCTTGGAGGAGGTTCAGCTGTCCTTCTTGGTATCGTCCTTGGTGGAA
TGATGGCTGTTGACATGGGTGGACCAGTTAATAAAGCAGCTTATGTCTTTG
GTACAGGTACGCTTGCAGCAACTGTTTCTTCAGGTGGTTCTGTAGCCATGG
CAGCAGTTATGGCTGGAGGAATGGTGCCACCACTTGCAATCTTTGTCGCAA
CTCTTCTTTTCAAAGATAAATTTACTAAGGAAGAACGTAACTCTGGTTTGA
CAAACATCATCATGGGCTTGTCATTTATCACTGAGGGAGCGATTCCATTTG
GTGCCGCTGACCCAGCTCGTGCGATTCCAAGCTTCATCCTTGGTTCAGCAG
TAGCAGGTGGACTCGTTGGTCTTACTGGTATCAAACTCATGGCGCCACACG
GAGGAATCTTCGTTATCGCCCTTACTTCAAATGCTCTCCTTTACCTCGTTT
CTGTCTTGGTAGGAGCAATCGTAAGTGGTGTGGTTTATGGTTACCTACGCA
AACCACAAGCATAA 4175.6
(SEQ. ID. NO. 308)
ATGGCAAACAAGAATACAAGTACAACAAGACGGAGACCGTCTAAAGCAGAA
CTGGAAAGAAAAGAAGCGATTCAACGAATGTTGATTTCGTTAGGAATTGCG
ATTTTATTGATTTTCGCAGCCTTCAAATTAGGGGCTGCAGGTATAACCCTT
TATAATTTAATTCGCTTGCTAGTGGGTAGCCTAGCTTATCTGGCGATATTC
GGCCTATTAATCTATCTCTTCTTTTTTCAAGTGGATACGAAAACAGGAAGGA
CTCTTATCTGGCTTTTTCACCATATTTGCTGGCTTACTCTTGATTTTTGAG
GCCTACTTGGTTTGGAAATATGGTTTGGACAAGTCCGTTCTAAAAGGGACC
ATGGCTCAGGTTGTGACAGATCTGACTGGTTTTCGAACGACTAGCTTTGCT
GGAGGGGGCTTGATCGGGGTCGCTCTTTATATTCCACAGCCTTTCTCTTTT
CAAATATCGGAACTTACTTTATTGGTTCTATCTTGATTTTAGTGGGTTCTC
TCCTAGTCAGCCCTTGGTCTGTTTACGATATTGCTGAATTTTTCAGTAGAG
GCTTTGCCAAATGGTGGAAGGGCACGAGCGTCGAAAAGAGGAACGCTTTG
TCAAACAAGAAGAAAAGCTCGCCAAAAGGCTGAGAAAGAGGCTAGATTAG
AACAAGAAGAGACTGAAAAAGCCTTACTCGATTTGCCTCCTGTTGATATGG
AAACGGGTGAAATTCTGACAGAGGAAGCTGTTCAAAATCTTCCACCTATTC
CAGAAGAAAAGTGGGTGGAACCAGAAATCATCCTGCCTCAAGCTGAACTTA
AATTCCCTGAACAGGAAGATGACTCAGATGACGAAGATGTTCAGGTCGATT TTTCAGCCAAAGAAGCCCTTGAATACAAACTTCCAAGCTTACAACTCTTTG
CACCAGATAAACCAAAAGATCAGTCTAAAGAGAAGAAAATTGTCAGAGAAA
ATATCAAAATCTTAGAAGCAACCTTTGCTAGCTTTGGTATTAAGGTAACAG
TTGAACGGGCCGAAATTGGGCCATCAGTGACCAAGTATGAAGTCAAGCCGG
CTGTTGGTGTAAGGGTCAACCGCATTTCCAATCTATCAGATGACCTCGCTC
TAGCCTTGGCTGCCAAAGATGTCCGGATTGAAGCACCAATCCCTGGGAAAT
CCCTAATCGGAATTGAAGTGCCCAACTCCGATATTGCCACTGTATCTTTCC
GAGAACTATGGGAACAATCGCAAACGAAAGCAGAAAATTTCTTGGAAATTC
CTTTAGGGAAGGCTGTTAATGGAACCGCAAGAGCTTTTGACCTTTCTAAAA
TGCCCCACTTGCTAGTTGCAGGTTCAACGGGTTCAGGGAAGTCAGTAGCAG
TTAACGGCATTATTGCTAGCATTCTCATGAAGGCGAGACCAGATCAAGTTA
AATTTATGATGGTCGATCCCAAGATGGTTGAGTTATCTGTTTACAATGATA
TTCCCCACCTCTTGATTCCAGTCGTGACCAATCCACGCAAAGCCAGCAAGG
CTCTGCAAAAGGTTGTGGATGAAATGGAAAACCGTTATGAACTCTTTGCCA
AGGTGGGAGTTCGGAATATTGCAGGTTTTAATGCCAAGGTAGAAGAGTTCA
ATTCCCAGTCTGAGTACAAGCAAATTCCGCTACCATTCATTGTCGTGATTG
TGGATGAGTTGGCTGACCTCATGATGGTGGCCAGCAAGGAAGTGGAAGATG
CTATCATCCGTCTTGGGCAGAAGGCGCGTGCTGCAGGTATCCACATGATTC
TTGCAACTCAGCGTCCATCTGTTGATGTCATCTCTGGTTTGATTAAGGCCA
ATGTTCCATCTCGTGTAGCATTTGCGGTTTCATCAGGAACAGACTCCCGTA
CGATTTTGGATGAAAATGGAGCAGAAAAACTTCTTGGTCGAGGAGACATGC
TCTTTAAACCGATTGATGAAAATCATCCAGTTCGTCTCCAAGGCTCCTTTA
TCTCGGATGACGATGTTGAGCGCATTGTGAACTTCATCAAGACTCAGGCAG
ATGCAGACTACGATGAGAGTTTTGATCCAGGTGAGGTTTCTGAAAATGAAG
GAGAATTTTCGGATGGAGATGCTGGTGGTGATCCGCTTTTTGAAGAAGCTA
AGTCTTTGGTTATCGAAACACAGAAAGCCAGTGCGTCTATGATTCAGCGTC
GTTTATCAGTTGGATTTAACCGTGCGACCCGTCTCATGGAAGAACTGGAGA
TAGCAGGTGTCATCGGTCCAGCTGAAGGTACCAAACCTCGAAAAGTGTTAC
AACAATAA 4176.1
(SEQ. ID. NO. 309)
ATGAGTTATTTTAAAAAATATAAATTCGATAAATCCCAGTTCAAACTTGGT
ATGCGAACCTTTAAAACAGGTATTGCTGTTTTTCTAGTTCTCTTGATTTTT
GGCTTTTTTGGCTGGAAAGGTCTTCAAATTGGTGCTTTGACAGCCGTTTTT
AGCCTGAGGGAGAGTTTTGATGAGAGTGTTCATTTTGGGACTTCGCGTATT
CTAGGAAATAGTATCGGTGGACTCTATGCCTTGGTCTTCTTCTTATTAAAT
ACCTTTTTCCACGAAGCCTTTTGGGTGACCTTGGTAGTTGTTCCAATCTGC
ACCATGTTAACCATTATGACAAATGTAGCCATGAATAACAAAGCAGGGGTT
ATTGGTGGTGTAGCAGCTATGTTAATCATTACCCTATCAATTCCAAGTGGT
GAGACAATTTTGTACGTGTTTGTGCGTGTATTAGAAACGTTTATGGGAGTT
TTTGTCGCAATTATCGTAAATTACGATATTGATCGTATTCGTCTCTTTTTA

GAGAAAAAAGAAAAATAA 4178.2
(SEQ. ID. NO. 310)
ATGAATAAATCAGAACACCGCCACCAACTTATACGCGCTCTTATCACAAAA
AACAAGATTCATACACAGGCTGAGTTGCAAGCCCTTCTTGCTGAGAACGAC
ATTCAAGTAACCCAGGCAACCCTCTCACGCGACATCAAAAATATGAACCTA
TCAAAAGTCCGCGAAGAAGATAGCGCTTATTATGTTCTTAACAATGGTTCC
ATCTCAAAATGGGAAAAACGTCTCGAACTCTACATGGAAGACGCCCTTGTC
TGGATGCGCCCAGTTCAACACCAAGTCCTACTAAAAACCCTTCCTGGACTG
GCTCAATCCTTTGGTTCTATCATTGATACTTTGAGCTTCCCTGACGCTATC
GCTACCCTTTGTGGTAATGATGTCTGTCTTATCATCTGTGAAGATGCAGAT
ACTGCTCAAAAGTGCTTTGAAGAACTGAAAAAATTCGCCCCACCATTTTTC
TTTGAAGAATAA 4179.1
(SEQ. ID. NO. 311)
ATGAAAAGTATAAAATTAAATGCTCTATCTTACATGGGAATTCGTGTCTTG
AATATTATTTTTCCCATCCTAACTGGAACCTATGTCGCGCGTGTCTTGGAC
CGAACTGACTATGGTTACTTCAACTCAGTCGACACTATTTTGTCATTTTTC
TTGCCCTTTGCAACTTATGGTGTCTATAACTACGGTTTAAGGGCTATCAGT
AATGTCAAGGATAACAAAAAAGATCTTAACAGAACCTTTTCTAGTCTTTTT
TATTTGTGCATCGCTTGTACGATTTTGACCACTGCTGTCTATATCCTAGCC
TATCCTCTCTTCTTTACTGATAATCCAATCGTCAAAAGGTCTACCTTGTT
ATGGGGATTCAACTCATTGCCCAGATTTTTTCAATCGAATGGGTCAATGAA
GCTCTGGAAAATTACAGTTTTCTCTTTTACAAAACTGCCTTCATCCGTATC
CTGATGCTGGTCTCTATTTTCTTATTTGTTAAAAATGAACACGATATTGTT
GTCTATACACTTGTGATGAGTTTATCGACGCTGATTAACTACCTGATTAGT
TATTTTTGGATTAAAAGAGACATCAAACTTGTTAAAATTCACCTAAGTGAT
TTTAAACCACTCTTTCTCCCTCTGACAGCCATGTTAGTCTTTGCCAATGCC
AATATGCTCTTCACTTTTTTAGATCGCCTCTTCCTCGTTAAAACAGGGATT
GATGTCAACGTTAGTTACTATACCATAGCTCAGCGAATTGTGACCGTTATA
GCTGGGGTTGTAACAGGTGCAATTGGAGTGAGTGTGCCTCGTCTCAGTTAC
TATCTGGGGAAAGGAGACAAAGAAGCCTATGTTTCTCTGGTTAATAGAGGT
AGTCGAATCTTTAACTTCTTTATCATTCCACTGAGTTTTGGACTCATGGTT
TTAGGACCAAATGCCATCCTACTTTACGGTAGTGAAAAATATATCGGAGGC
GGCATCTTGACCTCTCTCTTCGCTTTTCGTACGATTATCCTGGCCTTAGAT
ACCATTCTTGGTTCCCAAATTCTCTTTACCAATGGCTATGAAAAACGTATC
ACAGTCTATACAGTCTTTGCTGGGCTACTCAATTTGGGCTTGAATAGTCTC
CTTTTTTTCAACCATATCGTGGCTCCTGAATACTACTTACTGACAACTATG
CTATCAGAGACTTCTCTACTTGTTTTCTATATCATTTTCATCCATAGAAAA
CAACTCATCCACTTGGGACATATCTTTAGCTATACTGTTCGATACTCTCTC
TTTTCACTTTCCTTTGTAGCAATTTATTTCCTGATTAATTTCGTGTATCCT
GTAGATATGGTCATTAATTTGCCATTTTTGATTAATACTGGTTTGATTGTC

TTGCTATCAGCTATCTCTTATATTAGTCTACTTGTCTTCACAAAAGATAGC
ATTTTCTATGAATTTTTAAACCATGTCCTAGCCTTAAAAAATAAATTTAAA
AAATCATAG 4179.2
(SEQ. ID. NO. 312)
ATGAAACAACTAACCGTTGAAGATGCCAAACAAATTGAATTAGAAATTTTG
GATTATATTGATACTCTCTGTAAAAAGCACAATATCAACTATATTATTAAC
TACGGTACTCTGATTGGGGCGGTTCGACATGAGGGCTTTATCCCTTGGGAC
GACGATATTGATCTGTCCATGCCTAGAGAAGACTACCAACGATTTATTAAC
ATTTTTCAAAAGGAAAAAAGCAAGTATAAGCTCCTATCCTTAGAAACTGAT
AAGAACTACTTTAACAACTTTATCAAGATAACCGACAGTACGACTAAAATT
ATTGATACTCGAAATACAAAAACCTATGAGTCTGGTATCTTTATCGATATT
TTCCCTATAGATCGCTTTGATGATCCTAAGGTCATTGATACTTGTTATAAA
CTGGAAAGCTTCAAACTGCTGTCTTTCAGTAAACATAAAAATATTGTCTAT
AAGGATAGCCTTTTAAAAGATTGGATACGAACAGCCTTCTGGTTACTCCTT
CGACCGGTTTCTCCTCGTTATTTTGCAAATAAAATCGAGAAAGAAATTCAA
AAATATAGTCGTGAAAATGGGCAATATATGGCTTTTATCCCTTCAAAATTT
AAGGAAAAGGAAGTCTTCCCAAGTGGTACCTTTGATAAAACAATCGATTTA
CCCTTTGAGAATTTAAGCCTTCCTGCACCTGAAAAATTTGATACTATTTTG
ACACAATTTTATGGAGATTATATGACCCTACCACCAGAAGAAAACGCTTC
TACAGTCATGAATTTCACGCTTATAAATTGGAGGATTAG 4179.3
(SEQ. ID. NO. 313)
ATGATAAAAATCAATCATCTAACCATCACACAAAACAAAGATTTACGAGAT
CTTGTATCTGACCTAACCATGACCATCCAAGACGGGGAAAAGGTTGCTATT
ATTGGTGAAGAAGGAAATGGCAAATCAACCCTTACTTAAAATTTTAATGGGG
GAAGCTTTGTCTGATTTCACTATCAAGGGAAACATCCAATCTGACTATCAG
TCACTGGCCTACATTCCTCAAAAAGTCCCTGAGGACCTAAAAAAGAAAACT
TTACACGACTACTTCTTTTTAGATTCTATTGATTTAGACTACAGTATCCTC
TATCGTTTGGCGGAGGAATTGCATTTTGATAGCAATCGTTTCGCAAGTGAC
CAAGAGATTGGCAATCTATCAGGGGGCGAAGCTTTGAAAATTCAGCTTATC
CATGAGTTAGCCAAACCCTTTGAGATTCTATTTTTAGATGAACCTTCAAAT
GACCTAGACCTTGAGACAGTTGATTGGCTAAAAGGCCAGATTCAAAAGACC
AGGCAAACCGTTATTTTCATTTCCCATGATGAAGACTTTCTTTCTGAAACG
GCAGACACTATTGTTCACTTGCGACTGGTCAAACACCGTAAAGAAGCGGAA
ACGCTAGTAGAGCATTTAGACTATGATAGCTATAGTGAGCAGAGAAAGGCT
AATTTTGGCAAACAAAGTCAGCAAGCTGCTAACAACCAAAGAGCCTACGAT
AAAACCATGGAAAACATCGGAGAGTTAAGCAAAATGTAGAAACTGCGCTT
CGAGCTACCAAAGATAGTACTGCCGGTCGCCTATTGGCTAAAAAGATGAAA
ACTGTCCTCTCACAAGAAAAACGCTACGAAAAGGCAGCTCAGTCCATGACT
CAAAAGCCACTTGAAGAGGAACAAATCCAACTTTTCTTTTCAGACATCCAA
CCATTACCAGCTTCTAAAGTCTTAGTCCAACTGGAAAAAGAAAATTTGTCC

TABLE 3-continued

ATTGACGACCGAGTTTTGGTTCAAAAACTACAACTAACTGTCCGTGGCCAA
GAAAAAATCGGTATTATCGGGCCAAATGGTGTTGGGAAATCAACTCTGTTA
GCCAAGTTACAGAGACTTCTGAATGATAAAAGAGAGATTTCACTTGGTTTT
ATGCCACAAGATTACCACAAAAAACTGCAATTGGATTTATCCCCAATAGCC
TATCTCAGTAAAACTGGGGAAAAAGAGGAACTACAGAAAATCCAATCTCAC
CTAGCTAGTCTCAATTTCAGTTATCCAGAAATGCAGCATCAAATTCGCTCC
TTATCTGGCGGACAACAGGGAAAACTCCTGCTTTTGGATTTAGTCCTGCGC
AAACCAAACTTTCTCCTGCTGGATGAACCCACACGAAACTTTTCTCCCACT
TCTCAACCCCAAATCAGAAAACTCTTTGCTACCTATCCAGGCGGTCTCATC
ACTGTTTCGCATGACCGTCGTTTCTTAAAAGAAGTCTGCTCGATCATCTAT
CGCATGACAGAACACGGTTTGAAGCTAGTTAATTTAGAAGATTTATAA 4179.4
(SEQ. ID. NO. 314)
ATGAAACCAAAAACATTTTACAACTTGCTTGCCGAGCAGAATCTTCCACTT
TCGGACCAGCAAAAAGAACAATTTGAACGTTATTTTGAGCTCTTGGTCGAG
TGGAATGAGAAGATTAATTTGACGGCGATTACGGACAAGGAAGAAGTTTAT
CTCAAACATTTTTACGATTCGATTGCACCCATTCTTCAAGGTTTGATTCCC
AATGAAACTATCAAACTTCTTGATATCGGGGCTGGGGCAGGATTTCCTAGT
CTACCAATGAAAATTCTCTATCCGGAGTTAGATGTGACCATTATTGATTCA
CTCAATAAGCGCATCAACTTCCTACAACTCTTGGCTCAAGAACTGGATTTG
AACGGAGTTCATTTCTACCACGGACGTGCCGAAGATTTTGCCCAAGACAAG
AACTTCCGTGCTCAATATGATTTTGTAACAGCTCGTGCGGTTGCCCGTATG
CAGGTCCTATCTGAATTGACTATTCCCTACCTTAAGGTTGGTGGCAAACTA
TTAGCACTCAAGGCTAGCAATGCGCCTGAGGAATTATTAGAAGCTAAGAAT
GCCCTCAATCTCCTTTTTAGTAAGGTCGAAGACAATCTCAGctACGCCCTA
CCGAATAGAGATCCGCGCTATATCACAGTGGTAGAAAAGAAAAAAGAAACA
CCAAATAAATATCCACGTAAGGCTGGTATGCCAAATAAACGCCCACTTTAA 4179.6
(SEQ. ID. NO. 315)
ATGAGTATTAAACTAATTGCCGTTGATATCGACGGAACCCTTGTCAACAGC
CAAAAGGAAATCACTCCTGAAGTTTTTTCTGCCATCCAAGATGCCAAAGAA
GCTGGTGTCAAAGTCGTGATTGCAACTGGCCGCCCTATCGCAGGCGTTGCC
AAACTTCTAGACGACTTGCAGTTGAGAGACGAGGGGGACTATGTGGTAACC
TTCAACGGTGCCCTTGTCCAAGAAACTGCTACAGGACATGAGATTATCAGC
GAATCCTTGACTTATGAGGATTATCTAGATATGGAATTCCTCAGTCGCAAG
CTCGGTGTCCACATGCATGCCATTACCAAGGACGGTATCTATACTGCAAAT
CGCAATATCGGAAAATACACTGTACACGAATCAACCCTCGTCAGCATGCCT
ATCTTCTACCGTACCCCTGAAGAAATGGCTGGCAAAGAAATTGTTAAATGT
ATGTTTATCGATGAACCAGAAATTCTCGATGCTGCGATTGAAAAAATTCCA
GCAGAATTTTACGAGCGCTACTCCATCAACAAATCTGCTCCTTTCTACCTC
GAACTCCTTAAAAAGAATGTAGACAAGGGTTCAGCCATTACTCACTTGGCT
GAAAAACTCGGATTGACCAAAGATGAAACCATGGCAATCGGTGATGAAGAA

AATGACCGTGCCATGCTGGAAGTCGTTGGAAACCCCGTTGTCATGGAAAAT
GGAAATCCAGAAATCAAAAAAATCGCCAAATACATCACCAAAACAAATGAC
GAATCCGGCGTTGCCCATGCCATCCGAACATGGGTACTGTAA 4179.7
(SEQ. ID. NO. 316)
ATGACTTGGATTATTCTTGGAGTTATCGCTCTTATTGTTATTTTTGTGATT
GTTAGCTATAACGGTTTGGTTAAAAATCGTATGCAAACCAAGGAGGCTTGG
AGTCAGATTGATGTTCAGTTGAAACGTCGCAATGACCTCTTGCCAAACTTG
ATTGAGACTGTAAAAGGTTATGCCAAATATGAAGGTTCTACCCTTGAAAAG
GTGGCAGAACTACGTAACCAAGTGGCGGCAGCGACTTCACCAGCAGAAGCT
ATGAAAGCCAGTGATGCCCTCACTCGTCAGGTTTCAGGTATTTTTGCAGTT
GCAGAAAGCTATCCAGATTTGAAAGCTAGTGCTAACTTTGTTAAATTGCAA
GAGGAGTTGACAAACACAGAAAATAAAATTTCTTACTCTCGTCAACTCTAT
AACAGTGTTGTCAGCAACTACAATGTAAAATTAGAAACTTTCCCGAGCAAT
ATTATCGCTGGAATGTTTGGATTTAAAGCGGCAGATTTCCTTCAAACACCT
GAAGAGGAAAAGTCGGTTCCTAAAGTTGATTTTAGCGGTTTAGGTGACTAA 4179.8
(SEQ. ID. NO. 317)
ATGTTGTTTGATCAAATTGCAAGCAATAAACGAAAAACCTGGATTTTGTTG
CTGGTATTTTTCCTACTCTTAGCTCTTGTTGGTTATGCGGTTGGTTATCTC
TTTATAAGATCTGGACTTGGTGGTTTGGTTATTGCACTGATTATCGGCTTT
ATCTACGCTTTGTCTATGATTTTTCAATCGACAGAGATTGTCATGTCCATG
AATGGAGCGCGTGAGGTGGATGAGCAAACGGCACCAGACCTCTACCATGTA
GTGGAAGATATGGCTCTGGTCGCTCAGATTCCTATGCCCCGTGTTTTCATC
ATTGATGATCCAGCCTTAAATGCCTTTGCGACAGGTTCTAATCCTCAAAAT
GCGGCTGTTGCTGCGACTTCAGGTCTACTAGCTATCATGAATCGTGAAGAA
CTAGAAGCTGTTATGGGACATGAAGTCAGTCATATTCGTAATTATGATATC
CGTATTTCGACTATTGCAGTTGCCCTTGCTAGTGCTATCACCATGCTTTCT
AGTATGGCAGGTCGTATGATGTGGTGGGGTGGAGCAGGTCGCAGACGAAGT
GATGATGACCGAGATGGAAATGGTCTTGAAATCATTATGCTAGTGGTTTCC
CTACTAGCTATTGTACTGGCACCTCTCGCTGCAACCTTGGTTCAGCTCGCT
ATTTCTCGTCAGAGGGAATTTCTGGCAGATGCATCTAGTGTCGAGCTGACT
CGCAATCCCCAGGGAATGATTAATGCCCTAGATAAGTTGGACAATAGCAAA
CCTATGAGTCGCCACGTCGATGATGCTAGCAGTGCCCTTTATATCAATGAT
CCTAAGAAAGGTGGGGGGTTCCAAAAACTCTTTTATACCCACCCACCTATC
TCAGAACGGATTGAACGTTTAAAACAGATGTAA 4179.9
(SEQ. ID. NO. 318)
ATGAAATTAAATATTCAAGAAATTCGTAAGCAGTCTGAAGGTTTGAACTTT
GAACAAACGTTAGATTTAGTTGATGACCTGCGTGCACGTAATCAAGAAATT
TTAGATGTAAAAGATATCCTTGCAGTTGGGAAAGTACAATATGAAGACCGT
ATGTATTTCTTAGATTATCAACTATCTTATACCATTGTTCTTGCTTCGAGT
CGCAGTATGGAGCCAGTTGAGTTAGTTGAATCTTATCCAGTCACGGAAGTT

TABLE 3-continued

TTCATGGAAGGCGCAACTAACCAGCTAGATCAAGAAGTTTTAGATGATGAC
TTGGTCTTGCCCATCGAAAATGGGGAGCTTGACCTTGCTGAGAGTGTATCA
GACAATATCCTGCTAAACATTCCTATCAAGGTCTTGACGGCTGAAGAAGAA
GCTGGTCAAGGATTATCTCAGGAAATGACTGGCAAATCATGACAGAGGAA
GAATACCAAGCTCAAAAAGCAGTAAAGAAAGAAGAAAACAGTCCTTTTGCT
GGCTTACAAGGACTATTTGACGGAGATGAATAA 4179.12
(SEQ. ID. NO. 319)
ATGGAGTTATTTATGAAAATCACAAACTATGAAATCTATAAGTTAAAAAAA
TCAGGTTTGACCAATCAACAGATTTTGAAAGTGCTAGAATACGGTGAAAAT
GTTGATCAGGAGCTTTTGTTGGGTGATATTGCAGATATCTCAGGTTGCCGT
AATCCAGCCGTTTTTATGGAACGTTATTTTCAGATAGACGATGCGCATTTG
TCGAAAGAGTTTCAAAAATTTCCATCTTTCTCTATTTTAGATGACTGTTAT
CCCTTGGGATTTGAGTGAAATATATGATGCGCTGTACTTTTATTTTACAAG
GGAAATCTTGACCTCCTGAAATTCCCGAAGGTAGCGGTCGTGGGCAGTCGT
GCTTGTAGCAAACAGGGAGCTAAGTCAGTTGAAAAAGTCATTCAAGGCTTG
GAAAATGAACTGGTTATTGTCAGTGGTCTGGCCAAGGGCATTGACACAGCA
GCTCATATGGCAGCTCTTCAGAATGGCGGAAAAACCATTGCAGTGATTGGA
ACAGGACTGGATGTGTTTTATCCTAAAGCCAATAAACGCTTGCAAGACTAC
ATCGGCAATGACCATCTGGTTCTAAGTGAATATGGACCTGGTGAACAACCT
CTGAAATTTCATTTTCCTGCCCGTAATCGCATCATTGCTGGACTTTGTCGT
GGTGTGATTGTAGCAGAGGCTAAGATGCGTTCAGGTAGTCTCATTACGTGT
GAGCGAGCAATGGAAGAAGGACGCGATGTCTTTGCTATTCCTGGTAGCATT
TTAGATGGACTATCAGACGGTTGCCATCATTTGATTCAAGAAGGAGCAAAA
TTGGTCACCAGTGGGCAAGATGTTCTTGCGGAATTTGAATTTTAA 4181.1
(SEQ. ID. NO. 320)
ATGAAACGTCAATTAGCCTTGGTCGTCTTTAGTGGTGGTCAAGATTCAACA
ACCTGCCTTTTCTGGGTCATGCAACACTATGAAACAGTCGAAGCTGTCACC
TTTGCCTACGGCCAACGTCATCACCTCGAAATTCAAATTACTAGAGAAATC
GCTAAGGAACAGGGCATTCGTCACCATATCCTCGATATGTCTCTGCTGGA
CAAATCACTGCTCAGCCAGACTTTGCGACGATTCATATTTCCTACATTCCT
GACAAGCTCTGTGTCGAGTCAAAATCCCTCAAACTATATCTATTTAGCTAC
CGAAACCACGGAGATTTCCACGAAAACTGTATCAACACCATCGGGAAAGAC
TTGGTCAACTTGCTAGACCCTCGCTATTTAGAAGTCTGGGGAAAATTCACT
CCGCGCGGTGGCATTTCAATCGACCCCTACTACAACTACGGTAAGCAAGGA
ACTAAGTATGAGGGCTTGGCAGAACAACGCCTCTTCCAACACGACCTTTAT
CCAGAGAAAATTGACAACCGCTAA 4181.2
(SEQ. ID. NO. 321)
ATGACCGAAACGGTAGAAGATAAAGTAAGTCATTCAATTACTGGGCTTGAT
ATCCTCAAGGGGATAGTTGCTGCGGGAGCTGTCATAAGTGGAACCGTTGCA
ACTCAAACGAAGGTATTTACAAATGAGTCAGCAGTACTTGAAAAAACTGTA

GAGAAAACGGATGCTTTGGCAACAAATGATACAGTAGTTCTAGGTACGATA
TCTACAAGTAATTCAGCGAGTTCAACTAGTTTGTCAGCTTCAGAGTCGGCA
AGTACATCTGCATCTGAGTCAGCCTCAACCAGCGCTTCGACCTCAGCAAGT
ACAAGTGCATCAGAATCAGCAAGTACATCGGCTTCGACAAGTATTTCTGCA
TCATCTACTGTGGTAGGTTCACAAACAGCTGCCGCTACAGAAGCAACTGCT
AAGAAGGTCGAAGAAGATCGTAAGAAACCAGCTAGTGATTATGTAGCATCA
GTTACAAATGTCAATCTCCAATCTTATGCTAAGCGACGCAAGCGTTCAGTG
GATTCCATCGAGCAATTGCTGGCTTCTATAAAAAATGCTGCTGTTTTTTCT
GGCAATACGATTGTAAATGGCGCCCCTGCAATTAATGCAAGTCTAAACATT
GCTAAAAGTGAGACAAAAGTTTATACAGGTGAAGGTGTAGATTCGGTATAT
CGTGTTCCAATTTACTATAAATTGAAAGTGACAAATGATGGTTCAAAATTG
ACCTTTACCTATACGGTTACGTATGTGAATCCTAAAACAAATGATCTTGGT
AATATATCAAGTATGCGTCCTGGATATTCTATCTATAATTCAGGTACTTCA
ACACAAACAATGTTAACCCTTGGCAGTGATCTTGGTAAACCTTCAGGTGTA
AAGAACTACATTACTGACAAAAATGGTAGACAGGTTCTATCCTATAATACA
TCTACAATGACGACGCAGGGTAGTGGGTATACTTGGGGAAATGGTGCCCAA
ATGAATGGTTTCTTTGCTAAGAAAGGATATGGATTAACATCATCTTGGACT
GTACCAATTACTGGAACGGATACATCCTTTACATTTACCCCTTACGCTGCT
AGAACAGATAGAATTGGAATTAACTACTTCAATGGTGGAGGAAAGGTAGTT
GAATCTAGCACGACCAGTCAGTCACTTTCACAGTCTAAGTCACTCTCAGTA
AGTGCTAGTCAAAGCGCCTCAGCTTCAGCATCAACAAGTGCGTCGGCTTCA
GCATCAACCAGTGCCTCGGCTTCAGCGTCAACCAGTGCGTCAGCTTCAGCA
AGTACCAGTGCTTCAGTCTCAGCATCAACAAGTGCTTCAGCCTCAGCATCG
ACAAGTGCCTCGGCTTCAGCAAGCACATCAGCATCTGAATCAGCGTCAACC
AGTGCTTCGGCTTCAGCAAGTACCAGTGCTTCAGCTTCAGCATCAACCAGC
GCCTCGGCCTCAGCAAGCACCTCAGCTTCTGAATCGGCCTCAACCAGCGCC
TCGGCCTCAGCAAGCACCTCAGCTTCTGAATCGGCCTCAACCAGCGCCTCA
GCCTCAGCATCAACGAGTGCTTCGGCTTCAGCAAGCACAAGCGCCTCGGGT
TCAGCATCAACGAGTACGTCAGCTTCAGCGTCAACCAGTGCTTCAGCCTCA
GCATCAACAAGTGCGTCAGCCTCAGCAAGTATCTCAGCGTCTGAATCGGCA
TCAACGAGTGCGTCTGAGTCAGCATCAACGAGTACGTCAGCCTCAGCAAGC
ACCTCAGCTTCTGAATCGGCCTCAACCAGTGCGTCAGCCTCAGCATCGACA
AGCGCCTCAGCTTCAGCAAGTACCAGTGCTTCAGCCTCAGCGTCGACAAGT
GCGTCGGCCTCAACCAGTGCATCTGAATCGGCATCAACCAGTGCGTCAGCC
TCAGCAAGTACTAGTGCATCGGCTTCAGCATCAACCAGTGCCTCGGCTTCA
GCGTCAACCAGTGCGTCAGCTTCAGCAAGTACCAGTGCTTCAGTCTCAGCA
TCAACAAGTGCTTCAGCCTCAGCATCGACAAGTGCCTCGGCTTCAGCAAGC
ACATCAGCATCTGAATCAGCGTCGACAAGCGCCTCAGCTTCAGCAAGTCCC
AGTGCGTCAGCTTCAGCATCAACCAGCGCCTCGGCCTCAGCAAGCACCTCA
GCTTCTGAATCGGCCTCAACCAGCGCCTCGGCCTCAGCAAGCACCTCAGCT

TABLE 3-continued

TCTGAATCGGCCTCAACCAGCGCCTCAGCCTCAGCATCAACGAGTGCTTCG
GCTTCAGCAAGCACAAGCGCCTCGGGTTCAGCATCAACGAGTACGTCAGCT
TCAGCGTCAACCAGTGCTTCAGCCTCAGCATCAACAAGTGCGTCAGCCTCA
GCAAGTATCTCAGCGTCTGAATCGGCATCAACGAGTGCGTCTGAGTCAGCA
TCAACGAGTACGTCAGCCTCAGCAAGCACCTCAGCTTCTGAATCGGCCTCA
ACCAGTGCGTCAGCCTCAGCATCGACAAGCGCCTCAGCTTCAGCAAGTACC
AGTGCTTCAGCCTCAGCTCGACAAGTGCGTCGGCCTCAACCAGTGCATCTG
AATCGGCATCAACCAGTGCGTCAGCCTCAGCAAGTACTAGTGCATCAGCTT
CAGCATCAACGAGTGCATCGGCTTCAGCATCAACCAGTGCCTCGGCTTCAG
CGTCAACCAGTGCGTCAGCTTCAGCAAGTACCAGTGCTTCAGTCTCAGCAT
CAACAAGTGCTTCAGCCTCAGCATCGACAAGTGCcTCGGCTTCAGCAAGCA
CATCAGCATCTGAATCAGCGTCGACAAGCGCcTCAGCTTCAGCAAGTACCA
GTGCGTCAGCCTCAGCGTCGACAAGTGCGTCAGCCTCAGCAAGTACTAGTG
CATCAGCTTCAGCATCAACGAGTGCATCGGCTTCGGCGTCAACCAGTGCAT
CAGAGTCAGCAAGTACCAGTGCGTCAGCTTCCGCATCAACAAGTGCCTCGG
CTTCAGCAAGCACCAGTGCGTCGGCTTCAGCAAGTACTAGCGCCTCAGCCT
CAGCCTCAACCAGTGCGTCAGCCTCAGCAAGTATCTCAGCGTCTGAATCGG
CATCAACGAGTGCGTCCGCTTCAGCAAGTACTAGCGCCTCAGCCTCAGCGT
CAACAAGTGCATCGGCTTCAGCGTCAACGAGTGCGTCTGAATCGGCATCAA
CGAGTGCGTCCGCTTCAGCAAGTACTAGCGCCTCAGCCTCAGCGTCAACAA
GTGCATCGGCTTCAGCATCAACGAGTGCGTCCGCTTCAGCAAGTACTAGCG
CCTCAGCCTCAGCGTCAACAAGTGCATCGGCTTCAGCGTCAACGAGTGCGT
CTGAGTCAGCATCAACGAGTGCGTCAGCCTCAGCAAGCACATCAGCTTCTG
AATCTGCATCAACCAGTGCGTCAGCCTCAGCATCGACAAGCGCCTCAGCTT
CAGCAAGTACCAGTGCGTCAGCCTCAGCGTCGACAAGTGCGTCGGCTTCAG
CAAGTACCAGTGCGTCAGCCTCAGCAAGTACCAGTGCGTCAGCCTCAGCGT
CGACAAGTGCGTCGGCCTCAACCAGTGCATCTGAATCGGCATCAACCAGTG
CGTCAGCCTCAGCAAGTACTAGTGCATCAGCTTCAGCATCAACGAGTGCAT
CGGCTTCAGCATCAACCAGTGCATCAGAGTCAGCAAGTACCAGTGCGTCAG
TTCCGCATCAACAAGTGCCTCGGCTTCAGCAAGTACTAG 4183.1
(SEQ. ID. NO. 322)
ATGGGGGTCGAAACTTGGTTTTATTCTAGCATCTGCTGGCTGGCCATCGGG
CTTGGTTCCGTTTGGAAGTTTCCCTACATGACTGCTGCTAATGGCGGTGGA
GGCTTTTTACTAATCTTTCTCATTTCCACTATTTTAATCGGTTTCCCTCTC
CTGCTGGCTGAGTTTGCCCTTGGCCGTAGTGCTGGCGTTTCCGCTATCAAA
ACCTTTGGAAAACTGGGCAAGAATAACAAGTACAACTTTATCGGTTGGATT
GGCGCCTTTGCCCTCTTTATCCTCTTATCTTTTTACAGTGTTATCGGAGGA
TGGATTCTAGTCTATCTAGGTATTGAGTTTGGGAAATTGTTCCAACTTGGT
GGAACGGGTGATTATGCTCAGTTATTTACTTCAATCATTTCAAATCCAGCC
ATTGCCCTAGGAGCTCAAGCGGCCTTTATCCTATTGAATATCTTCATTGTA

TCACGTGGGGTTCAAAAAGGGATTGAAAGAGCTTCGAAAGTCATGATGCCC
CTGCTCTTTATCGTCTTTGTTTTTATCATCGGTCGCTCTCTCAGTTTGCCA
AATGCCATGGAAGGGGTTCTTTACTTCCTCAAACCAGACTTTTCAAAACTG
ACTAGCACTGGTCTCCTCTATGCTCTGGGACAATCTTTCTTTGCCCTCTCA
CTAGGGGTTACAGTCATGTTGACCTATGCTTCTTACTTAGACAAGAAAACC
AATCTAGTCCAGTCAGGAATCTCCATCGTAGCCATGAATATCTCGATATCC
ATCATGGCAGGTCTAGCCATTTTCCAAGCTCGATCCCCCTTCAATATCCAG
TCTGAAGGGGGACCCAGCCTGCTCTTTATCGTCTTGCCTCAACTCTTTGAC
AAGATGCCTTTTGGAACCATTTTCTACGTCCTCTTCCTCTTGCTCTTCCTT
TTTGCGACAGTCACTTTTTCTGTCGTGATGCTGGAAATCAATGTAGACAAT
ATCACCAACCAGGATAACAGCAAACGTGCCAAATGGAGTGTTATTTTAGGA
ATTTTGACCTTTGTCTTTGGCATTCCTTCAGCCCTATCTTACGGTGTCATG
GCGGATGTTCACATTTTTGGTAAGACCTTCTTTGACGCTATGGACTTCTTG
GTTTCCAATCTCCTCATGCCATTTGGAGCTCTCTACCTTTCACTTTTTACA
GGCTATATCTTTAAAAAGGCTCTTGCAATGGAGGAACTCCATCTCGATGAA
AGAGCATGGAAACAAGGACTGTTCCAAGTCTGGCTCTTCCTTCTTCGTTTC
TTCGTTTCGTCATTCCAATCATCATCATTGTGGTCTTCATTGCCCAATTTA
TGTAATCAAAAAGGACTTGAGTAG 4183.5
(SEQ. ID. NO. 323)
ATGTTGAAAAAATGGCAGTTAAAAGATGTTATCTTGCTTGCTTTCTTGTCT
ATCTTTTTTGGTGGGGTTTTCGTTGGTTCAGGATATGTGTATAATATTCTC
AGTCTACTCTTAACACCTCTTGGTTTGCAGGCCTTTGCCAATGAAATCCTC
TTCGGTCTCTGGTGTATGGCTGCGCCCATTGCTGCCATCTTTGTTCCGAGA
GTCGGAAGTGCAACGATTGGAGAAGTGCTAGCTGCGCTTGCTGAAGTCCTT
TATGGTAGCCAATTTGGTCTAGGAGCTCTTTTGTCTGGCTTTGTTCAAGGT
TTGGGAAGTGAATTTGGTTTTATCGTAACTAAGAATCGCTATGAAAGTTGG
CTCTCTCTAACTGCTAATAGTATTGGGATTACGCTTGTTAGCTTTGTCTAT
GAATACATTAAGTTAGGTTACTACGCCTTTTCCCTTCCGTTTGTCCTTTCC
TTGCTTGTGGTACGTTTTATTTCTGTTTATTTCTTCTGTACCATCTTGGTT
CGTGCCATTGTCAAACTCTATCATCAGTTTGCAACTGGAGGAAAAGCATAG 4183.6
(SEQ. ID. NO. 324)
ATGGTCAAAGTAGCAACCCAGACACCGATTATCAGTCTCTTCTTGCTGATT
TTATCCTTGGAAACATCTTTCATTCCTTCGATTGCTCTGACTCTTTCGGTA
GTCGCATTTTGTATTCTCTTTATGCTCTATTACCGTCGATTTAAAATGTTA
GCTTGGATGATCATACTTGCCATTTTACCATCTTTTGCCAACTACTGGGCA
GTTCAGTTACACGGAGATGCTTCACAGGCAGTCATGCTTGGAACGAGGGCC
TTTGTGACAGTTTGTATCGGCCTTGTCTTTGTTTCCTCTGTTTCACTAAAA
GAGCTTCTCTTGTACTTGGCTCAAAAGGGGCTATCACGCTCTTGGTCCTAT
GCCTTGATTGTGGTATTCAATTCTTTTCCCTCTCATTCAGCAAGAAATCAAG
TCCCTCAAAGAAGCTTGCCTATTACGTGGTCAAGAACTACATTTTTGGTCG

TABLE 3-continued

CCCTTGATTTACAGTAAGGTTCTGATGACAGTCTTTAGGTGGCGCCATCTT
TACCTGAGAGCTCTATCTGCTCACGGATATGACGAACATGCACAGTTGAAG
AATAGCTATCGGACTTTTTATATTCCTAAAAAAACAAAATTAATCTACCTG
CTTTTCTTTTTATTGCTTCAAACCAGTCTATTTTATAA 4183.7
(SEQ. ID. NO. 325)
ATGAGAAAGCACCAATTACAAGTTCACAAATTAACCATTTTATCTATGATG
ATTGCCCTTGATGTAGTCCTTACACCTATCTTTCGAATTGAGGGAATGGCA
CCGATGTCCAGTGTAGTCAATATTCTAGCAGGAATCATGATGGGACCTGTT
TATGCCTTGGCTATGGCTACAGTCACAGCCTTTATCCGTATGACGACTCAA
GGGATTCCGCCTTTAGCTCTCACAGGAGCGACTTTTGGAGCCCTTCTAGCA
GGTCTCTTTTATAAGTACGGTCGAAAATTTCACTATTCTGCTCTAGGAGAG
ATTTTGGGAACAGGTATTATTGGTTCCATTGTTTCCTATCCTGTTATGGTA
CTCTTTACAGGATCAGCTGCTAAGCTTAGCTGGTTTATCTACACGCCTCGA
TTTTTCGGAGCAACCTTGATTGGTACAGCGATTTCCTTTATTGCCTTTCGA
TTTTTAATCAAGCAGGAATTCTTTAAAAAAGTGCAGGGATATTTCTTTAGT
GAAAGGATAGACTGA 4183.8
(SEQ. ID. NO. 326)
ATGCAGGAATTTACAAATCCCTTTCCTATAGGCTCTAGTTCCCTCATTCAC
TGCATTACCAATGAGATTTCTTGTGAGATGCTGGCAAATGGGATTTTGGCT
CTGGGATGCAAACCTGTCATGGCAGATGATTCCCGTGAAGTTCTTGATTTT
ACTAAGCAAAGTCAGGCTCTCTTCATCAATTTGGGGCATTTGTCAGCTGAG
AAGGAAAAAGCAATCCGCATGGCAGCTTCGTATGCAAACCAATCTTCTCTC
CCGATGGTAGTAGATGCGGTTGGCGTAACGACTTCATCCATTCGTAAGAGC
TTAGTTAAAGACCTTTTAGACTATAGACCTACGGTCCTTAAAGGAAACATG
TCAGAAATTCGAAGTCTTGTTGGATTAAAGCACCACGGCGTTGGGGTCGAT
GCGAGTGCTAAAGATCAAGAAACGGAGGATTTGCTTCAAGTCTTGAAAGAC
TGGTGTCAGACCTATCCTGGTATGTCTTTCTTAGTCACAGGTCCCAAGGAC
CTCGTCGTTTCGAAAAATCAGGTCGCTGTACTGGGAAATGGCTGTACTGAA
TTAGACTGGATAACAGGGACAGGAGACTTGGTTGGAGCCTTAACAGCTGTT
TTTCTCAGCCAAGGAAAGACTGGTTTTGAAGCTTCTTGCTTAGCAGTCTCT
TATCTCAATATCGCTGCTGAGAAAATAGTTGTTCAAGGAATGGGATTGGAA
GAATTTCGTTACCAAGTACTCAATCAGCTTTCGCTCCTAAGAAGAGATGAA
AATTGGCTAGATACCATCAAAGGAGAGGTTTATGAATAG 4185.3
(SEQ. ID. NO. 327)
ATGAACCATAAAATCGCAATTTTATCAGATGTTCATGGCAATGCGACGGCG
CTAGAAGCAGTGATTGCAGATGCTAAAAATCAAGGGGCCAGTGAATATTGG
CTTCTGGGAGATATTTTCTTCCTGGTCCAGGCGCAAATGACTTAGTCGCC
CTGCTAAAGGACCTTCCTATCACAGCAAGTGTTCGAGGCAATTGGGATGAT
CGTGTCCTTGAGGCTTTAGATGGGCAATATGCTTAGAAGACCCACAGGAA
GTTCAGCTCTTGCGTATGACACAGTATTTGATGGAGCGAATGGATCCTGCA

ACGATTGTCTGGCTACGAAGCTTGCCTTTGCTGGAAAAGAAAGAAATTGAC
GGATTGCGCTTTTCTATCTCTCATAATTTACCTGACAAAAACTATGGTGGT
GACTTGCTAGTTGAGAATGATACAGAGAAATTTGACCAACTGCTAGATGCG
GAAACGGACGTGGCAGTTTATGGTCATGTTCACAAGCAGTTGCTTCGTTAT
GGAAGTCAAGGGCAACAAATCATCAATCCAGGGTCGATTGGCATGCCCTAT
TTTAATTGGGAGGCGTTAAAAAATCACCGTTCCCAGTATGCCGTGATAGAA
GTTGAAGATGGGGAATTACTCAATATCCAATTTCGTAAAGTTGCTTATGAT
TACGAAGCTGAGTTAGAATTGGCCAAGTCCAAGGGGCTTCCCTTTATCGAA
ATGTATGAAGAACTGCGTCGTGACGATAACTATCAGGGGCACAATCTGGAA
TTATTAGCCAGCTTAATAGAAAAGCATGGGTATGTAGAGGATGTGAAGAAT
TTTTTTGATTTTTTGTAA 4186.1
(SEQ. ID. NO. 328)
ATGAATGTAAATCAGATTGTACGGATTATTCCTACTTTAAAAGCTAATAAT
AGAAAATTAAATGAAACATTTTATATTGAAACCCTTGGAATGAAGGCCTTG
TTAGAAGAATCGGCCTTTCTGTCACTAGGTGACCAAACGGGTCTTGAAAAG
CTGGTTTTAGAAGAAGCTCCCAGTATGCGTACTCGTAAGGTAGAGGGAAGA
AAAAAACTAGCTAGATTGATTGTCAAGGTGGAAAATCCCTTAGAAATTGAA
GGAATCTTATCTAAACAGATTCGATTCATCGATTATATAAAGGTCAAAAT
GGCTACGCTTTTGAAATTTTCTCACCAGAAGATGATTTGATTTTGATTCAT
GCGGAAGATGACATAGCAAGTCTAGTAGAAGTAGGAGAAAAAGCCTGAATTT
CAAACAGATTTGGCATCAATTTCTTTAAGTAAATTTGAGATTTCTATGGAA
TTACATCTCCCAACTGATATCGAAAGTTTCTTGGAATCATCTGAAATTGGG
GCATCCCTTGATTTTATTCCAGCTCAGGGGCAGGATTTGACTGTGGACAAT
ACGGTTACCTGGGACTTATCTATGCTCAAGTTCTTGGTCAATGAATTAGAC
ATAGCAAGTCTTCGCCAGAAGTTTGAGTCTACTGAATATTTTATTCCTAAG
TCTGAAAAATTCTTCCTTGGTAAAGATAGAAATAATGTTGAATTGTGGTTT
GAAGAAGTATGA 4186.2
(SEQ. ID. NO. 329)
ATGAAGTGGACCAAGATTATTAAAAAAATAGAAGAACAAATCGAGGCAGGG
ATTTATCCCGGAGCCTCTTTTGCGTATTTTAAGGACAATCAATGGACAGAG
TTCTATTTAGGCCAGAGTGACCCAGAGCATGGCTTGCAGACTGAGGCAGGA
CTAGTTTATGACCTAGCTAGTGTCAGCAAGGTTGTTGGGGTTGGCACAGTT
TGTACCTTCTTGTGGGAAATAGGTCAATTAGATATTGATAGACTGGTAATA
GATTTTTTACCTGAGAGTGATTATCCAGACATCACTATTCGCCAGCTCTTG
ACTCATGCAACAGACCTTGATCCTTTTATTCCTAATCGTGATCTTTTAACA
GCCCCTGAATTAAAGGAAGCGATGTTTCATCTCAACAGACGAAGTCAGCCA
GCCTTTCTTATTCGGATGTCCATTTTTTGCTGTTGGGCTTTATTTTGGAA
AGAATTTTAATCAAGATTTGGATGTGATTTTAAAGGATCAAGTCTGGAAA
CCTTGGGGAATGACGGAAACTAAGTTTGGGCCAGTTGAGCTTGCTGTTCCA
ACAGTTAGAGGTGTAGAGGCAGGCATAGTGCATGATCCCAAGGCTCGTCTC

CTGGGTAGACATGCTGGGAGTGCTGGTTTATTTTCGACTATAAAGGATTTA

CAAATCTTTTTAGAACACTATTTAGCAGATGATTTTGCAAGAGACTTAAAT

CAAAATTTTTCTCCTTTGGATGACAAGGAACGTTCTTTAGCATGGAATTTG

GAAGGAGATTGGCTAGACCATACGGGCTATACAGGTACCTTTATCATGTGG

AATCGTCAGAAGCAAGAAGCCACTATTTTCCTATCGAATCGTACCTATGAA

AAGGACGAGAGAGCTCAATGGATATTAGACCGCAATCAAGTGATGAACTTG

ATTCGCAAAGAAGAGTAA 4187.2

(SEQ. ID. NO. 330)
ATGATGAAGAAGACTTATAATCATATTTTGGTCTGGGGAGTCATTTTCTAT

AGCATTTGCATTGTCTGTTTTTGCTTTACTCCTCAAGAACAATCTACCGTG

GGAGTGGGAACTCCAGGTATTCAGCATCTTGGACGCCTGGTTTTTCTTTTG

ACTCCTTTCAATTCTCTCTGGAAACTGGGCGAAGTGAGTGACATTGGACAA

TTATGTTGGATTTTTTTACAAAATATCCTCAATGTCTTCTTGTTTTTTCCT

CTGATTTTCCAACTCCTTTATCTATTTCCAAATTTGCGGAAAACAAAAAAG

GTCCTTCTTTTTAGTTTTCTTGTGAGTCTTGGAATCGAGTGTACGCAATTA

ATCTTGGACTTTTTCTTTGATTTCAATCGCGTCTTTGAGATTGATGATTTG

TGGACCAACACTTTGGGTGGCTATCTGGCTTGGCTCCTTTATAAACGATTA

CATAAAAACAAGGTAAGGAATTAA 4188.1

(SEQ. ID. NO. 331)
ATGAAGATTCCTCTCTTAACTTTTGCAAGGCATAAATTTGTTTATGTCTTG

CTTACTTTGCTTTTTCTTGCTTTGGTTTATCGTGATGTTTTGATGACTTAT

TTCTTTTTTGATATTCATGCGCCCGATCTAGCTAAATTCGATGGACAAGCA

ATTAAAAATGACTTATTAAAATCAGCATTAGATTTTCGTATTCTCCAGTTC

AATCTAGGTTTTTATCAATCATTTATTATTCCAATCATCATTGTTTTGCTA

GGTTTTCAATATATTGAGCTGAAAAATAAAGTTTTACGATTGAGTATTGGA

AGAGAAGTGAGTTATCAAGGGTTAAAAAGAAAGTTGACTTTGCAAGTTGCA

AGTATCCCTTGTTTGATATATTTAGTGACTGTGCTGATAATTGCAATTATA

ACCTATTTCTTTGGGACTTTTTCTCCTCTTGGATGGAATTCTCTATTTTCT

GATGGAAGTGGTTTACAAAGACTCCTAGATGGAGAGATAAAAAGCTATTTG

TTCTTTACTTGTGTCCTACTAATCGGTATTTTCATCAATGCAATCTATTTT

TTACAAATAGTTGATTATGTGGGGAATGTGACTCGTTCGGCAATCACCTAT

TTGATGTTTCTTTGGCTTGGTTCTATGCTGCTTTATAGTGCCTTGCCTTAC

TATATGGTTCCTATGACGAGTTTGATGCAAGCTAGCTATGGGGATGTAAGT

TTGATGAAACTCTTTACTCCTTATATCCTTTATATTGTCCCTTACATGGTG

CTTGAAAAATATGAAGATAATGTTTAA 4188.2

(SEQ. ID. NO. 332)
ATGAAGATAATGTTTAAGAATTTTAACATATTTTGCTAAATATAGAAAGATT

GTTTTACTACTTCGTATAGTTCTGATGATGATTTTGATAAACCATCTATTG

TCAACAGCGGTTCAAAGCAGGATGCTGTTATCTTTTTCAAGAGAGAATTGA

TTTCAATTTTTTCCTATAATGACTATTCTGAAGCGAATTTAGAAATCCCCA

AACTATTGTTAAACCTTTCGCTTTTCATGGTAGGATGGCTCTCTGTCATTT

TACTTGAAAGTGATTTGGCAGACCATTACCATCACTTGATTCGCTATCAAT

CAAGCTCCTTTTTCGATTATACAAGGAAACGATTGGTTGTCATTTCTAAAT

TTTTTACTCAAGATTTGTTTGTCTGGTTTCTTGGTTTACTTCCTCTAGGAA

TTCATTTCAAAACAGTCGCACTTTTCTTTTTACTTGCTCAGTTAATGATGT

TGTACTTACTACTGTCTTATCTGATAGCACTGATTAGTGCGGGCGCTGGTT

TTTCCTTTTTTCTCTATTTTTTAGCATTTGTGGGACAAGAATGGATGATGG

ATCATATTGTAACAGTGTATTTAGTACTCTTAAGTTTATTAGTTATGTTGA

TTGTTAGTCGCTTGGAAGAGAAATTTAAGAAAGGATAA 4188.5

(SEQ. ID. NO. 333)
ATGGGCAAAGGAGAGATGGGCAAAGGAGTTATTGGCTTGGAGTTCGACTCA

GAAGTATTGGTCAACAAGGCTCCAACCCTTCAATTGGCAAATGGTAAAACA

GCGACTTTCCTAACCCAGTATGATAGCAAGACCTTGTTGTTTGCAGTAGAT

AAGGAAGATATCGGACAGGAATTATTGGTATAGCTAAAGGAAGCATCGAA

AGTATGCATAATCTTCCTGTAAATCTAGCAGGTGCCAGAGTTCCTGGCGGA

GTAAATGGTAGCAAAGCAGCGGTGCATGAAGTTCCAGAATTTACAGGGGGA

GTTAATGGTACAGAGCCAGCTGTTCATGAAATCGCAGAGTATAAGGGATCT

GATTCGCTTGTAACTCTTACTACAAAAAAAGATTATACTTACAAAGCTCCT

CTTGCTCAGCAGGCACTTCCTGAAACAGGAAACAAGGAGAGTGACCTCCTA

GCTTCACTAGGACTAACAGCTTTCTTCCTTGGTCTGTTTACGCTAGGGAAA

AAGAGAGAACAATAA 4188.10

(SEQ. ID. NO. 334)
ATGTTTAAAGTTTTACAAAAAGTTGGAAAAGCTTTTATGTTACCTATAGCT

ATACTTCCTGCAGCAGGTCTACTTTTGGGGATTGGTGGTGCACTTTCAAAC

CCAACCACGATAGCAACTTATCCAATACTAGACAATAGTATTTTTCAATCA

ATATTCCAAGTAATGAGCTCTGCAGGAGAGGTTGTATTCAGTAAATTTGTCA

CTACTTCTCTGTGTGGGATTATGTATTGGCTTAGCGAAACGAGATAAAGGA

ACCGCTGCGTTAGCAGGAGTAACTGGTTACTTAGTTATGACTGCAACGATC

AAAGCTTTGGTAAAACTTTTTATGGCAGAAGGATCTGCAATTGATACTGGA

GTTATTGGAGCATTAGTTGTCGGAATAGTTGCCGTATATTTGCACAACCGA

TATAACAATATTCAATTACCTTCCGCTTTAGGATTCTTTGGAGGTTCACGC

TTCGTTCCTATTGTTACATCGTTCTCTTCTATCTTGATTGGCTTTGTCTTC

TTTGTTATTTGGCCACCTTTCCAACAACTTCTTGTTTCTACAGGTGGATAT

ATTTCTCAGGCGGGTCCAATTGGAACTTTTCTATATGGATTTTTAATGAGA

CTTTCTGGAGCAGTAGGCTACATCATATAATTTACCCTATGTTTTGGTAT

ACTGAACTTGGTGGTGTTGAAACTGTTGCAGGACAAACAGTGGTTGGAGCT

GCAAAAAATATTTTTTGCTCAATTAGCCGATTTGCCCATTCTGGATTATTT

ACAGAAGGAACAAGGTTTTTTGCAGGTCGTTTCTCAACAATGATGTTCGGT

TTACCGGCTGCCTGTTTAGCGATGTACCATAGTGTTCCTAAAAATCGTCGT

AAAAAATACGCGGGTTTGTTTTTTGGAGTTGCTTTAACATCTTTTATTACC

GGTATTACAGAACCAATTGAATTTATGTTTCTATTCGTCAGTCCGGTTCTA
TATGTTGTTCACGCATTCCTTGATGGTGTTAGCTTCTTTATTGCAGACGTC
TTAAATATTTCAATAGGAAACACATTTTCAGGAGGTGTAATCGATTTCACT
TTATTTGGAATTTTGCAGGGGAACGCTAAGACGAATTGGGTTCTTCAGATT
CCATTTGGACTTATTTGGAGTGTTTTGTATTATATTATTTTTAGATGGTTC
ATTACTCAATTCAACGTTCTAACGCCAGGGCGAGGAGAAGAAGTAGATTCT
AAAGAAATTTCTGAATCCGCAGATTCAACTTCAAATACTGCAGATTATTTA
AAACAGGATAGCCTACAAATTATCAGAGCCTTGGGTGGATCAAATAATATA
GAAGATGTAGATGCTTGTGTGACACGTTTACGTGTAGCTGTAAAAGAAGTT
AATCAAGTTGATAAAGCACTTTTAAAACAAATTGGTGCAGTTGATGTCTTA
GAAGTGAAGGGTGGCATTCAAGCAATCTATGGAGCAAAAGCAATCTTATAT
AAAAATAGTATTAATGAAATTTTAGGTGTAGATGATTAA 4188.11

(SEQ. ID. NO. 335)
ATGAAATTTAGAAAATTAGCTTGTACAGTACTTGCGGGTGCTGCGGTTCTT
GGTCTTGCTGCTTGTGGCAATTCTGGCGGAAGTAAAGATGCTGCCAAATCA
GGTGGTGACGGTGCCAAAACAGAAATCACTTGGTGGGCATTCCCAGTATTT
ACCCAAGAAAAAACTGGTGACGGTGTTGGAACTTATGAAAAATCAATCATC
GAAGCGTTTGAAAAAGCAAACCCAGATATAAAAGTGAAATTGGAAACCATC
GACTTCAAGTCAGGTCCTGAAAAAATCACAACAGCCATCGAAGCAGGAACA
GCTCCAGACGTACTCTTTGATGCACCAGGACGTATCATCCAATACGGTAAA
AACGGTAAATTGGCTGAGTTGAATGACCTCTTCACAGATGAATTTGTTAAA
GATGTCAACAATGAAAACATCGTACAAGCAAGTAAAGCTGGAGACAAGGCT
TATATGTATCCGATTAGTTCTGCCCCATTCTACATGGCAATGAACAAGAAA
ATGTTAGAAGATGCTGGAGTAGCAAACCTTGTAAAAGAAGGTTGGACAACT
GATGATTTTGAAAAAGTATTGAAGCACTTAAAGACAAGGGTTACACACCA
GGTTCATTGTTCAGTTCTGGTCAAGGGGAGACCAAGGAACACGTGCCTTT
ATCTCTAACCTTTATAGCGGTTCTGTAACAGATGAAAAAGTTAGCAAATAT
ACAACTGATGATCCTAAATTCGTCAAAGGTCTTGAAAAAGCAACTAGCTGG
ATTAAAGACAATTTGATCAATAATGGTTCACAATTTGACGGTGGGGCAGAT
ATCCAAAACTTTGCCAACGGTCAAACATCTTACACAATCCTTTGGGCACCA
GCTCAAAATGGTATCCAAGCTAAACTTTTAGAAGCAAGTAAGGTAGAAGTG
GGTAGAAGTACCATTCCCATCAGACGAAGGTAAGCCAGCTCTTAGTACCTT
GTAAACGGGTTTGCAGTATTCAACAATAAAGACGACAAGAAAGTCGCTGCA
TCTAAGAAATTCATCCAGTTTATCGCAGATGACAAGGAGTGGGGACCTAAA
GACGTAGTTCGTACAGGTGCTTTCCCAGTCCGTACTTCATTTGGAAAACTT
TATGAAGACAAACGCATGGAAACAATCAGCGGCTGGACTCAATACTACTCA
CCATACTACAACACTATTGATGGATTTGCTGAAATGAGAACACTTTGGTTC
CCAATGTTGCAATCTGTATCAAATGGTGACGAAAAACCAGCAGATGCTTTG

AAAGCCTTCACTGAAAAAGCGAACGAAACAATCAAAAAAGCTATGAAACAA
TAG 4188.12

(SEQ. ID. NO. 336)
ATGCAATCTACAGAAAAAAAACCATTAACAGCCTTTACTGTTATTTCAACA
ATCATTTTGCTCTTGTTGACTGTGCTGTTCATCTTTCCATTCTACTGGATT
TTGACAGGGGCATTCAAATCACAACCTGATACAATTGTTATTCCTCCTCAG
TGGTTCCCTAAAATGCCAACCATGGAAAACTTCCAACAACTCATGGTGCAG
AACCCTGCCTTGCAATGGATGTGGAACTCAGTATTTATCTCATTGGTAACC
ATGTTCTTAGTTTGTGCAACCTCATCTCTAGCAGGTTATGTATTGGCTAAA
AAACGTTTCTATGGTCAACGCATTCTATTTGCTATCTTTATCGCTGCTATG
GCGCTTCCAAAACAAGTTGTCCTTGTACCATTGGTACGTATCGTCAACTTC
ATGGGAATCCATGATACTCTCTGGGCAGTTATCTTGCCTTTGATTGGATGG
CCATTCGGTGTCTTCCTCATGAAACAGTTCAGTGAAAATATCCCTACAGAG
TTGCTTGAATCAGCTAAAATCGACGGTTGTGGTGAGATTCGTACCTTCTGG
AGTGTAGCCTTCCCGATTGTGAAACCAGGGTTTGCAGCCCTTGCAATCTTT
ACCTTCATCAATACTTGGAATGACTACTTCATGCAATTGGTAATGTTGACT
TCACGTAACAATTTGACCATCTCACTTGGGGTTGCGACCATGCAGGCTGAA
ATGGCAACCAACTATGGTTTGATTATGCAGGAGCTGCCCTTGCTGCTGTT
CCAATCGTCACAGTCTTCCTAGTCTTCCAAAAATCCTTCACACAGGGTATT
ACTATGGGAGCGGTCAAAGGATAA 4191.1

(SEQ. ID. NO. 337)
ATGAAAAAACTTTTTTCTTACTGGTGTTAGGCTTGTTTTGCCTTCTTCCA
CTCTCTGTTTTTGCCATTGATTTCAAGATAAACTCTTATCAAGGGGATTTG
TATATTCATGCAGACAATACGGCAGAGTTTAGACAGAAGATAGTTTACCAG
TTTGAGGAGGACTTTAAGGGCCAAATCGTGGGACTTGGACGTGCTGGTAAG
ATGCCTAGCGGGTTTGACATTGACCCTCATCCAAAGATTCAGGCCGCGAAA
AACGGTGCAGAACTAGCAGATGTGACTAGCGAAGTAACAGAAGAAGCGGAT
GGTTATACTGTGAGAGTCTATAATCCAGGTCAGGAGGGCGACATAGTTGAA
GTTGACCTCGTCTGGAACTTAAAAAATTTACTTTTCCTTTATGATGATATC
GCTGAATTAAATTGGCAACCTCTGACAGATAGTTCAGAGTCTATTGAAAAG
TTTGAATTTCATGTAAGGGGAGACAAGGGGGCTGAAAAACTCTTTTTCCAT
ACAGGGAAACTTTTTAGAGAGGGAACGATTGAAAAGAGTAACCTTGATTAT
ACTATCCGTTTAGACAATCTTCCGGCTAAGCGTGGAGTTGAGTTGCATGCC
TATTGGCCTCGGACCGATTTTGCTAGCGCTAGGGATCAGGGATTGAAAGGG
AATCGTTTAGAAGAGTTTAATAAGATAGAAGACTCGATTGTTAGAGAAAAA
GATCAGAGTAAACAACTCGTTACTTGGGTCCTCCCTTCGATCCTTTCCATC
TCCTTGTTATTGAGTGTCTGCTTCATTTTATTTATAGAAGAAAGACCACT
CCTTCAGTCAAATATGCCAAAAATCATCGTCTCTATGAACCACCAATGGAA
TTAGAGCCTATGGTTTTATCAGAAGCAGTCTACTCGACCTCCTTGGAGGAA
GTGAGTCCCTTGGTCAAGGGAGCTGGAAAATTCACCTTTGATCAACTTATT

CAAGCTACCTTGCTAGATGTGATAGACCGTGGGAATGTCTCTATCATTTCA
GAAGGAGATGCAGTTGGTTTGAGGCTAGTAAAAGAAGATGGTTTGTCAAGC
TTTGAGAAAGACTGCCTAAATCTAGCTTTTTCAGGTAAAAAGAAGAAACT
CTTTCCAATTTGTTTGCGGATTACAAGGTATCTGATAGTCTTTATCGTAGA
GCCAAAGTTTCTGATGAAAAACGGATTCAAGCAAGAGGGCTTCAACTCAAA
TCTTCTTTTGAAGAGGTATTGAACCAGATGCAAGAAGGAGTGAGAAAACGA
GTTTCCTTCTGGGGGCTCCCAGATTATTATCGTCCTTTAACTGGTGGGGAA
AAGGCCTTGCAAGTGGGTATGGGTGCCTTGACTATCCTGCCCCTATTTATC
GGATTTGGTTTGTTCTTGTACAGTTTAGACGTTCATGGCTATCTTTACCTC
CCTTTGCCAATACTGGTTTTCTAGGGTTAGTTTTGTCTGTTTTCTATTAT
TGGAAGCTTCGACTAGATAATCGTGATGGTGTTCTAAATGAAGCGGGAGCT
GAGGTCTACTATCTCTGGACCAGTTTTGAAAATATGTTGCGTGAGATTGCA
CGATTGGATCAGGCTGAACTGGAAAGTATTGTGGTCTGGAATCGCCTCTTG
GTCTATGCGACCTTATTTGGCTATGCGGACAAGGTTAGTCATTTGATGAAG
GTTCATCAGATTCAAGTGGAAAATCCAGATATCAATCTCTATGTAGCTTAT
GGCTGGCACAGTACGTTTTATCATTCAACAGCACAAATGAGCCATTATGCT
AGTGTCGCAAATACAGCAAGCACCTACTCTGTATCTTCTGGAAGTGGAAGT
TCTGGTGGTGGCTTCTCTGGAGGCGGAGGTGGCGGCAGTATCGGTGCCTTT
TAA 4191.2

(SEQ. ID. NO. 338)
ATGAAAAAAGTAAGAAAGATATTTCAGAAGGCAGTTGCAGGACTGTGCTGT
ATATCTCAGTTGACAGCTTTTTCTTCGATAGTTGCTTTAGCAGAAACGCCT
GAAACCAGTCCAGCGATAGGAAAAGTAGTGATTAAGGAGACAGGCGAAGGA
GGAGCGCTTCTAGGAGATGCCGTCTTTGAGTTGAAAAACAATACGGATGGC
ACAACTGTTTCGCAAAGGACAGAGGCGCAAACAGGAGAAGCGATATTTTCA
AACATAAAACCTGGGACATACACCTTGACAGAAGCCCAACCTCCAGTTGGT
TATAAACCCTCTACTAAACAATGGACTGTTGAAGTTGAGAAGAATGGTCGG
ACGACTGTCCAAGGTGAACAGGTAGAAAATCGAGAAGAGGCTCTATCTGAC
CAGTATCCACAAACAGGGACTTATCCAGATGTTCAAACACCTTATCAGATT
ATTAAGGTAGATGGTTCGGAAAAAAACGGACAGCACAAGGCGTTGAATCCG
AATCCATATGAACGTGTGATTCCAGAAGGTACACTTTCAAAGAGAATTTAT
CAAGTGAATAATTTGGATGATAACCAATATGGAATCGAATTGACGGTTAGT
GGGAAAACAGTGTATGAACAAAAAGATAAGTCTGTGCCGCTGGATGTCGTT
ATCTTGCTCGATAACTCAAATAGTATGAGTAACATTCGAAACAAGAATGCT
CGACGTGCGGAAAGAGCTGGTGAGGCGACACGTTCTCTTATTGATAAAATT
ACATCTGATTCAGAAAATAGGGTAGCGCTTGTGACTTATGCTTCCACTATC
TTTGATGGGACCGAGTTTACAGTAGAAAAAGGGGTAGCAGATAAAAACGGA
AAGCGATTGAATGATTCTCTTTTTTGGAATTATGATCAGACGAGTTTTACA
ACCAATACCAAAGATTATAGTTATTTAAAGCTGACTAATGATAAGAATGAC
ATTGTAGAATTAAAAAATAAGGTACCTACCGAGGCAGAAGACCATGATGGA

AATAGATTGATGTACCAATTCGGTGCCACTTTTACTCAGAAAGCTTTGATG
AAGGCAGATGAGATTTTGACACAACAAGCGAGACAAAATAGTCAAAAAGTC
ATTTTCCATATTACGGATGGTGTCCCAACTATGTCGTATCCGATTAATTTT
AATCATGCTACGTTTGCTCCATCATATCAAAATCAACTAAATGCATTTTTT
AGTAAATCTCCTAATAAAGATGGAATACTATTAAGTGATTTTATTACGCAA
GCAACTAGTGGAGAACATACAATTGTACGCGGAGATGGGCAAAGTTACCAG
ATGTTTACAGATAAGACAGTTTATGAAAAAGGTGCTCCTGCAGCTTTCCCA
GTTAAACCTGAAAAATATTCTGAAATGAAGGCGGCTGGTTATGCAGTTATA
GGCGATCCAATTAATGGTGGATATATTTGGCTTAATTGGAGAGAGAGTATT
CTGGCTTATCCGTTTAATTCTAATACTGCTAAAATTACCAATCATGGTGAC
CCTACAAGATGGTACTATAACGGGAATATTGCTCCTGATGGGTATGATGTC
TTTACGGTAGGTATTGGTATTAACGGAGATCCTGGTACGGATGAAGCAACG
GCTACTAGTTTTATGCAAAGTATTTCTAGTAAACCTGAAAACTATACCAAT
GTTACTGACACGACAAAAATATTGGAACAGTTGAATCGTTATTTCCACACC
ATCGTAACTGAAAAGAAATCAATTGAGAATGGTACGATTACAGATCCGATG
GGTGAGTTAATTGATTTGCAATTGGGCACAGATGGAAGATTTGATCCAGCA
GATTACACTTTAACTGCAAACGATGGTAGTCGCTTGGAGAATGGACAAGCT
GTAGGTGGTCCACAAAATGATGGTGGTTTGTTAAAAAATGCAAAAGTGCTC
TATGATACGACTGAGAAAAGGATTCGTGTAACAGGTCTGTACCTTGGAACG
GATGAAAAAGTTACGTTGACCTACAATGTTCGTTTGAATGATGAGTTTGTA
AGCAATAAATTTTATGATACCAATGGTCGAACAACCTTACATCCTAAGGAA
GTAGAACAGAACACAGTGCGCGACTTCCCGATTCCTAAGGATTCGTGATGTG
CGGAAGTATCCAGAAATCACAATTTCAAAAGAGAAAAAACTTGGTGACATT
GAGTTTATTAAGGTCAATAAAAATGATAAAAAACCACTGAGAGGTGCGGTC
TTTAGTCTTCAAAAACAACATCCGGATTATCCAGATATTTATGGAGCTATT
GATCAAAATGGCACTTATCAAAATGTGAGAACAGGTGAAGATGGTAAGTTG
ACCTTTAAAAATCTGTCAGATGGGAAATATCGATTATTTGAAAATTCTGAA
CCAGCTGGTTATAAACCCGTTCAAAATAAGCCTATCGTTGCCTTCCAAATA
GTAAATGGAGAAGTCAGAGATGTGACTTCAATCGTTCCACAAGATATACCA
GCGGGTTACGAGTTTACGAATGATAAGCACTATATTACCAATGAACCTATT
CCTCCAAAGAGAGAATATCCTCGAACTGGTGGTATCGGAATGTTGCCATTC
TATCTGATAGGTTGCATGATGATGGGAGGAGTTCTATTATACACACGGAAA
CATCCGTAA 4191.3

(SEQ. ID. NO. 339)
ATGAAATCAATCAACAAATTTTTAACAATGCTTGCTGCCTTATTACTGACA
GCGAGTAGCCTGTTTTCAGCTGCAACAGTTTTTGCGGCTGGGACGACAACA
ACATCTGTTACCGTTCATAAACTATTGGCAACAGATGGGGATATGGATAAA
ATTGCAAATGAGTTAGAAACAGGTAACTATGCTGGTAATAAAGTGGGTGTT
CTACCTGCAAATGCAAAGAAATTGCCGGTGTTATGTTCGTTTGGACAAAT
ACTAATAATGAAATTATTGATGAAAATGGCCAAACTCTAGGAGTGAATATT

TABLE 3-continued

GATCCACAAACATTTAAACTCTCAGGGGCAATGCCGGCAACTGCAATGAAA

AAATTAACAGAAGCTGAAGGAGCTAAATTTAACACGGCAAATTTACCAGCT

GCTAAGTATAAAATTTATGAAATTCACAGTTTATCAACTTATGTCGGTGAA

GATGGAGCAACCTTAACAGGTTCTAAAGCAGTTCCAATTGAAATTGAATTA

CCATTGAACGATGTTGTGGATGCGCATGTGTATCCAAAAAATACAGAAGCA

AAGCCAAAAATTGATAAAGATTTCAAAGGTAAAGCAAATCCAGATACACCA

CGTGTAGATAAAGATACACCTGTGAACCACCAAGTTGGAGATGTTGTAGAG

TACGAAATTGTTACAAAAATTCCAGCACTTGCTAATTATGCAACAGCAAAC

TGGAGCGATAGAATGACTGAAGGTTTGGCATTCAACAAAGGTACAGTGAAA

GTAACTGTTGATGATGTTGCACTTGAAGCAGGTGATTATGCTCTAACAGAA

GTAGCAACTGGTTTTGATTTGAAATTAACAGATGCTGGTTTAGCTAAAGTG

AATGACCAAAACGCTGAAAAAACTGTGAAAATCACTTATTCGGCAACATTC

AATGACAAAGCAATTGTAGAAGTACCAGAATCTAATGATGTAACATTTAAC

TATGGTAATAATCCAGATCACGGGAATACTCCAAAGCCGAATAAGCCAAAT

GAAAACGGCGATTTGACATTGACCAAGACATGGGTTGATGCTACAGGTGCA

CCAATTCCGGCTGGAGCTGAAGCAACGTTCGATTTGGTTAATGCTCAGACT

GGTAAAGTTGTACAAACTGTAACTTTGACAACAGACAAAAATACAGTTACT

GTTAACGGATTGGATAAAAATACAGAATATAAATTCGTTGAACGTAGTATA

AAAGGGTATTCAGCAGATTATCAAGAAATCACTACAGCTGGAGAAATTGCT

GTCAAGAACTGGAAAGACGAAAATCCAAAACCACTTGATCCAACAGAGCCA

AAAGTTGTTACATATGGTAAAAAGTTTGTCAAAGTTAATGATAAAGATAAT

CGTTTAGCTGGGGCAGAATTTGTAATTGCAAATGCTGATAATGCTGGTCAA

TATTTAGCACGTAAAGCAGATAAAGTGAGTCAAGAAGAGAAGCAGTTGGTT

GTTACAACAAAGGATGCTTTAGATAGAGCAGTTGCTGCTTATAACGCTCTT

ACTGCACAACAACAAACTCAGCAAGAAAAGAGAAAGTTGACAAAGCTCAA

GCTGCTTATAATGCTGCTGTGATTGCTGCCAACAATGCATTTGAATGGGTG

GCAGATAAGGACAATGAAAATGTTGTGAAATTAGTTTCTGATGCACAAGGT

CGCTTTGAAATTACAGGCCTTCTTGCAGGTACATATTACTTAGAAGAAACA

AAACAGCCTGCTGGTTATGCATTACTAACTAGCCGTCAGAAATTTGAAGTC

ACTGCAACTTCTTATTCAGCGACTGGACAAGGCATTGAGTATACTGCTGGT

TCAGGTAAAGATGACGCTACAAAAGTAGTCAACAAAAAAATCACTATCCCA

CAAACGGGTGGTATTGGTACAATTATCTTTGCTGTAGCGGGGGCTGCGATT

ATGGGTATTGCAGTGTACGCATATGTTAAAAACAACAAAGATGAGGATCAA

CTTGCTTAA 4191.4

(SEQ. ID. NO. 340)
ATGACAATGCAGAAAATGCAGAAAATGATTAGTCGTATCTTCTTTGTTATG

GCTCTGTGTTTTTCTCTTGTATGGGGTGCACATGCAGTCCAAGCGCAAGAA

GATCACACGTTGGTCTTGCAATTGGAGAACTATCAGGAGGTGGTTAGTCAA

TTGCCATCTCGTGATGGTCATCGGTTGCAAGTATGGAAGTTGGATGATTCG

TATTCCTATGATGATCGGGTGCAAATTGTAAGAGACTTGCATTCGTGGGAT

GAGAATAAACTTTCTTCTTTCAAAAAGACTTCGTTTGAGATGACCTTCCTT

GAGAATCAGATTGAAGTATCTCATATTCCAAATGGTCTTTACTATGTTCGC

TCTATTATCCAGACGGATGCGGTTTCTTATCCAGCTGAATTTCTTTTTGAA

ATGACAGATCAAACGGTAGAGCCTTTGGTCATTGTAGCGAAAAAACAGAT

ACAATGACAACAAAGGTGAAGCTGATAAAGGTGGATCAAGACCACAATCGC

TTGGAGGGTGTCGGCTTTAAATTGGTATCAGTAGCAAGAGATGTTTCTGAA

AAAGAGGTTCCCTTGATTGGAGAATACCGTTACAGTTCTTCTGGTCAAGTA

GGGAGAACTCTCTATACTGATAAAAATGGAGAGATTTTTGTGACAAATCTT

CCTCTTGGGAACTATCGTTTCAAGGAGGTGGAGCCACTGGCAGGCTATGCT

GTTACGACGCTGGATACGGATGTCCAGCTGGTAGATCATCAGCTGGTGACG

ATTACGGTTGTCAATCAGAAATTACCACGTGGCAATGTTGACTTTATGAAG

GTGGATGGTCGGACCAATACCTCTCTTCAAGGGGCAATGTTCAAAGTCATG

AAAGAAGAAAGCGGACACTATACTCCTGTTCTTCAAAATGGTAAGGAAGTA

GTTGTAACATCAGGGAAAGATGGTCGTTTCCGAGTGGAAGGTCTAGAGTAT

GGGACATACTATTTATGGGAGCTCCAAGCTCCAACTGGTTATGTTCAATTA

ACATCGCCTGTTTCCTTTACAATCGGGAAAGATACTCGTAAGGAACTGGTA

ACAGTGGTTAAAAATAACAAGCGACCACGGATTGATGTGCCAGATACAGGG

GAAGAAACCCTTGTATATCTTGATGCTTGTTGCCATTTTGTTGTTTGGTAG 4191.5

(SEQ. ID. NO. 341)
ATGAGCCACATATACTTATCTATTTTCACAAGTCTCTTGCTGATGCTAGGA

CTTGTCAATGTTGCTCAAGCCGATGAATATTTACGCATCGGTATGGAAGCA

GCATATGCTCCCTTTAACTGGACCCAGGATGATGATAGCAACGGAGCTGTC

AAAATCGATGGGACCAATCAGTATGCCAACGGATACGATGTTCAAATCGCC

AAGAAAATCGCTAAGGACTTAGGTAAAGAACCTTTGGTTGTTAAAACCAAG

TGGGAAGGTCTAGTCCCTGCCCTTACTTCTGGTAAGATTGACATGATTATC

GCAGGTATGAGTCCAACTGCAGAACGCAAACAAGAAATTGCCTTTTCGAGC

AGTTACTATACTAGCGAACCAGTTTTGCTTGTCAAAAAAGATTCTGCCTAC

GCAAGTGCTAAATCTTTGGATGACTTTAACGGTGCAAAAATCACTTCTCAA

CAAGGGGTCTACCTTTATAACTTGATTGCACAAATCCCAGGTGCTAAAAAA

GAAACAGCCATGGGAGACTTCACTCAAATGCGACAAGCTCTTGAGGCTGGT

GTCATTGATGCTTATGTTTCTGAACGTCCAGAAGCACTGACTGCTGAAGCT

GCGAACTCTAAGTTCAAGATGATTCAAGTAGAACCTGGTTTCAAAACTGGG

GAAGAAGATACAGCTATCGCTATCGGGCTTCGTAAAAATGACAATCGTATT

AGCCAAATCAATGCCAGCATTGAAACCATTTCAAAAGATGACCAAGTTGCC

TTGATGGATCGTATGATCAAGGAACAACCTGCCGAAGCTACAACAACTGAA

GAGACTAGCAGTAGTTTCTTTAGCCAAGTTGCTAAAATTCTTTCTGAAAAC

TGGCAACAACTCTTGCGTGGTGCTGGTATCACTCTTTTAATCTCTATCGTC

GGAACCATCATAGGTCTCATTATTGGACTTGCCATTGGTGTCTTCCGTACT

GCTCCTCTCTCTGAAAACAAAGTCATTTACGCCTACAAAAACTAGTCGGC

TGGGTTCTCAATGTCTACATTGAAATTTTCCGTGGTACGCCAATGATTGTT

TABLE 3-continued

CAATCGATGGTTATCTACTATGGAACTGCCCAAGCTTTCGGGATCAACCTT

GACCGTACACTGGCTGCTATCTTCATCGTTTCAATCAATACCGGTGCCTAC

ATGACTGAAATCGTCCGTGGTGGTATCCTAGCAGTTGACAAGGGACAATTT

GAAGCTGCGACTGCTCTTGGTATGACCCATAACCAGACCATGCGTAAGATT

GTCCTACCTCAGGTAGTCCGTAACATCCTACCTGCAACTGGTAATGAATTT

GTCATCAATATCAAAGATACATCTGTATTGAACGTTATCTCTGTTGTCGAA

CTTTATTTCTCAGGAAATACCGTGGCAACACAAACCTATCAATACTTCCAG

ACATTTACAATCATCGCCGTGATTTACTTTGTCCTCACCTTCACCGTAACA

CGTATCCTACGCTTTATCGAGCGCAGAATGGACATGGATACCTACACTACA

GGTGCTAACCAAATGCAAACGGAGGATTTGAAATAA 4191.6

(SEQ. ID. NO. 342)

ATGACACAAGCAATCCTTGAAATTAAACACCTCAAAAAATCCTATGGACAA

AACGAAGTGCTAAAAGACATTTCACTCACTGTCCACAAGGGAGAGGTCATC

TCTATCATCGGAAGCTCTGGAAGCGGAAAATCGACCTTCCTACGCTCCATT

AACCTACTTGAAACACCAACTGATGGACAAATCCTTTATCATGGACAAAAC

GTCCTCGAAAAAGGCTATGACCTCACGCAATACCGTGAAAAGTTGGGGATG

GTTTTCCAATCCTTTAACCTCTTTGAAAATCTCAATGTTCTTGAAAACACA

ATCGTCGCTCAGACAACTGTCCTAAAACGCGAACGCACAGAAGCTGAAAAG

ATTGCCAAAGAAAACCTGGAAAAGGTCGGCATGGGAGAACGCTACTGGCAA

GCCAAACCAAAACAACTCTCAGGTGGTCAAAAACAACGTGTGGCCATCGCT

CGTGCCCTCTCCATGAATCCGGACGCTATTCTCTTTGATGAACCAACATCA

GCTCTCGATCCAGAAATGGTTGGAGAAGTCCTCAAAATCATGCAGGACCTG

GCTCAGGAAGGCTTGACCATGATTGTCGTAACCCATGAAATGGAATTTGCC

CGTGATGTCTCTCACCGTGTTATCTTTATGGATAAGGGCGTGATCGCTGAA

GAAGGTAAACCAGAAGACCTCTTCACCAATCCTAAAGAAGACCGAACAAAA

GAGTTCCTTCAACGCTATCTCAAATAA 4192.3

(SEQ. ID. NO. 343)

ATGAAAAAGTATCAACTTCTATTCAAAATAAGTGCAGTCTTCTCTTACTTA

TTTTTCGTATTTAGTCTTTCTCAGCTGACGCTTATCGTCCAAAACTATTGG

CAATTTTCTTCTCAGATAGGCAATTTATTCTGGATTCAAAATATCTTGAGT

TTACTTTTTATTGGAGTCATGATTGTGGTTCTTGTTAAGACAGGCCATGGT

TATCTCTTCCGCATTCAAGAAAAAAATGGCTTTGGTATTCGATTTTGACA

GTATTAGTGCTAGTGTTCCAGATCTCTTTTAACGTTCAGACAGCTAAACAT

GTTCAGTCAACTGCGGAAGGTTGGGCTGTATTGATTGGTTATAGTGGGACT

AACTTTGCAGAGCTAGGTATTTATATAGCCCTGTTCTTTCTGGTTCCACTG

ATGGAAGAATTGATTTATAGAGGATTACTGCAACATGCTTTCTTTAAGCAT

TCGCGATTTGGTCTTGATTGCTTCTTCCTTCTATTTTATTTGCTCTCCCT

CATTTTTCAAGCCTGCCTAGTCTGTTAGATATCTTCGTCTTTGCAACAGTT

GGAATCATCTTTGCTGGTTTGACCCGCTATACCAAGAGCATTTATCCATCC

TATGCGGTGCATGTGATCAATAATATTGTAGCGACCTTCCCGTTTTTGCTC

ACTTTTCTACATAGGGTCTTGGGGTAA 4193.1

(SEQ. ID. NO. 344)

ATGAACAAGAAACAATGGCTAGGTCTTGGCCTAGTTGCAGTGGCAGCAGTT

GGACTTGCTGCATGTGGTAACCGCTCTTCTCGTAACGCAGCTTCATCTTCT

GATGTGAAGACAAAAGCAGCAATCGTCACTGATACTGGTGGTGTTGATGAC

AAATCATTCAACCAATCAGCTTGGGAAGGTTTGCAGGCTTGGGGTAAAGAA

CACAATCTTTCAAAAGATAACGGTTTCACTTACTTCCAATCAACAAGTGAA

GCTGACTACGCTAACAACTTGCAACAAGCGGCTGGAAGTTACAACCTAATC

TTCGGTGTTGGTTTTGCCCTTAATAATGCAGTTAAAGATGCAGCAAAAGAA

CACACTGACTTGAACTATGTCTTGATTGATGATGTGATTAAAGACCAAAAG

AATGTTGCGAGCGTAACTTTCGCTGATAATGAGTCAGGTTACcTTGCAGGT

GTGGCTGCAGCAAAAACAACTAAGACAAAACAAGTTGGTTTTGTAGGTGGT

ATCGAATCTGAAGTTATCTCTCGTTTTGAAGCAGGATTCAAGGCTGGTGTT

GCGTCAGTAGACCCATCTATCAAAGTCCAAGTTGACTACGCTGGTTCATTT

GGTGATGCGGCTAAAGGTAAAACAATTGCAGCCGCACAATACGCAGCCGGT

GCAGATATTGTTTACCAAGTAGCTGGTGGTACAGGTGCAGGTGTCTTTGCA

GAGGCAAAATCTCTCAACGAAAGCCGTCCTGAAAATGAAAAGTTTGGGTT

ATCGGTGTTGATCGTGACCAAGAAGCAGAAGGTAAATACACTTCTAAAGAT

GGCAAAGAATCAAACTTTGTTCTTGTATCTACTTTGAAACAAGTTGGTACA

ACTGTAAAAGATATTTCTAACAAGGCAGAAAGAGGAGAATTCCCTGGCGGT

CAAGTGATCGTTTACTCATTGAAGGATAAAGGGGTTGACTTGGCAGTAACA

AACCTTTCAGAAGAAGGTAAAAAAGCTGTCGAAGATGCAAAAGCTAAAATC

CTTGATGGAAGCGTAAAAGTTCCTGAAAAATAA 4193.3

(SEQ. ID. NO. 345)

ATGTCTAAAAAATTACAACAAATTTCGGTTCCCTTGATTTCTGTATTCCTA

GGAATTTTACTCGGAGCCATTGTCATGTGGATCTTCGGTTATGATGCTATT

TGGGGCTACGAAGAATTGTTCTATACAGCCTTTGGCAGTCTGCGTGGGATT

GGAGAAATCTTCCGTGCTATGGGTCCTCTGGTCTTGATTGGTCTTGGTTTT

GCCGTTGCCAGTCGAGCTGGTTTCTTTAACGTCGGACTTCCTGGTCAGGCT

TTGGCAGGTTGGATTCTCAGTGGTTGGTTTGCCCTGTCGCATCCAGATATG

CCCCGTCCCTTGATGATTCTAGCAACCATCGTGATTGCCTTGATTGCTGGT

GGGATTGTCGGAGCGATTCCAGGTATTCTTAGGGCCTATCTAGGGACGTCA

GAGGTTATTGTAACCATCATGATGAACTACATTGTCTTGTATGTAGGGAAT

GCCTTTATCCATGCTTTCCCTAAAGACTTCATGCAAAGTACAGATTCGACC

ATTCGTGTTGGGGCTAATGCAACCTATCAGACACCTTGGTTGGCTGAGTTG

ACTGGTAACTCACGGATGAATATTGGTATTTTCTTTGCCATCATTGCCGTT

GCAGTTATTGGTTCATGCTCAAGAAAACAACTCTTGGTTTTGAAATCCGT

GCAGTTGGTCTTAATCCACATGCTTCAGAATATGCTGGTATTTCTGCCAAG

CGGACTATTATCCTATCTATGATTATTTCAGGTGCCTTGGCAGGTCTTGGT

TABLE 3-continued

GGAGCTGTTGAAGGTTTGGGAACCTTCCAGAACGTCTATGTTCAAGGTTCG

TCATTAGCTATCGGATTTAACGGAATGGCGGTTAGTTTGCTTGCGGCCAAC

TCACCAATTGGTATACTCTTTGCAGCCTTCCTATTTGGCGTTCTCCAAGTT

GGGGCTCCTGGTATGAATGCGGCGCAGGTACCATCTGAGCTTGTCAGCATT

GTAACAGCGTCTATTATCTTCTTTGTCAGTGTTCATTACCTTATCGAACGC

TTTGTCAAACCGAAAAAACAAGTTAAAGGAGGTAAGTAA 4194.1

(SEQ. ID. NO. 346)
ATGGGAGTGAAAAAGAAACTAAAGTTGACTAGTTTGCTAGGACTGTCTCTG

TTAATCATGACAGCCTGTGCGACTAATGGGGTAACTAGCGATATTACAGCC

GAATCGGCTGATTTTTGGAGTAAATTGGTTTACTTCTTTGCGGAAATCATT

CGCTTTTTATCGTTTGATATTAGTATCGGAGTGGGGATTATTCTCTTTACG

GTCTTGATTCGTACAGTCCTCTTGCCAGTCTTTCAGGTGCAAATGGTGGCT

TCTAGGAAAATGCAGGAAGCTCAGCCACGCATTAAGGCGCTTCGAGAACAA

TATCCAGGTCGAGATATGGAAAGCAGAACCAAACTAGAGCAGGAAATGCGT

AAAGTATTTAAAGAAATGGGTGTCAGACAGTCAGACTCTCTTTGGCCGATT

TTGATTCAGATGCCGGTTATTTTGGCCCTGTTCCAAGCCCTATCAAGAGTT

GACTTTTTAAAGACAGGTCATTTCTTATGGATTAACCTTGGTAGTGTGGAT

ACAACCCTTGTTCTTCCGATTTTAGCAGCAGTATTCACCTTTTTAAGTACT

TGGTTGTCCAACAAAGCTTTGTCTGAGCGAAATGGCGCTACGACTGCGATG

ATGTATGGGATTCCAGTCTTGATTTTTATCTTTGCAGTTTATGCGCCAGGT

GGAGTCGCCCTATACTGGACAGTGTCTAATGCTTATCAAGTCTTGCAAACC

TATTTCTTGAATAATCCATTCAAGATTATCGCAGAGCGCGAGGCCGTAGTA

CAGGCACAAAAAGATTTGGAAAATAGAAAAAGAAAAGCCAAGAAAAAGGCT

CAGAAAACGAAATAA 4194.4

(SEQ. ID. NO. 347)
ATGGTTATCGATCCATTTGCTATCAACGAACTAGACTATTACTTAGTTTCA

CACTTCCACAGTGATCATATCGACCCATACACAGCTGCAGCAATTCTCAAT

AATCCTAAGTTAGAGCATGTTAAGTTTATCGGTCCTTACCACTGTGGACGA

ATCTGGGAAGGATGGGGTGTTCCAAAAGAACGTATCATCGTTGTTAAACCA

GGTGACACTATCGAATTAAAAGATATGAAGATTCATGCAGTAGAATCATTT

GACCGTACTTGCTTGGTAACTCTCCCAGTGAACGGTGCTGATGAGACAGGC

GGTGAACTTGCTGGCTTGGCTGTTACAGATGAAGAAATGGCTCAAAAGGCT

GTTAACTATATCTTTGAAACACCAGGTGGAACCATCTATCATGGTGCAGAT

TCTCACTTCTCAAACTATTTTGCAAAACATGGTAAAGACTTTAAAATTGAT

GTTGCTTTGAATAACTATGGTGAAAATCCGGTAGGTATCCAAGACAAAATG

ACATCTATCGACCTTCTTCGTATGGCAGAAAATCTGCGTACCAAAGTCATT

ATCCCAGTTCACTATGATATCTGGTCTAACTTCATGGCTTCTACTAATGAG

ATTCTAGAACTTTGGAAAATGCGAAAAGATCGCTTGCAATACGATTTCCAT

CCATTTATCTGGGAAGTTGGCGGTAAGTACACTTATCCTCAAGATCAACAC

TTAGTAGAATACCATCATCCACGTGGTTTTGATGATTGTTTGAACAAGAC

TCTAACATTCAATTTAAAGCTTTGCTATAA 4196.2

(SEQ. ID. NO. 348)
ATGTTCCTTTCAGGCTGGTTGTCTAGTTTTGCTAATACTTATATCCATGAT

TTACTGGGGGTTCTTTTCCCAGATAGTCCATTTTTAAATGCCTTTGAAAGT

GCTATTGCGGCTCCTTTGGTAGAAGAACCCTTGAAATTATTGTCACTTGTT

TTTGTTTTGGCTTTGATTCCTGTGCGAAAATTAAAATCTTTGTTTTTACTT

GGAATTGCTTCCGGTTTGGGATTCCAAATGATTAAGGATATTGGTTATATT

CGTACGGATTTGCCAGAGGGCTTTGACTTTACTATTTCGCGAATTTTAGAG

CGTATCATCTCAGGAATTGCCTCTCACTGGACTTTTTCAGGTCTAGCTGTA

GTAGGTGTTTACTTGCTTTACAGAGCCTATAAAGGACAGAAGGTTGGCAAG

AAACAGGGCCTTATTTTTCTAGGTTTAGCCTTGGGAACTCACTTCTTGTTT

AACTCTCCTTTTGTGGAGTTGGAAACAGAGTTGCCTTTAGCGATTCCAGTG

GTTACGGCTATTGCTCTCTATGTTTTTATCATGCTTATTGCTTTGTTGAG

AAACACAATGAGTTGATGACCTAG 4197.1

(SEQ. ID. NO. 349)
ATGAAGGTGGAACCACGTTGCGACGTCCTTTCGAGGATGTCGCATTTTTTT

ATTAGGATACTAATTATGGAGTTGCAAGAATTAGTGGAGCGCAGTTGGGCA

ATCCGACAAGCTTATCACGAACTGGAAGTTAAGCATCATGATTCCAAGTGG

ACGGTAGAAGAAGACCTCTTGGCTTTATCTAATGATATTGGAAATTTCCAA

CGACTGGTGATGACAAAGCAAGGACGCTACTATGATGAAACACCCTACACA

CTGGAACAAAAACTTTCAGAAAATATCTGGTGGCTATTAGAACTTTCTCAA

CGTTTGGATATAGACATTCTGACGGAAATGGAAAACTTCCTCTCTGATAAA

GAAAAGCAATTGAACGTTAGGACTTGGAAGTAG 4197.4

(SEQ. ID. NO. 350)
ATGCTTGATTGGAAACAATTTTTTTCTAGCCTATCTGCGCTCCCGTAGTCGT

CTTTTTATCTATCTGCTTTCTTTGGCATTTCTTGTCTTACTCTTTCAGTTT

TTATTTGCCAGTCTAGGAATTTACTTCCTCTACTTTTTCTTCTTGTGTTGC

TTTGTAACCATATTATTTTTCACTTGGGACATATTGGTGGAAACGCAGGTC

TATCGCCAGGAACTTCTCTATGGAGAGAGGGAAGCCAAGTCTCCTTTGGAA

ATAGCTTTAGCAGAAAAATTAGAAGCGCGTGAGATGGAACTCTATCAGCAG

AGGTCAAAAGCAGAAAGAAACTGACGGATTTGCTGGATTACTATACCTTG

TGGGTCCATCAGATAAAGACCCCCATTGCAGCCAGTCAACTCTTAGTTGCA

GAAGTGGTCGACCGCCAACTGAAGCAGCAGCTAGAACAGGAAATTTTCAAA

ATCGACTCCTATACCAACCTAGTTTTACAGTACCTGCGTTTAGAAAGTTTC

CATGATGATTTGGTCTTAAAGCAGGTTCAAATTGAGGACTTGGTCAAGGAA

ATAATTCGTAAATATGCTCTTTTCTTTATTCAAAAAGGCTTAAATGTCAAT

CTACATGACCTTGATAAAGAAATCGTGACGGATAAAAGTGGCTGCTAGTG

GTTATTGAGCAAATCATCTCAAACAGTCTCAAGTACACCAAGGAAGGTGGT

CTGGAGATTTATATGGATGACCAAGAGCTTTGTATCAAAGATACGGGAATC

TABLE 3-continued

```
GGGATAAAAAACAGTGATGTCCTCCGAGTATTTGAACGTGGCTTTTCAGGA
TACAATGGCCGTTTGACCCAGCAGTCCTCTGGACTTGGCCTTTATCTATCT
AAGAAAATTTCTGAAGAACTGGGGCACCAGATTCGTATCGAGTCTGAGGTC
GGAAAAGGAACGACAGTGCGGATTCAGTTTGCTCAAGTGAACTTAGTCCTT
GAGTAA
```

4211.2
(SEQ. ID. NO. 351)
```
ATGGAACTTAATACACACAATGCTGAAATCTTGCTCAGTGCAGCTAATAAG
TCCCACTATCCGCAGGATGAACTGCCAGAGATTGCCCTAGCAGGGCGTTCA
AATGTTGGTAAATCCAGCTTTATCAACACTATGTTGAACCGTAAGAATCTC
GCCCGTACATCAGGAAAACCTGGTAAAACCCAGCTCCTGAACTTTTTTAAC
ATTGATGACAAGATGCGCTTTGTGGATGTGCCTGGTTATGGCTATGCTCGT
GTTTCTAAAAAGGAACGTGAAAAGTGGGGGTGCATGATTGAGGAGTACTTA
ACGACTCGGGAAAATCTCCGTGCGGTTGTCAGTCTAGTTGACCTTCGTCAT
GACCCGTCAGCAGATGATGTGCAGATGTACGAATTTCTCAAGTATTATGAG
ATTCCAGTCATCATTGTGGCGACCAAGGCGGACAAGATTCCTCGTGGTAAA
TGGAACAAGCATGAATCAGCAATCAAAAGAAATTAAACTTTGACCCGAGT
GACGATTTCATCCTCTTTTCATCTGTCAGTAAGGCAGGGATGGATGAGGCT
TGGGATGCAATCTTAGAAAAATTGTGA
```

4211.3
(SEQ. ID. NO. 352)
```
ATGACAAAGAAACAACTTCACTTGGTGATTGTGACAGGGATGAGTGGCGCA
GGGAAAACTGTAGCCATTCAGTCCTTCGAGGATCTAGGTTATTTCACCATT
GATAATATGCCGCCAGCTCTCTTGCCTAAGTTTTTGCAGCTGGTTGAAATT
AAGGAAGACAATCCTAAGTTGGCCTTGGTAGTGGATATGCGTAGCCGTTCT
TTCTTTTCAGAGATTCAAGCTGTTTTGGATGAGTTGGAAAATCAAGATGGT
TTGGATTTCAAAATCCTCTTTTTGGATGCGGCTGATAAGGAATTCCTCGCT
CGTTACAAGGAAACCAGACGGAGTCACCCACTAGCAGCAGACGGTCGTATT
TTAGATGGAATCAAGTTGGAACGTGAACTCTTGGCACCTTTGAAAAATATG
AGCCAAAATGTGGTGGATACGACTGAACTCACTCCACGTGAGcTGCGCAAA
ACCCTTGCAGAGCAGTTTTCAGACCAAGAACAAGCCCAGTCTTTCCGTATC
GAAGTCATGTCTTTCGGATTTAAGTATGGAATCCCGATTGATGCGGACTTG
GTCTTTGATGTCCGTTTCTTGCCAAATCCCTATTATTTACCAGAACTGAGA
AACCAAACGGGTGTGGATGAACCTGTTTATGATTATGTCATGAACCATCCT
GAGTCAGAAGACTTTTATCAACATTATTGGCCTTGATTGAGCCGATTCTG
CCAAGTTACCAAAAGGAAGGTAAGTCCGTTTTGACCATTGCCATGGGATGT
ACGGGTGGACAACACCGTAGTGTGGCATTTGCTAAACGCTTGGCGCAGGAC
TTATCCAAGAATTGGTCTGTTAATGAAGGGCATCGCGACAAAGACCGCAGA
AAGGAAACGGTAAACCGTTCATGA
```

4211.4
(SEQ. ID. NO. 353)
```
ATGAGAAAACCAAAGATAACGGTGATTGGTGGAGGGACTGGAAGTCCCGTC
ATTCTAAAAAGTCTGCGGGAAAAAGATGTGGAAATCGCAGCTATCGTGACG
```

```
GTGGCAGATGATGGTGGTTCTTCAGGTGAACTCCGAAAAAATATGCAACAG
TTGACACCGCCAGGTGATCTTCGTAATGTCCTTGTGGCCATGTCGGATATG
CCTAAGTTTTATGAGAAGGTCTTTCAGTATCGGTTCTCTGAGGATGCCGGA
GCCTTTGCTGGCCATCCATTGGGAAATCTCATCATTGCTGGCTTGTCAGAA
ATGCAGGGTTCAACCTATAATGCCATGCAGTTATTGAGCAAATTTTTCCAT
ACAACAGGGAAATTTATCCTTCCAGTGACCATCCTTTGACCCTTCATGCA
GTCTTTCAGGATGGGACGAAGTGGCTGGAGAGAGTCATATTGTAGACCAT
CGAGGCATAATTGACAATGTCTATGTGACCAATGCCCTAAACGATGATACG
CCTCTGGCCAGCCGTCGAGTAGTGCAGACCATCCTTGAAAGTGACATGATT
GTCCTAGGGCCAGGTTCCCTCTTTACCTCTATTTTGCCCAATATCGTGATT
AAGGAAATTGGGCGGGCTCTTTTGGAAACCAAGGCAGAAATTGCCTATGTC
TGCAATATCATGACCCAACGTGGGGAGACGGAACACTTTACAGATAGCGAC
CACGTGGAAGTCTTGCATCGTCACCTTGGTCGCCCTTTTATCGACACTGTC
TTGGTGAATATTGAAAAAGTGCCTCAGGAATACATGAATTCCAACCGTTTT
GATGAATACTTAGTGCAAGTGGAACACGATTTTGTAGGTCTTTGTAAGCAA
GTTTCGCGCGTGATTTCATCTAACTTCCTTCGTCTGGAAATGGCGGTGCC
TTCCACGATGGAGATTTGATTGTGGACGAGTTGATGCGCATTATACAGGTG
AAAAAATGA
```

4213.1
(SEQ. ID. NO. 354)
```
ATGAAAAATTTGATAAAGTTGCTAATAATTAGATTGATTGTTAACTTAGCA
GACAGTGTATTTTATATAGTAGCATTGTGGCACGTTAGCAATAATTATTCT
TCGAGCATGTTCTTAGGAATATTTATTGCAGTAAATTATCTACCGGATTTG
TTACTAATCTTTTTTGGACCAGTTATTGACAGAGTAAATCCGCAAAAAATT
CTTATAATATCAATTTTGGTTCAATTAGCAGTGGCTGTAATATTTTATTA
TTATTAAACCAAATATCATTTTGGGTGATAATGAGTCTAGTGTTTATTTCA
GTAATGGCTAGCTCCATAAGTTACGTGATAGAAGATGTGTTGATTCCTCAA
GTGGTAGAATATGATAAGATTGTATTTGCAAATTCTCTTTTTAGTATTTCG
TATAAAGTATTAGATTCTATTTTTAATTCATTCGCATCATTTTTACAGGTG
GCAGTAGGATTTATTTTATTGGTTAAGATAGATATAGGCATATTTTTACTT
GCTCTATTTATATTGTTGTTGTTAAAATTTAGAACTAGCAATGCGAATATA
GAAAACTTCTCTTTCAAATATTACAAGAGAGAAGTGTTGCAAGGTACAAAG
TTTATTTTAAATAATAAATTATTATTTAAAACCAGTATTTCTTTAACGCTT
ATAAACTTTTTTATTCATTTCAGACAGTAGTTGTACCGATTTTTTCTATTC
GATATTTTGATGGTCCGATTTTTTATGGTATTTTTTAACTATTGCTGGTT
TGGGTGGTATATTGGGAAATATGCTAGCGCCAATCGTAATAAAATATTTAA
AATCGAATCAAATTGTTGGTGTATTTCTTTTTTTGAACGGCTCAAGTTGGT
TAGTAGCAATTCTTATAAAAGACTATACTTTATCACTTATTTTATTTTTCG
TTTGTTTTATGTCTAAAGGAGTCTTCAATATTATTTTTAATTCGTTGTACC
AACAAATACCTCCACATCAACTTCTTGGTAGGGTAAATACTACCATTGATT
CTATTATTTCTTTTGGAATGCCAATTGGTAGTTTAGTTGCAGGAACGCTTA
```

TABLE 3-continued

TTGATTTGAATATTGAATTAGTGTTAATTGCTATTAGCATACCTTATTTTT

TGTTTTCTTATATTTTTTATACGGATAATGGATTGAAAGAATTTAGTATAT

ATTAG 4213.2

(SEQ. ID. NO. 355)
ATGATGTCTAACAAAAATAAGGAAATTCTGATTTTTGCGATTCTCTATACA

GTCCTCTTTATGTTTGATGGCGTTAAATTGCTGGCTTCTTTAATGCCATCT

GCCATTGCAAATTATCTTGTTTATGTAGTTTTAGCTCTATATGGCTCCTTC

TTGTTCAAGGATAGATTGATCCAACAATGGAAGGAGATTAGAAAGACTAAA

AGAAAATTCTTCTTTGGAGTCTTAACAGGATGGCTCTTTCTCATTCTGATG

ACTGTTGTCTTTGAATTTGTATCAGAGATGTTGAAGCAGTTTGTGGGACTA

GATGGACAAGGTCTAAATCAGTCTAATATTCAAAGTACCTTTCAAGAACAA

CCACTACTGATAGCTGTTTTTGCTTGTGTCATTGGACCTCTGGTAGAAGAA

TTATTTTTCCGTCAGGTCTTATTGCATTACTTGCAGGAACGGTTGTCAGGT

TTACTAAGCATTATTCTGGTAGGACTTGTTTTTGCTCTGACTCATATGCAC

AGTTTGGCTCTATCAGAGTGGATTGGTGCAGTTGGTTACTTAGGTGGAGGC

CTTGCCTTTTCTATTATTTATGTGAAAGAAAAAGAGAATATCTACTATCCC

CTACTTGTTCACATGTTAAGCAACAGCCTCTCCTTAATCATTTTAGCTATC

AGTATAGTAAAATGA 4224.1

(SEQ. ID. NO. 356)
TTGAAAAAGCCAATTATCGAATTCAAAAACGTCTCTAAAGTTTTTGAAGAC

AGCAACACCAAGGTTCTCAAAGACATCAACTTTGAGTTGGAAGAAGGGAAA

TTCTACACCCTTCTAGGTGCATCTGGTTCGGGGAAATCAACTATCCTAAAC

ATTATTGCAGGTTTACTGGATGCGACGACAGGAGATATCATGCTAGACGGT

GTTCGTATCAATGATATTCCAACCAACAAGCGCGACGTACATACCGTCTTC

CAATCCTATGCCTTGTTCCCACATATGAATGTGTTTGAAAATGTTGCCTTT

CCACTTCGCTTGCGTAAAATTGATAAGAAAGAAATCGAGCAGCGTGTAGCG

GAAGTTCTCAAGATGGTTCAGTTGGAAGGTTATGAAAAACGTTCCATCCGC

AAACTTTCTGGAGGACAACGTCAGCGTGTGGCCATCGCCCGTGCTATCATC

AACCAACCCCGTGTGGTCTTGTTGGACGAGCCTTTATCAGCGCTGGACTTG

AAATTGAGAACAGACATGCAGTACGAATTGCGTGAATTACAACAACGATTG

GGCATTACCTTTGTCTTTGTCACTCACGATCAGGAAGAAGCTCTTGCCATG

AGTGACTGGATTTTCGTTATGAATGATGGCGAGATTGTCCAGTCTGGAACC

CCTGTGGACATCTACGATGAGCCAATCAACCACTTTGTTGCCACCTTTATC

GGGGAGTCAAACATCTTGCCAGGTACCATGATTGAGGACTACTTGGTCGAA

TTTAACGGCAAACGCTTTGAAGCGGTTGATGGTGGGATGAAGCCAAATGAA

CCTGTTGAGGTCGTTATTCGTCCAGAGGACTTGCGCATTACCCTTCCTGAA

GAAGGCAAGCTCCAAGTTAAGGTCGATACCCACTTTTCCGTGGAGTTCATT

ATGAAATTATCGCCTATGACGAACTTGGAAATGAATGGATGATCCACTCAA

CCCGTAAGGCTATCGTGGGTGAGGAAATCGGTCTGGACTTTGAACCAGAAG

ACATCCACATCATGCGTCTCAATGAAACCGAAGAAGAGTTCGATGCTCGTA

TTGAGGAGTACGTAGAAATCGAAGAGCAAGAAGCAGGTTTGATCAATGCAA

TCGAGGAGGAAAGAGATGAAGAAAACAAGCTCTAA 4252.1

(SEQ. ID. NO. 357)
ATGAAATCAATGAGAATCTTATTTTTGTTAGCTTTAATTCAAATCAGTTTG

AGTAGCTGTTTCCTATGGAAGGAATGCATCTTGTCCTTTAAACAAAGTACA

GCTTTTTTCATCGGAAGCATGGTTTTCGTTTCAGGAATCTGTGCTGGAGTA

AATTATCTTTATACCCGTAAGCAAGAAGTCCATAGTGTCCTAGCCAGTAAG

AAGTCGGTGAAGCTTTTTTACAGTATGTTACTCTTAATTAATTTGTTAGGA

GCTGTTCTTGTTTTGTCAGATAACTTGTTCATCAAAAATACGCTGCAGCAA

GAATTAGTTGACTTTTTATTGCCATCCTTCTTTTTCCTATTTGGGCTAGAT

TTGCTGATTTTTTTACCCTTGAAAAAATACGTGCGCGATTTTCTTGCTATG

CTGGACAGAAAAAAGACAGTGTTGGTGACTATTTTAGCAACACTTCTTTTC

TTAAGAAATCCAATGACCATTGTCTCACTTCTGATTTATATTGGACTGGGC

TTGTTTTTTGCAGCCTATCTTGTCCCAAATTCGGTTAAGAAGGAAGTTTCC

TTTTTATGGTCATATTTTCCGAGATCTTGTATTGGTCATTGTTACGCTCAT

TTTCTTTTAG 4252.2

(SEQ. ID. NO. 358)
ATGGTTAAAAAAATTATTGGAATGGTGCTAGCTTTACTTTCTGTAACTGTA

GTAGGAGTAGGTGTTTTTGCTTATACTATTTATCAACAAGGGACAGAAACC

TTAGCTAAAACCTATAAAAAAATCGGTGAAGAAACCAAGGTTATTGAAGCG

ACTGAACCTCTAACCATTCTGTTAATGGGAGTGGACACCGGAAATGTTGAA

CGAACTGAAACTTGGGTCGGTAGAAGTGATAGCATGATCTTGATGACAGTG

AATCCTAAAACGAAAAAAACAACAATGATGAGTTTAGAGCGGGATATTCGA

CGCGCATTGAATCAGGGAATGGTCAGGCTCATGAAGCGAAACTGAACTCAG

CATATGCAGATGGTGGAGCAGAGCTTGCTATAGAAACCATTCAAAAAATGA

TGAATATCCATATTGATCGCTATGTGATGGTCAATATGAGAGGATTGCAAA

AACTAGTGGATGCAGTAGGAGGTATTACAGTCAATAATATCCTAGGTTTCC

CAATTTCTATCAGTGACCAAGAAGAATTTAATACTATTTCTATCGGTGTTG

GGGAGCAACATATTGGGGGAGAAGAAGCCCTAGTCTATGCACGAATGCGTT

ACCAAGATCCTGAGGGGGATTATGGTCGTCAAAAACGTCAACGTGAAGTTA

TTCAAAAAGTCATGGAAAAAGCTCTCAGTTTAAATAGCATTGGTCATTATC

AAGAGATTCTAAAAGCTTTGAGTGACAATATGCAGACCAATATTGATTTGT

CTGCAAAAAGTATCCCTAACTTGCTAGGCTATAAAGATTCATTTAAAACCA

TTGAAACTCAGCAGTTGCAGGGTGAAGGAGAGATACTTCAAGGTGTTTCTT

ACCAGATTGTTTCGAGAGCACATATGTTGGAAATGCAAAATCTACTCCGAC

GTTCTTTGGGACAAGAAGAAGTTACTCAGCTTGAAACCAATGCGGTTTTAT

TTGAAGATTTATTTGGCAGAGCACCTGTTGGTGATGAAGATAATTAA 4256.2

(SEQ. ID. NO. 359)
ATGAAAAAACAAGCCTATGTCATTATTGCTCTCACCTCCTTCCTATTTGTC

TTTTTTTTCTCCCACAGCTTGCTGGAAATACTTGATTTTGACTGGTCTATC

TABLE 3-continued

TTTTTGCACGATGTCGAAAAAACAGAAAAATTTGTCTTTTTATTGTTGGTT
TTCAGCATGTCCATGACCTGTCTCTTAGCCCTGTTTTGGCGAGGGATCGAA
GAGCTTTCTCTAAGAAAAATGCAGGCTAATCTCAAGCGTTTATTAGCAGGG
CAAGAAGTGGTTCAGGTTGCAGATCCAGATTTGGATGCCAGTTTCAAGTCC
TTATCAGGTAAACTTAACCTTTTGACAGAGGCTCTTCAAAAAGCTGAAAAT
CAGAGCCTTGCTCAGGAAGAGGAAATCATCGAGAAGGAACGGAAGCGAATT
GCTCGGGATTTGCACGATACAGTCAGTCAGGAGTTGTTTGCGGCCCACATG
ATTTTATCGGGTATCAGTCAGCAGGCTTTGAAATTGGATAGAGAAAAGATG
CAGACCCAGTTGCAGAGTGTCACAGCTATTTTAGAAACAGCCCAGAAGGAT
TTGCGGGTTTTGCTCTTGCATTTGCGACCAGTTGAACTGGAGCAGAAGAGC
TTGATAGAAGGGATTCAAATTCTTTTAAAAGAGCTTGAGGACAAGAGTGAT
CTTAGGGTTAGTCTCAAGCAGAATATGACGAAATTGCCTAAGAAAATCGAG
GAGCATATCTTCCGTATCCTGCAAGAGTTGATTAGCAATACCCTCCGCCAT
GCCCAGGCATCTTGCCTAGATGTCTACCTCTATCAGACAGATGTTGAATTG
CAACTGAAGGTGGTGGACAATGGGATTGGTTTCCAGTTAGGGAGCTTAGAC
GACTTGAGTTATGGACTGCGAAATATCAAGGAGCGGGTTGAAGATATGGCT
GGAACAGTTCAACTCTTGACAGCTCCCAAGCAAGGGCTGGCGGTTGATATC
CGTATTCCCCTGTTAGATAAGGAATGA 4263.1
(SEQ. ID. NO. 360)
ATGATTGTTTCCATTATTTCTCAAGGATTTGTCTGGGCTATTCTAGGTCTG
GGAATCTTTATGACATTTAGGATTTTAAACTTTCCAGATATGACGACAGAA
GGTTCCTTCCCTCTTGGGGGAGCTGTTGCTGTCACTTTGATAACCAAAGGC
GTGAACCCATTTTTAGCGACACTTGTTGCTGTAGGAGCAGGTTGTTTGGCT
GGAATGGCAGCAGGCCTTCTTTATACAAAAGGGAAGATCCCAACCTTGCTC
TCAGGGATTTTGGTGATGACTTCTTGTCACTCAATCATGCTCTTGATTATG
GGACGTGCGAATTTAGGCCTGCTTGGAACCAAGCAAATTCAGGATGTTTTG
CCTTTTGATTCGGATTTGAATCAACTCTTGACAGGTCTCATCTTTGTGAGT
ATTGTTATTGCTCTCATGCTCTTTTTCTTGGACACTAAACTCGGACAAGCC
TATATTGCTACAGGGGATAATCCTGATATGGCTAGAAGTTTCGGGATTCAT
ACTGGACGCATGGAGCTCATGGGCTTGGTCTTATCAAATGGTGTGATTGCC
CTTGCAGGTGCCCTCATTGCTCAGCAAGAAGGTTATGCCGATGTGTCTCGA
GGGATCGGGGTTATCGTTGTGGGCTTGCAAGTTTGATTATTGGAGAAGTT
ATTTTCAAGAGTTTGAGCTTGGCAGAGCGTTTGGTTACTATCGTTGTAGGT
TCTATCGCTTATCAATTTTTAGTGTGGGCAGTTATCGCACTTGGCTTTAAT
ACAAGTTACCTTCGTTTATACAGTGCCTTGATTTTAGCAGTCTGCCTCATG
ATTCCAACATTTAAGCAAACAATCTTGAAAGGAGCCAAGTTAAGCAAATGA 4346.1
(SEQ. ID. NO. 361)
ATGAAAAAAATGAAAGTTTGGTCTACTGTACTTGCAACGGGAGTTGCTCTT
ACTACACTTGCTGCTTGCTCTGGAGGTTCAAATTCTACGACTGCTTCTTCA
TCTGAAGAAAAGCTGATAAAAGTCAAGAATTAGTTATCTATTCGAACTCA

GTCTCAAATGGTCGTGGTGATTGGTTAACTGCTAAAGCAAAAGAAGCTGGT
TTTAATATAAAAATGGTTGATATCGCTGGCGCTCAATTAGCAGACCGTGTT
ATTGCTGAGAAGAATAATGCAGTTGCAGATATGGTATTTGGAATTGGTGCT
GTTGATTCAAATAAAATTAGAGATCAAAAATTACTAGTACAGTACAAGCCT
AAATGGTTAGATAAAATTGATCAATCTTTATCAGATAAAGATAATTATTAT
AATCCTGTGATTGTTCAACCATTAGTTTTAATTGGGGCGCCTGATGTAAAA
GAAATGCCTAAAGATTGGACTGAATTAGGTAGTAAGTATAAAGGTAAATAT
TCAATTTCTGGTCTTCAAGGAGGTACAGGACGGGCAATTCTAGCAAGTATC
TTAGTTCGATACCTTGATGATAAAGGTGAATTAGGTGTTTCCGAAAAAGGT
TGGGAAGTAGCAAAAGAATATTTGAAAAATGCATACACTCTTCAAAAGGGA
GAAAGTTCAATTGTTAAGATGTTAGACAAAGAAGATCCAATACAATATGGA
ATGATGTGGGGTTCTGGTGCATTAGTTGGACAAAAAGAACAAAATGTTGTT
TTCAAAGTTATGACTCCTGAGATTGGTGTACCATTTGTAACTGAACAAACT
ATGGTTTTAAGCACTAGTAAAAAACAAGCGTTAGCTAAAGAATTTATTGAT
TGGTTTGGTCAATCAGAAATTCAAGTAGAATATAGTAAGAACTTTGGATCT
ATTCCTGCAAATAAAGATGCCCTCAAAGATCTACCTGAAGATACGAAGAAA
TTTGTTGATCAAGTGAAACCACAAAATATTGACTGGGAAGCTGTTGGAAAG
CATTTGGATGAATGGGTAGAAAAAGCTGAATTAGAATACGTACAATAA 4346.2
(SEQ. ID. NO. 362)
ATGATTAAATTTGATAATATTCAAATTAAATATGGTGATTTTGTTGCAATT
GATAATCTGAATTTAGATATACATGAAGGGGAATTTTTTACATTTCTTGGG
CCTTCAGGATGTGGTAAATCAACTACTTTGAGAGCATTGGTAGGTTTTCTA
GATCCATCATCAGGAAGTATTGAAGTTAATGGAACAGATGTCACTCATTTG
GAACCTGAAAAGCGTGGAATTGGTATTGTATTTCAATCTTATGCGCTATTT
CCAACTATGACTGTTTTTGATAATATTGCATTTGGTTTAAAGTTAAGAAGG
TAGCTCCAGATGTTATTAAAGCTAAAGTATCAGCAGTGGCAGCAAAAATTA
AGATCTCTGATCAACAGTTACAGCGTAATGTATCAGAATTATCTGGGGGTC
AACAACAAAGGGTAGCATTGGCTCGTGCTCTGGTTCTTGAACCTAAAATTC
TTTGTCTAGATGAACCATTGTCAAACCTTGACGCAAAATTACGTGTAGATT
TGAGAAAAGAGTTGAAAAGACTTCAAAAAGAGTTAGGTATTACTACTTTAT
ATGTTACTCATGATCAAGAGGAAGCCTTGACTTTATCTGATAGAATTGCAG
TCTTTAACAATGGATACATCGAACAGGTCGGTACACCAGTAGAGATTTATC
ATAATTCTCAAACTGAATTTGTATGTGATTTTATTGGAGATATTAATGTTT
TGACCGATGAAACAGTCCACGAAGTATTATTGAAAAATACAAGCGTTTTCT
TAGAGGATAAAAAGGATACATTCGATTAGAGAAAGTTCGATTCAATCGTG
AAACTGAACAAGATTTTATTCTAAAAGGGACAATTATTGATGTTGAGTTTT
CTGGAGTTACAATTCACTATACAATAAAAGTTTCTGAAAGTCAGATTCTTA
ATGTAACAAGTATTGATAGTCAGGCTGCTATTAGATCTGTCGGAGAAAGTG
TGGAATTATTTATCACACCATCAGACGTTCTGCAATTTTAA

TABLE 3-continued 4346.3
(SEQ. ID. NO. 363)
ATGCGTCATAAATTAAATTTAAAAGATTGGCTTATTCGTTTAGGGTTAATC
TGGTTCTTAGTAACATTTATTATTTATCCAAACTTTGATCTAGTAGTGAAT
GTATTTGTAAAAGGAGGAGAATTTTCCCTTGATGCTGTACATCGTGTTCTA
AAATCTCAGAGGGCACTTCAGAGTATTATGAACAGTTTTAAGTTAGCATTT
TCACTCATTATTACAGTTAATGTCGTAGGTATTCTTTGTGTTCTATTTACA
GAGTACTTTGATATTAAAGGTGCTAAAATTTTAAAATTAGGTTATATGACC
TCTTTAATTTATGGAGGAGTGGTTTTAGCGACTGGATATAAATTTGTCTAT
GGTCCTTATGGATTGATTACAAAATTTTTACAAAATGTTATCCCTTCTTTA
GACCCTAACTGGTTTATTGGGTATGGTGCAGTCTTATTCATTATGACATTT
TCAGGAACTGCTAATCATACATTGTTTTTAACAAATACAATTCGAAGCGTT
GACTATCACACTATTGAGGCTGCTCGAAATATGGGAGCAAAACCATTTACT
GTTTTCCGAAAAGTAGTGTTACCAACCTTAATTCCAACTCTATTTGCACTT
ACTATTATGGTTTTTCTTAGTGGTTTATCTGCAGTAGCAGCACCCATGATT
GTTGGTGGTAAAGAATTTCAAACTATAAATCCAATGATTATTACATTTGCA
GGGATGGGGAATTCTCGTGATTAGCTGCCCTACTTGCAATTATTTTAGGT
ATTGCAACTACAATTTTGCTTACTATCATGAATAAGATAGAAAAAGGTGGA
AATTATATTTCTATCTCTAAGACTAAAGCGCCTCTTAAAAAACAAAAAATT
GCGTCTAAGCCTTGGAATATCATTGCTCACATTGTAGCATATGGATTGTTC
ACAGTTTTCATGCTTCCACTAATTTTTATAGTATTATACTCATTTACAGAT
CCAGTTGCAATTCAAACAGGTAACTTAACATTATCAAACTTTACTTTAGAA
AATTATCGCTTATTCTTTAGTAATAGTGCGGCATTCTCTCCATTCTTGGTC
AGCTTTATTTATTCTATTATTGCTGCGACAACAGCAACAATTCTCGCAGTT
GTATTTGCTCGTGTTGTCAGAAAACATAAATCTCGTTTTGATTTCTTATTT
GAATATGGTGCTCTACTTCCTTGGTTACTACCAAGTACACTTTTAGCAGTA
AGTTTATTATTTACTTTTAATCAGCCACAATTTCTTGTCTTGAATCAGATT
TTGGTAGGTAGTTTGGTAATTCTACTTATTGCATATATAGTTGTAAAAATC
CCATTTTCTTATAGAATGGTACGTGCTATTTTATTTAGTGTTGATGATGAG
ATGGAAGATGCAGCAAGAAGTATGGGTGCTTCACCTTTTTATACTATGATG
AAGGTTATCATTCCATTTATTTTACCGGTTGTTCTCTCTGTTATTGCTTTA
AACTTTAACTCTTTATTAACTGACTTCGACTTATCTGTATTCCTTTACCAT
CCCCTAGCTCAACCATTAGGTATTACGATTCGATCTGCAGGTGATGAAACA
GCAACATCTAATGCACAAGCTCTGGTATTTGTTTATACAATTGTTCTGATG
ATTATTTCTGGAACGGTATTATACTTCACACAAAGACCGGGCGTAAAGTAA
GGAAATAA

TABLE 4

(SEQ ID. NO. 1)
MEELVTLDCLFIDRTKIEANANKYSFVWKKTTEKFSAKLQEQIQVYFQEE
ITPLLIKYAMFDKKQKRGYKESAKNLANWHYNDKEDSYTHPDGWYYRFHH

TABLE 4-continued

TKYQKTQTDFQQEIKVYYADEPESAPQKGLYMNERYQNLKAKECQALLSP
QGRQIFAQRKIDVEPVFGQIKASLGYKRCNLRGKRQVRIDMGLVLMANNL
LKYSKMKZ (SEQ ID. NO. 2)
MGKGHWNRKRVYSIRKFAVGACSVMIGTCAVLLGGNIAGESVVYADETLI
THTAEKPKEEKMIVEEKADKALETKNIVERTEQSEPSSTEAIASEKKEDS
AVTPKEEKVSAKPEEKAPRIESQASNQEKPLKEDAKAVTNEEVNQMIEDR
KVDFNQNWYFKLNANSKEAKPDADVSTWKKLDLPYDWSIFNDFDHESPAQ
NEGGQLNGGEAWYRKTFKLDEICDLKKNVRLTFDGVYMDSQVYVNGQLVG
HYPNGYNQFSYDITKYLQKDGRENVIAVHAVNKQPSSRWYSGSGIYRDVT
LQVTDKVHVEKNGTTILTPKLEEQQHGKVETHVTSKIVNTDDKDHELVAE
YQIVERGGHAVTGLVRTASRTLKAHESTSLDAILEVERPKLWTVLNDKPA
LYELITRVYRDGQLVDAKKDLFGYRYYHWTPNEGFSLNGERIKFHGVSLH
HDHGALGAEENYKAEYRRLKQMKEMGVNSIRTTHNPASEQTLQIAAELGL
LVQEEAFDTWYGGKKPYDYGRFFEKDATHPEARKGEKWSDFDLRTMVERG
KNNPAIFMWSIGNEIGEANGDAHSLATVKRLVKVIKDVDKTRYVTMGADK
FRFGNGSGGHEKIADELDAVGFNYSEDNYKALRAKHPKWLIYGSETSSAT
RTRGSYYRPERELKHSNGPERNYEQSDYGNDRVGWGKTATASWTFDRDNA
GYAGQRWTGTDYIGEPTPWHNQNQTPVKSSYFGIVDTAGIPKHDFYLYQS
QWVSVKKKPMVHLLPHWNWENKELASKVADSEGKIPVRAYSNASSVELFL
NGKSLGLKTFNKKQTSDORTYQEGANANELYLEWKVAYQPGTLEAIARDE
SGKEIARDKITTAGKPAAVRLIKEDHAIAADGKDLTYIYYEIVDSQGNVV
PTANNLVRPQLHGQGQLVQVDNGEQASRERYKAQADGSWIRKAFNGKGVA
IVKSTEQAGKFTLTAHSDLLKSNQVTVFTGKKEGQEKTVLGTEVPKVQTI
IGEAPEMPTTVPFVYSDGSRAERPVTWSSVDVSKPGIVTVKGMADGREVE
ARVEVIALKSELPVVKRIAPNTDLNSVDKSVSYVLIDGSVEEYEVDKWEI
AEEDKAKLAIPGSRIQATGYLEGQPIHATLVVEEGNPAAPAVPTVTVGGE
AVTGLTSQKPMQYPXLAYGAKLPEVTASAKNAAVTVLQASAANGMRASII
IQPKDGGPLQTYAIQFLEEAPKIAHLSLQVEKADSLKEDQTVKLSVRAHY
QDGTQAVLPADKVTFSTSGEGEVAIRKGMLELHKPGAVTLNAEYEGAKDQ
VELTIQANTEKKIAQSIRPVNVVTDLHQEPSLPATVTVEYDKGFPKTHKV
TWQAIPKEKLDSYQTFEVLGKVEGIDLEARAKVSVEGIVSVEEVSVTTPI
AEAPQLPESVRTYDSNGHVSSAKVAWDAIRPEQYAKEGVVVNGRLEGTQL
TTKLHVRVSAQTEQGANISDQWTGSELPLAFASDSNPSDPVSNVNDKLIS
YNNQPANRWTNWNRTNPEASVGVLFGDSGILSKRSVDNLSVGFHEDHGVG
VPKSYVIEYYVGKTVPTAPKNPSFVGNEDHVFNDSANWKPVTNLKAPAQL
KAGEMNHFSFDKVETYAVRIRMVKADNKRGTSITEVQIFAKQVAAAKQGQ
TRIQVDGKDLANFNPDLTDYYLESVDGKVPAVTASVSNNGLATVVPSVRE
GEPVRVLAKAENGDILGEYRLHFTKDKSLLSHKPVAAVKQARLLQVGQAL
ELPTKVPVYFTGKDGYETKDLTVEWEEVPAENLTKAGQFTVRGRVLGSNL

TABLE 4-continued

VAEITVRVTDKLGETLSDNPNYDENSNQAFASATNDIDKNSHDRVDYLND
GDHSENRRWTNWSPTPSSNPEVSAGVIFRENGKIVERTVTQGKVQFFADS
GTDAPSKLVLERYVGPEFEVPTYYSNYQAYDADHPFNNPENWEAVPYRAD
KDIAAGDEINVTFKAIKAKAMRWRMERKADKSGVAMIEMTFLAPSELPQE
STQSKILVDGKELADFAENRQDYQITYKGQRPKVSVEENNQVASTVVQSG
EDSFPVLVRLVSESGKQVKEYRIHLTKEKPVSEKTVAAVQEDLPKIEFVE
KDLAYKTVEKKDSTLYLGETRVEQEGKVGKERIEFAINPDGSKEEKLREV
VEVPTDRIVLVGTKPVAQEAKKPQVSEKADTKPIDSSEASQTNKAQLPST
GSAASQAAVAAGLTLLGLSAGLVVTKGKKEDZ (SEQ. ID. NO. 3)
MKIMKXKYWTLAILFFCLFNNSVTAQEIPKNLDGNITHTQTSESFSESDE
KQVDYSNKNQEEVDQNKFRIQIDKTELPVTTDKHLEKNCCKLELEPQINN
DIVNSESNNLLGEDNLDNKIKENVSHLDNRGGNIEHDKDNLESSIVRXYE
WDIDKVTGGGESYKLYSKSNSKVSIAILDSGVDLQNTGLLKNLSNMSKNY
VPNKGYLGKEEGEEGIISDIQDRLGHGTAVVAQIVGDDNINGVNPHVNIN
VYRIFGKSSASPDWIVKAWDAVDDGNDHNLSTGQYLMIDGEYEDGTNDFE
TFLKYKKAIDYANQKGVIIVAALGNDSLNVSNQSDLLKLISSRIZKVRKP
GLVVVDVPSYFSSTISVGGIDRIGNLSDFSNKGDSDAIYAPAGSTLSLSEL
GLNNFINAEKYKEDWIFSATLGGYTYLYGNSFAAPKVSGAIAMIIDKYKL
KDQPYNYMFVKKFWKKHYQZ (SEQ. ID. NO. 4)
MKKTWKVFLTLVTALVAVVLVACGQGTASKDNKEAELKXVDFILDWTPNT
NHTGLYVAKEKGYFKEAGVDVDLKLPPEESSSDLVINGKAPFAVYFQDYM
AKKLEKGAGITAVAAIVEHNTSGILSRKSDNVSSPKDLVGKKYGTWNDPT
ELAMLKTLVESQGGDFEKVEKVPNNDSNSITPIANGVFDTAWIYYGWDGI
LAKSQGVDANFMYLKDYVKEFDYYSPVIIANNDYLKDNKEEARKVIQAIK
KGYQYAMEHPEEAADILIKNAPELKEKRDFVIESQKYLSKEYASDKEKWG
QFDAARWNAFYKWDKENGILKEDLTDKGFTNEFVKZ (SEQ. ID. NO. 5)
MKRTWRNSFVTNLNTPFMIGNIEJPNRTVLAPMAOVTNSAFRTIAKELGA
GLVVMEMVSDKGIQYNNEKTLHMLHIDEGENPVSIQLFGSDEDSLARAAE
FIQENTKTDIVDINMGCPVNKIVKNEAGAMWLKDPDKIYSIINIVQSVLD
IPLTVKMRTGWADPSLAVENALAAEEAAGVSALAMHGRTREQMYTGHADLE
TLYKVAQALTICIPFIANGDIRTVQEAKQRIEEVGADAVMIGRAAMGNPY
LFNQINHYFETGEILPDLTFEDKMKIAYEHLKRLINLKGENVAVRERGLA
PHYLRGTSGTSGAAKLRGAISQASTLAEIETLLQLEKAZ (SEQ. ID. NO. 6)
MIKNPKLLTKSFLRSFAILGGVGLVIHIAIYLTFPFYYIQLEGEKFNESA
RVFTEYLKTKTSDEIPSLLQSYSKSLTISAHLKRDIVDKRLPLVHDLDIK
DGKLSNYIVMLDMSVSTADGKQVTVQFVHGVDVYKEAKNILLLYLPYTFL
VTIAPSFVFSYFYTKRLLNPLFYISEVTSKMQDLDDNIRFDERJCDEVGE
VGKQINGMYEELLKVIYELESRNEQIVKLQNQKVSFVRGASHELKTPLAS

LRMLENMQHNIGDYKDHPKYIAKSINKIDQMSHLLEEVLESSKFQEWTEC
RETTVKPVLVDILSRYQELAHSIGVTIENQLTDATRVVMSLRALDKVLTN
LISNAIKYSDKNGRVHSEQDGYLSIKNTCAPLSDQELEHLFDFYHSQIVT
DKDESSGLGLY1VNNILESYQMDYSFLPYEHGMEFKISLZ (SEQ. ID. NO. 7)
MYLGDLMEKAECGQFSILLQESQTTVKAVMEETGFSKATLTKYVTLLNDK
ALDSGLELAIHSEDENLRLSIGAATKGRDIRSLFLESAVKYQILVYLLYH
QQFLAHQLAQELVISEATLGRHLAGLNQILSEFDLSIQNGRWRGPEHQIH
YFYFCLFKVWSSQEWEGHMQKPERKQEIANLEEICGASLSAGQKLDLVLW
AHISQQRLRVNACQFQVIEEKMRCYPDNIFYLRLLRKVPSFFAGQHIPLG
VEDGEMMIFFSFLLSHRILPLHTMEYILGFGGQLADLLTQLIQEMKKEEL
LGDYTEDHVTYELSQLCAQVYLYKGYILQDRYKYQLENRHPYLLMEHDFK
ETAEEIFHALPAFQQGTDLDKKILWEWLQLIEYMAEGGQHMRIGLDLTSG
FLVFSRMAAILKRYLEYNRFITTIEAYDPSRHYDLLVTNNPIHKKEQTPV
YYLKNDLDMEDLVAIRQLLFTZ (SEQ. ID. NO. 8)
MEFSKKTRELSIKKMQERTLDLLHGGGITGAGVALQAAASGLETGLIEMQ
DFAEGTSSRSTKLVHGGLRYLKQFDVEVVSDTVSERAVVQQIAPHIPKSD
PMLLPVYDEDGATFSLFRLKVAMDLYDLLAGVSNTPAANKVLSKDQVLER
QPNLKKEGLVGGGVYLDFRNNDARLVIENIKRANQDGALANHKAEGFLFD
ESGKITGVVARDLLTDQVFEIKARLVINTTGPWSDKVRNLSNKGTQPSQM
RKGVHLVVDSSKIKVSQPVYFDTGLGDGRMVFVLPRENKTYEGTTDTDYT
GDLEHPKVTQEDVDYLLGIVNNRFPESNITIDDIESSWAGLRPLIAGNSA
SDYNGGNNGTISDESFDNLIATVESYLSKEKTREDVESAVSKLESSTSEK
HLDPSAVSRGSSLDRDDNGLLTLAGGKITDYRKMAEGAMERVVDIICAEF
DRSFKLINSKTYPVSGGELNPANVDSEIEAFAQLGVSRGLDSKEAHYLAN
LYGSNAPKVFALAHSLEQAPLSLADTLSHYAMRNELLTLSPVDFLLRRTN
HMLFMRDSLDSIVEPILDEMGRFYDWTEEEKATYRADVEAALANNDLAEL
KNZ (SEQ. ID. NO. 9)
MMNELFGEFLGTLIILLGNGVVAGVVLPKTKSNSSGWIVITMGWGIAVAV
AVFVSGKLSPAYLNPAVTIGVALKGGLPWASVLPYILAQFAGAMLGQILV
WLQFKPHYEAEENAGNILATFSTGPAIKDTVSNLISEILGTFVLVLTIPA
LGLYDFQAGIGTFAVGTLIVGIGLSLGGTTGYALNPARDLGPRIMHSILP
IPNKGDGDWSYAWIPVVGPVIGAALAVLVFSLFZ (SEQ. ID. NO. 10)
MTKKKERISVIHREKILWLKWYFMRDKEQPKYSVLERKMFDAAKNQDMLA
YQKYATIKQTSEADIRVQTSEADILEAVKEVYVYNHMNVIGACQRILFIS
QSPAYDKLNKWPNIYSDLYFSVVPLPKMGVYHEMVGIZ (SEQ. ID. NO. 11)
MKNSNEAEMKLLYTDIRTSLTEILTREAEELVAAGKRVFYIAPNSLSFEK
ERAVLEYLSQQASFSITVTRFAQMARYLVLNDLPAKTTLDDIGLGLAFYK

TABLE 4-continued

CLAELDPKDLRVYGAIKQDPQLIQQLIELYHEMTKSQMSFLDLENLTDED
KRADLLLIFEKVTAYLNQGQLAQESQLSHLIEAIENDKVSSDFNQIALVI
DGFTRFSAEEERVVDLLHGKGVEWIGAYASKKAYTSPFSEGNLYQAVKFL
HHLASKYQTPAQDCSQTHEKMDSFDKASRLLESSYDFSELALDVDEKDRE
NLQIWSCLTQKEELELVARSIRQKLHENSDLSYKHFRJLLGGDVASYQLSL
KTIFDQYQIPFYLGRSEAMAHHPLTQFVESILALKRYRPRQEDLINLLRT
DLYTDLSQSDIDAFEQYIRYLGINGLPAFQQTFTKSHHGKFNLERLNVLR
LRILAPLETLFASRKQKAEKLLQKWSVFLKEGAVTKQLQDLTITLEAVEQ
ERQAEVWKAFCNVLEQFATVFAGSQVSLEDFLALLHSGMSLSQYRTIPAT
VDTVLVQSYDLIAPLTADFVYAIGLTQDNLPKISQNTSLLTDEERQNLNQ
ATEEGVQLLIASSENLKKNRYTMLSLVNSARKQLFLSAPSLFNESESKES
AYLQELIHFGFRRREKRMNHKGLSKEDMGSYHSLLSSLVAYHQQGEMSDT
EQDLTFVKVLSRVIGKKLDQQGLENPAIPTSPSSKTLAKDTLQALYPAKQ
EFYLSTSGLTEFYRNEYSYFLRYVLGLQEELRLHPDARSHGNFLHRFEAL
QLPNEDSFDQRLEQAIQETSQERBFSAIYQESLEAQITKEVLLDVARTTG
HILRHNPAIETIKEEANFGGKDQAFIQLDNGRSVFVRGKVDRIDRLKANG
AIGVVDYKSSLTQFQFPHFFNGLNSQLPTYLAALKREGEQNFFGAMYLEM
AEPVQSLMAVKSLAGAVVEASKSMKYQGLFLEKESSYLGEFYNKNKANQL
TDEEFQLLLDYNAYLYKKAAEKILAGRFAINPYTENGRSIAPYVQQHQAI
TGFEANYHLGQARFLEKLDLADGKRLVGEKLKQAWLEKIREELNRZ
(SEQ. ID. NO. 12)
MKLIPFLSEEEIQKLQEAEANSSKEQKKTAEQIEAIYTSAQNILVSASAG
SGKTFVMAERLDQLARGVEISQLFISTFTVKAATELKERLEKJCISKKIQ
ETDDVDLKQHLGRQLADLPNAAIGTMDSFTQKFLGKHGYLLDIAPNFRIL
QNQSEQULENEVFHEVFEAHYQGKQKETFSHLLKNFAGRGKDERGLRQQV
YKIYDFLQSTSNPQKWLSESFLKGFEKADFTSEKEKLTEQIKQALWDLES
FFRYHLDNDAKEIAKAAYLENVQLILDEEGSLNQESDSQAYQAVLARVVA
ISKEKNGRALTNASRKADLKPLADAYNEERKTQFAKLGQISDQIAILDYQ
ERYHGDTWKLAKTFQSFMSDFVEAYRQRKRQENAPEFADISHYTIEILEN
FPQVRESYQERFHEVMVDEYQDTNHIQERMLELLSNGHNRFMVGDIKQSI
YRFRQADPQCFNEKFQRYAQNPQEGRLIILKENFRSSSEVLSATNDVFER
LMDQEVGEINYDNKHQLVFANTKLTPNPDNKAAFLLYDKDDTGEEEESQR
ETKLTGEMRLVIKEILKLHQEKGVAFKRIALLTSSRSRNOQILLALSEYG
EPVKTDGEQNNYLQSLEVQVMLDTLRVIHNPLQDYALVALMKSPMFGFDE
DELARLSLQKAEDGVHENLYEKLVNAQKMASSQKGLIHTALAEKLKQFMD
ILASWRLYAKTHSLYDLIWKIYNDRFYYDYVGALPNGPARQANLYALALR
ADQFEKSNFEKGLSRFIRMIDQVLEAQHDLASVAVAPPKDAVELMTIHKS
KGLEFPYVFILNMDQDINKQDSMSEVILSRQNGLGVKYIAKMETGAVEDH
YPKTIKLSIPSLTYRQNEEELQLASYSEQMRLLYVAMTRAEKKLYLVGKG
SREKLESKEYPAAKNGKLNSNTRLQARNFQDWLWAISKVFTKDKLNFSYR
FIGEDQLTREAIGELETKSPLQDSSQADNRQSDTIKEALEMLKEVEVYNT
LHRAAIELPSVQTPSQUCKPYEPVMDMEGVEIAGQGQSVGKKISFDLPDF
STKEKVTGAEIGSATHELMQRIDLSQQLTLASLTETLKQVQTSQAVRDKI
NLDKILAFFDTVLGQEILANTDHLYREQPFSMLKRDQKSQEDFVVRGILD
GYLLYENKIVLFDYKTDRYDEPSQLVDRYRGQLALYEEALSRAYSIENIE
KYLILLGKDEVQVVKVZ
(SEQ. ID. NO. 13)
MELARHAESLGVDALATIPPIYFRLPEYSVAKYWNDISSAAPNTDYVCYN
IPQLAGVALTPSLYTEMLKNPRVIGVKNSSMPVQDIQTFVSLGGEDMIVF
NGPDEQFLGGRLMGARAGIGGTYGAMPELFLKLNQLIADKDLETARELQY
AINAHGKLTSAHGNMYGVIKEVLKINBGLNIGSVRSPLTPVTEEDRPVVE
AAAALIRETKERFLZ
(SEQ. ID. NO. 14)
MYKTKCLREKLVLFLKIFFPIUYQFANYSASFVDTAMTGQYNTMDLAGVS
MATSTWNPPFTPLTGIVSALVPIIGHHLGRGKKEEVASDFYQFIYLALGL
SVVLLGMVLPLAPIILNHIGLEAAVAAVAVRYLWFLSIGIIPLLLFSVIR
SLLDSLGLTKLSMYLMLLLLPLNSGFNYLLIYGAFGVPELGGAGAGLGTS
LAYWVLLGISVLVLFKQEKLKALHLEKRIPLNMDKIKEGVRLGLPIGGTV
FAEVAIFSVVGLIMAKFSPLIIASHQSAMNFSSLMYAFPMSISSAMAIVV
SYEVGAKRFDDAKTYIGLGRWTALIFAAFTLTFLYIFRGNVASLYGNDPK
FIDLTVRFLTYSLFFQLADTFAAPLQGILRGYKDTVIPFYLGLLGYWGVA
IPVYAIZ
(SEQ. ID. NO. 15)
MSTLAKIEALLFVAGEDGIRVRQLAELLSLPPTGIQQSLGKLAQKYEKDP
DSSLALIETSGAYRLVTKPQFAEILKEYSKAPINQSLSRALETLIIAYKQ
PITRIEIDAIRGVNSSGALAKLQAFDLIKEDGKKEVLGRPNLYWITDYFL
DYMGINHLEELPVIDELEIQAQESQLFGERIEEDENQZ
(SEQ. ID. NO. 16)
MDTMISRFFRHLPEALKSLKRNGWMTVAAVSSVMITLTLVAIFASVIFNT
AKLATDIENNVRVVVYIRKDVEDNSQTIEKEGQTVTNNDYHKVYDSLKNM
STVKSVTFSSKEEQYEKLTEIMGDNWKIFEGDANPLYDAYIVEANTPNDV
KTIAEDAKKIEGVSEVQDGGANTERLFKLASFIRVWGLGIAALLIFIAVF
LISNTIRITIISRSREIQIMRLVGAKNSYIRGPFLLEGAFIGLLGAIAPS
VLVFIVYQIVYQSVNKSLVGQNLSMISPDLFSPLMIALLFVIGVFIGSLG
SQGISMRRFLKIZ
(SEQ. ID. NO. 17)
MKKVRFIFLALLFFLASPEGAMASDGTWQGGQYLKEDGSQAANEWVFDTH
YQSWFYIKADANYAENEWLKQGDDYFYLKSGGYMAKSEWVEDKGAFYYLD
QDGKMKRNAWVGTSYVGATGAKVIEDWVYDSQYOAWFYIKADGQHAEKEW
LQIKGKDYYFKSGGYLLTSQWINQAYVNASGAKVQQGWLFDKQYQSWFYI
KBNGNYADKEWIFENGFHYYYLKSGGYMAANEWEWDKESWFYLKFDGKMA
EKEWVYDSHSQAWYYFKSGGYMTANEWIWDKESWFYLKSDGKIAEKEWVY

DSHSQAWYYFKSGGYMTANEWIWDKESWFYLKSDGKIAEKEWVYDSHSQA
WYYFKSGGYMAKNETVDGYQLGSDGKWLGGKTTNENAAYYQVVPVTANVY
DSDGEKLSYISQGSVVWLDKDRKSDDKRLAITISGLSGYMKTEDLQALDA
SKDFIPYYESDGHRFYHYVAQNASIPVASHLSDMEVGKKYYSADGLHFDG
FKLENPFLFICDLTEATNYSAEELDKVFSLLNINNSLLENKGATFKEAEE
HYHINALYLLAHSALESNWGRSKIAKDKNNFFGITAYDITPYLSAKTFDD
VDKGILGATKWIKENYIDRGRTFLGNKASGMNVEYASDPYWGEKIASVMM
KINEKLGGKDZ (SEQ. ID. NO. 18)
MKKVLQKYWAWAFVVIPLLLQAIPFYVPMFQGAFYSFTNWTGLTYNYKFV
GLNNFKLLFMDPKFMNAIGFTAIIAIAMVVEIALCIARVLNSKIKGQTFF
RAWFHPAVLSGLTVALIFKQVFNYGLPAIGNALHIEFFQTSLLGTKWGAI
FAAVFVLLWQOVAMPEIIFLAGLQSIPTEITEAARIDGATSKQVFWNIEL
PYLLPSVSMVFELALKGGLTAFDQVFAMTGGGPNNATTSLGLLVYNYAFK
NNQFGYANAIAVILFFLIVVISHQLRVSKKFEIZ (SEQ. ID. NO. 19)
MMKQDERKALIGKYILLILGSVLILVPLLATLFSSFKPTKDIVDNFFGFF
TNFTWDNFSRLLADGIGGYYWNSVVITVLSLLAVMIFIPMAAYSIARNMS
KRKAFTIMYTLLILGIFVPFQVIMIPITVMMSKLGLANTPGLILLYLTYA
IPQTLFLYVGYIKISIPESLDEAAEIDGANQFTTYFRIIFPMMKPMHATT
MIINALWFWNDFMLPLLVLNRDSKMWTLPLFQYNYAGQYFNDYGPSFASY
VVGIISITIVYLFFQRHIHSGMSNGAVKZ (SEQ. ID. NO. 20)
MKSILQKMGEHPMLLLFLSYSTVISILAQNWMGLVASVGMFLFTIFFLHY
QSILSHKFFRLILQFVLFGSVLSAAFASLEHPQIVKKPNYAPLSPNMQVW
HQNRAEVTFFNPNYYGIICCFCIMIAPYLFTTTKLNWLKVFCVIAGPVNL
FGLNFTQNRTAFPAIIAGAIIYLFTTTKNWKAFWLSIGVFAIGLSFLFSS
DLGVRMGTLDSSMEERISIWDAGMALFKQNPFWGEGPLTYMNSYPRIHAP
YHEHAHSLYIDTILSYGIVGTILLVLSSVAPVRLMMDMSQESGKRPIIGL
YLSFLTVVAVHGIFDLALFWIQSGFIFLLVMCSIPLEHRMLVSDMTDZ (SEQ. ID. NO. 21)
MSKMDVQKIIAPMMKFVNMRGIIALIKDGMLAILPLTVVGSLFLIMGQLP
FEGLNKSIASVFGANWTEPPMQVYSGTFAIMGLISCFSIAYSYAKNSGVE
ALPAGVLSVSAFFILLRSSYIPKQGEAIGDAISKVWFGGQGHGAHIGLVV
GSIYTFFIKRKIVIKMPEQVPQAIAKQFEAMIPAVIFLSSMIVYILAKSL
TNGGTFIEMIYSAIQVPLQGLTGSLYGAIGIAFFISFLWWFGVHGQSVVN
GVTALLLSNLDANKAMLASANLSLENGAHIVTQQFLDSFLILSGSGITFG
LVVAMLFAAKSKQYQALGKVAAFPAIFNVNEPVVFGFPEVMNPVMFVPFI
LVPVLAAVIVYGAIATGFMQPFSGVTLPWSTPAILSGFLVGGWQGVETQL
VILAMSTLVYFPFFKVQDRLAYQNEIKQSZ (SEQ. ID. NO. 22)
MKKKDLVDQLVSEIETGKVRTLGIYGHGASGKSTFAQELYQALDSTTVNL
LETDPYITSGRHLVVPKDAPNQKVTASLPVAHELESLQRDILACRRVWMS
Z (SEQ. ID. NO. 23)
MKKRYLVLTALLALSLAACSQEKTKNEDGETKTEQTAKADGTVGSKSQGA
AQKKAEVVNKGDYYSIQGKYDEIIVANKHYPLSKDYNPGENPTAKAELVK
LIKAMQEAGPPISDHYSGFRSYETQTKLYQDYVNQDGKAAADRYSARPGY
SEHQTGLAFDVIGTDGDLVTEEKAAQWLLDHAADYGFVVRYLKGKEKETG
YMAEEWHLRYVGKEAIKEIAASGLSLEEYYGFEGGDYVDZ (SEQ. ID. NO. 24)
MREPDFLNHFLKKGYFKKHAKAVLALSGGLDSMFLFKVLSTYQKELEEEL
ILAHVNHKQRIESDWEEKELRKLAAEAELPIYISNFSGEFSEARARNFRY
DFFQEVMKKTGATALVTAHHADDQVETIFMRLIRGTRLRYLSGIKEKQVV
GEIEIIRPFLHFQKKDFPSIFHFEDTSNQENHYFRNRIRNSYLPELEKEN
PRFRDAILGIGNEILDYDLAIAELSNNINVEDLQQLPSYSESTQRVLLQT
YLNRFPDLNLTKAQFAEVQQILKSKSQYRHPIKNGYELEKEYQQFQICKI
SPQADEKBDELVLHYQNQVAYQGYLFSFGLPLEGELIQQIPVSRETSIHI
RHRKTGDVLIKNGHRKKLRRLFIDLKIPMEKRNSALIIEQFGEIVSILGI
ATNNLSKKTKNDIMNTVLYIEKIDRZ (SEQ. ID. NO. 25)
MRKPLIILLLPSFLTISKVVSTEKEVVYTSKEIYYLSQSDFGIYFRBKLS
SPMVYGEVPVYANEDLVVESGKLTPKTSFQITEWRLNKQGIPVPKLSNHQ
FIAADKRFLYDQSEVTPTIICKVWLESDFKLYNSPYDLKEVKSSLSAYSQ
VSIDKTMFVEGREFLHIDQAGWVAKESTSEEDNRMSKVQEMLSEKYQKDS
FSIYVKQLTTGKSAGINQDEKMYAASVLKLSYLYYTQEKINEGLYQLDTT
VKYVSAVNDFPGSYKPEGSGSLPKKEDNKEYSLKDUTKVSKESDNVAHNL
LGYYISNQSDATFKSKMSAIMGDDWDPKEKLISSKMAGKFMEAIYNQNGF
VLESLTKTDFDSQRIAKGVSVKVAHKIGDADEFKHDTGVVYADSPFILSI
FTKNSDYDTISKIAKDVYEVLKZ (SEQ. ID. NO. 26)
MKKQNNGLIKNPFLWLLFIFFLVTGFQYFYSGNNSGGSQQINYTELVQEI
TDGNVKELTYQPNGSVIEWSGVYKNPKSTKEETGIQFFIPSVTKVEKFTS
TILPADITVSELQKLATDHKAEVTVKHBSSSGIWINLLVSWPFGILFFFL
FSNIMGNMGGGNGRNPMSFGRSKAXANKBDIKVRFSDVAGAEEEKQELVE
VVEFLKDPKRFKLGARIPAGVLLEGPPGTGKLLLAKAVAGEAGVPFFSDS
GSDLVEMFVGVGASRVRSLFEDAKKAAPAIIFIDEIDAVGRQRGVGLGGG
NFRTRQTLNQLLIEMDGFEGNEGIIVIAATNSDVLDPALLRPGRFDRKVL
VGRPDVKGEAILKVHAKNKPLAEDVDLKLVAQQTPGFGFVGADLENVLNE
AALVAARRNSIIDASDIDEAEDRVIAGPSKKKDKTVSQKERELVAYHEAG
HIVGLVLSNARVVHKVTIVPRGRAGGYMIALPKEDQMLEDMKEQLAGLMG
GRVAEEIIFNVQITGASNDFEQATQMARAMVTEYGMSEKLGPVQYEGNHA

TABLE 4-continued

```
MLGAQSPQSEQTAYEIDEEVRSLLNEARNKAAEHQSNRETHKLLEALLKY
ETLDSTQIKALYETGKMPEAVEEESHALSYDEVKSKMNDEKZ
```
(SEQ. ID. NO. 27)
```
MKRSSLLVRMVISIFLVFLILLALVGTFYYQSSSSAIEATIEGNSQSQTS
HFIQSYIKKLETTSTGLTQQTDVLAYAENPSQDKVEGIRDLFLTILKSDK
DLKTVVLVTKSGQVISTDDSVQMKTSSDMMAEDWYQKAIHQGAMPVLTPA
RKSDSQWVISVTQELVDAKGANLGVLRLDSYETLEAYLNQLQLGQQGFAF
IINENHEFVYHPQHTVYSSSSKMEAMKPYDTGQGYTPGHKSYVSQEKIAG
TDWTVLGVSSLEKLDQVRSQLLWTLLGASVTSLLVCLCLVWFSLKRWIAP
LKDLRETMLEIASGAQNLRAKEVGAYELREVTRQFNAMLDQIDQLMVAIR
SQEETTRQYQLQALSSQINPHFLYNTLDTIIWMAEFHDSQRVVQVTKSLA
TYFRLALNQGKDLICLSDEINHVRQYLFIQKRYGDKLEYEINENVAFDN
LVLPKLVLQPLVENALYHGIKEKEGQGHIKLSVQKQDSGLVIREDDGVGF
QDAGDSSQSQLKRGGVGLQNVDQRLKLHPGANYHMKIDSRPQKGTKVEIY
INRIETSZ
```
(SEQ. ID. NO. 28)
```
MKRSSLLVRMVISIFLVFLILLALVGTIYYQSSSSAIEATIEGNSQTTIS
QTSHFIQSYIKKLETTSTGLTQQTDVLAYAENPSQDKVEGIRDLFLTILK
SDKDLKTVVLVTKSGQVISTDDSVQMKTSSDMMAEDWYQKAIHQGAMPVL
TPARKSDSQWVISVTQELVDAKGANLGVLRLDISYETLEAYLNQLQLGQQ
GFAFIINENHEFVYHPQHTVYSSSSKMEAMKPYIDTGQGYTPGHKSYVSQ
EKIAGTDWTVLGVSSLEKLDQVRSQLLWTLLGASVTSLLVCLCLVWFSLK
RWIAPLKDLRETMLEIASGAQNLRKEVGAYELREVTRQFNAMLDQIDQLM
VA1RSQEET1RQYQLQALSSQINPHFLYNTLDTUWMAEFHDSQRVVQVTK
SLATYFRLALNQGKDLICLSDENHVRQYLPIQKRYGDKLEYEINENVAF
DNLVLPKLVLQPLVENALYHGIKEKEGQGHIKLSVQKQDSGLVIRIEDDG
VGFQDAGDSSQSQLKRGGVGLQNVDQRLKLHFGANYHMKIDSRPQKGTKV
EIYINRIETSZ
```
(SEQ. ID. NO. 29)
```
MFFKLLREALKVKQVRSKILETIFWLVFRIGTSITVPGVNANSLNALSGL
SFLNMLSLVSGNALKNFSIFALGVSPYITASIVVQLLQMDILPKFVEWGK
QGEVGRRKLNQATRYIALVLAFVQSIGITAGFNTLAGAQLIKTALTPQVF
LTIGIILTAGSMIVTWLGEQETDKGYGNGVSMHFAGWSSIPEMIQGIYVD
YFVNVPSSRITSSIIFVHLIITVLLIIYFTTYVQQAEYKIPIQYTKVAQG
APSSSYLPLKVNPAGVIPVIFASSITAAPAAILQFLSATGHDWAWVRVAQ
EMLATTSPTGIAMYALLIILFTFFYTFVQINPEKAAERYKRVVPISMEFV
LVKVQKNICLNFFVVLQLLVPSSLVZ
```
(SEQ. ID. NO. 30)
```
MDIRQVTETIAMIEEQNFDIRTITMGISLLDCIDPDENRAAEKIYQKITT
KAANLVAVGDEIAAELGIPIVNKRVSVTPISLIGAATDATDYVVLAKALD
KAAKE1GVDFIGGFSALVQKGYQICGDEILINSIPRALAETDKVCSSVNI
GSTKSGINMTAVADMGRIIKETANLSDMGVAKLVVFANAVEDNPFMAGAF
HGVGEADVIINVGVSGPGVVKRALEKVRGQSPDVVAETVKKTAFKITRIG
QLVGQMASERLGVEFGIVDLSLAPTPAVGDSVARVLEEMGLETVGTHGTT
AALALLNDQVKKGGVMACNQVGGLSGAFIPVSEDEGMEAAVQNGSLNLEK
LEAMTAICSVGLDMIAIPEDTPAETIAAMIADEAAIGVINMKTTAVRIIP
KGKEGDMIEIGGLLGTAPVMKVNGASSVDFISRGGQIPAPIHSFKNZ
```
(SEQ. ID. NO. 31)
```
MTQIIDGKALAAKLQGQLAEKTAKLKEETGLVPGLVVILVGDNPASQVYV
RNKERSALAAGFRSEVVRVPETITQEELLDLIAKYNQDPAWHGILVQLPL
PKHIDEEAVLLAIDPEKDVDGFHPLNMGRLWSGHPVMIPSTPAGIMEMFH
EYGIDLEGKNAVVIGRSNIVGKPMAQLLLAKNATVTLTHSRTHNLSKVAA
XADILVVAIGRAKFVTADFVKPGAVVIDVGMNRDENGKLCGDVDYEAVAP
LASHITPVPGGVGPMTITMLMEQTYQAALRTLDRKZ
```
(SEQ. ID. NO. 32)
```
MSKFNRIHLVVLDSVGIGAAPDANNFVNAGVPDGASDTLGHISKTVGLNV
PNMAKIGLGNIPRETPLKTVAAESNPTGYATKLEEVSLGKDTTGHWEIMG
LNITEPFDTFWNGFPEE1LTKIEEFSGRKVIREANKPYSGTAVIYDFGPR
QMSTGELHYTSADPVLQIAAHEDIIPLDELYRICEYARSITLERPALLGR
IIARPYVGEPGNFTRTANRRDLAVSPFFPTVLDKLNEAGIDTYAVGKIND
IFNGAGINHDMGHNKSNSHGIDTLLKTMGLAEFEKGFSFTNLVDFDALYG
HRRNAHGYRDCLHEPDERLPEHAAMRENDLLLITADHGNDPTYAGTDHTR
EYIPLLAYSPAFKGNGLIPVGHFADISATVADNFGVETAMIGESFLDKLV
Z
```
(SEQ. ID. NO. 33)
```
MFISISAGLVTFLLTLVEPAFIQFYRKAQITGQQMNEDVKQHQAKAGTPT
MGGLVPLITSVLVAFFFALFSSQFSNNVGMILFILVLYGLVGFLDDFLKV
FRKINEGLNPKQKLALQLLGGVIFYLFYERGGDILSVPGYPVHLGFFYIP
FALFWLVGFSNAVNLTDGVDGLASISVVISLSAYGVIAYVQGQMDLLLVI
LAMIGGLLGFFIPNHKPAKVFMGDVGSLALGGMLAAISMALHQEWTLLUG
IVYVFEFTSVMMQVSYFKLTGGKPIFRMTPVHHHFELGGLSGKGNPWSEW
KVDFFFWGVGLLASLLTLAILYLMZ
```
(SEQ. ID. NO. 34)
```
LFKKNKDELNIALPAMGENFLQMLMGMVDSYLVAHLGLIAISGVSVAGNI
MYQAIRALGAAISSVLSKSIGQKDQSKLAYNVTEALKITLLLSILLGFLS
IFAGKSMIGLLGTERDVAESGGLYLSLVGGSIVLLGLMTSLGALIRATHN
PRLPLYVSFLSNALNILFSSLAIFVLDMGIAGVAWGTIVSRLVGLVILWS
QLKLPYGKPTFGLDKELLTLALPAAGERLMMRAGDVVHALVVSFGTEAVA
GNAIGEVLTQFNYMPAFGVATATVMLLARAVGEDDWKRVASLSKQTLFLS
LFMLPLSFSIYVLGVPLTHLYTDSLAVEASVLVTLFSLLGTPMTTGTVIY
TAVWQGLGNARLPFYATSIGMWCIRIGTGYLMGIVLGWGLPGIWAGSLLD
NGFRWLFLRYRYQRYMSLKGZ
```
(SEQ. ID. NO. 35)
```
MQTQEKRSQAAVLGLQHLAMYSGSILVPIMIATALGYSAEQLTYLISTDI
FMCGVATFLQLQLNKYFGIGLPVVLGVAFQSVAPLIMIGQSHGSGAMFGA
```

TABLE 4-continued

LIASGIYVVLVSGIFSKVANLFPSIVTGSVITTIGLTLIPVAIGNMGNNV
PEPTGQSLLAAITVLIILINIFTKGFIKSISILIGLVVGTAIAATMGLVD
FSPVAVAPLVHPTPLYFG,PTFEISSIVMMCIIATVSMVESTGVYLALSD
ITKDPIDSTRLRNGYREGLAVLLGGIFNTFPYTGFSQNVGLVKLSGIKKR
LPIYYAAGFLVLLGLLPKFGALAQIIPSSVLGGAMLVMFGFVSIQGMQIL
ARVDFANNEHNFLIAAVSIAGVGLNNSNLFVSMPTAFQMFFSNGIVVASL
LAIVLNAVLNHKKKZ (SEQ. ID. NO. 36)
MKDRKEYLQDKGKVTVNDLAQALGKDSSKDFRELIKTLLMERKHQIRFEE
DGSLTLEIKKKHEITLKGIFHAHKNGFGFVSLEGEEDDLFVGKNDVNYAI
DGDTVEVVHCKVADRNKGTAAEAKIIDILEHSLTTVVGQIVLDQEKPKYA
GYISKNQK1SQPIYVKKPALKLEGTEVLKVPEDKYPSKKHDFFVASVLDV
VGHSTDVGIDVLEVLESMDIVSEFPEAVVKEAESVPDAPSQKDMEGRLDL
RDEDGADAKDLDQAVHIKALKNGNLEPGVHADVSYYEGSALDKEALNRTS
VYVTDRVVPMLPERSNGICSLNPQVDRLTQSAIMEIDKHGRVVNTQTVIK
TSFRMTYSDVNDILAGDEEKEYHKIVSSIELMAKLHETLENMRVKRGALN
FDTNEAKILVDKQGKPVDIVLRQRGIAERMIESFMLMANETVAEHFSKLD
LPRYIHEBPKAEKVQKFIDYASSFGLRIYGTASELSQEALQDIMRAVEGB
PYADVLSMMLRSMQQARYSEHNHGHYGLAADYYTHFTSPIRRYPDLLVHR
MIRDYGRSKEIAEHFEQVIPEIATQSSNRERRAIEAEREVEAMKKAEYME
EYVGEEYDAVVSSIVKFGLFVELPNTVEGLINTNLPEFYHFNERDLTLRG
EKSGITFRVGQQIRIRVERADKMTGEIDFSFVPSEDFDVIEKGLKQSSRS
GRGRDSNRRSDKKEDKRKSGRSNDKRKHSQKDKKKKGKKPFYKEVAKKGA
KHGKGRGKGRRTKZ (SEQ. ID. NO. 37)
MGTTGFTIIDLIILIVYLLAVLVAGIYFSKKEMKGKEFFKGDGSVPWYVT
SVSIFATMLSPISFLGLAGSSYAGSWLWFAQLGMVVAIPLTHIILPIFAR
DIDTAYDYLDKRFNSKALRISALLFIIYQLGRMSUMYLPSAGLSVLTGID
INILIILMGVVAIVYSYTGGLKSVLWTDFIQGVILJSGVVLALFVLIANI
KGGFGAVAETLANGKFLAANEKLFDPNLLSNSIFLIVMGSGPTILSSYAS
SQDLVQRFTTTQNIKKLNKMLFTNGVLSLATAVFYLIGTGLYVFYQVQNA
DSAASNIPQDQIFMYFIAYQLPVGITGLILAAIYAASQSTISTGLNSVAT
SWTLDIQDVISKNMSDNRRTKIAQFVSLAVGLPSIGVSIVMAHSDIKSAY
EWFNSFMGLVLGLLGGVRLGVSKKANKQGAYAALPIVMVFICYFLPPTAV
SYWAYSLISISVSVVSGYIVSVLTGNKVSAPKYTTIEDITEIKADSSWEV
RMZ (SEQ. ID. NO. 38)
MKFSKKYAGSAVIVSLSLCAYALNQHRSQENKDNNRVSYVDGSQSSQKSE
NLTPDQVSQKEGIQAEQAEQIVIKITDQGYVTSHGDHYHYYNGKVPYDAL
FSEELLMKDPNYQLKDADIVNEVKGGYUKVDGKYYVYLKDAAHADNVRTK
DEINRQKQEHVKDNEKVNSNVAVARSQGRYTNDGYVPNPADIIEDTGNAY
IVPHGGHYHYIPKSDLSASELAAAKAHLGKNMQPSQLSYSSTASDNNTQS
VAKGSTSKPANKSENLQSLLKELYDSPSAQRYSESDGLVIDPAKIISRTP
NGVAIPHGDHYHPIPYSKLSALEEKTARVPISGTGSTVSTNAKPNEVVSS
LGSLSNPSSLTTSKELSSASDGYIFNPKDIVEETATAYWRHGDHFHYIPK
SNQIGQPTLPNNSLATPSPSLPINPGTSHEKHEEDGYGFDANRIIAEDES
GFVMSHGDHNHYFFKKDLTEEQIKVRKNIZ (SEQ. ID. NO. 39)
MKKRAIVAVIVLLLIGLDQLVKSYIVQQIPLGEVRSWIPNFVSLTYLQNR
GAAPSILQDQQLLFAVITLVVVIGAIWYLHKHMEDSFWMVLGLTLUAGGL
GNFIDRVSQGPVVDMFHLDFINFAIFNVADSYLTVGVIILLIAMLKEEIN
GNZ (SEQ. ID. NO. 40)
MNTNLASFIVGLHDENDRFYFVQKDGQTYALAKEEGQHTVGDTVKGFAYT
DMKQKLRLTTLEVTATQDQFGWGRVTEVRKDLGVFVDTGLPDKEIVVSLD
ILPELKELWPKXGDQLYIRLEVDKKDRIWGLLAYQEDFQRLARPAYNNMQ
NQNWPAIVYRKLSGTFVYLPENNNMLGFIHPSERYAEPRLGQVLDARVIG
FREVDRTLNLSLKPRSFEMLENDAQMILTYLSSNGGFMTLNDKSSPDDIK
ATFGISKGQFKKALGGLMKAGKIKQDQFGTELIZ (SEQ. ID. NO. 41)
MKDVSLFLLKKVFKSRLNWIVLALFVSVLGVTFYLNSQTANSHSLESRLE
SR1AANERAINENEEKLSQMSDTSSEEYQFAXNNLDVQKNLLTRKTEILT
LLKEGRWKEAYYLQWQDEBKNYEFVSNDPTASPGLKMGVDRERKIYQALY
PLNIKAHTLEFPTHGIDQIVWILEVIIPSLFVVAIIFMLTQLFAERYQNH
LDTAHLYPVSKVTFAISSLGVGVGYVTVLFIGICGFSPLVGSLISGFGQL
DYPYNYSLVNQEVTIGKIQDVLFPGLLLAFLAFIVIVEVVYLIAYPFKQK
MPVLFLSLIGIVGLLFGIQTIQPLQRIAHLIPFTYLRSVEILSGRLPKQI
DNVDLNWSMGMVLLPCLIIFLLLGILFISRWGSSQKICEFFNRFZ (SEQ. ID. NO. 42)
MMKFILDIVSTPAILVALIAILGLVLQKKKLPDIIKGGIKTFVGFLVVSG
GAGIVQNSLNPFGTMPEHAPHLSOVVPNNEAIVAVAUITYGSATAMIMFA
GMVFNILIARFTRFKYIFLTGHHTLYMACMIAVILSVAGFTSLPLILLGG
LALGUMSISPAFVQKYMVQLTGNDKVALGHFSSLGYWLSGFTGSLIGDKS
KSTEDIICPPKSLAPLRDSTVSITLSMAVIYUVAIFAGSEYIEKEISSGT
SGLVYALQLAGQFAAGVFVLAGVRLILGEIVPAPKGISERLVPNSKPALD
CPIVYTYAPNAVLIGFTSSFVGGLVSMVIMIASGTVVILPGVVPHFFCGA
TAGVTGNASGGVRGATIGAPLQGILISFLPVFLMPVLGGLGFQGSTFSDA
DFGLSGIILGMLNQFGSQAGIVIGLVLILAVMFGVSPIKKPSATEEZ (SEQ. ID. NO. 43)
MIKTFLSALSVILFSIPIITYSFPPSSNLNZWLSTQPILAQIYAFPLATA
TMAAILSFLFFFLSFYKKNKQIRFYSGILLLLSLILLLFGTDKTLSSASN
KTKTLKLVTWNVANQIEAQHIERIFSKFDADMAIFPELATNIRGEQENQR
IKLLFHQVGLSMANYDIFTSPPTNSGIAPVTVIVKXSYGFYTEAKTFHTT

TABLE 4-continued

RFGTIVLHSRKQNIPDIIALHTAPPLPGLMEIWKQDLNIIHNQLASKYPK
AIIAGDFNATMRHGALAKISSHRDALNALPPFERGTWNSQSPKLFNATID
HILLPKNHYYVKDLDIVSFQNSDHRCIFTEITFZ (SEQ. ID. NO. 44)
MNPIQRSWAYVSRKRLRSFLILLVLLAGISACLTLMKSNKTVESNLYKSL
NTSPSIKKIENGQTFKLSDLASVSKIKGLENVSPELEVAKLKDKEAVTGE
QSVERDDLSAADNNLVSLTALEDSSKDVTFTSSAFNLKEGRLHLQKGDSK
GKILHEELAKKNGSLHDKIGLDAGQSESGKQTVEFEIIGWSGKKQEKFTG
LSSDFSENQVFTDYESSQTLLGNSEAQVSAARFYVENPKEMDGLMKQVEN
IALENQGYQVEKENKAFEQIDSVATFQTPLTIFLYGMLIAGAGALILVLS
LWLRERVYEVGILLALGKGKSS1FLQFCLEVVLVSLGALLPAFVAGNAIT
TYLLQTLLASGDQASLQDTLAKASSLTSILSFAESYVFLVLLSCLSVALC
FLFLFRKSPKEILSSISZ (SEQ. ID. NO. 45)
MLHNAFAYVTRKFFKSIVTFLIILLMASLSLVGLSIKGATAKASQETFKN
ITNSFSMQINRRVNQGTPRGAGNEKGEDIKKITENKAIESYVKRINAIGD
LTGYDLIETPETKKNLTADRAKRFGSSLMITGVNDSSKEDKFVSGSYKLV
EGEHLTNDDKDKILLHKDLAAKHGWKVGDKVKLDSNIYDADNEKGAKETV
EVTIKGLFDGHNKSAVTYSQELYENTAITDIHTAAKLYGYTEDTAIYGDA
TFFVTADKNLDDVMKELNGISGINWKSYTLVKSSSNYPALEQSISGMYXM
ANLLFWGSLSPSVLLLALLLSLWINARRKEVGILLSIGLKQASILGQFIT
ESILIAIPALVSAYFLANYTARAIGNTVLANVTSGVAKQASKAAQASNLG
GGAEVDGFSKTLSSLD1SIQTSDFIIIFVLALVLVVLVMALASSNLLRKQ
PKELLLDGEZ (SEQ. ID. NO. 46)
MSQDKQMKAVSPLLQRVINISSIVGGVGSLIFCIWAYQAGILQSKETLSA
FIQQAGIWGPPLFIFLQILQTVVPIIPGALTSVAGVFIYGHIIGTIYNYI
GIVIGCAIIFYLVRLYGAAFVQSVVSKRTYDKYIDWLDKGNRFDRFFIFM
MIWPISPADFLCMLAALTKMSFKRYMTIIILTKPFTLVVYTYGLTYIIDF
EWQMLZ (SEQ. ID. NO. 47)
MRNMWVIKETYLRHVESWSFFFMVISPFLFLGISVGIGHLQGSSMAKNNK
VAVVTTVPSVAEGLKNVNGVNFDYKDEASAKEAIKEEKLKGYLTIDQEDS
VLKAVYHGETSLENGIKFEVTGTLNELQNQLNRSTASLSQEQEKRLAQTI
QFTEKIDEAKENXKFIQTIAAGALGFFLYMILITYAGVTAQEVASEKGTK
IMEVVFSSIRASHYFYARMMALFLVILTHIGIYVVGGLAAVLLFKDLPFL
AQSGILDHLGDAISLNTLLFILISLFMYVVLAAFLGSMVSRPEDSGKALS
PLMILIMGGFFGVTALGAAGDNLLLKIGSYIPFISTFFMPFRTINDYAGG
AEAWISLALTVWAVVATGFIGRMYASLVLQTDDLGIWKTFKRALSYKZ (SEQ. ID. NO. 48)
MTETIKLMIKAHTSVRRFKEQEIPQVDLNEILTAAQMASSWKNFQSYSVI
VVRSQEKKDALYELVPQEAIRQSAVFLLFVGDLNRAEKGARLHTDTFQPQ
GVEGLLISSVDAALAGQNALLAAESLGYGGVHGLVRYKSEEVAELFNLPD
YYTYSVFGMALGVPNQHHDMKPRLPLENVVFEEEYQEQSTEAIQAYDRVQ
ADYAGARATTSWSQRLAEQFGQAEPSSTRKNLEQKKLLZMLKLIAIVGTN
SKRSTNRQLLQYMQKHFTDKAEIELVEIKAIPVFNKPADKQVPAEILEIA
AKIEEADGVHGTPEYDHSIPAVLMSALAWLSYGIYPLLNKPIMITGASYG
TLGSSRAQLQLRQILNAPEIKANVLPDEFLLSHSLQAFNPSGDLVDLDVI
KKLDAIFDDPRIFVKITEKLRNAQELLRKDAEDFDWENLZ (SEQ. ID. NO. 49)
MNTYQLNNGVEIPVLGFGTFICAKDGEEAYRAVLEALKAGYRHIDTAAIY
QNEESVGQAIKDSGVPREEMFVTTKLWNSQQTYSQTRQALEKSIEKLGLD
YLDLYLIHWPNPKPLRENDAWFTRNAEVWRAMEDLYQEGKIRAIGVSNFL
PHHLDALLETATIVPAVNQVRLAPGVYQDQVVAYCREKGILLEAWGPPGQ
GELFDSKQVQEIAANHGKSVAQLALAWSLAEGFLPLPKSVTTSRIQANLD
CFGIELSHEERETLKTIAVQSGAPRVDDVDFZ (SEQ. ID. NO. 50)
MRCKMLDPIAIQLGPLAIRWYALCIVTGLILAVYLTMKEAPRKKIIPDDL
DPILVAFPLAILGARLYYVIFRFDYYSQNLGEIFAIWNGGLAIYGGLITG
ALVLYIFADRKLINTWDFLDIAAPSVMIAQSLGRWGNFFNQEAYGATVDN
LDYLPGRRDQMYIEGSYRQPTFLYESLWNLLGFALILIFRRKWKSLRRGH
ITAFYLIWYGFGRMVIEGMRTDSLMFFGFRVSQWLSVVLIGLGIMIVIYQ
NRKKAPYYITEEENZ (SEQ. ID. NO. 51)
MGKLSSILLGTVSGAALALFLTSDKGKQVCSQAQDPLDDLREDPEYAKEQ
VCEKLTEVKEQATDFVLKTKEQVESGEITVDSILAQTKSYAFQATEASKN
QLNNLKEQWQEKAEALDDSEEIVIDITEEZ (SEQ. ID. NO. 52)
MKTKLIFWGSMLFLLSLSILLTIYLAWIFYPMEIQWLNLTNRVYLKPETI
QYNFHILMNYLTNPFSQVLQMPDFRSSAAGLNHFAVVKNLFHLVQLVALV
TLPSFYVFVNRIVKKDFLSLYRKSLLALVVLPVMIGLGGVLIGFDQFFTL
FHQILFVGDDTWLFDPAKDPVEVILPETFFLHAFLLFFALYENFFGYLYL
KSRRKZ (SEQ. ID. NO. 53)
MTYHFTEEYDHVIGAGHAGVEASLAASRMGCKVLLATINIEMLAFMPCNP
SIGGSAKGIVVREVDALGGEMAKTIDKTYIQMKMLNTGKGPAVRALRAQA
DKELYSKEMRKTVENQENLTLRQTMIDEILVEDGKVVGVRTATHQEYAAK
AVNTTGTALRGEIIIGDLKYSSGPNHSLASINLADNLKELGLEIGRFKTG
TPPRVKASSINYDVTEIQPGDEVPNHFSYTSRDEDYVKDQVPCWLTYTNG
TSHEUQNNLHRAPMFTGVVKGVGPRYCPSIEDKIVRFADKERHQLFLEPE
GRNTEEVYVQGLSTSLPEDVQRDLVHSIKGLENAEMMRTGYAIEYDMVLP
HQLRATLETKKISGLFTAGQTNGTSGYEEAAGQGUAGINAALKIQGKPEL
ILKRSDGYIGVMIDDLVTKGTIEPYRLLTSRAEYRLILRHDNADMRLTEM
GREIGLVDDERWARFEIKKNQFDNEMKRLDSIKLKPVKETNAKVEEMGFK
PLTDAVTAKEFLRRPEVSYQDVVAFIGPAAEDLDDKIIELIETEIKYEGY

TABLE 4-continued

ISKAMDQVAKMKRMEEKRIPANIDWDDIDSIATEARQKFKUNPETIGQAS
RISGVNPADISILMVYLEGKNRSISKTLQKSKZ (SEQ. ID. NO. 54)
MTKQVLLVDDEEHILKLLDYHLSKEGFSTQLVTNGRKALALAETEPFDFI
LLDIMLPQLDGMEVCKRLRAKGVKTPIMMVSAKSDEFDKVLALELGADDY
LTKPFSPRELLARVKAVLRRTKGEQEGDDSDNIADDSWLFGTLKVYPERH
EVYKANKLLSLTPKEFESDKNPFFEVFKVSKVTAQZ (SEQ. ID. NO. 55)
MTTFKDGFLWGGAVAAHQLEGGWQEGGKGISVADVMTAGRHGVAREITLG
VLEGKYYPNHEAIDFYHRYKEDIALFAEMGFKCPRTSIAWTRFPKGDELE
PNEEGLQFYDNLPDECLKNGIEPVITLSHFEMPYHLVTEYGGWKNRKLID
FPAREAEVVFKRYKDKVKYWMTFNEINNQANYQEDFAPFTNSGIVYEEGD
NREAIMYQAAHYELVASARAVKIGHEINPDFQIYYMSFAIDSHRENNPYD
YLETEDLVKNNYVKASEWEWQIDPEGLRYALNWFTDHYHLPLFNENGFGM
DQVAADGMVHDDYREYLGAHIREMKKAVVEDGVDLMGYTPWGCIDLVSAG
TGEMRKRYGFIYVDKDDNGKGSYNRSPKKFGWYKEVISSNGESVEZ (SEQ. ID. NO. 56)
MDQQNGLFGFLENHVMGPMGKLAQPKVVLTAAGMAAVPFWGSMFLVFSIL
PQAPSPPWADIFSASFDKFTSLYMVANYATMGSLSLYFVLSLAYELTKIY
AEEEELNMNPLNGALLALMAFVMTVPQUFDGGMMKTSLKEGAVIADGWAM
GNVVARFGTTGIFTAHMAIVTVLIYRMCVKHNWVIKMPEAVPEGVSRGPT
ALVPGFVVAFVVIFINGLLVAMGTDIKVLMPFGFVSNLTNSWIGLMUYLL
TQLLWWGIHGANIVFAFVSPIALANMAENAAGGHFAVAGEFSNMFLVIAG
GSGATLGLCLYIAFASKSEQLKIGRSVVPALFNINEPLILGLPIIYNPAL
AIPFILAPMVTATIYYVANSLNFIKPIIAQVPWPTPVGIGAFLGTADLRA
VLVALVCAFAAPLVYLPFTRVYDQKLVKEEQGIZ (SEQ. ID. NO. 57)
MKKFYVSPIFPILVGLIAFGVLSTFIIFVNNNLLTVLILPLFVGGYVFLF
KKLRVHYTRSDVEQIQYVNHQAEESLTALLEQMPVGVMKLNLSSGEVEWF
NPYAELILTKEGDFDLEAVQTIIKASVGNPSTYAKLGEKRYAVHMDASSG
VLYFVDVSREQAITDELVTSRPVIGVSVDNYDDLEDETSESDISQENSFV
ANFISEFSEKHMMFSRRVSMDRFYLFTDYTVLEGLMNDKFSVTDAFREES
KQRQLPLTLSMGFSYGDGNHDEIGKVALLNLNLAEVRGGDQVVVKENDST
KNPVYFGGGSAASTIKRTRTRTRAMMTASDKIRSVDQVFVVGHKNLDMDA
LGSAVGMQLFASNVIENSYALYDEEQMSPDIERAVSFIEKEGVTKLLSVK
DAMGMVTNRSLLILVDHSKTALTLSKEFYDLFTQTIVIDHHRRPQDFPDN
AVITYIESGASSASELVTELIQPQNSKKNRLSRMQASVLMAOMMLDTKNF
TSRVTSRTFDVASYLRTRGSDSIAIQEIAATDFEEYREVNEULQGRKLGS
DVLIAEAKDMKCYDTVVISKAADAMLAMSGIEASFVLAKNTQOFISLSAR
SRSKLNVQR1MEELGGGGHFNLAAAQIKDVTLSEAGEKLTEIVLNEMKEK
EKEEZ (SEQ. ID. NO. 58)
MKEKNMWKELLNRAGWILVFLLAVLLYQVPLVVTSILTLKEVALLQSGLI
VAGLSIVVLALFIMGARKTKLASFNFSFFRAKDLARLGLSYLVIVGSNIL
GSILLQLSNETTTANQSQINDMVQNSSIISSFFLLALLAPICEEILCRGI
VPKKIFRGKENLGFVVGTIVFALLHQPSNLPSLLIYGGMSTVLSVIAYKT
QRLEMSILLHMIVNGIAFCLLALVVIMSRTLGISVZ (SEQ. ID. NO. 59)
MKEKNMWKELLNRAGWILVFLLAVLLYQVPLVVTSILTLKEVALLQSGLI
VAGLSIVVLALFIMGARKTKLASFNFSFFRAKDLARLGLSYLVIVGSNLG
SILLQLSNETITANQSQINDMVQNSSLISSPFLLALLAPICEEILCRGIV
PKKIPRGKENILGFVVGTWFALLHQPSNLPSLLIYGGMSTVLSWAYKTQR
LEMSILLHMIVNGIAFCLLALVVIMSRTLGISVZ (SEQ. ID. NO. 60)
MDTQKIEAAVKMUEAVGEDANREGLQETPARVARMYQEIFSGLGQTAEEH
LSKSFEIIDDNMVVEKDIFFHTMCEHHFLPFYGRAHIAYIPDGRVAGLSK
LARTVEVYSKKPQIQERLNIEVADALMDYLGAKGAFVVIEAEHMCMSMRG
VRKPGTATUTVARGLFETDKDLRDQAYRLMGLZMKDLFLKRKQAFRKECL
GYLRYVLNDHFVLFLLVLLGFLAYQYSQLLQHFPENHWPILLFVGITSVL
LLLWGGTATYMEAPDKLFLLVGEEEIKLHLKRQTGISLVFWLFVQTLFLL
LFAPLFLAMGYGLPVFLLYVLLLGVGKYFHFCQKASKFFTETGLDWDYVI
SQESKRKQVLLRFFALFTQVKGISNSVKRRAYLDFILKAVQKVPGKIWQN
LYLRSYLRNGDLFALSLRLLLLSLLAQVFIEQAWIATAVVVLFNYLLLPQ
LLALYHAFDYQYLTQLFPLDKGQKEKGLQEVVRGLTSFVLLVELVVGLIT
FQEKLALLALLGAGLVLLVLYLPYQVKRQMQDZ (SEQ. ID. NO. 61)
MRKSIVLAADNAYLIPLETTIKSVLYHNRDVDFYILNSDIAPEWFKLLGR
KMEVVNSTIRSVHIDKELFESYKTGPHINYASYFRFFATEVVESDRVLYL
DSDIIVTGELATLFEIDLKGYSIGAVDDVYAYEGRKSGFNTGMLLMDVAK
WKEHSIVNSLLELAAEQNQVVNLGDQSILNIYFEDNWLALDKTYNYMVGI
DEYHLAQECERLDDNPPTIVHYASHDKPWNTYSISRLRELWWVYRDLDWS
EIAFQRSDLNYFERSNQSKKQVMLVTWSADIKHLEYLVQRLPDWHPHLAA
PCDCSEELTSLSQYTNVTVYQNVLHSRIDWLLDDSEVYLDINTGGEVFNV
VTRAQESGKICIFAFDITRKSMDDGLYDGIFSVERPDDLVDRMKNIEIEZ (SEQ. ID. NO. 62)
MTKIYSSIAVKKGLFTSFLLFIYVLGSRIILPFVDLNTKDFLGGSTAYLA
FSAALTOGNLRSLSIFSVGLSPWMSAMILWQMFSFSKRLGLTSTSIEIQD
RkKMYLTLLIAVIQSLAVSLRLPVQSSYSAILVVLMNTILLIAGTFFLVW
LSDLNASMGIGGSIVILLSSMVLNIPODVLETFQTVHIPTGHVLLALLTL
VFSYLLALMYRARYLVPVNKIGLHNRFKRYSYLEIMLNPAGGMPYMYVMS
FLSVPAYLFILLGFIFPNHSGLAALSKEIMVGKPLWVYVYISVLFLFSII
FAFVTMNGEEIADRMKKSGEYIYGIYPGADTSRFINRLVLRFSVIGGLFN

TABLE 4-continued

VIMAGGPMLFVLFDEKLLRLAMIPGLFMMFGGMIFTIRDEVKALRLNETY
RPLIZ (SEQ. ID. NO. 63)
MSSLSDQELVAKTVEFRQRLSEGESLDDILVEAFAVVREADKRILGMFPY
DVQVMGAIVMHYGNVAEMNTGEGKTLTATMPVYLNAPSGEGVMVVTPNEY
LSKRDAEEMGQVYRFLGLTXGVPFTEDPKKEMKASEKKLIYASDWTTINS
NLGPDYLNDNLASNEEGKFLRPFNYVUDEIDDILLDSAQTPLIIAGSPRV
QSNYYAIIDTLVTTLVEGWYIPKEEKEEVWLTTKGAKSAENELGIDNLYK
EEHASFARHLVYAIRAHKLFTKDKDYHRGNEMVLVDKGTGRLMEMTKLQG
GLHQAIEAKEHVKLSPETRAMASITYQSLPKMFNKISGMTGTGKVAEKEF
IETYNMSVVRIPTNRPRQRIDYPDNLYITLPEKVYASLEYIKQYHAKGNP
LLVFVGSVEMSQLYSSLLFREGIAHNVLNANNAAREAQIISESGQMGAVT
VATSMAGRGTDCKLGKGVAELGGUVIGTERMESQRIDLQIRGRSGRQGDP
GMSKFFVSLEDDVIKKFGPSWVHKKYKDYQVQDMTQPEVLKGRKYRKLVE
KAQHASDSAGRSARRQTLEYAESMNIQRDIVYKERNRLIDGSRDLEDVVV
DIIERYTEEVAADHYASRELLFWPIVTNISFHVKEVPDYIDVTDKTAVRS
FMKQVIDKELSEKKELLNQHDLYEQPLRLSLLKAIDDNWVEQVDYLQQLS
MAIGGQSASQKNPEVEYYQEAYAGFEAMKEQIHADMVRNLLMGLVEVTPK
GEIVTHFPZ (SEQ. ID. NO. 64)
MIGTFAAALVAVLANRVPIEITPNSANTEIAPPDGIGQVLSNLLLKLVDN
PVNALLTANYIRILSWAVIFGIAMREASKNSQELLKTIADVTSKIVEWII
NLAPFGILGLVFKISDKGVGSLANYGILLVLLVTTMLPVAPVVNPLIAPF
FMRRNPYPLVWNCLRVSGVTAPFTRSSATNTPVNMKLCMDLGLNPDTYSV
SIPLOSTINMAGVAITINLLTLAAVNTLGTPVDFATAFVLSVVAAISSCD
ASGIAGGSLLUPVACSLFGISNDIAIQIVGVGPVIGVQDSCETALNSSTD
VLFTAVAEYAATRKKZ (SEQ. ID. NO. 65)
MSISQRTTKLILATCLACLLAYFLNLSSAVSAGIIALLSLSDTRRSTLKL
ARNRLFSMLLALAIGVLAFHLSGFHIWSLGLYLAVPLAYKMGWEIGITPS
TVLVSHLLVQESTSPDLLVNEFLLFAIGTGFALLVNLYMPSREEEIQHYH
TLVEEKDILQRFKYYLSRGDGRNRAQLVAELDTLLKEALRLVYLDHSDHL
FHQTDYHIHYFEMRQRQSRILRNMAQQINTCHLAASESLILAQLFSKAGQ
LSQTNPASDLLDEIERYLEVFRNRSLPKTREEPETRATLLQLLREAKTFI
QVKVDFYQKYRQZ (SEQ. ID. NO. 66)
MEIMSLAIAVFAVIIGLVIGYVSISAKM1SSQEAAELMLLNAEQEATNLR
GQAEREADLLVNEAKRESKSLKKEALLEAKEEARKYREEVDAEFKSERQE
LKQIESRLTERATSLDRXDDNLTSKEQTLEQKEQSISDRAKNLDAREEQL
EEVERQKEAELERIGALSQAEARDIILAQTSENLTREIASRIREAEQEVK
ERSDKMAKDILVQAMQRIAGEYVAESTNSTVHLPDDTMKGRIIGREGRNI
RTFESLTGVDVIIDDTPEVVTLSGFDPIRREIARMTMEMLLKDGRIHPAR

IEELVEKNRQEIDNKIREYGEAAAYEIGAPNLHPDLMKIMGRLQPRTSYG
QNVLRHSIEVAKLAGIMASELGENAALARRAGFLHDIGKAIDHEVEGSHV
EIGMELARKYKEPPVVVNTIASHHGDVEAESVIAVIVAAADALSAARPGA
RSESLESYIKRLHDLEEIANGFEGVQTSFALQAGREIRIMVNPGKIKDDK
VTILAHKVRKKIENNLDYPGNIKVTVIRELRAVDYAKZ (SEQ. ID. NO. 67)
MMLKPSIDTLLDKVPSKYSLVILBAKRAHELEAGAPATQGFKSEKSTLRA
LEEIESGNVTIHPDPEGKREAVRRRIEEEKRRKEEEEKKIKEQIAKEKED
GEKIZ (SEQ. ID. NO. 68)
MSAYQLPTVWQDEASNQGAFTGLNRPTAGARFEQNLPKGEQAFQLYSLGT
PNGVKVTILLEELLEAGFKEAAYDLYKIAIMDGDQFGSDPFKLNPNSKIP
ALLDQSGTENVRVFESAHILLYLAEKFGAFLPSNPVEKVEVLNWLFWQAG
AAPFLGGGFGHFFNYAPEKLEYPINRFTMEVKRQLDLLLDKELAQKPYIAG
NDYTIADIAIWSWYGQLVQGNLYQGSAKFLDASSYQNLVKWAEKANRPAV
KRGLEVTYTEIKZ (SEQ. ID. NO. 69)
LASLITSIIMFYVGFDVLRDTIQKILSREETVIDPLGATLGIISAAIMFV
VYLYNTRLSKKSNSNALKAAAKDNLSDAVTSLGTAIAILASSFNYPIVDK
LVAIIITFFILKTAYDIFIESSFSLSDGFDDRLLEDYQKAIMEIPKISKV
KSQRGRTYGSNIYLDITLEMNPDLSVFESHEIADQVESMLEERPGVFDTD
VHIEPAPIPEDEILDNVYKKLLMREQLIDQGNQLEELLTDDFVYIRQDGE
QMDKEAYKTKKELNSAIKDIQITSISQKTKLICYELDGIIHTSIWRRMET
WQNIFHQETKKEZ (SEQ. ID. NO. 70)
MTIKLVATDMDGTFLDGNGRFDMDRLKSLLVSYKEKGIYFAVASGRGFLS
LEKLFAGVRDDIIFIAENGSLVEYQGQDLYEATMSRDFYLATFEKLKTSP
YVDINKLLLTGKKGSYVLDTVDETYLKVSQHYNENIQKVASLEDITDDIF
KFTTNFTEETLEDGEAWVNENVPGVKAMTTGFESIDIVLDYVDKGVAIVE
LVKKLGITMDQVMAFGDNLNDLHMMQVVGHPVAPENARPEILELAKTVIG
HHKERSVIAYMHGLZ (SEQ. ID. NO. 71)
MADIKLIALDLDGTLLITTDKRLTDRTKETLQAARDRGIKVVLTTGRPLK
AMDFFLHELGTDGQEDEYTITFNGGLVQKNTGEILDKTVFSYDDVARLYE
ETEKLSLPLDAISEGTVYQIQSDQELYAKFNPALTFVPVDFEDLSSQMTY
NKCVTAFAQEPLDAAEQKISPELFDQYEIFKSREMLLEWSPKNVHKATGL
AKLISHLGIDQSQVMACGDEANDLSMIEWAGLGVAMQNAVPEVKAAANVV
TPMTNDEEAVAWAIEEYVLKENZ (SEQ. ID. NO. 72)
MESLLILLLIANLAGLFLIWQRDRQEKHLSKSLEDQADHLSDQLDYRFD
QARQASQLDQKDLEVVVSDRLQEVRKELHQGLTQVRQEMTDNLLQTRDKT
DQRLQALQESNEQRLEQMRQTVEEKLEKTLQTRLQASFETVSKQLESVNR
GLDEMQTVARDVGALNKVLSGTKTRGALGELQLGQHEDIMTPAQYEREYA

TABLE 4-continued

TVENSSERVEYAIKLPGQGDQEYVYLPIDSKFPLADYYRLEEAYETGDKD
EIERCRKSLLASVKRFARDIRNKYIAPPRTTNFGVLFVPTEGLYSEIVRN
PVFFDDLRREEQIWAGPSTLSALLNSLSVGFKTLNIQKSADHISKTLASV
KTEFGKFGGILVKAQKHLQHASGNIDELLNRRTIAIERTLRHIELSEGEP
ALDLLHFQENEEEYEDZ (SEQ. ID. NO. 73)
MKISHMKKDELFEGFYLIKSADLRQTRAGKNYLAFTFQDDSGEIDGKLWD
AQPHNIEAFTAGKVVHMKGRREVYNNTPQVNQITLRLPQAGEPNDPADFK
VKSPVDVIKEIRDYMSQMIFKIENPVWQRIVRNLYTKYDKEFYSYPAAIC
TNHHAFETGLAYHTATMVRLADALSEVYQLNKSLLYAGIMLHDLAKVIEL
TGPDQTEYTVRGNLLGHIALIDSEITKTVMELGIDDTKEEVVLLRHVILS
HHGLLEYGSPVRPRIMEAEIIHMIDNLDASMMMMSTALALVDKGEMTNKI
FAMDNRSFYKPDLDZ (SEQ. ID. NO. 74)
MSEKAKKGFKMPSSKTVLLIIIAIMAVLTFIPAGAPIEGIYETQPQNPQG
IWDVLMAPIRAMLGTHPEEGSLIKBTSAAIDVAPRLMVGGFLGIVNKTGA
LDVGIASIVKKYKGREKMLILVLMPLFALGGTTYGMGEETMAFYPLLVPV
MMAVGFDSLTGVAIILLGSQIGCLASTLNPFATGIASATAGVGTGDGVLR
LIFWVTLTALSTWFVYRYADKIQKDPTKSLVYSTRKEDLKHFNVEESSSV
ESTLSSKQKSVLFLPVLTFILMVLSRPWTDLGVTIPDDFNTWLTGLPVIG
NIVGSSTSALGTWYFPEGAMLFAFMGILIGVIYGLKEDKUSSFMNGAADL
LSVALIVAIARGIQVIMNDGMITDTILNWGKEGLSGISSQVFIVVTYIFY
LPMSFLIPSSSGLASATMGIMAPLGEFVNVRPSLIITAYQSASGVLNLIA
PTSGIVMGALALGRINIGTWWKFMGKLVVAIIVVTIALLLLGTPLPFLZ (SEQ. ID. NO. 75)
MSNSFVKLLVSQLFANLADIFFRVTIIANIYUSKSVIATSLVPILIGISS
FVASLLVPLVTKRLALNRVLSLSQFGKTILLAILVGMPTVMQSVAPLVTY
LFVVAISILDGFAAPVSYAIVPRYATDLGKANSALSMTGEAVQLIGWGLG
GLLFATIGLLPTTCINLVLYIISSFLMLFLPNAEVEVLESETNLEILLKG
WKLVARNPRLRLIWSANLLEFSNTIWVSSHLVFVTELLNKTESYWGYSNT
AYSIGIIISGLLRISEKFLAAKWEPQLFTPNLIVFIQNPCLSLDPGWFLF
SPNGCFLLDKKEFPLYGISVEKNTKRKETHMNSLPNHHIQNKSFYQLSFD
GGHLTQYGGLIFFQELFSQLKLKERISKYLVTNDQRRYCRYSDSDILVQP
LPQLLTGYGTDYACKELSADAYFPKLLEGGQLASQPRFSRTDEETVHSLR
CLNLELVEFFLQPHQLNQLIVDEDSTHFTTYGKQEGVAYNAHYRAHGYHP
LYAFEGKTGYCFNAQLRPGNRYCSEEADSFTTPVLERFNQLLFRMDSGFA
TPKLYDLIEKTGQYYUKLKKNTVLSRLGDLSLPCQDEDLTILPHSAYSET
LYQAGSWSHKRRVCQFSERKEONLPYDVISLVTNMTSGTSQDQFQLYRGR
GQAENFIKEMKBGFFGDKTDSSTLIKNEVRMMMSCIAYNLYLFLKHLAGG
DFQTLTIKRFRMLHVVGKCVRTGRKQLLKLSSLYAYSELFSALYSRIRKV
NLNLPVPYEPPRRKASLMMHZ (SEQ. ID. NO. 76)
MMEFFQQLPHLEPYGNPQYFVYVIAATLPIFIGLFFKKRFAWYEVLVSLF
FIVTMLVGGKTNQLAALGIYLCWEILLLLFYKHYRKDGKWVFYLVSFLSL
LPIIFVKVQPAINGTQSLLGFLGISYLTPRSVGIVIELRDGVIKDPTLWE
FLRFLLFMPTFSSGPIDRFKRFNENYQAIPERDELMDMLDESVRYIMWGF
LYKFILAHVLGETLLPPLKNLALQSGGFFNLYALAVMYTFGLELFFDFAG
YSMPALAISNLMGIRSPINFNKPFLSRDLKEFWNRWHMSLSFWFRDFVPM
RMVMVLTRKKVFKNRNVTSSMAYIVNMLMGFWHGVTWYYIAYGLFHGLGL
VINDAWVRKKKTLNKERKKAGKAALPENRWIQLLGMVVTFHVVMLSFLIF
SGFLNNLWFKKZ (SEQ. ID. NO. 77)
MLKRLWMIFGPVLIAGLLVFLLIFFYPTEMHHNLGAEKRSAVATTIDSFK
ERSQKVRALSDPNVRFVPFFGSSEWLRFDGAHPAVLAEKYNRSYRYLLGQ
GGAASLNQYFGMQQMLPQLENKQVVYVISPQWFSKNGYDPAAPQQYPNGD
QLTSFLKHQSGDQASQYAATRLLQQPPNVAMKDLVQKLASKEELSTADNE
MIELLARFNERQASFFGQFSVRGYVNYDKHVAKYLKILPDQPSYQAIEDV
VKADAEKTSNNEMGMENYPYNEQIKKDLKKLKDSQKSPTYLKSPEYNDLQ
LVLTQFSKSKVNPIFIIPPVNKKWMNYAGLREDMYQQTVQKIRYQLESQG
FTNIADFSKDGGEPFFMKDTIHLGWLGWLAFDKAVDPFLSNPTPAPTYHL
NERFFSKDWATYDGDVKEFQZ (SEQ. ID. NO. 78)
MEKNLKALKQTTDQEGPAIEPEKAEDTKTVQNGYFEDAAVKDRTLSDYAG
NWQSVYPFLEDGTFDQVFDYKAKLTGKMTQAEYKAYYTKGYHTDVTKINI
TDNTMEFVQGGQSKKYTYKYVGKKILTYKKGNRGVRFLFEATDADAGQFK
YVQFSDHNVAPVKAEHFHIFFGGTSQEALFEEMDNWPTYYPDNLSGQEIA
QEMLAHZ (SEQ. ID. NO. 79)
MKDGHLLAHHIRLLNGRIFQKLLSQDPEALYRGEQGKILAVLWNSETGCA
TATDIALATGLANNTLTTMIKKLEEQKLVIVSPCGKDKRKKYLVLTELGK
SQKEVGHRVSQKLDTIFYKGFSEEEIHQFEGFQERILANLKEKGNEVZ (SEQ. ID. NO. 80)
MTNLIATFQDRFSDWLTALSQHLQLSLLTLLLAILLAIPLAVFLRYHEKL
ADWVLQIAGIFQTIPSLALLGLFTIPMGIGTLPALTALVLYAIFPILQNT
GLKGIDPNLQEAGIAFGMTRWERLKIFEIPLAMPVIMSGIRTAAVLIGTA
TLAALIGAGGLGSPILLGIDRNNASLILIGALSSAVLAIAFNFLLKVMEK
KLRTSGFALVALLLGLSYSPALLVQKEKENLVIAGKIGPEPEILANMYKL
LIEENTSMTATVKPNPGKTSFLYEALKKGDIDIYPEETGTVTESLLQPSP
KVSHEPEQVYQVARDGIAKQDHLAYLICPMSYQNTYAVAVPKKIAQEYGL
KTISDLKKVEGQLKAGFTLEFNDREDGNKGLQSMYGLNLNVATIEPALRY
QAIQSGDIQITDAYSTDAELERYDLQVLEDDKQLFPPYQGAPLMKEALLK
KHPELERVLNTLAGKITESQMSQLNYQVGVEGKSAKQVAKEFLQEQGLLK
KZ

TABLE 4-continued (SEQ. ID. NO. 81)
MMHTYLQKKIENIKTTLGEMSGGYRRMVAAMADLGFSGTMKAIWDDLPAH
YLLVLGSFPLWLELVYEHRIVDWIGMICSLTGIICVIFVSEGRSNYLFGL
RSFAQWIINSVIYLILALQKGFYGEVLTTLYFTVMQPIGLLVIYQAFKK
EKQEFVARKLDGKGWTKYLSISVLWWLAFGFIYQSIGANRPYRDSITDAT
NGVGQILMTAVYREQWIFWAATNVFSIYLWWGESLQIQGKYLIYLINSLV
GWYQWSKAAKQNTDLLNZ (SEQ. ID. NO. 82)
MRNMKAKYAVWVAPFLNLTYAIVEFIAGGVFGSSAVLADSVHDLGDAIAI
GISAFLETISNREEDNQYTLGYKRFSLLGALVTAVILVTGSVLVILENVT
KILHPQPVNDEGILWLGILTINLLSLVVGKGKTKNESILSLHFLEDTLGW
VAVILMAIVLRFTDWYILDPLLSLVISFFILSKALPRFWSTLKIFLDAVP
EGLDIKQVKSGLERDNVASLNQLNLWTMDALEKNAIVHVCLKEMEHMETC
KESIRIFLKDCGFQNITIEIDADLETHQTHKRKVCDLERSYEHQHZ (SEQ. ID. NO. 83)
MIEYKNVALRYTEKDVLRDVNLQIEDGEFMVLVGPSGSGKTTMLKMINPL
LEPTDGNIYMDGKRIKDYDERELRLSTGYVLQAIALIPNLTVAENIALIP
EMKGWSKEEITKKTEELLAKVGLPVAEYGHRLPSELSGGEQQRVGIVLRA
MIGQPICIFLMDEPFSALDAISRKQLQVLTKELIEFGMTTIFVTHDTDEA
LKLADRJAVLQDGEIRQVANPETILKAPATDFVADLPGGSVHDZ (SEQ. ID. NO. 84)
MSAVAISAMTKVMQETHGNPSSIHGHGRQAGKLLREARQELAQLLRTKPQ
HIFFTSGGTEGNNTTIIGYCLRHQEQGKHIITTAIEHHAVLETIDYLVQH
FGFEATIIQPENQEITAQQIQKALRDDTILVSTMFVNNETGNLLPIAEIG
QILKQHPAAYHVDAVQAIGKIPHSEELGIDFLTASAHKFHGPKGIGFLYA
SSMDFDSYLHGGDQEQKRAGTENLPAIVGMVAALKEDLEKQEEHFQHVQN
LETAFLAELEGIQYYLNRGKHHLPYVLNIGFPGQKNDLLLLRLDLAGIST
GSACTAGVVQSSHVLEAMYGANSERLKESLRISLSPQNTVEDLQTLAKTL
KEUGGZ (SEQ. ID. NO. 85)
MLFKLSKEKIELGLSRLSPARRIFLSFALVILLGSLLLSLOFVQVESSRA
TYFDHLFTAVSAVCVTGLSTLPVAHTYNIWGQIICLLLIQIGGLGLMTFI
GVFYIQSKQKLSLRATIQDSFSYGSLRFVYSIFLTTFLVESLGAILLSFR
LIPQLGWGRGLFSSIFLAISAFCNAGPDNLGSTSLFAFQTDLLVNLVIAG
LIITGGLGPMVWFDLAGHVGRKKKGRLHFHTKLVLLLTIGLLLFGTATTL
FLEWNNAGTIGNLPVADKVLVSFFQTVTMRTAGFSTIDYTQAHPVTLLIY
ILQMFLGGAPGGTAGGLKITTFFVLLVFARSELLGLPHANVARRTIAPRT
VQKSFSFIIFLMSFLIGILLGITAKGNPPFIHLVFETISALSTVGVTANL
TPDLGKLALSVIMPLMFMGRIGPLTLFVSLADYXPEKKDMIHYMKADISI
GZ (SEQ. ID. NO. 86)
MSDRTIGILGLGIFGSSVLAALAKQDMNIIAIDDHAERINQFEPVLARGV
IGDITDEELLRSAGIDTCDTVVVATGENLESSVLAVMHCKSLGVPTVIAK VKSQTAKKVLEKIGADSVISPEYEMGQSLAQTILFHNSVDVFQLDKNVSI
VEMKIPQSWAGQSLSKLDLRGKYNLNILGFREQENSPLDVEFGPDDLLKA
DTYILAVINNQYLDTLVALNSZ (SEQ. ID. NO. 87)
MKLLSIAISSYNAAAYLHYCVESLVIGGEQVGILIINDGSQDQTQEIAEC
LASKYPNIVRAIYQENKCHGGAVNRGLVEASGRYFKVVDSDDWVDPRAYL
KILETLQELESKGQEVDVFVTNFVYEKEGQSRKKSMSYDSVLPVRQIFGW
DQVGNFSKGQYTMMHSLIYRTDLLRASQFZ (SEQ. ID. NO. 88)
MKFNPNQRYTRWSRRLSVGVASVVVASGFFVLVGQPSSVRADGLNPTPGQ
VLPEETSGTKEGDLSEKPGDTVLTQAKPEGVTGNTNSLPTPTERTEVSEE
TSPSSLDTLPBKDEEAQKNPELTDVLXETVDTADvDGTQASPAEERRPEQV
KGGVKENTKDSIDVPAAYLEKAEGKGPFTAGVNQVIPYELFAGDGMLTRL
LLKASDNAPWSDNGTAKNPALPPLEGLTICGKYFYEVDLNGNTVGKQGQA
UDQLRANGTQTYKATVKVYGNKDGKADLTNLVATKNVDININGLVAKETV
QKAVADNVKDSIIDVPAAYLEKGEGPTAGVNHVIPYELFAGDGMLTRLLL
LSDKAPWSDNGDAKNPALSPLGENVKTKGQYFYQVALDGNVAGKEKQALI
DQFRANGTQTYSATVNVYGNKDGKPDLDNIVATKKVTLNNGLSKETVQKA
VADNVKDSIDVPAAYLEKAKGEGPFTAGVNHVIPYELFAGDGMLTRLLLK
ASDKAPWSDNGDAKNPALSPLGENVKTKGQYFYQLALDGNVAGKEKQALI
DQFRANGTQTYSATVNVYGNKDGKPDLDNIVATKXVTININGLISKETVQ
KAVADNVKTVSMFQQPTZ (SEQ. ID. NO. 89)
MKLKSYILVGYIISTLLTILVVFWAVQKMLIAKGEIYFLLGMTIVASLVG
AGISLFLLLPVFTSLGKLKEHAKRVAAKDFPSNLEVQGPVEFQQLGQTFN
EMSHDLQVSFDSLEESEREGLMIAQLSHDIKTPITSIQATVEGILDGIIK
ESEQAHYLATIGRQTERLNKLVEELNFLTLNTARNQVETTSKDSIFLDKL
LIECMSEFQFLIEQERRDVHLQVIPESARIEGDYAKLSRJLVNEITVSSQ
YGLGSTETLVLNLSGSENKAZ (SEQ. ID. NO. 90)
MFGQTAQHGLTNSLKDFWIFLLNIGPQLAFFCQMLRCSRSVEQGTGNHRR
EFNMIQQIFSHFGMTHLGQIKLVYQESIDLELLVNALNHHLLIDRLVLTP
NQITIEIDRQIVHGLDLLKGRXDKEIIDIKSMFRQLELASTQQICPNQRV
HHGILAFGEISDLVPAKNLPNRQDZ (SEQ. ID. NO. 91)
MEHLATYPSTYGGAPAALGWLAVGLSGMGSAYGVGKAGQSAAALLKEQPE
KFASALILQLLPGTQOLYGFVIGLIWLQLTPSLPLEKGVAYFVALPIA1V
GYFSAKHQGNVAVAGMQILAKRPKEFMKGAILAAMVETYAILAIWVSFIL
TLRVZ (SEQ. ID. NO. 92)
MLKSEKQSRYQMLNEELSFLLEGETNVLANLSNASALIKSRFPNTVFAGF
YLFDGKELVLGPFQGGVSCIIRIALGKGVCGEAAGHFQETVIVGDVTTYL TABLE 4-continued

NYISCDSLAKSEIVVPMMKNGQLLGVLDLDSSEIEDYDAMDRDYLEQFVA
ILLEKTAWDFTMFEEKSZ (SEQ. ID. NO. 93)
MSVLEKDLHVEIEGKEILKGVNLTLTGEAAIMGPNGTGKSAAIMGNPNYE
VTKGEVLFDGVNILELEVDERARMGLFLAMQYPSEIPGITNAEFLRAAMN
AGKEDDEKISVREFITKLDEKMELLNMKEEMAERYLNEGFSGGEKKRNEI
LQLLMLEPTFALLDEIDSGLDIDALKVVSKGVNAMRGEGFGAMIITTHYQ
RLLNYITPDVVHVMMEGRVVLSGGPELAARLEREGYAKLAEELGYDYKEE
LZ (SEQ. ID. NO. 94)
MPYKRQRSFSMALSKLDSLYMAVVADHSKNPHHQGKLEDAEQISLNNPTC
GDVINLSVKFDAEDRLEDIAFLNGCTISTASASMMTDAVLGKKQEILELA
T1FSEMVQGQKDERQDQLGDAAGVAKFPQPJKCATWNALKIENQEKQZ (SEQ. ID. NO. 95)
MKIQDLLRKDVMLLDLQATEKTAVIDEMIKNLTDHGYVTDEFETFKEGIL
AREALTSTGLGIAMPHSKNAAVKEATVLFAKSNKGVDYESLDGQATDLFF
MIAAPEGANDTHLAALAELSQYLMKDGFADKLRQATSADQVIELFDQASE
KTEELVQAPANDSGDFIVAVTACTTGIAHTYMAQEALQKVAAEMGVGIKV
ETNGASGVGNQLTAEDIRKAKAIIAADKAVEMDRFDGKPLINRPVADGI
RKTEELINLALSGDTEVYRANGAJ(AATASNEKQSLGGALYLMSGVSQML
PFVIGGGIMIALAFLIDGALGVPNENLGNLGSYHELASMFMKIGGAAFGL
MLPVFAGYVAYSIAEKPGLVAGFVAGALAKEGFAFGKIPNDFLGGLGGGS
AVLLGIVLGGMMAVDMGGPVNKAAYVFGTGTLAATVSSGGSVAMAAVMAG
GMVPPLAIFVATLLFVLVGAIVSGVVYGYLRKPQAZ (SEQ. ID. NO. 96)
MANKNTSTTRRRPSKAELERKEAIQRMLISLGIAILLIFAAFKLGAAGIT
LYNLIRLLVGSLAYLAIFGLLIYLFFFKWIRKQEGLLSGFFTIFAGLLLI
FEAYLVWKYGLDKSVLKGTMAQVVTDLTGFRTTSFAGGGLIGVALYPTAF
LFSNIGTYFIGSLILVGSLLVSPWSVYDIAEFSRGFAKWWEGHERRXEER
FVKQEEKARQKAEKEARLEQEETEKALLDLPPVDMETGEILTEEAVQNLP
PIPEEKWVEPEIILPQAELKFPEQEDDSDDEDVQVDFSAKEALEYKLPSL
QLFAPDKPKDQSKEKKWRENIKILEATFASFGIKVTVERAEIGPSVTKYE
VKPAVGVRVNRISNLSDDLALALAAKDVRIEAPIPGKSUGTEVPNSDIAT
VSFELWEQSQTKAENFLEIPLGKAVNGTARAFDLSKMPHLLVAGSTGSGK
SVAVNGIIASILMKARPDQVKFMMVDPKMVELSVYNDIPILLJPVVTNPR
KASKALQKVVDEMENRYELFAKVGVRNIAGFNAKVEEFNSQSEYKQIPLP
FIVVIVDELADLMMVASKBVEDAIIRLGQKARAAGIHMILATQRPSVDVI
SGUKANVPSRVAFAVSSGTDSRTLDNGAEKLLGRGDMLFKPIDENHPVRL
QGSFISDDDVERIVNPIKTQADADYDESFDPGEVSENEGEFSDGDAGGDP
LFEEAXSLVIETQKASASMIQRRLSVGFNRATRLMEELEIAGVIGPAEGT
KPPJCVLQQZ (SEQ. ID. NO. 97)
MSYFKKYKFDKSQFKLGMRTKTGIAVFLVLLIFGFGWKGLQIGALTAVFS
LRESFDESVHFGTSRILGNSIGGLYALVFLLNTFFWEAWVTLVVVPICTM
LTIMTNVAMNNCAGVIGGVAAMLHTLSPSGETILYVFVRVLETFMGVFVA
UVNYDIDRIRLFLEKKEKZ (SEQ. ID. NO. 98)
MNKSEHRHQLIRAUTKNKIHTQAELQALLAENDIQVTQATLSRDIKNMNL
SKVREEDSAYYVLNNGSISKWEKRLELYMEDALVWMRPVQHQVLLKTLPG
LAQSFGSHDTLSFPDAATLCGNDVCLIICEDADTAQKCFEELKKFAPPFF
FEEZ (SEQ. ID. NO. 99)
MCSIKLNALSYMGRVLNIFPItTGTYVARVLDRTDYGYFNSVDTILSFFL
PFATYGVYNYGLRAISNVKDNKKDLNRTFSSLFYLCIACTILTRAVYILA
YPLFFTDNPIVKKVYLVMGIQLIAQFSIEWVNBALENYSILFYKTAFRIL
MLVSIFLPVKNEHDEVVYTLVMSLTLINYLSYFWKRDIKLVKIHLSDFKP
LFLPLTAMLVANANMLFTTLDRLFLVICTGIDVNVSYAQRJVTVIAGVVT
GAIGVSVPRLSYYLGKGDKEAYVSLVNRCSRIFNPFHPLSFGLMVLGNAI
LLYGSEKYIGGGILTSLFAFRTULALDTILGSQILFTNGYHKRTVYTVFA
GLLNLGLNSLLFFNHVAPEYYLLTRMLSETSLLVFYIIFEHRKQLIHLGH
IFSYTVRYSLFSLSWAIYFUNFVYPVDMVINLPFLINTGLIVLLSAISYI
SLLVFRKDStFYEFLNHVLALKNKFKKSZ (SEQ. ID. NO. 100)
MELFMKITNYEIYXLKKSGLTNQQILICVLEYGENVDQELLLGDIADISG
CRNPAVFMERYPQIDDAHLSKEFQKFPSPSILDDCYPWDLSEIYDAPVLL
FYKGNLDLLKFPKVAVVGSRACSKQGAKSVEKVIQGLENELVIVSGLAXG
DTAAHMAALQNGGKTAVIGTGLDVFPKANKRLQDYIGNDHLVLSEYGPGE
QPLKHFPARNRIAGLCRGVIVAEAKMRSGSLTCERAMEEGRDVFAIPGSI
LDGLSDGCIIMLIQEGAKLVTSGQDVLAEFEPZ (SEQ. ID. NO. 101)
MKQLTVEDAKQIELEILDYIDTLCKKIININYIINYGTLIGAVRHEGFIP
WDDDIDLSMPRBDYQRFINIFQKEKSKYKLLSLERDKNYNNFIKTDSTRK
IIDTRNTKTYESGIIDIFPDRFDDPKVIDTCYKESKLLSFSKHKNVVYKD
SLLKDWIRTAFWLLLRPVSPRYFANKIEKEIQKYSRENGQYMAFIPSKFK
EKEVFPSGTFDKTIDLPPENLSLPAPEKPDTILTQFYGDYMTLPPEEKRF
YSHEFHAYKLEDZ (SEQ. ID. NO. 102)
MIKINHLTITQNKDLRDLVSDLTMTIQDGEKVAIIGEEGNGKSTLLKLMG
EALSDFTIKGNIQSDYQSLAYPQKVPEDLKKKTLHDYFFLDSIDLDYSIL
YRLAEELHFDSNRFASDQEIGNLSGGEALKIQLIHELAICPFEILFLDEP
SNDLDLETVDWLKGQIQKTRQTVTFISHDEDPLSETADTIVLRLVKHRKE
AETHVEHLDYDSYSEQRKANFAKQSQQAANNQRAYDKTMEKIRRVKQNVE
TALRATKDSTAGRRLLAKKMKTVLSQEKRYEKAAQSMTQKPLEEEQIQLFF
SDIQPLPASKVLVQLEKENLSIDDRVLVQKLQLTVRGQEKIGIIGPNGVG

TABLE 4-continued

KSTLLAKLQRLLNDKREISLGIMPQDYHXJCLQLDLSPIAYLSKTGEKEE
LQKQSHLASLNFSYPMQHRSLSGGQQGKLLLLDLVLRKPNFLLLDEPTR
NPSPTSQPQIRKLFATYPGGLITVSHDRRFLKEVCSIIYRMTEHGLKLVN
LEDLZ (SEQ. ID. NO. 103)
MKPKTFYNLLAEQNLPLSDQQKEQFERYFELLVEWNEKINLTAITDKEEV
YLKNFYDSIAPILQGLIPNETIKLLDIGAGAGFPSLPMKILYPELDVTII
DSLNKRINFLQLLAQELDLNGVHFYHGRAEDFAQDKNFRAQYDFVTARAV
ARMQVLSELTIPYLKVGGKLLALKASNAPEELLEAKNALNLLFSKVEDNL
SYALPNRDPRYITVVEKKKETPNKYPRKAGMPNKRPLZ (SEQ. ID. NO. 104)
MSIKUAVDIDGTLVNSQKEITPEVFSAIQDAKEAGVKVVIATGRPIAGVA
ICLLDDLQLRDEGDYVVTFNGALVQETATGHEIISSLTYEDYLDMEFLSR
KLGVHMHAITKDGIYTANRNIGKYTVHESTLVSMPYRTPEEMAGKJVKCM
FIDEPEIPEIKKIAKYITKTNDESGVAHAIRTWVLZ (SEQ. ID. NO. 105)
MTWIILGVIALIVIIVSYNGLVKNRMQTKEAWSQIDVQLKRRNDLLPNLI
ETVKGYAYEGLEKVAELRNQVTSPAEAMKASDALTRQVSGIFAVAESYPD
LKASANPVICLQEELTNTENKSYSRQLYNSVVSNYNVKLETFSNIIAGMF
GFKAADFLQTPEEEKSVPKVDPSGLGDZ (SEQ. ID. NO. 106)
MLFDQIASNKRKTWILLLVFFLLLALVGYAVGYLIRSGLGGLVIALIIGF
IYALSMIFQSTEVMSMNGAREVDEQTAPDLYHVVEDMALVAQIPMPRVFI
IDDPALNAFATGSNPQNAAVAATSGLLAIMNREELEAVMGHEVSHIRNYD
IRISTIAVALASAITMLSSMAGRMMWWGGAGRRRSDDDRDGNGLEIIMLV
VSLLAIVLAPLAATLVQLAISRQREFLADASSVELTRNPQGMINALDKLD
NSKPMSRHVDDASSALYINDPKKGGGFQKLFYTHPPtSERIERLKQMZ (SEQ. ID. NO. 107)
MKLNIQEIRKQSEGLNFEQTLDLVDDLRARNQEILDVKDILAVGKVQYED
RMYFLDYQLSYTIVLASSRSMEPVELVESYPVTEVFMEGATNQLDQEVLD
DDLVLPIENGELDLAESVSDNLLNIPIKVLTAEEBAGQCPISGNDWQIMT
EEEYQAQKAVKKEENSPFAGLQGLFDGDEZ (SEQ. ID. NO. 108)
MKRQLALVVPSGGDSRTCLWVMQHYETVEAVTFAYGQRMHLEQRRREIAK
EQGRHHILDMSLLGQITAQPDFATIHSYIPDKLCVESKSLKLYLFSYRNH
GDFHENCNTIGKDLVNLLDPRYLEVWGKFTPRGGISDPYYNYGKQGTKYE
GLAEQRLFQHDLYPEKIDNRZ (SEQ. ID. NO. 109)
MTETVEDKVSHSn*GLDILLKGIVAAGAVISGTVATQTKVFTNESAVLEK
TVEKTDALATNDTVVLGTISTSNSASSTSLSASESASTSASESASTSAST
SASTSASESASTSASTSISASSTVVGSQTAAATEATAKXVEEDRKKPASD
YVASVTNVNLQSYAgRRKRSVDSIEQLLASIKNAAVSGNTVNGAPAINAS
LNLAKSETKVYTGEGVDSVYRVPIYYKLKVTNDGSKLTFTYTVTYVNPKT

NDLGNISSMRPGYSYNSGTSTQTMLTLGSDLGKPSGVKNYITDKNGRQVL
SYNTSTMTRQGSGYTWGNGAQMNGFFAKXGYGLTSSWTVPITGTDTSFTF
TPYAARTDRIGINYFNGGGKVVESSITSQSLSQSKSLSVSASQSASASAS
TSASASASTSASASTSASASASTSASVSASTSASASASTSASASASTS
ASESASTSASASASTSASASASTSASASASTSASESASTSASASASTSAS
ESASTSASASASTSASASASTSASGSASTSTSASASTSASASASTSASAS
ASISASESASTSASESASTSTSASASTSASESASTSASASASTSASASAS
TSASASASTSASASTSASESASTSASASASTSASASASTSASASASTSAS
ASASTSASVSASTSASASASTSASASASTSASESASTSASASASTSASAS
ASTSASASASTSASESASTSASASASTSASESASTSASASASTSASASAS
TSASGSASTSASASASTSASASASTSASASASISASESASTSASESASTS
TSASASTSASESASTSASASASTSASASASTSASASARQVRRPQPVHLNR
MQPVRQPQQVLVHQLQHQRVHRLQHPVPRLQRQPVRQLQQVPVLQSQHQ
QVLQPQHRQVPRLQQAHQHLNQRRQAPQLQQVPVRQPQRRQVRQPQQVLV
HQLQHQRVHRLRRQPVHQSQQVPVRQLPHQQVPRLQQAPVRRLQQVLAPQ
PQPQPVRQPQQVSQRLNRIIQRVRPLQQVLAPQPQRQQVHRLQRQRVRLN
RHQRVRPLQQVLAPQPQRQQVHRLQHRVRPLQQVLAPQPQRQQVHRLQR
QRVRLSQHQRVRQPQQAHQLLNLHQPVRQPHRQAPQLQQVPVRQPQRRQ
VRRLQQVPVRQPQQVPVRQPRRQVRRPQPVHLNRNQPVRQPQQVLVHQL
QMQRVHRLQHQPVHQSQQVPVRQPRINKCLGFSKYZ (SEQ. ID. NO. 110)
MGVETWFYSSICWLALGLGSVWKFPYMTAANGGGGFLLIFLLSTILIGPL
LLAEALGRSAGVSAIKTFGKLGKNNKYNIGWIGAFALFLLSFYSVIGGWT
LVYLGIEFGKLFQLGGTGDYAQLFTSfLSNPAIALGAQAAPILLNIFIVS
RGVQKGIERASKVMMPLLFIVFVFIIGRSLSLPNAMEGVLYPDSKLTSTG
LLYALGQSFALSLGVTVMLTYASYLDKXTNLVQSGISIVAMNISISIMAG
LAFQARSPFNQSEGGPSLLVLPQLIDKMPFGTUYVLFLLLFLFATVTFSV
VMLEINVDNITNQDNSKRAXWSVILGLTFVFGTPSALSYGVMADVHIFGK
TFFDAMDFLVSNLLMPFGALYLSLTGYTFKKALAMEELHLDERAWKQGLF
QVWLFLLRFFVSSFQSSSLWSSLPNLCNQKGLEZ (SEQ. ID. NO. 111)
MLKKWQLKDVILLAFLSIFFC3GVFVGSGYVYNELSLLLTPLGLQAFANE
ILFGLWCMAAPIAAIFVPRVGSATIGEVLAALAEVLYGSQFGLGALLSGF
VQGLGSEFGFIVTKNRYESWLSLTANSIGITLVSFVYEYIKLGYYAFSLP
FVLSLLVVRFISVYFFCTILVRAIVKLYHQFATGGKAZ (SEQ. ID. NO. 112)
MVKVATQTPHSLLLILSLETSFIPSIALTLSVVAPCILFMLYYRRFKMLA
WMLLLAILPSFANYWAVQLHGDASQAVMLGTRAFVTVCIGLVFVSSVSLK
ELLLYLAQKGLSRSWSYALIVVFNSFPLQQEIKSLKEACLLRGQELHFWS
PLIYSKVLMTVFRWRHLYLRALSAHGYDEHAQLKNSYRTFYPKKTKLIYL
LFFLLLQTSLLZ

TABLE 4-continued (SEQ. ID. NO. 113)
MRKHQLQVHKLTLSMMALDVVLTPRIEGMAPMSSVVNLAGIMMGPVYALA
MATVRAFXRNfFRQGIPPLALTGATFGALLAGLFYKYGRKFHYSALGEIL
GTGUGSIVSYPVMVLFTGSAAKLSWFEYTPREFGATLIGTALSFIAFRFL
KQEFFKKVQGYFFSERIDZ (SEQ. ID. NO. 114)
MQETNPFPIGSSSLIHCFLNEISCEMLANGILALGCKPVMADDSREVLDF
IKQSQALNLGHLSAEKEKJJRMAASYANQSSLPMVVDAVGVRSSIRKSLV
KDLLDYRPRVLKGNMSEIRSLVGLKHHGVGVDASAJCDQETEDLLQVLKD
WCQTYPGMSFLVTGPKDLVSKNQVAVLGNGCTELDWITGTGDLVGALTA
VFLSQGKTGPEASCLAVSYLNIAAEKIVVQOMGLEEFRYQVLNQLSLLRR
DENWLDTIKGEVYEZ (SEQ. ID. NO. 115)
MNHKAILSDVMGNATALEAVL&DAXNQGASEYWLLGDIFLPGPGANDLVA
LLKDLPPASVRGNWDDRVLEALDGQYGLEDPQEVQLLRMTQYLMERMDPA
TIVWLRSLPLLEKKEIDGLRFSISHNLPDKNYGGDLLVENDTEKFDQLLD
AETDVAVYGHVHKQLLRYGSQGQQIINPGSIGMPYFNWEALKNHRSQYAV
IEVEDGELLNIQFRKVAYDYEAELELAKSKGLPFIEMYEELRRDDNYQGH
NLELLASLIEKHGYVEDVKNFFDFLZ (SEQ. ID. NO. 116)
MNVQIVRIIPTLKANNRKLNETFYIETLGMKALLEESAFLSLGDQTGLEK
LVLEEAPSMRTRKVEGRKKLARLIVKVENPLEIEGTTDSIHRLYKGQNGY
AFEIPSPEDDLILIHAEDDIASLVEVGEKPEQTDLASKEISMELHLDIFL
ESSEIGASLDFIPAQGQDLTVDNTVTWDLSMLKFLVNELDLSLRQKFEST
EYFIPKSEKGKDNVELWEVZ (SEQ. ID. NO. 117)
MKWTKHIIKKIEEQIEAGIYPGASFAYFKDNQWTEFYLGQSDPEHGLQTE
AGLVYDLASVSKVVGVGTVCTFLWEIGQLDIDRLVIDFLPESDYPDTIRQ
LLTRATDLDPPIPNRDLLTAPELKEAMFHLNRSQPAFLYSDVHPLLLGFL
EFNQDLDVILKDQVWKPWGMTETKFGPVELAVPTVRGVEAGIVHDPKARL
LGREAGSAGLFSTIKDLQIFLEHYLADDFALNQNFSPLDDKERSLAWNLE
GDWLDHTGYTGTFIMWNRQKQEATFLSNRTYEKDERAQWILDRNQVMNLI
EEZ (SEQ. ID. NO. 118)
MMKKTYNHILVWGVIFYSICIVCFCFTPQEQSTVGVGTPGIQHLGRLVFL
LTPFNSLWKLGEVSDIGQLCWIFLQNILNVFLFFPLIFQLLYLFPNLRKT
KKVLLFSFLVSLGIECTQLILDFFFDFNRVFEIDDLWTNTLGGYLAWLLY
KRLHKVRNZ (SEQ. ID. NO. 119)
MKIPLLTFLARHKFVYVLLTLLFLALVYRDVLMYFFDIHAPDLAKFDGQA
IKNDLLKSALDFRILQNLGQSFIIPIIVLLGFQYIELKNXVLRLSRBVS
YQGLKRKLTLQVASIPCLIYLVTVLUAHTYFFGTFSPLGWNSLSDGSGLQ
RLLDGEIKSYLFFTCVLLIGIFINAIYFLQIVDYVGNVTRSAITYLMFLW
LGSMLLYSALPYYMVPMTSLMQASYGDVSLMKLPYILYIVPYMVLEICYE
DNVZ (SEQ. ID. NO. 120)
MFKVLQKVGKAFMLPIAILPAAGLLLGLGGALSNPRTIATYPILDNSIFQ
SIFQVMSSAGEVVFSNLSLLLCVGLCIGLAKRDKGTAALAGVTGYLVMTA
TUALVKLFMAEGSAIDTGVIGALVVGIVAVYLHNRYNNIQLPSALGGGSP
PISFSSILIGFVFFVWPPFQQLLVSTGGYSQAGPIGTLYGFLMRLSGAVG
LHHIIYPMTYTELGGVETVAGQTVGAQKIPAQLADLAHSGLFREGTREAG
RFSTMMFGLPAACLAMYHSVPKNRRKKYAGLFGVALTSFITGITEPIEFM
FLPVSPVLYVHAFLDGVSPFIADVLNISIGNTFSGGVIDFRLFGILQGNA
KTNWVLQIPGLIWSVLYYIIFRWFTQNVLTRGEEVDSKEISESADSTSNT
ADYLKQDSLQIIRALGGSNNIEDVDACVTRLRVAVEVNQVDKALLKQIGA
VDVIEVKGGIQAIYGAKAILYKNSINEILGVDDZ (SEQ. ID. NO. 121)
MKFRKLACVLAGAAVLGLAACGNSGGSKDAAKSGGDGAKTEITWWAFPVF
TQEKTGDGVGTYEKSUEAFEKANPDIKVKLETDFKSGPEKNTAIEAGTAP
DVLFDAPGRIIQYGKNGKLAELNDLFTDEFVKDVNNENRVQASKAGDKAY
MYPISSAPFYMAMNKKMLEDAGVANLVKEGWITDDFEKVLKALKDKGYTP
GSLFSSGQGGDQGTRAFISNLYSGSVTDEKVSKYTRDDPKFVKGLEKATS
WIKDNLINNGSQFDGGADIQNFANGQTSYTILWAPAQNGIQAKLLEASKV
EVVEVPFPSDEGKPALEYLVNGFAVNNKDDKKVAASKKIQFIADDKEWGP
KDVVRTGAFPVRTSFGKLYEDKRMETSGWTQSPYYNTIDGFAEMRTLWPM
LQSVSNGDEKPADALKAFTEKANETIKKAMKQZ (SEQ. ID. NO. 122)
MQSTEKKPLTAFTVISTIILLLLTVLFIPPFYWILTGAFKSQPDTIVIPP
QWFPKMPTMENFQQLMVQNPALQWMWNSVFISLVTMFLVCATSSLAGYVL
AKKRFYGQRILFAIFIAAMALPKQVVLVPLVRIVNFMGHDTLWAVILPLI
GWPFGVFLMKQFSENIPTELLESAKIDGCGEIRTFWSVAPPVKPGFAALA
IPTFINTWNDYFMQLVMLTSRNNLTISLGVATMQAEMATNYGLMAGAALA
AVPIVTVFLVFQKSTQGITMGAVKGZ (SEQ. ID. NO. 123)
MKIMFKNFNNILLNRCIVLLLRIVLMMILINHLLSTAVQKQDAVIFFKRE
LSFSYNDYSEANLEIPICLLLNLSIFMVGWLSVILLESDLADHYHHLIRY
QSSSFFDYTRKRLVVISKFFTQDLFVWFLGLLPGIHFKTVALFFLLAQL
MMLYLLLSYUALISAGAGFSFFLYPLAFVGQEWMMDHIVTVYLVLLSLLV
MLVSRLESKFKKGZ (SEQ. ID. NO. 124)
MGKGEMGKGVIGLEFDSEVLVNKAPTLQLANGKTATFLTQYDSICTLLPA
VDKEDIGQEIIGIAKGSIESMHNLPVNLAGARVPGVNGSKAAVHEVPEFT
GGVNGTEPAVHEIAEYKGSDSLVTLTTGKDYTYKAPLAQQALPETGNKES
DLLASLGLTAFLGLFTLGKXREQZ TABLE 4-continued (SEQ. ID. NO. 125)
MKKTFFLLVLGLFCLLPLSVIAIDFKINSYQGDLYIHADNTAEFRQKIVY
QFEEDFKGQIVGLGRAGKMPSGFDIDPHPKIQAAKNGAELADVTSEVTEA
DGYTVRVYNPGQEGDIVEVDLVWNL,KNLLPLYDDIAELNWQPLTDSSES
IEKFEFHVRGDKGAEKLFFTGKLBGTIEKSNLDYTIRLDNLPAKRGVELH
AYWPRTDFASARDQGLKGNRLEENKIEDSIVREKDQSKQLVTWVLPSILS
ISLLLSVCYFIYRRKTRPSVKYAKNHRLYEPPMELEPMVLSEAVY5TSLE
EVSPLVKGAGKFTFDQLIQATLLDVIDRGNVSIISEGDAVGLRLVKEDGL
SSFEKDCLNLAFSGKICEETLSNLFADYKVSDSLYRRAKVSDEKRIQARG
LQLKSSPEEVLNQMQEGVRKRVSFWGLPDYYRPLTGGEKALQVGMGALTL
PLFIGFGLFLYSLDVNGYLYLPLPILGFLGLVLSVFYYWKLRLDNRDGVL
NBAGAEVYYLWTSFENMLRIARLDQAELESVVWNRLLVYATLFGYADKVS
HLMKVNQIQVENPDINLYVAYGWHSTYHSTAQMSHYASVANTASTYSVSS
GSGSSGGGFSGGGGGGSIGAFZ (SEQ. ID. NO. 126)
MKKVRKIFQKAVAGLCCISQLTASSIVALAETPETSPAIGKVVIKBTOEG
GALLGDAVFELKNNTDGTTVSQRTEAQTGEAIFSNIKPGTYTLTEAQPPV
GYKPSTKQWTVEVEKNGRTTVQGEQVENREEALSDQYPQTGTYPDVQTPY
QUCVDGSEKNGQHKALNPNPYERVPEGTLSKRIYQVNNLDDNQYGIELTV
SGKTVYEQKDKSVPLDVVILLDNSNSMSNIRNKNARRAERAGEATRSLID
KTSDSENRVALVTYASTIFDGTEFTVBKGVADKNGKRLNDSLFwNYDQTS
VITNTKDYSYLKLTNDKNDIVELKNKVPTEAEDHDGNRLMYQFGATFTQK
ALMKADEILTQQARQNSQKVIFHITDGVPTMSYPINFNHATFAPSYQNQL
NAFFSKSPNKDGLLSDRTQATSGEITIVRGDGQSYQMFTDKTVYEKGAPA
AFPVKPEKYSEMKAAGYAVGDPNGGYWLNWRESILAYPFNSNTAKITNHG
DPTRWYYNGNIAPDGYDVFTVGIGINGDPGTDEATATSFMQSISSKPENY
TNVTDTRKILEQLNRYFHTIVTEKKSENGTITDPMGELIDLQLGTDGRFD
PADYTLTANDGSRLENGQAVGGPQNDGGLLKNAKVLYDRREKRIRVTGLY
LGTDEKVTLTYNVRLNDEFVSNKFYDTNGIfLRLHPKEVEQNTVRDFPIP
KIRDVRKYPEITSKEKKLGDIBFIKVNKNDKKPLRGAVFSLQKQHPDYPD
IYGAIDQNGTYQNVRTGEDGKLTFKNLSDGKYRLFENSEPAGYKPVQNKP
IVAFQIVNGEVRDVTSVPQDIPAGYEFTNDKHYRRNEPIPPKREYPRTGG
IGMLPFYLIGCMMMGGVLLYRRKHPZ (SEQ. ID. NO. 127)
MKSINKFLTMLAALLLTASSLFSAATVFAAGTTTTSVTVHKLLATDGDMD
KIANELETGNYAGNKVGVLPANAKEIAGTLTGSKAVPIEIELPLNDVVDA
HVYPKNTEAKPKIDKDFKGKANPDTPRVDKDTPVNHQVGDVVEYEIVTKI
PALANYATANWSDRMTEGLAFNKGTVVTVDDVALEAGDYALTEVATGFDL
KLTDAGLAKVNDQNAEKTVKITYSATLNDKAIVEVPESNDVTINYGNNPD
HGNTPKPNKPNENGDLTLTKTWVDATGAPIPAGAEATFDLVNAQTGKVVQ
TVTLDKNTVTVNGLDKNTEYKFVERSIKGYSADYQEITTAGEIAVKNWKD
ENPKPLDTEPKVVTYGKKFVKVNDKDNRIAGAEFEWVADKDNENVVKLVS
TGLLAGTYYLEETKQPAGYALLTSRQKFEVTATSYSATGQGIEYTAGSGK
DAQGRFEIDDATKVVNKKITIPQTGGIGTIIFAVAGAAIMGIAVYAYVKN
NKDEDQLAZ (SEQ. ID. NO. 128)
MTMQKMQKMSRJFFVMALCPSLVWGAHAVQAQEDHTLVLQLENYQEVVSQ
LPSRDGHRLQVWKLDDSYSYDDRVQIVRDLHSWDENKLSSFKKTSFEMTF
LENQIEVSHIPNGLYYVRSUQTDAVSYPAEPLFEMTDQTVEPLVIVAKJC
TDTMVKLIKVDQDHNRLEGVGFKLVSVARDVSEKEVPLIGEYRYSSSGQV
GRTLYTDKGEIPVRNLPLGNYRYKEVELAGYAVTTLDTDVQLVDHQLVTI
TVVNQKLPRGNVDFMKVDORTNTSLQGAMFKVMKEESGHYTPVLQNGKEV
VVTSGKDGRFRVEGLEYGTYYLWELQAPTGYVQLTSPVSFTIGKDTRKEL
VTVVKNNKRRJDVPDTGEETLVYLDACCHVVWZ (SEQ. ID. NO. 129)
MSHIYLSIFTSLLLMLGLVNVAQADEYLRIGMEAAYAPFNWTQDDDSNGA
VKIDGTNQYANGYDVQIAKKAKDLGKEPLVVKTKWEGLVPALTSGKIDMI
IAGMSAERICQEIAFSSSYYTSEPVLLVKKDSAYAS&YLDDPNGAKITSQ
QGVYLYNLL4QIPGAKICITAMGDFAQMRQALEAGVDAYVSERPEALTAE
AANSKFKMIQVEPGFKGEEDTAIAIGLRKNDNRISQINASIETSKDDQVA
LMDRMIKEQPAEATITEETSSSFFSQVAKILSENWQQLLRGAGITLLISV
GTIIGLIIGLAIGVFRTAPLSENKVIYGLQKLVGWVLNVYIEIRGTPMVQ
SMVIYYGTAQAFGINLDRTLAAIFIVSINTGAYMTEVRGGILAVDKGQFE
AATALGMTHNQTMRKWLPQVVRNILPATGNEFVINIKDTSVLNVISVVEL
YFSGNTVATQTYQYFQTFRIIAVIYFVLTFTVTRILRFIERRMDMDTYTR
OANQMQTEDLKZ (SEQ. ID. NO. 130)
MTQAILEIKHLLKKSYGQNEVLKDSLTHKGEVISIIGSSGSGKSTFLRINL
LETPTDGQYHGQNVLEKGYDLTQYREKLGMVFQSFNLFENLNVLENTIVA
QTRVLKRERTEAEKIAKENLEKVGMGERYWQAKPKQLSGGQKQRVALARA
LSMNPDAILFDETSALDPEMVGEVLKIMQDLAQEGLTMIVVTHEMEFARD
VSHRVFMDKGVLAEEGKPEDLFTNPKEDRTKEFLQRYLKZ (SEQ. ID. NO. 131)
MKKYQLLFSAVFSYLFFVFSLSQLTLIVQNYWQFSSQGNLPWIQNILSLL
FIGVMIVVLVQGHGYLFPJPPJCKWLWYSLTVLVLVQISFNVQTAKHVQS
TAEGWAVLIGYSGTNFAELGIYALFFLVPLMEELYRGLLQHAFFKRFGLD
LLLPSILFALPHFSSLPSLLDIFVFATVGIIFAGLTRYTKSIYPSYAVHV
INNIVATFPFLLTFLHRVLGZ (SEQ. ID. NO. 132)
MNKKQWLGLGLVAVAAVGLAACGNRSSRNAASSSDVKTKIVTDTGGVDDK
SFNQSAWEGLQAWGKEHNKDNGFTYFQSTSEADYANNLQQAAGSYNLIFG
VGFALNNAVKDAAKEHTDLNYYLIDDVIKDQKNVASVTFADNESGYLAGV
AAAKTTKTKQVGFVGGIESEVISRFEAGFKAGVASVDPISKVQVDYAGSF TABLE 4-continued GDAAKGKTIAAQYAAGADIVYQVAGGTGAGVFAEAKSLNESRPENEKVWI
GVDRDQEAEGKYTSKDGKESNFVLVSTLKQVGTTVKDISNKAERGEFPGG
QVIVYSLKDKGVDLAVTNLEEGKKAVEDAKAKILDGSVKPEKZ (SEQ. ID. NO. 133)
MSKKLQQISVPLISVFLGILLGAIVMWIFGYDAIWGYEELPYTAFGSLRG
IGEIFRAMGPLVLIGLGFAVASRAGFPNVGLPGQALAGWILSGWFALSHP
DMPRPLMILATIVIALIAGGIVGAIPGILRAYLGTS2VIVTIMMNYIVLY
VGNAPIHAPPKDFMQSTDSTIRVGANATYQTPWLAELTGNSRMNIGIFFA
IIAVAVIWFMLKKTRLGFEIRAVGLNPMASEYAGISAKRTHLSMIISGAL
AGLGGAVEGLGTFQNVYVQGSSLAIGFNGMAVSLLAANSPIGILPAAFLF
GVLQVGAPGMNAAQVPSELVSIVTASIIFFVSVEYLIERPVKPKKQVKGG
KZ (SEQ. ID. NO. 134)
MGVKKLKLTSLLGSLLITACATNGVTSDITAESADWSKLVYFFAEIIRFL
SFDISIGVGuLFRVLIRTVLLPVQVQMVASRKMQEAQPRIKALREQYPGR
DMESRTKLEQEMRKVFKEMGVRQSDSLWPILIQMPVILALFQALSRVDFL
KTGHFLWINLGSVDTRLYLPILAAVFTFLSTWLSNKALSERNGATTAMMY
GIPVLIRPAVYAPGGVALYWTVSNAYQVLQTYFLNNPFKIIAEREAVVQA
QKDLENRKRKAKKKAQKTKZ (SEQ. ID. NO. 135)
MVIDPFANELDYYLVSHFHSDHIDPYTAAAILNNPKLEHVKFIGPYHCGR
IWEGWGVKERFLVVKPGDTIELKDMKIHAVESFDRTCLVTLPVNGADETG
GELAGLAVTDEEMAQKAVNYIPETPGGTIYHGADSHFSNYFAJCHGKDFK
IDVALNNYGENPVGIQDKMTSIDLLRMAENLRTKVIIPVHYDIWSNFMAS
TNEILELwKMRKDRLQYDFHPFIwEVGGKYTYPQDQHLVEYHHPRGFDDC
FEQDSNIQFKALLZ (SEQ. ID. NO. 136)
MFLSGWLSFANYIHDLLVLFPDSPFLNAFESAIAAPLVEELSCVFVTM4P
VRXKSTLTGIASOLCFQMIKNGYIRTDLPEGFDFTISRILERJISGIASH
WTFSGLAVVGVYLLYRAYKC3QKVGKKQGLIFLGLALGTHFLFNSPFVEL
ETEIPLAIPVVTAIALYGFYMAYCFVEKHNELMTZ (SEQ. ID. NO. 137)
MKVEPRCDVLSRMSHFFIRILIMLQELVERSWAIRQAYHELEVKHHDSKV
RRVEEDLLALSNDIGNPQRLVMTKQGRYYDETPYTLEQKLSENIWWLLEL
SQRLDIDILTEMENFLSDKEKQLNVRTWKZ (SEQ. ID. NO. 138)
MLDWKQFFLAYLRSRSRLFIYLLSLAFLVLLFQFLASLGIYFLYFPPLCC
FVTILFRWDILVETQVYRQELLYGEREAKSPLEIALAEKLEAREMELYQQ
RSKAERKLTDLLDYYTLWVHQIKTPIAASQLLVAEVVDRQLKQQLEQEIF
ICIDSYTNLVLQYLRLESPHDDLVLKQVQIEDLVKEIIRKYALFRQKGLN
VNLHDLDKEIVTDKJCwLLVVIEQIISNSLKYTKEGGLEIYMDDQELCIK
DTGIGIKNSDVLRVFERGFSGYNGRLTQQSSGLGLYLSKKISEELGHQIR
IESEVGKGTRVRIQFAQVNLVLEZ (SEQ. ID. NO. 139)
MELNTHNAEILLSAANKSHYPQDELPEIALAGRSNVGKSSFINTMLNRXN
LARTSGKPGQLLNFFNIDDKMRFVDVPGYGYARVSKKEREKWGCMIEEYL
TRRENLAVVSLVDLRHDPSADDVQMYEFLKYYEIPVIRVATKADKIPRGK
WNKHESAIKKKLNFDPSDDFILFSSVSKAGMDEAWDAILEKLZ (SEQ. ID. NO. 140)
MTKKQLHLVVTGMSGAGKTVAIQSFBDLGYFEDNMPPALLPKFLQLVEIK
EDNPKLALVVDMRSRSFFSEIQAVLDELENQDGLDPKILLDAADKELVAR
YKETRRSHPLAADGRLDGIgLRELLAPLKNMSQNVVDRRELTPRELRITL
AEQFSDQEQAQSFPJEVMSFGIKYGIPIDADLVFDVRFLPNPYYLPELRN
QTGVDEPVYDYVMNHPESEDFYQHLLALIEPILPSYQKEGKSVLTIAMGC
TGGQMRSVAFAKRLAQDLSKNWSVNEGHPDKDRRKETVNRSZ (SEQ. ID. NO. 141)
MRKPKITVIGGGTGSPVTLKSLREKDVEAAIVTVADDGGSSGELRKNMQQ
LTPPGDLRNVLVAMSDMPKFYEKVFQYRFSEDAGAFAGHPLGNLUAGLEM
QGSTYNAMQLLSKFPHRGKYPSSDHPLTLVFQTEVAGHIVDMRGIIDNEV
LHRLRPFIDTVLVNEKVPEYMNSNRPDEYLVQVEHDFVGLCKQVSRVISS
NPLPENGGAIDLIVDELMRIQVKKZ (SEQ. ID. NO. 142)
MKNLIKLLIUVNLADSVFYIVALWHVSNNYSSSMFLGFIAVNYLPDLLLI
GPVDRVNPQKILIILVQLAVAVIFTLLLNQISFWVIMSLVFSVMASSISY
VIEDVLIQVVEYDKIVFANSLFSISYKVLDSFNSFFLQVAVGILLVKIDI
GIPLLALFILLLLKRTSNANIENFSFKYYKREVLQGTHFILNNGLLFTSI
SLTLINFFYSFQTVVVPFSIRYGPIJYGIPLTGLGGILGNMLAPIVIKYL
KSNQVGVFLFLNGSSWLVAIVIKDYTLSLILFFVCFMSKGVNIINSLYQQ
IPPHQLLGRVNTTIDSIISFGMPIGSLVAGTLIDLNIELVLIAISIPYFL
FSYLFYTDNGLKEFSIYZ (SEQ. ID. NO. 143)
MMSNKNKEILIFAILYTVLFMFDGVKLLASLMPSAIANYLVYVVLALYGS
FLFKDRLIQQWKEIRKTKRKFFFGVLTGWLFLILMTVVFEFVSEMLKQFV
GLDGQGLNQSNIQSTFQEQPLLIAVFACVIGPLVEELFFRQVLLHYLQER
LSGLLSIILVGLVFALTHMHSLALSEWIGAVGYLGGGLAFSIIYVKEKEN
IYYPLLVHMLSNSLSLIILAISIVKZ (SEQ. ID. NO. 144)
LKKPIIEFKNVSKVFEDSNTCVLKDNFELEEGICYTLLGASGSGKSTILN
HAGLLDATRGDIMLDGVRINDPTIKRDVHTVFQSYALFPHMNVFENVAFP
LRLRKIDKKEIEQRVAEVLKMVQLEGYEKRSLRKLSGGQRQRVAIARAII
NQPRVVLLDEPLSALDLKLRTDMQYELRELQQRLGITFVFVTHDQEALAM
SDWTVMNDGETVQSGTPVDIYDEPINHFVATFGBSNILPGTMIEDYLVEF
NGKREAVDGGMKPNEPVEVVIRPEDLRTLPEEGKLQVKVDTQLFRGVHYE
UAYDELGNEWMIHSTRKAVGEEGLDFBPEDIHIMRLNETEEEFDAPJEEY
VEIEEQEAGLINAIEEERDEENKLZ TABLE 4-continued (SEQ. ID. NO. 145)
MKSMRILFLLALIQISLSSCFLWKECILSFKQSTAFFIGSMVFVSGICAG
VNYLYTRKQEVHSVLASKKSVKLFYSMLLLNLLGAVLVLSDNLFKNLQQE
LVDFLLPSFFLFGLDLLIFLPLKXYVRDFLAMLDRXTVLVTILATLLFLR
NPMTVSLLIYIGLGLFFAAYLVPNSVKKEVSFYGHIRDLVLVIVTLIFFZ (SEQ. ID. NO. 146)
MVKKIIGMVLALLSVTVVGVGVFAYTIYQQGTETLAIZTYKKIGEETKVI
EATEPLTILLMGVURGNVERTETWVGRSDSMILMTVNPKTKRITMMSLER
DILTRIESGNGQAHEAKLNSAYADGGAELAIETIQKMMNIHIDRYVMVNM
RGLQKLVDAVGGRRVNNLGFPISSDQEENTSIGVGEQHIGGEEALVYARM
RYQDPEGDYGRQKRQREVIQKVMEKALSLNSIGHYQEILKALSDNMQTNI
DLSAKSPNLLGYPZDSFKTIETQQLQGEGEILQGVSYQIVSRAHMLEMQN
LLRRSLGQEEVTQLETNAVLFEDLFGRAPVGDEDNZ (SEQ. ID. NO. 147)
MKKQAYVUALTSFLFVFFFSHSLLEILDFDWSIFLHDVEKTEKFVFLLLV
FSMSMTCLLALFwRGIEELSLRKMQANLKRLLAGQEVVQVADPDLDASFK
SLSGKLNLLTEALQKAENQSLAQEEEIIEKERKRIARDLHDTVSQELFAA
HMILSGISQQALKLDREKMQTQLQSVTAILETAQKDLRVLLLHLRPVELE
QKSLIEGIQILLKELEDKSDLRVSLKQNMTKLPKKLEEHIFRJLQELSNT
LRHAQASCLDVYLYQTDVELQLKVVDR4GIGFQLGSLDDLSYGLRNIKER
VEDMAGTVQLLTAPKQGLAVDIRIPLLDKEZ (SEQ. ID. NO. 148)
MIVSIISQGFVWAILGLGIFMTFRILNFPDMTTEGSIPLGGAVAVTLITK
GVNPFLATLVAVGAGCLAGMAAGLLYTKGKIPTLLSGILVMTSCHSWILL
IMGRANLGLLGTKQIQDVLPFDSDLNQLLTGLRFVSRVXALMLPLLDTIC
LGQAYIATGDNPDMARSFGHTGRMELMGLVLSNGVIALAOALAQQEGYAD
VSRGGVIVVGLASLIIGEVISLAEPVTIVVGSIAYQFLVWAVIAIOFNTS
YLRLYSALILAVCLMUTFKQTILKGAJCLSKZ (SEQ. ID. NO. 149)
MKKMKVWSTVLATGVALTRLAACSGGSNSTTASSSEEKADKSQELVIYSN
SVSNGRGDWLTAXAEAGFNIKMVDIAGAQLADRVLAEKNNAVADMVFGIG
AVDSNKIRDQKLLVQYKPKWLDKIDQSLSDKDNYYNPVIVQPLVLIGAPD
VKEMPKDWTELGSKYKGKYSISGLQGGTGRALASILVRYLDDKGELGVSE
KGWEVAICEYLKNAYTLQKOESSIVKMLDKEDPIQYGMMWGSGALVGQKE
QNVVPKVMTPEIGVPFVTEQTMVLSTSKKQALAKEFIDWFGQSEIQVEYS
KNFGSIPANKDALKDLPEDTKKFVDQVKPQNIDWEAVGKHLDEWVEKAEL
EYVQZ (SEQ. ID. NO. 150)
MIKFDNIQIKYGDFVAIDNLNLDHEGEFTFLGPSGCGKSTLRALVGFLDP
SSGSIEVNGTDVTHLEPEKRGIGVFQSYALFPTMTVDNIAFGLKVKKVAP
DVIKAKVSAVAAKIKISDQQLQRNVSELSGGQQQRVALARLVLEPKILCL
DEPLSNLDAKLRVDLRKELKRLQKELGRITLYVTHDQEEALTLSDRIAVF
NNGYIEQVGTPVEIYHNSQTEVCDPIGDNVLTDETVHEVLLKNTSVFLED

KKGYIRLEKVRFNRETEQDFLKGTUDVEFSGVTEHYTIKVSESQILNVTS
IDSQAARSVGESVELFITPSDVLQFZ (SEQ. ID. NO. 151)
MRHKLNLKDWLRLGLRWFLVTRIYPNFDLVVNVFVKGGESLDAVHRVLKQ
PALQSMNSPSLIVNVVGILCVLFTEYFDIKGAKZLKLGYMTSLIYGGVVL
ATGYKFVYGPYGLITKFLQNVIPSLDPNWPIGYGAVLFIMTFSGTANHTL
FLTNTHSVDYTIEARNMGKPVFRICVVLPTLITLFALTIMVFLSGLSAVA
APMIVGGKEFQTTNPMIITFAGMGNSRDLAALLAIILGIATTILLTIMNK
IEKGGNYISISKTKAPLKKQKIASKPWNIIAHIVAYGLFTVFMLPLIFIV
LYSPTDPVVIALNFNSLLTDFDLSVFLYHPLAQPLGITIPSAGDETATSN
AQALVF\RYTIVLMIISGTVLYPTQPJGPJVPJ CZ

TABLE 5

ID201 - 4106.4

(SEQ. ID. NO. 168)
ATGATAAAAATCCTAAATTATTAACCAAGTCTTTTTTAAGAAGTTTTGC
AATTCTAGGTGGTTGGTCTAGTCATTCATATAGCTATTTATTTGACCTTT
CCTTTTTTATTATATTCAACTGGAGGGGAAAAGTTTAATGAGAGCGCAAG
AGTGTTTACGGAGTATTTAAAGACTAAGACATCTGATGAAATTCCAAGCT
TACTCCAGTCTTATTCAAAGTCCTTGACCATATCTGCTCACCTTAAAAGA
GATATTGTAGATAAGCGGCTCCCTCTTGTGCATGACTTGGATATTAAAGA
TGGAAAGCTATCAAATTATATCGTGATGTTAGATATGTCTGTTAGTACAG
CAGATGGTAAACAOGTAACCGTGCAATTTGTTCACGGGGTGGATGTCTAC
AAAGAAGCAAAGAATATTTTGCTTTTGTATCTCCCATATACATTTTTGGT
TACAATTGCTTTTTCCTTTGTTTTTTCTTATTTTTATACTAAACGCTTGC
TCAATCCTCTTTTTACATTTCAGAAGTGACTAGTAAAATGCAAGATTTG
GATGACAATATTCGTTTTGATGAAAGTAGGAAAGATGAAGTTGGTGAAGT
TGGAAAACAGATTAATGGTATGTATGAGCACTTGTTGAAGGTTATTTATG
AGTTGGAAAGTCGTAATGAGCAAATTGTAAAATTGCAAAATCAAAAGGTT
TCCTTTGTCCGCGGAGCATCACATGAGTTGAAAACCCCTTTAGCCAGTCT
TAGAATTATCCTAGAGAATATGCAGCATAATATTGGAGATTACAAAGATC
ATCCAAATATATTGCAAAGAGTATAAATAAGATTGACCAGATGAGCCAC
TTATTAGAAGAAGTACTGGAGTCTTCTAAATTCCAAGAGTGGACAGAGTG
TCGTGAGACCTTGACTGTTAAGCCAGTTTTAGTAGATATTTTATCACGTT
ATCAAGAATTAGCTCATTCAATAGGTGTTACAATTGAAAATCAATTGACA
GATGCTACCAGGGTCGTCATGAGTCTTAGGGCATTGGATAAGGITTTGAC
AAACCTGATTAGTAATGCAATTAAATATTCAGATAAAATGGGCGTGTAA
TCATATCCCAGCAAGATGGCTATCTCTCTATCAAAAATACATGTGCGCCT
CTAAGTGACCAAGAACTAGAACATTTATTTGATATATTCTATCATTCTCA
AATCGTGACAGATAAGGATGAAAGTTCCGGTTTGGGTCTTTACATTGTGA

TABLE 5-continued

ATAATATTTTAGAAAGCTATCAAATGGATTATAGTTTTCTCCCTTATGAA

CACGGTATCGAATTTAAGATTACCTTATAG (SEQ. ID. NO. 152)
MIKNPKLLTKSFLRSFAILGGVGLVIHIAIYLTFPFYYIQLEGEKFNESA
RVFTEYLKTKTSDEIPSLLQSYSKSLTISAHLKRDIVDKRLPLVHDLDIK
DGKLSNYIVMLDMSVSTADGKQVTVQFVHGVDVYKEAKNILLLYLPYTFL
VTIAFSFVFSYFYTKRLLNPLFYISEVTSKMQDLDDNIRFDESRKDEVGE
VGKQINGMYEHLLKVIYELESRNEQIVKLQNQKVSFVRGASHELKTPLAS
LRIILENMQHNIGDYKDHPKYIAKSINKIDQMSHLLEEVLESSKFQEWTE
CRETLTVKPVLVDILSRYQELAHSTGVTTENGLTDATRVVMSLRALDKVL
TNLTSNATTCYSDJGRVIISEQDGYLSIKINITCAPLSDQELEHLFDIFY
HSQIVTDKDESSGLGLYIVNNILESYQMDYSFLPYEHGMEFKISLZ

ID202 - 41069

(SEQ. ID. NO. 169)
ATGGATAAAATTATTAAAACTATATCAGAAAGCGGAGCCTTTCGTGCTTT
TGTCCTTGATAGCACTGAAACCGTCCGCACTGCTCAAGAAAAACATCAAA
CCCAAGCTAGCTCAACTGTAGCGCTTGGTCGAACTCTTATCGCTAGCCAG
ATTCTCGCAGCCAATGAAAAGGAAATACCAAACTTACAGTTAAGGTGTT
GGGATCTAGCTCTCTAGGTGCTATTATCACCGTCGCTGATACCAAGGGGA
ACGTCAAAGGCTATGTTCAAAATCCTGGTGTTGACATCAAAAAGACTGCG
ACTGGTGAAGTCCTAGTCGGACCTTTTGTTGGAAATGGTCAATTCCTCGT
TATCACAGACTACGGTACTGGAAATCCTTACAACTCTATAACTCCCCTCA
TCTCTGGAGAAATCGGTGAAGACCTTGCCTTTTACCTTACTGAAAGCCAA
CAAACGCCTTCAGCGGTCGGCCTCAATGTCCTTTTGGACGAGGAAGACAA
GGTCAAGGTTGCAGGTGGTTTCCTAGTTCAAGTCTTGCCAGGAGCCAAGA
AGAAGGAGATTGCTCGCTTTGAAAAACGCATCCAAGAAATGCCAGCTATC
TCTACTCTTCTCGAAACGTTTCCAATGTGACTGTAGCCATGAACGCTTTA
TGAACGCTCTTGCCAGCCTTCCAAGCTCAGACTTACAGGAAATGAAAGAG
GAAGACCACGGGGCAGAAATCACTTGTCAATTCTGCCAAACTACTTACAA
CTTTGATGAAAAGGACCTGGAGGAACTCATTCGTGACAAATCTTAA (SEQ. ID. NO. 153)
MDKIIKTISESGAFRAFVLDSTETVRTAQEKHQTQASSTVALGRTLIASQ
ILAANEKGNTKLTVKVLGSSSLGAIITVADTKCNV1CGYVQPCVDTKKTA
TGEVLVGPFVGNGQFLVTTDYGTG&PYNSTTPLTSGETGEDLAFYLTESQ
QTPSAVGLNLLDEEDKVKVAGGFLVQVLPGAKKEETARFETCRTQEMPAT
STLLESDDHIEALLKATYGDEAYKRLSEEEIRFQCDCSHERFMNALASLP
SSDLQEMKEEDHGAEITCQFCQTTYNFDEKDLEELIRDKSZ

ID203 - 4115

(SEQ. ID. NO. 170)
ATGAAATCAATAACTAAAAAGATTAAAGCAACTCTTGCAGGAGTAGCTGC
CTTGTTTGCAGTATTTGCTCCATCATTTGTATCTGCTCAAGAATCATCAA
CTTACACTGTTAAAGAAGGTGATACACTTTCAGAAATCGCTGAAACTCAC

TABLE 5-continued

AACACAACAGTTGAAAAATTGGCAGAAAACAACCACATTGATAACATTCA
TTTGATTTATGTTGATCAAGAGTTGGTTATCGATGGCCCTGTAGCGCCTG
TTGCAACACCAGCGCCAGCTACTTATGCGGCACCAGCCGCTCAAGATGAA
ACTGTTTCAGCTCCAGTAGCAGAAACTCCAGTAGTAAGTGAAACAGTTGT
TTCAACTGTAAGCGGATCTGAAGCAGAAGCCAAAGAATGGATCGCTCAAA
AAGAATCAGGTGGTAGTATACAGCTACAAATGGACGTTATATCGGACGTT
ACCAATTAA (SEQ. ID. NO. 154)
MKSITKKIKATLAGVAALFAVFAPSFVSAQESSTYTVKEGDTLSEIAETH
NTTVEKLAENNHTDNTHLTYVDQELVIDGPVAPVATPAPATYAAPAAQDE
TVSAPVAETPVVSETVVSTVSGSEAEAKEWIAQKESGGSIQLQMDVISDV
TNZ

ID204 - 4111.7

(SEQ. ID. NO. 171)
ATGAATTTAGGAGAATTTTGGTACAATAAAATAAATAAGAACAGAGGAAG
AAGGTTAATGAAGAAAGTAAGATTTATTTTTTTAGCTCTGCTATTTTTCT
TAGCTAATCCAGAGGGTGCAATGGCTAGTGATGGTACTTGGCAAGGAAAA
CAGTATCTGAAAGAAGATGGCAGTCAAGCAGCAAATGAGTGGGTTTTTGA
TACTCATTATCAATCTTGGTTCTATATAAAAGCAGATGCTAACTATGCTG
AAAATGAATGGCTAAAGCAAGGTGACGACTATTTTTACCTCAAATCTGGT
GGCTATATGGCCAAATCAGAATGGGTAGAAGACAAGGGAGCCTTTTATTA
TCTTGACCAAGATGGAAAGATGAAAAGAAATGCTTGGGTAGGAACTTCCT
ATGTTGGTGCAACAGGTGCCAAAGTAATAGAAGACTGGGTCTATGATTCT
CAATACGATGCTTGGTTTTATATCAAAGCAGATGGACAGCACGCAGAGAA
AGAATGGCTCCAAATTAAAGGGAAGGACTATTATTTCAAATCCGGTGGTT
ATCTACTGACAAGTCAGTGGATTAATCAAGCTTATGTGAATGCTAGTGGT
GCCAAAGTACAGCAAGGTTGGCTTTTTGACAAACAATACCAATCTTGGTT
TTACATCAAAGAAAATGGAAACTATGCTGATAAAGAATGGATTTTCGAGA
ATGGTCACTATTATTATCTAAAATCCGGTGGCTACATGGCAGCCAATGAA
TGGATTTGGGATAAGGAATCTTGGTTTTATCTCAAATTTGATGGGAAAAT
GGCTGAAAAGAATGGGTCTACGATTCTCATAGTCAAGCTTGGTACTACT
TCAAATCCGGTGGTTACATGACAGCCAATGAATGGATTTGGGATAAGGAA
TCTTGGTTTTATCTCAAATCTGATGGAAAATAGCTGAAAAAGAATGGGT
CTACGATTCTCATAGTCAAGCTTGGTACTACTTCAAATCCGGTGGTTACA
TGACAGCCAATGAATGGATTTGGGATAAGGAATCTTGGTTTTACCTCAAA
TCTGATGGGAAAATAGCTGAAAAAGAATGGGTCTACGATTCTCATAGTCA
AGCTTGGTACTACTTCAAATCGGTGGCTACATGGCGAAAATGAGACAG
TAGATGGTTATCAGCTTGAAGCGATGGTAAATGGCTTGGAGGAAAAACT
ACAAATGAAAATGCTGCTTACTATCAAGTAGTGCCTGTTACAGCCAATGT
TTATGATTCAGATGGTGAAAAGCTTTCCTATATATCGCAAGGTAGTGTCG
TATGGCTAGATAAGGATAGAAAAAGTGATGACAAGCGCTTGGCTATTACT

TABLE 5-continued

ATTTCTGGTTTGTCAGGCTATATGAAAACAGAAGATTTACAAGCGCTAGA
TGCTAGTAAGGACTTTATCCCTTATTATGAGAGTGATGGCCACCGTTTTT
ATCACTATGTGGCTCAGAATGCTAGTATCCCAGTAGCTTCTCATCTTTCT
GATATGGAAGTAGGCAAGAAATATTATTCGGCAGATGGCCTGCATTTTGA
TGGTTTTAAGCZTGAGAATCCCTTCCTTTTCAAAGATTTAACAGAGGCTA
CAAACTACAGTGCTGAAGAATTGGATAAGGTATTTAGTTTGCTAAACATT
AACAATAGCCTTTTGGAGAACAAGGGCGCTACTTTTAAGGAAGCCGAAGA
ACATTACCATATCAATGCTCTTTATCTCCTTGCCCATAGTGCCCTAGAAA
GTAACTGGGAAGAAGTAAAATTGCCAAAGATAAGAATAATTTCTTTGGC
ATTACAGCCTATGATACGACCCCTTACCTTTCTGCTAAGACATTTGATGA
TGTGGATAAGGGAATTTTAGGTGCAACCAAGTGGATTAAGGAAAATTATA
TCGATAGGGGAAGAACTTTCCTTGGAAACAAGGCTTCTGGTATGAATGTG
GAATATGCTTCAGACCCTTATTGGGGCGAAAAAATTGCTAGTGTGATGAT
GAAAATCAATGAAAGCTAGGTGGCAAAGATTAG (SEQ. ID. NO. 155)
MNLGEFWYNKINKNRGRRLMKKVRFIFLALLFFLASPEGAMASDGTWQGK
QYLKEDGSQAANEWVFDTHYQSWFYIKADANYAENEWLKQGDDYFLKSG
GYMAKSEWVEDKGAFYYLDQDGKMKRNAWVGTSYVGATGAKVIEDWVYDS
QYDAWFYIKADGQHAEKEWLQIKGKDYYFKSGGYLLTSQWINQAYVNASG
AKVQQGWLFDKQYQSWFYTKENGNYADKEWIFENGHYYYLKSGGYMAANE
WIWDKESWFYLKFDGKMAEKEWVYDSHSQAWYYFKSGGYMTANEWTWDKE
SWFYLKSDGKIAEKEWVYDSHSQAWYYFKSGGYMTANEWIWDKESWFYLK
SDGKIAEKEWVYDSHSQAWYYFKSGGYMAKNETVDGYQLGSDGKWLGGKT
TNENAAYYQVVPVTANVYDSDGEKLSYISQGSVVWLDKDRKSDDKRLAIT
ISGLSGYMKTEDLQALDASKDFIPYYESDGHRFYHYVAQNASIPVASHLS
DMEVGKKYYSADGLHFDGFKLENPFLFKDLTEATNYSAEELDKVFSLLNI
NNSLLENKGATFKEAEEHYHINALYLLAHSALESNWGRSKIAKDKNNFFG
ITAYDTTPYLSAKTFDDVDKGILGATKWIKENYIDRGRTFLGNKASGMNV
EYASDPYWGEKIASVMMKINEKLGGKDZ

ID205 - 41181.1

(SEQ. ID. NO. 172)
ATGAAAAAATTAGGTACATTACTCGTTCTCTTTCTTTCTGCAATCATTCT
TGTAGCATGTGCTAGCGGAAAAAAAGATACAACTTCTGGTCAAAAACTAA
AAGTTGTTGCTACAAACTCAATCATCGCTGATATTACTAAAAATATTGCT
GGTGCAAAATTGACCTTCATAGTATCGTTCCGATTGGGCAAGACCCACAC
GAATACGAACCACTTCCTGAAGACGTTAAGAAACTTCTGAGGCTAAATT
TGATTTTCTATAACGGTATCAACCTTGAAACAGGTGGCAATGCTTGGTTT
ACAAAATTGGTAGAAAATGCCAAGAAAACTGAAAACAAAGACTACTTCGC
AGTCAGCGACGGCGTTGATGTTATCTACCTTGAAGGTCAAATGAAAAAG
GAAAAGAAGACCCACACGCTTGGCTTAACCTTGAAAACGGTATTATTTTT
GCTAAAAATATCGCCAAACAATTGAGCGCCAAAGACCCTAACAATAAAGA

ATTCTCATGAAAAAAATCTCAAAGAATATACTGATAAGTTAGACAAACTT
GATAAAGAAAGTAAGGATAAATTTAATAAGATCCCTGCTGAAAAGAAACT
CCATTGTAACCAGCGAAAGGAGCATTCAAATACTTCTCTAAAGCCTATGG
TGTCCCAAGTGCTTTACATCTGGGAAATCAATACTGAAGAAGAAGGAACT
CCTGAACAAATCAAGACCTTGGTTGAAAAACTTCGCCAAACAAAACTTCC
ATCACTCTTTGTAGAATCAAGTGTGGATGACCGTCCAATGAAAACTGTTT
CTCAAGACACAAACATCCCAATCTACGCTCAAATCTTTACTGACTCTATC
GCAGAACAAGGTCCCGAAGGCGACAGCTACTACAGCATGATGAAATACAA
CCTTGACAAGATTGCTGAAGGATTGGCAAAATAA (SEQ. ID. NO. 156)
MKKLGTLLVLFLSAI ILVACASGKKDTTSGQKLKVVATNSIIADITKNIA
GDKIDLHSIVPIGQDPHEYEPLPEDVKKTSEANLIFYNGINLETGGNAWF
TKLVENAKKTENKDYFAVSDGVDVIYLEGQNEKGKEDPHAWLNLENGIIF
AKNIAKQLSAKDPNNKEFYEKNLKEYTDKLDKLDKESKDKFNKIPAEKKL
IVTSEGAFKYFSKAYGVPSAYIWEINTEEEGTPEQIKTLVEKLRQTKVPS
LFVESSVDDRPMKTVSQDTNIPIYAQIFTDSIAEQGKEGDSYYSMMKYNL
DKIAEGLAKZ

ID206 - 41191.1

(SEQ. ID. NO. 173)
ATGGAATGGTATAAAAAAATCGGACTTCTTGCAACTACAGGTTTAGCTTT
GTTTGGGCTCGGCGCTTGCTCCAACTATGGTAAATCTGCGGATGGCACAG
TGACCATCGAGTATTTCAACCAGAAAAAAGAAATGACCAAAACCTTGGAA
GAAATCACTCGTGATTTTGAGAAGGAAAACCCTAAGATCAAGGTCAAAGT
CGTCAATGTACCAAATGCTGGTGAAGTATTGAAGACACGCGTTCTCGCAG
GAGATGTGCCTGATGTGGTCAATATTTACCCACAGTCCATCGAACTGCAA
GAATGGGCAAAAGCAGGTGTTTTTGAAGATTGACCAACAAAGACTACCTG
AAACGCGTGAAAATGGCTACGCTGAAAAATATGCTGTAAACGAAAAAGTT
TACAACGTTCCTTTTACAGCTAATGCTTATGGAATTTACTACAACAAAGA
TAAATTCGAAGAACTGGGCTTGAAGGTTCCTGAAACCTGGGATGAATTTG
AACAGTTAGTCAAAGATATCGTTGCTAAAGGACAAACACCATTTGGAATT
GCAGGTGCAGATGCTTGGACACTCAATGGTTACAATCAATTAGCCTTTGC
GACAGCAACAGGTGGAGGAAAAGAAGCAAATCAATACCTTCGTTATTCTC
AACCAAATGCCATTAAATTGTCGGATCCGATTATGAAAGATGATATCAAG
GTCATGGACATCCTTCGCATCAATGGATCTAAGCAAAAGAACTGGGAAGG
TGCTGGCTATACCGATGTTATCGGAGCCTTCGCACGTGGGGATGTCCTCA
TGACACCAATGGGTCTTGGCGATCACAGCGATTAATGAACAAAACCGA
ACTTTAAGATTGGGACCTTCATGATTCCAGGAAAAGAAAAAGGACAAAGC
TTAACCGTTGGTGCGGGAGACTTGGCATGGTCTATCTCAGCCACCACCAA
ACATCCAAAAGAAGCCAATGCCTTTGTGGAATATATGACCCGTCCAGAAG
TCATGCAAAAATACTACGATGTGGACGGATCTCCAACAGCGATCGAAGGG
GTCAAACAAGCAGGAGAAGATTCACCGCCTTGCTGGTATGACCGAATATG

TABLE 5-continued

CCTTTACGGATCGTCACTTGGTCTGGTTGCAACAATACTGGACCAGTGAA
GCAGACTTCCATACCTTGACCATGAACTATGTCTTGACCGGTGATAAACA
AGGCATGGTCAATGATTTGAATGCCTTCTTTAACCCGATGAAAGCGGATG
TGGATTAG (SEQ. ID. NO. 157)
MEWYKKIGLLATTGLALFGLGACSNYGKSADGTVTIEYFNQKKEMTKTLE
EITRDFEKENPKIKVKVVNVPNAGEVLKTRVLAGDVPDVVNIYPQSIELQ
EWAKAGVFEDLSNKDYLKRVKNGYAEKYAVNEKVYNVPFTANAYGIYYNK
DKFEELGLKVPETWDEFEQLVKDIVAKGQTPFGIAGADAWTLNGYNQLAF
ATATGGGKEANQYLRYSQPNAIKLSDPIMKDDIKVMDILRTNGSKQKNWE
GAGYTDVIGAFARGDVLMTPNGSWAITAINEQKPNFKIGTFMIPGKEKGQ
SLTVGAGDLAWSISATTKHPKEANAFVEYMTRPEVMQKYYDVDGSPTAIE
GVKQAGEDSPLAGMTEYAFTDRHLVWLQOYWTSEADFHTLTMNYVLTGDK
QGMVNDLNAFFNPMKADVDZ

ID207 - 4123.1

(SEQ. ID. NO. 174)
ATGAAGAAAATCAAACCGCATGGACCGTTACCAAGTCAGACTCAGCTAGC
TTATCTGGGAGATGAACTAGCAGCTTTTATCCACTTCGGTCCTAATACCT
TTTATGACCAAGAATGGGGGACTGGACAGGAGGATCCTGAGCGCTTTAAC
CCGAGTCAGTTGGATGCGCGTGAGTGGGTTCGTGTGCTCAAGGAAACGGG
CTTCAAAAAGTTGATTTTGGTGGTCAAGCACCACGATGGCTTTGTCCTTT
ATCCGACAGCTCACACAGATTATTCGGTTAAGGTCAGTCCITGGAGGAGA
GGAAAGGGCGAGTTGCTCCTTGAAGTATCCCAAGCTGCCACAGAGTTTGA
TATGGATATGGGGGTCTACCTGTCACCGTGGGATGCCCATAGTCCCCTCT
ATCATGTGGACCGAGAAGCGGACTACAATGCCTATTATCTGGCTCAGTTG
AAGGAAATCTTATCAAATCCTAACTATGGGAATGCTGGTAAGTTCGCTGA
GGTTTGGATGGATGGTGCCAGAGGAGAGGGCGCGCAAAAGGTTAATTATG
AATTTGAAAATGGTTTGAAACCATTCGTGACCTGCAGGGCGATTGCTTG
ATTTTTTCAACAGAAGGCACCAGTATCCGCTGGATTGGCAATGAACGAGG
GTATGCAGGTGATCCACTGTGGCAAAAGGTGAATCCTGATAAACTAGGAA
CAGAAGCAGAGCTGAACTATCTTCAGCACGGGGATCCCTCGGGCACGATT
TTTTCAATCGGAGAGGCAGATGTTTCCATCCGTCCAGGCTGGTTCTACCA
TGAGGATCAGGATCCTAAGTCTCTCGAGGAGTTGGTCGAAATCTACTTTC
ACTCAGTAGGGCGAGGAACTCCACTCTTGCTTAATATTCCGCCGAATCAA
GCTGGGCTCTTTGATGCAAAGGATATTGAACGACTTTATGAATTTGCGAC
CTATCGCAATGAGCTCTATAAAGAAGATTTGGCTCTGGGAGCTGAGGTAT
CTGGTCCAGCTCTTTCCGCAGACTTTGCTTGTCGCCATTTGACAGACGGC
CTTGAGACCAGCTCTTGGGCAAGCGATGCAGACTTGCCCATCCAGTTAGA
ACTCGACTTAGGTTCTCCTAAAACTTTTGATGTAATTGAGTTAAGAAGG
ATTTGAAGCTAGGGCCCGAATCGCTGCTTTTCATGTGCAAGTAGAGGTGG
ATGGTGTCTGGCAGGAGTTTGGTTCGGGTCATACTGTTGGTTACAAACGT

CTCTTACGAGGAGCAGTTGTTGAGGCACAGAAGATACGTGTAGTCATTAC
AGAATCACAGGCCTTTGCCTTTGTTGACCAAGATTTCCCTTTATAAAACT
CCTGGATTATCAAAAAAAGAAGTTGTTCAGGAACTAGCATTTGCAGAAAA
AAGCCTAGCTGTGGCAAAGGGAGAAAATGCCTATTTTACAGTTAAGCGCA
GAGAATGTAGTGGTCCTTTAGAAGCTAAGATTTCGATTCAACCGGGGAC
AGGTGTCCATGGTGTCGCCTATCAGGATGAGATTCAAGTCCTTGCGTTTC
AAACTGGTGAGACTGAAAAAAGTCTGACGCTACCAACCTTGTATTTCGCA
GGAGATAAAACCTTGGATTTCTATCTGAACCTAACGGTGGATGGTCAGCT
TGTGGATCAACTTCAAGTCCAAGTTTCATAA (SEQ. ID. NO. 158)
MKKIKPHGPLPSQTQLAYLGDELAAFIHFGPNTFYDQEWGTGQEDPERFN
PSQLDAREWVRVLKETGFKKLILVVKHHDGFVLYPTAHTDYSVKVSPWRR
GKGDLLLEVSQAATEFDMDMGVYLSPWDAHSPLYHVDREADYNAYYLAQL
KEILSNPNYGNAGKFAEVWMDGARGEGAQKVNYEFEKWFETIRDLQGDCL
IFSTEGTSIRWIGNERGYAGDPLWQKVNPDKLGTEAELNYLQHGDPSGTI
FSIGEADVSIRPGWFYHEDQDPKSLEELVEIYFHSVGRGTPLLLNIPPNQ
AGLFDAKDIERLYEFATYRNELYKEDLALGAEVSGPALSADFACRHLTDG
LETSSWASDADLPIQLELDLGSPKTFDVIELREDLKLGQRIAAFHVQVEV
DGVWQEFGSGHTVGYKRLLRGAVVEAQKTRVVTTESQALPLLTKTSLYKT
PGLSKKEVVQELAFAEKSLAVAKGENAYFTVKRRECSGPLEAKISIQPGT
GVHGVAYQDEIQVLAFQTGETEKSLTLPTLYFAGDKTLDFYLNLTVDGQL
VDQLQVQVSZ

ID208 - 4125.12

(SEQ. ID. NO. 175)
ATGCTTGAAAGACTGAAAAGAATACATTATATGTTTTGGATCAGTTTAAT
TTTTATGATTTTCCCCATCCTGTCTGTAGTGACTGGGTGGCTTTCTGCCT
GGCATTTATTGATTGATATTCTATTTGTAGTGGCATATTTGGGTGTTTTA
ACAACTAAGAGCCAGCGCCTATCTTGGCTATATTGGGGCCTCATGCTGAC
TTATGTAGTTGGGAATACTGCCTTTGTTGCTGTTAATTATATCTGGTTTT
TCTTTTTCCTATCCAATCTCTTAAGTTATCATTTCAGCGTACGTAGTTTA
AAGTCTTTACATGTCTGGACTTTTCTTCTTGCTCAAGTCCTTGTTGTGGG
GCAACTGTTGATTTTTCAGAGAATCGAAGTTGAGTTTCTATTCTATCTAC
TTGTAATTCTTACTTTTGTCGATTTAATGACTTTTGGATTGGTTCGGATT
CGTATTGTCGAGGATTTGAAAGAAGCTCAGGTCAAGCAAATGCTCAGAT
AAATCTATTGCTTGCTGAAAATGAACGTAGTCGTATCGGTCAGGATTTGC
ATGATAGTCTGGGACATACCTTTGCTATGCTGAGTGTCAAGACAGATTTA
GCCTTGCAGTTATTTCAGATGGAGCTTATCCACAGGTGGAAAGGAATTAA
AGAAATTCACCAGATAGCAGGATCCATGA (SEQ. ID. NO. 159)
MLERLKRTHYMFWTSLTFMTFPTLSVVTGWLSAWHLLTDTLFVVAYLGVL
TTKSQRLSWLYWGLMLTYVVGNTAFVAVNYIWFFFFLSNLLSYHFSVRSL

TABLE 5-continued

KSLHVWTFLLAQVLVVGQLLIFQRIEVEFLFYLLVILTFVQLMTFGLVRI
RIVEDLKEAQVKQNAQINLLLAENERSRIGQDLHDSLGHTFAMLSVKTDL
ALQLFQMEAYPQVEKELKEIHQISKDPZ

ID209 - 4126.3

(SEQ. ID. NO. 176)
ATGAATGATAAGTTAAAAATCTTCTTGTTGCTAGGAGTATTTTTTCTAGC
CATAACCGGTTTCTATGTTCTATTGATACGAAATGCAGGGCAGACAGATG
CCTCGCAAATTGAAAAGGCGGCAGTTAGCCAAGGAGGAAAAGCAGTGAAA
AAAACAGAAATTAGTAAAGACGCAGACTTGCACGAAATTTATCTAGCTGG
AGGTTGTTTCTGGGGAGTGGAGGAATATTTCTCACGTGTTCCCGGGGTGA
CGGATGCCGTTTCAGGCTATGCAAATGGTAGAGGAGAAACAACCAAGTAC
GAATTGATTAACCAAACAGGTCATGCAGAAACCGTCCATGTCACCTATGA
TGCCAAGCAAATTTCTCTCAAGGAAATCCTGCTTCACTATTTCCGCATTA
TCAATCCAACCAGCAAAAATAAACAAGGAAATGATGTGGGGACCCAGTA
CCGTACTGGTGTTTATTACACAGATGACAAGGATTTGGAAGTGATTAACC
AAGTCTTTGATGAGGTGGCTAAGAAATACGATCAACCTCTAGCAGTTGAA
AAGGAAAACTTGAAGAATTTTGTGGTGGCTGAGGATTACCATCAAGACTA
TCTAAAGAAAAATCCAAATGGCTACTGCCATATCAATGTTAATCAGGCGG
CCTATCCTGTCATTGATGCCAGCAAATATCCAAAACCAAGTGATGAGGAA
TTGAAAAAGACCCTGTCACCTGAGGAGTATGCAGTTACCCAGGAAAATCA
AACAGAACGAGCTTTCTCAAACCGTTACTGGGATAAATTTGAATCCGGTA
TCTATGTGGATATAGCAACTGGGGAACCTCTCTTTTCATCAAAAGACAAA
TTTGAGTCTGGTTGTGGCTGGCCTAGTTTTACCCAACCCATCAGTCCAGA
TGTTGTCACCTACAAGGAAGATAAGTCCTACAATATGACGCGTATGGAAG
TGCGGAGCCGAGTAGGAGATTCTCACCTTGGGCATGTCTTTACGGATGGT
CCACAGGACAAGGGCGGCTTACGTTACTGTATCAATAGCCTCTCTATCCG
CTTTATTCCCAAAGACCAAATGGAAGAAAAAGgcTACGCTTATTTACTAG
ATTATGTTGATTAA (SEQ. ID. NO. 160)
MNDKLKIFLLLGVFFLAITGFYVLLIRNAGQTDASQIEKAAVSQGGKAVK
KTEISKDADLHETYTAGGCFWGVEEYFSRVPGVTDAVSGYANGRGETTKY
ELINQTGHAETVHVTYDAKQISLKEILLHYFRIINPTSKNKQGNDVGTQY
RTGVYYTDDKDLEVINQVFDEVAKKYDQPLAVEKENLKNFVVAEDYHQDY
LKKNPNGYCHINVNQAAYPVIDASKYPKPSDEELKKTLSPEEYAVTQENQ
TERAFSNRYWDKFESGIYVDIATGEPLFSSKDKFESGCGWPSFTQPISPD
VVTYKEDKSYNMTRMEVRSRVGDSHLGMVFTDGPQDKGGLRYCINSLSIR
FIPKDQMEEKGYAYLLDYVDZ

ID210 - 4127.1

(SEQ. ID. NO. 177)
ATGAAAAAGAAATGGATGTATTATGCTGCTTGTTCTTCTAATGAATCTGC
CGATGACAGTTCATCTGATAAAGGAGACGGCGGTTCGCTAGTCGTTTATT

CACCAAACTCAGAGGGCTTAATTGGAGCAACTATTCCTGCCTTTGAAGAA
AAATATGGTATCAAAGTAGAACTGATTCAAGCTGGTACTGGAGAACTTTT
CAAAA)ACTAGAGTCAGAAAAAGAAGTTCCTGTAGCTGATGTTATCTTTG
GTGGTTCTTATACACAATATACTACCCACGGAGAACTCTTTGAAAACTAT
ACTTCAAAAGAAAATGATAATGTTATCAAAGAATATCAAAACACAACTCG
CTACTCTACTCCTTATACACTAGATGGTAGTGTTTTAATCGTCAACCCTG
ATTTAACTAAAGGCATGAACATCGAAGGATATAACGATCTTTTCAAACCT
GAACTAAAAGGAAAAATCGCAACTGCTGACCCAGCAAACTCTTCTAGCGC
CTTTGCTCAATTAACAAATATGCTACAAGCTCAAGGTGGTTAACAAAGAT
GATAAGGCTTGGTCTTATGTAAAAGATCTTTTCACACTTATTGATGGTAA
AATCGGTTCAGTTCATCTAGTGTCTATAAAGTAGTCGCTGATGGAGAAAT
GGCTGTTGGTCTCTCTTATGAAGATCCAGCAGTTAAACTCTTAAATGACG
GAGCTAACATTAAGGTAGTCTATCCAAAAGAAGGAACCGTCTTCCTACCT
GCTAGTGCTGCTATCGTTAAAAAATCTAAAAATATGGAAAATGCCAAGAA
ATTTATCGATTTTATTATCTCTCAAGAAGTACAAGATACACTTGGTACAA
CCACTACTAACCGTCCTGTTCGTAAAAATGCTAAAACAAGCGAAAACATG
AAACCAATTGACAAAATCAAAACACTCACTGAAGATTATGATTATGTCAT
CAAGAATAAATCAGATATCGTTAAGAAATACAACGAAGTCTTTACAGATA
TCCAATCTAAACAGTAA (SEQ. ID. NO. 161)
MKKKWMYYAACSSNESADDSSSDKGDGGSLVVYSPNSEGLIGATIPAFEE
KYGIKVELIQAGTGELFKKLESEKEVPVADVIFGGSYTQYTTHGELFENY
TSKENDNVIKEYQNTTGYSTPYTLDGSVLIVNPDLTKGMNIEGYNDLFKP
ELKGKIATADPANSSSAFAQLTNMLQAQGGYKDDKAWSYVKDLFTLIDGK
IGSSSSSVYKVVADGEMAVGLSYEDPAVKLLNDGANIKVVYPKEGTVFLP
ASAAIVKKSKNMENAKKFIDFIISQEVQDTLGTTTTNRPVRKNAKTSENM
KPIDKIKTLTEDYDYVIKNKSDIVKKYNEVFTDIQSKQZ

ID211 - 4127.2

(SEQ. ID. NO. 178)
ATGAGTGAGATCAAAATTATTAACGCCAAAAAAATCTACCACGATGTCCC
TGTTATTGAGAATTTGAACATTACAATTCCAAAAGGAAGTCTCTTTACCC
TTCTTGGAGCTTCAGGATGTGGGAAAACGACCCTTCTTCGTATGATTGCA
GGTTTCAACAGTATCGAAGGTGGAGAATTTTACTTCGATGATACAAAAAT
CAATAATATGGAACCCAGCAAACGCAATATCGGGATGGTTTTCCAAAACT
ACGCTATTTTCCCACATTTGACTGTCCGAGACAACGTTGCTTTTGGTCTT
ATGCAAAGAAGGTTCCAAAAGAAGAATTGATTCAACAGACCAACAAGTA
TCTTGAACTCATGCAAATTGCTCAATATGCGGATCGAAAGCCCGATAAAC
TCAGTGGTGGACAACAACAACGTGTCACCTTGGCATGCGCCTTAGCGGTT
AATCCAAGTGTTCTCCTCATGGACGAGCCACTTAGTAATCTGGAGGCCAA
ACTTCGCTTGGATATGCGTCAAGCCATCCGAGAAATCCAACACGAAGTGG
GAATTACAACTGTTTATGTAACCCACGACCAAGAAGAAGCCATGGCTATT

TABLE 5-continued

TCAGACCAAATTGCTGTTATGAAAGATGGGGTGATCCAACAAATCGGCCG

ACCAAAAGAACTCTATCATAAACCAGCTAATGAGTTTGTGGCAACCTTTA

TCGGACGCACAAATATTATCCCTGCCAATCTTGAAAAACGGAGCGACGGC

GCTTATATCGTCTTTTCAGATGGCTATGCCCTTCGAATGCCAGCTCTTGA

TCAGGTTGAGGAGCAAGCTATTCATGTAAGCATTCGTCCCGAAGAGTTTA

TCAAAGATGAATCTGGAGATATTGAAGGAACTATTAGAGATAGCGTCTAT

CTTGGACTAAATACGGATTATTTCATTGAGACAGGTTTTGCCTCAAAAAT

TCAAGTTAGTGAAGAATCAACTTTTGAAGAAGATCTACAAAAAGGCAATC

GTATTCGTCTACGAATCAATACGCAAAAATTAAACATCTTTTCTGCAGAT

GGTTCCCAAAACCTGATAAAAGGAGTCAACCATGGAACGTAA (SEQ. ID. NO. 162)
MSEIKIINAKKIYHDVPVIENLNITIPKGSLFTLLGASGCGKTTLLRMIA
GFNSIEGGEFYFDDTKINNMEPSKRNIGMVFQNYAIFPHLTVRDNVAFGL
MQKKVPKEELIQQTNKYLELMQIAQYADRKPDKLSGGQQQRVTLACALAV
NPSVLLMDEPLSNLEAKLRLDMRQAIREIQHEVGITTVYVTHDQEEAMAI
SDQIAVMKDGVIQQIGRPKELYHKPANEFVATFIGRTNIIPANLEKRSDG
AYIVFSDGYALRMPALDQVEEQAIHVSIRPEEFIKDESGDIEGTIRDSVY
LGLNTDYFIETGFASKIQVSEESTFEEDLQKGNRIRLRINTQKLNIFSAD
GSQNLIKGVNHGTZ

ID212 - 4136.1

(SEQ. ID. NO. 179)
ATGAAGAAAAAATTATTGGCAGGTGCCATCACACTATTATCAGTAGCAAC
TTTAGCACGTTGTTCGAAAGGGTCAGAAGGTGCAGACCTTATCAGCATGA
AAGGGGATGTCATTACAGAACATCAATTTTATGAGCAAGTGAAAACGAAC
CCTTCAGCCCAACAAGTCTTGTTAAATATGACCATCCAAAAAGTTTTTGA
AAAACAATATGGCTCAGAGCTTGATGATAAAGAGGTTGATGATACTATTG
CCGAAGAAAAAAAACAATATGGCGAAAACTACCAACGTGTCTTGTCACAA
GCAGGTATGACTCTTGAAACACGTAAAGCTCAAATTCGTACAAGTAAATT
AGTTGAGTTGGCAGTTAAGAAGGTAGCAGAAGCTGAATTGACAGATGAAG
CCTATAAGAAAGCCTTTGATGAGTACACTCCAGATGTAACGGCTCAAATC
ATCCGTCTTAATAATGAAGATAAGGCCAAAGAAGTTCTCGAAAAAGCCAA
GGCAGAAGGTGCTGATTTTGCTCAATTAGCCAAAGATAATTCAACTGATG
AAAAAACAAAAGAAAATGGTGGAGAAATTACCTTTGATTCTGCTTCAACA
GAAGTACCTGAGCAAGTCAAAAAAGCCGCTTTCGCTTTAGATGTGGATGG
TGTTTGTGATGTGATTACAGCAACTGGCACACAAGCCTACAGTAGCCAAT
ATTACATTGTAAAACTCACTAAGAAAACAGAAAAATCATCTAATATTGAT
GACTACAAAGAAAAATTAAAAACTGTTATCTTGACTCAAAAACAAAATGA
TTCAACATTTGTTCAAAGCATTATCGGAAAAGAATTGCAAGCAGCCAATA
TCAAGGTTAAGGACCAAGCCTTCCAAAATATCTTTACCCAATATATCGGT
GGTGGAGATTCAAGCTCAAGCAGTAGTACATCAAACGAATAG (SEQ. ID. NO. 163)
MKKKLLAGAITLLSVATLAACSKGSEGADLISMKGDVITEHQFYEQVKSN
PSAQQVLLNMTIQKVFEKQYGSELDDKEVDDTIAEEKKQYGENYQRVLSQ
AGMTLETRKAQIRTSKLVELAVKKVAEAELTDEAYKKAFDEYTPDVTAQI
IRLNNEDKAKEVLEKAKAEGADGAQLAKDNATDEKTKENGGEITFDSAST
EVPEQVKKAAFALDVDGVSDVITATGTQAYSSQYYIVKLTKKTEKSSNID
DYKEKLKTVILTQKQNDSTFVQSIIGKELQAANIKVKDQAFQNIFTQYIG
GGDSSSSSSTSNEZ

ID213 - 4137.3

(SEQ. ID. NO. 180)
ATGAAAAAAATATTAAACAATATGTAACCTTAGGTACTGTAGTGGTATT
ATCAGCATTTGTTGCTAACTCAGTTGCAGCTCAGGAGACTGAAACTTCTG
AAGTATCAACACCAAAGTTGGTGCAACCTGTTGCACCAACGACTCCGATT
TCGGAAGTACAACCTACATCGGATAACTCTTCGGAAGTTACTGTACAACC
TCGAACAGTTGAAACTACTGTTAAGGATCCATCTTCTACAGCGGAAGAAA
CTCCTGTCTTAGAAAAAAATAATGTTACTTTAACAGGGGGCGGAGAAAAT
GTTACTAAAGAGTTAAAGGATAAATTTACTAGCGGTGACTTTACTGTAGT
GATTAAGTACAATCAGTCAAGTGAGAAAGGCTTACAAGCTCTGTTTGGAA
TATCTAATTCCAAACCCGGTCAACAAAATAGTTATGTAGATGTGTTCCTT
AGAGACAATGGTGAGTTGGGGATGGAAGCGCGTGATACTTCTTCCAATAA
AAATAACCTAGTATCCAGACCTGCTTCAGTTTGGGGTAAGTACAAACAAG
AGGCTGTGACTAACACTGTTGCAGTAGTAGCAGATTCAGTCAAAAAAACA
TATTCTTTATACGCAAATGGTACAAAAGTAGTAGAAAAGAAAGTGGATAA
TTTCCTAAACATCAAGGATATTAAAGGTATTGATTACTATATGCTTGGGG
GAGTGAAACGTGCAGGAAAAACGGCGTTTGGTTTTAACGGAACACTAGAA
AATATCAAATTCTTTAATAGTGCATTGGATGAAGAAACTGTTAAAAAGAT
GACAACAAACGCTGTTACTGGACATTTAATTTATACGGCTAATGATACAA
CAGGTTCTAACTATTTCCGTATTCCAGTTCTGTATACTTTTAGCAATGGT
CGGGTATTTTCAACGATTGACGCTCGTTACGGTGGAACTCATGATTTCTT
GAATAAAATTAATATTGCTACAAGTTATAGTGATGATAATGGTAAGACAT
GGACTAAACCAAAATTAACATTGGCATTCGATGATTTTGCGCCAGTACCA
TTAGAATGGCCTCGTGAAGTTGGTGGACGTGACTTACAAATCAGCGGTGG
TGCAACCTATATTGACTCTGTTATTGTTGAAAAAAAGAACAAACAAGTAC
TCATGTTTGCTGATGTGATGCCTGCTGGAGTAAGTTTTAGAGAAGCAACT
AGAAAAGATTCAGGTTATAAACAAATTGATGGTAATTATTACCTTAAATT
AAGGAAACAAGGTGATACTGATTACAATTATACTATTCGTGAGAATGGTA
CTGTATACGACGATCGTACCAACAGACCAACTGAATTTTCAGTAGATAAA
AATTTCGGTATTAAACAAATGGTAATTATTTGACGGTAGAGCGG (SEQ. ID. NO. 164)
MKKNIKQYVTLGTVVVLSAFVANSVAAQETETSEVSTPKLVQPVAPTTPI
SEVQPTSDNSSEVTVQPRTVETTVKDPSSTAEETPVLEKNNVTLTGGGEN

TABLE 5-continued

VTKELKDKFTSGDFTVVIKYNQSSEKGLQALFGISNSKPGQQNSYVDVFL
RDNGELGMEARDTSSNKNNLVSRPASVWGKYKQEAVTNTVAVVADSVKKT
YSLYANGTKVVEKKVDNFLNIKDIKGIDYYMLGGVKRAGKTAFGFNGTLE
NIKFFNSALDEETVKKMTTNAVTGHLIYTANDTTGSNYFRIPVLYTFSNG
RVFSSIDARYGGTHDFLNKINIATSYSDDNGKTWTKPKLTLAFDDFAPVP
LEWPREVGGRDLQISGGATYIDSVIVEKKNKQVLMFADVMPAGVSFREAT
RKDSGYKQIDGNYYLKLRKQGDTDYNYTIRENGTVYDDRTNRPTEFSVDK
NFGIKQNGNYLTVER

ID214 - 4185

(SEQ. ID. NO. 181)
ATGAAAAAATTTAGCCTATTACTAGCTATCCTACCATTTTTGGTTGCCTG
TGAGAATCAAGCTACACCCAAAGAGACTAGCGCTCAAAAGACAATCGTCC
TTGCTACAGCTGGCGACGTGCCACCATTTGACTACGAAGACAAGGGCAAT
CTGACAGGCTTTGATATCGAAGTTTTAAAGGCAGTAGATGAAAAACTCAG
CGACTACGAGATTCAATTCCAAAGAACCGCCTGGGAGAGCATCTTCCCAG
GACTTGATTCTGGTCACTATCAGGCTGCGGCCAATAACTTGAGTTACACA
AAAGAGCGTGCTGAAAAATACCTTTACTCGCTTCCAATTTCCAACAATCC
CCTCGTCCTTGTCAGCAACAAGAAAAATCCTTTGACTTCTCTTGACCAGA
TCGCTGGTAAAACAACACAAGAGGATACCGGAACTTCTAACGCTCAATTC
ATCAATAACTGGAATCAGAAACACACTGATAATCCCGCTACAATTAATTT
TTCTGGTGAGGATATTGGTAAACGAATCCTAGACCTTGCTAACGGAGAGT
TTGATTTCCTAGTTTTTGACAAGGTATCCGTTCAAAAGATTATCAAGGAC
CGTGGTTTAGACCTCTCAGTCGTTGATTTACCTTCTGCAGATACGGGGAG
CAATTATATCATTTTCTCAAGCGACCAAAAAGAGTTTAAAGAGCAATTTG
ATAAAGCGCTCAAAGAACTCTATCAAGACGGAACCCTTGAAAAACTCAGC
AATACCTATCTAGGTGGTTCTTACCTCCCAGATCAATCTCAGTTACAATA
A (SEQ. ID. NO. 165)
MKKFSLLLAILPFLVACENQATPKETSAQKTIVLATAGDVPPFDYEDKGN
LTGFDIEVLKAVDEKLSDYEIQFQRTAWESIFPGLDSGHYQAAANNLSYT
KERAEKYLYSLPISNNPLVLVSNKKNPLTSLDQIAGKTTQEDTGTSNAQF
INNWNQKHTDNPATINFSGEDIGKRILDLANGEFDFLVFDKVSVQKIIKD
RGLDLSVVDLPSADSPSNYDFSSDQKEFKEQFDKALKELYQDGTLEKLSN
TYLGGSYLPDQSQLQZ

ID215 - 4211.1

(SEQ. ID. NO. 182)
ATGAAAAAAATAGTTTATATATCATATCCTCACTCTTTTTTGCTTGTGT
CTTATTTGTCTATGCTACGGCGACGAATTTTCAAAACAGTACCAGTGCTA
GGCAGGTAAAAACGGAAACCTATACTAATACAGTAACAAATGTCCCTATT
GACATACGCTATAATAGTGATAAGTATTTTATTAGCGGTTTTGCTTCAGA
AGTATCAGTGGTCTTGACTGGTGCAAATCGCCTATCGCTAGCTAGTGAAA

TGCAAGAAAGTACACGTAAATTCAAGGTTACTGCTGACCTAACAGATGCC
GGTGTTGGAACGATTGAAGTTCCTTTGAGCATTGAAGATTTACCCAATGG
GCTGACCGCTGTGGCGACTCCGCAAAAAATTACAGTCAAGATTGGTAAGA
AGGCTCAGAAGGATAAGGTAAAGATTGTACCAGAGATTGACCCTAGTCAA
ATTGATAGTCGGGTACAAATTGAAATGTCATGGTGTCAGATAAAGAAGT
GTCTATTACGAGTGACCAAGAGACATTGGATAGAATTGATAAGATTATCG
CTGTTTTGCCAACTAGCGAACGTATAACAGGTAATTACAGTGGTTCAGTA
CCTTTTGCAGGCAATCGACCGCAATGGTGTTGTCTTACCGGCAGTTATCAC
TCCGTTTGATACAATAATGAAGGTGACTACAAAACCAGTAGCACCAAGTT
CAAGCACATCAAATTCAAGTACAAGCAGTTCATCGGAGACATCTTCGTCA
ACGAAACGAACTAGTTCAAAAACGAATTAA (SEQ. ID. NO. 166)
MKKNSLYIISSLFFACVLFVYATATNFQNSTSARQVKTETYTNTVTNVPI
DIRYNSDKYFISGFASEVSVVLTGANRLSLASEMQESTRKFKVTADLTDA
GVGTIEVPLSIEDLPNGLTAVATPQKITVKIGKKAQKDKVKIVPEIDPSQ
IDSRVQIENVMVSDKEVSITSDQETLDRIDKIIAVLPTSERITGNYSGSV
PLQAIDRNGVVLPAVITPFDTIMKVTTKPVAPSSSTSNSSTSSSSETSSS
TKATSSKTNZ

ID216 - 4127.3

(SEQ. ID. NO. 183)
ATGTTGATTGGCGAAGGGTATCGGACTTTCCCTGTCCTGATTTATACCCA
ATTTATTAGCGAGGTTGGAGGAAATTCTGCTTTTGCAATTATGGCGATTA
TCATTGCCTTGGCAATTTTCCTTATCCAAAAACACATTGCAAACCGCTAC
AGTTTCAGCATGAATCTGCTCCATCCAATTGAGCCTAAAAAAACTACAAA
AGGAAAAATGGCTGCCATTTATGCAACAGTCTACGGAATTATCTTTATCT
CTGTTTTACCTCAAATCTACTTAATTTATACCTCTTTCCTAAAAACATCA
GGTATGGTATCTGTTAAAGGTTATTCTCCAAACAGTTACAAGGTAGCTTT
CCATCGTATGGGATCTGCTATTTTCAATACCATTCGTATCCCTTTGATTG
CCTTAGTTCTAGTTGTTCTATTTGCGACATTTATCTCCTACCTAGCCGTT
AGAAAACGGAATTTGTTTACAAACTTAATTGACAGCCTCAGTATGGTACC
TTATATTGTACCAGGAACCGTTCTAGGGATTGCCTTCATTTCTTCCTTCA
ATACTGGTCTATTTGGAAGTGGATTTCTTATGATTACAGGGACTGCTTTC
ATCTTGATTATGTCTCTATCTGCCAGAAGATTACCTTATACTATTCGCTC
ATCTGTTGCTAGCTTACAACAAATAGCACCAAGTATTGAAGAAGCTGCTG
AAAGCTTAGGAAGTAGTCGTCTCAATACCTTTGCTAAGATTACAACTCCA
ATGATGCTATCTGGTATCATTTCTGGAGCCATCTTATCTTGA (SEQ. ID. NO. 167)
MLIGEGYRTFPVLIYTQFISEVGGNSAFAIMAIIIALAIFLIQKHIANRY
SFSMNLLHPIEPKKTTKGKMAAIYATVYGIIFISVLPQIYLIYTSFLKTS
GMVSVKGYSPNSYKVAFHRMGSAIFNTIRIPLIALVLVVLFATFISYLAV
RKRNLFTNLIDSLSMVPYIVPGTVLGIAFISSFNTGLFGSGFLMITGTAF

TABLE 5-continued

ILIMSLSARRLPYTIRSSVASLQQIAPSIEEAAESLGSSRLNTFAKITTP
MMLSGIISGAILSZ

TABLE 6

ID301

(SEQ. ID. NO. 196)
ATGAATAAGAAAAAAATGATTTTAACAAGTCTAGCCAGCGTCGATATCTT
AGGGGCTGGTTTTGTTACGTCTCAGCCTACTTTTGTAAGAGCAGAAGAAT
CTCCACAAGTTGTCGAAAAATCTTCATTAGAGAAGAAATATGAGGAAGCA
AAAGCAAAAGCTGATACTGCCAAGAAAGATTACGAAACGGCTAAAAAGAA
AGCAGAAGACGCTCAGAAAAAGTATGAAGATGATCAGAAGAGAACTGAGG
AGAAAGCTCGAAAAGAAGCAGAAGCATCTCAAAAATTGAATGATGTGGCG
CTTGTTGTTCAAAATGCATATAAAGAGTACCGAGAAGTTCAAAATCAACG
TAGTAAATATAAATCTGACGCTGAATATCAGAAAAAATTAACAGAGGTCG
ACTCTAAAATAGAGAAGGCTAGGAAAGAGCAACAGGACTTGCAAAATAAA
TTTAATGAAGTAAGAGCAGTTGTAGTTCCTGAACCAAATGCGTTGGCTGA
GACTAAGAAAAAAGCAGAAGAAGCTAAAGCAGAAGAAAAGTAGCTAAGA
GAAAATATGATTATGCAACTCTAAAGGTAGCACTAGCGAAGAAAGAAGTA
GAGGCTAAGGAACTTGAAATTGAAAAACTTCAATATGAAATTTCTACTTT
GGAACAAGAAGTTGCTACTGCTCAACATCAAGTAGATAATTTGAAAAAAC
TTCTTGCTGGTGCGGATCCTGATGATGGCACAGAAGTTATAGAAGCTAAA
TTAAAAAAAGGAGAAGCTGAGCTAAACGCTAAACAAGCTGAGTTAGCAAA
AAAACAAACAGAACTTGAAAAACTTCTTGACAGCCTTGATCCTGAAGGTA
AGACTCAGGATGAATTAGATAAAGAAGCAGAAGAAGCTGAGTTGGATAAA
AAAGCTGATGAACTTCAAAATAAAGTTGCTGATTTAGAAAAAGAAATTAG
TAACCTTGAAATATTACTTGGAGGGGCTGATCCTGAAGATGATACTGCTG
CTCTTCAAAATAAATTAGCTGCTAAAAAAGCTGAGTTAGCAAAAAAACAA
ACAGAACTTGAAAAACTTCTTGACAGCCTTGATCCTGAAGGTAAGACTCA
GGATGAATTAGATAAAGAAGCAGAAGAAGCTGAGTTGGATAAAAAAGCTG
ATGAACTTCAAAATAAAGTTGCTGATTTAGAAAAAGAAATTAGTAACCTT
GAAATATTACTTGGAGGGGCTGATTCTGAAGATGATACTGCTGCTCTTCA
AAATAAATTAGCTACTAAAAAAGCTGAATGGAAAAAACTCAAAAGAAT
TAGATGCAGCTCTTAATGAGTTAGGCCCTGATGGAGATGAAGAAGAAACT
CCAGCGCCGGCTCCTCAACCAGAGCAACCAGCTCCTGCACCAAAACCAGA
GCAACCAGCTCCAGCTCCAAAACCAGAGCAACCAGCTCCTGCACCAAAAC
CAGAGCAACCAGCTCCAGCTCCAAAACCAGAGCAACCAGCTCCAGCTCCA
AAACCAGAGCAACCAGCTAAGCCGGAGAAACCAGCTGAAGAGCCTACTCA
ACCAGAAAAACCAGCCACTCCAAAAACAGGCTGGAAACAAGAAAACGGTA
TGTGGTATTTCTACAATACTGATGGTTCAATGGCAATAGGTTGGCTCCAA
AACAACGGTTCATGGTACTACCTAAACGCTAACGGCGCTATGGCAACAGG

TABLE 6-continued

TTGGGTGAAAGATGGAGATACCTGGTACTATCTTGAAGCATCAGGTGCTA
TGAAAGCAAGCCAATGGTTCAAAGTATCAGATAAATGGTACTATGTCAAC
AGCAATGGCGCTATGGCGACAGGCTGGCTCCAATACAATGGCTCATGGTA
CTACCTCAACGCTAATGGTGATATGGCGACAGGATGGCTCCAATACAACG
GTTCATGGTATTACCTCAACGCTAATGGTGATATGGCGACAGGATGGGCT
AAAGTCAACGGTTCATGGTACTACCTAAACGCTAACGGTGCTATGGCTAC
AGGTTGGGCTAAAGTCAACGGTTCATGGTACTACCTAAACGCTAACGGTT
CAATGGCAACAGGTTGGGTGAAAGATGGAGATACCTGGTACTATCTTGAA
GCATCAGGTGCTATGAAAGCAAGCCAATGGTTCAAAGTATCAGATAAATG
GTACTATGTCAATGGCTTAGGTGCCCTTGCAGTCAACACAACTGTAGATG
GCTATAAAGTCAATGCCAATGGTGAATGGGTTTAA (SEQ. ID. NO. 184)
MNKKKMILTSLASVAILGAGFVTSQPTFVRAEESPQVVEKSSLEKKYEEA
KAKADTAKKDYETAKKKAEDAQKKYEDDQKRTEEKARKEAEASQKLNDVA
LVVQNAYKEYREVQNQRSKYKSDAEYQKKLTEVDSKIEKARKEQQDLQNK
FNEVRAVVVPEPNALAETKKKAEEEAKAEEKVAKRKYDYATLKVALAKKEV
EAKELEIEKLQYEISTLEQEVATAQHQVDNLKKLLAGADPDDGTEVIEAK
LKKGEAELNAKQAELAKKQTELEKLLDSLDPEGKTQDELDKEAEEAELDK
KADELQNKVADLEKEISNLEILLGGADPEDDTAALQNKLAAKKAELAKKQ
TELEKLLDSLDPEGKTQDELDKEAEEAELDKKADELQNKVADLEKEISNL
EILLGGADSEDDTAALQNKLATKKAELEKTQKELDAALNELGPDGDEEET
PAPAPQPEQPAPAPKPEQPAPAPKPEQPAPAPKPEQPAPAPKPEQPAPAP
KPEQPAKPEKPAEEPTQPEKPATPKTGWKQENGMWYFYNTDGSMAIGWLQ
NNGSWYYLNANGAMATGWVKDGDTWYYLEASGAMKASQWFKVSDKWYYVN
SNGAMATGWLQYNGSWYYLNANGDMATGWLQYNGSWYYLNANGDMATGWA
KVNGSWYYLNANGAMATGWAKVNGSWYYLNANGSMATGWVKDGDTWYYLE
ASGAMKASQWFKVSDKWYYVNGLGALAVNTTVDGYKVNANGEWVZ

ID302

(SEQ. ID. NO. 197)
ATGTTTGCATCAAAAAGCGAAAGAAAGTACATTATTCAATTCGTAAATT
TAGTGTTGGAGTAGCTAGTGTAGTTGTTGCCAGTCTTGTTATGGGAAGTG
TGGTTCATGCGACAGAGAACGAGGGAGCTACCCAAGTACCCACTTCTTCT
AATAGGGCAAATGAAAGTCAGGCAGAACAAGGAGAACAACCTAAAAAACT
CGATTCAGAACGAGATAAGGCAAGGAAAGAGGTCCAGGAATATGTAAAAA
AAATAGTGGGTGAGAGCTATGCAAATCAACTAAAAAGCGACATACAATT
ACTGTAGCTGCCAGTCTTGTTATGGGAAGTGTGGTTCATGCGACAGAGAA
CGAGGGAGCTACCCAAGTACCCACTTCTTCTAATAAGATACTGATGATGG
AGAGTCGATCAAAGTAGATGAAGCTGTGTCTAAGTTTGAAAAGGACTCA
TCTTCTTCGTCAAGTTCGACTCTTCCACTAAACCGGAAGCTTCAGATAC
AGCGAAGCCAAACAAGCCGACAGAACCAGGAGAAAAGGTAGCAGAAGCTA
AGAAGAAGGTTGAAGAAGCTGAGAAAAAAGCCAAGGATCAAAAGAAGAA

TABLE 6-continued

```
GATCGTCGTAACTACCCAACCATTACTTACAAAACGCTTGAACTTGAAAT
TGCTGAGTCCGATGTGGAAGTTAAAAAAGCGGAGCTTGAACTAGTAAAAG
TGAAAGCTAACGAACCTCGAGACGAGCAAAAAATTAAGCAAGCAGAAGCG
GAAGTTGAGAGTAAACAAGCTGAGGCTACAAGGTTAAAAAAAATCAAGAC
AGATCGTGAAGAAGCAGAAGAAGAAGCTAAACGAAGAGCAGATGCTAGAT
GCGAAGTCTTCAGATTCTAGCGTAGGTGAAGAAACTCTTCCAAGCCCATC
CCTGAAACCAGAAAAAAGGTAGCAGAAGCTGAGAAGAAGGTTGAAGAAG
CTAAGAAAAAGCCGAGGATCAAAAAGAAGAAGATCGCCGTAACTACCCA
ACCAATACTTAGAAAACGCTTGAACTTGAAATTGCTGAGTCCGATGTGGA
AGTTAAAAAAGCGGAGCTTGAACTAGTAAAAGAGGAAGCTAAGGAACCTC
GAAACGAGGAAAAAGTTAAGCAAGCAAAAGCGGAAGTTGAGAGTAAAAAA
GCTGAGGCTACAAGGTTAGAAAAAATCAAGACAGATCGTAAAAAAGCAGA
AGAAGAAGCTAAACGAAAAGCAGCAGAAGAAGATAAAGTTAAAGAAAAAC
CAGCTGAACAACCACAACCAGCGCCGGCTCCAAAAGCAGAAAAACCAGCT
CCAGCTCCAAAACCAGAGAATCCAGCTGAACAACCAAAAGCAGAAAAACC
AGCTGATCAACAAGCTGAAGAAGACTATGCTCGTAGATCAGAAGAAGAAT
ATAATCGCTTGACTCAACAGCAACCGCCAAAAACTGAAAAACCAGCACAA
CCATCTACTCCAAAAACAGGCTGGAAACAAGAAAACGGTATGTGGTACTT
CTACAATACTGATGGTTCAATGGCGACAGGATGGCTCCAAAACAATGGCT
CATGGTACTACCTCAACAGCAATGGCGCTATGGCGACAGGATGGCTCCAA
AACAATGGTTCATGGTACTATCTAAACGCTAATGGTTCAATGGCAACAGG
ATGGCTCCAAAACAATGGTTCATGGTACTACCTAAACGCTAATGGTTCAA
TGGCGACAGGATGGCTCCAATACAATGGCTCATGGTACTACCTAAACGCT
AATGGTTCAATGGCGACAGGATGGCTCCAATACAATGGCTCATGGTACTA
CCTAAACGCTAATGGTGATATGGCGACAGGTTGGGTGAAAGATGGAGATA
CCTGGTACTATCTTGAAGCATCAGGTGCTATGAAAGCAAGCCAATGGTTC
AAAGTATCAGATAAATGGTACTATGTCAATGGCTCAGGTGCCCTTGCAGT
CAACACAACTGTAGATGGCTATGGAGTCAATGCCAATGGTGAATGGGTAA
ACTAA
```

(SEQ. ID. NO. 185)
MFASKSERKVHYSIRKFSVGVASVVVASLVMGSVVHATENEGATQVPTSS
NRANESQAEQGEQPKKLDSERDKARKEVEEYVKKIVGESYAKSTKKRHTI
TVALVENELNNIKNEYLNKIVESTSESQLQILMMESRSKVDEAVSGEKDS
SSSSSSDSSTKPEASDTAKPNKPTEPGEKVAEAKKKVEEAEKKAKDQKEE
DRRNYPTITYKTLELEIAESDVEVKKAELELVKVKANEPRDEQKIKQAEA
EVESKQAEATRLKKIKTDREEAEEEAKRRADAKEQGKPKGRAKRGVPGEL
ATPDKKENDAKSSDSSVGEETLPSPSLKPEKKVAEAEKKVEEAKKKAEDQ
KEEDRRNYPTNTYKTLELEIAESDVEVKKAELELVKEEAKEPRNEEKVKQ
AKAEVESKKAEATRLEKIKTDRKKAEEEAKRKAAEEDKVKEKPAEQPQPA
PAPKAEKPAPAPKPENPAEQPKAEKPADQQEEDYARRSEEEYNRLTQQQ
PPKTEKPAQPSTPKTGWKQENGMWYFYNTDGSMATGWLQNNGSWYYLNSN
GAMATGWLQNNGSWYYLNANGSMATGWLQNNGSWYYLNANGSMATGWLQY
NGSWYYLNANGSMATGWLQYNGSWYYLNANGDMATGWVKDGDTWYYLEAS
GAMKASQWFKVSDKWYYVNGSGALAVNTTVDGYGVNANGEWVNZ

ID303

(SEQ. ID. NO. 198)
ATGGTAAAAAGACGTATAAGGAGAGGGACGAGAGAACCTGAAAAAGTTGT
TGTTCCTGAGCAATCATCTATTCCTTCGTATCCTGTATCTGTTACATCTA
ACCAAGGAACAGATGTAGCAGTAGAACCAGCTAAAGCAGTTGCTCCAACA
ACAGACTGGAAACAAGAAAATGGTATGTGGTATTTTTATAATACTGATGG
TTCCATGGCAACAGGTTGGGTACAAGTTAATAGTTCATGGTACTACCTCA
ACAGCAACGGTTCTATGAAAGTCAATCAATGGTTCCAAGTTGGTGGTAAA
TGGTATTATGTAAATACATCGGGTGAGTTAGCGGTAATACAAGTATAGA
TGGCTATAGAGTCAATGATAATGGTGAATGGGTGCGTTAA (SEQ. ID. NO. 186)
MVKRRIRRGTREPEKVVVPEQSSIPSYPVSVTSNQGTDVAVEPAKAVAPT
TDWKQENGMWYFYNTDGSMATGWVQNSSWYYLNSNGSMKVNQWFQVGGK
WYYVNTSGELAVNTSIDGYRVNDNGEWVRZ

ID304

(SEQ. ID. NO. 199)
CTGAATACAAGTTTTGTTCATGCTGCTGATGGGATTCAATATGTCAFAGA
TGATACTAGAGATAAAGAAGAGGGAATAGAGTATGATGACGCTGACAATG
GGGATATTATTGTAAAAGTAGCGACTAAACCTAAGGTAGTAACCAAGAAA
ATTTCAAGTACGCGAATTCGTTATGAAAAAGATGAAACAAAAGACCGTAG
TGAAAATCCTGTTACAATTGATGGAGAGGATGGCTATGTAACTACGACAA
GGACCTACGATGTTAATCCAGAGACTGGTTATGTTACCGAACAGGTTACT
GTTGATAGAAAAGAAGCCACGGATACAGTTATCAAAGTTCCAGCTAAAAG
CAAGGTTGAAGAAGTTCTTGTTCCATTTGCTACTAAATATGAAGCAGACA
ATGACCTTTCTGCAGGACAGGAGCAAGAGATTACTCAGGAAAGAATGGG
AAAACAGTTACAACGATAACTTATAATGTAGATGGAAAGAGTGGACAAGT
AACTGAGAGTACTTTAAGTCAAAAAAAGACTCTCAAACAAGAGTTGTTA
AAAAAAGAACCAAGCCCCAAGTTCTTGTCCAAGAAATTCCAATCGAAACA
GAATATCTCGATGGCCCAACTCTTGATAAAGTCAAGAAGTAGAAGAAGT
AGGAGAAATTGGTAAATTACTCTTACTACAATCTATACTGTAG (SEQ. ID. NO. 187)
LNTSFVHAADGIQYVRDDTRDKEEGIEYDDADNGDIIVKVATKPKVVTKK
ISSTRIRYEKDETKDRSENPVTIDGEDGYVTTTRTYDVNPETGYVTEQVT

TABLE 6-continued

VDRKEATDTVIKVPAKSKVEEVLVPFATKYEADNDLSAGQEQEITLGKNG
KTVTTITYNVDGKSGQVTESTLSQKKDSQTRVVKKRTKPQVLVQEIPIET
EYLDGPTLDKSQEVEEVGEIGKLLLLQSILZ

ID305

(SEQ. ID. NO. 200)
ATGAAGCTTTTGAAAAAATGATGCAAATCGCACTAGCCACATTTTTCTT
CGGTTTGTTAGCGACAAATACAGTATTTGCAGATGATTCTGAAGGATGGC
AGTTTGTCCAAGAAAATGGTAGAACCTACTACAAAAAGGGGGATCTAAAA
GAAACCTACTGGAGAGTGATAGATGGGAAGTACTATTATTTTGATCCTTT
ATCCGGAGAGATGGTTGTCGGCTGGCAATATATACCTGCTCCACACAAGG
GGGTTACGATTGGTCCTTCTCCAAGAATAGAGATTGCTCTTAGACCAGAT
TGGTTTTATTTTGGTCAAGATGGTGTATTACAAGAATTTGTTGGCAAGCA
AGTTTTAGAAGCAAAAACTGCTACGAATACCAACAAACATCATGGGAAG
AATATGATAGCCAAGCAGAGAAACGAGTCTATTATTTTGAAGATCAGCGT
AGTTATCATACTTTAAAAACTGGTTGGATTATGAAGAGGGTCATTGGTA
TTATTTACAGAAGGATGGTGGCTTTGATTCGCGCATCAACAGATTCACGG
TTGGAGAGCTAGCACGTGGTTGGGTTAAGGATTACCCTCTTACGTATGAT
GAAGAGAAGCTAAAAGCAGCTCCATGGTACTATCTAAATCCAGCAACTGG
CATTATGCAAACAGGTTGGCAATATCTAGGTAATAGATGGTACTACCTCC
ATTCGTCAGGAGCTATGGCAACTGGCTGGTATAAGGAAGGCTCAACTTGG
TACTATCTAGATGCTGAAAATGGTGATATGAGAACTGGCTGGCAAAACCT
TGGGAACAAATGGTACTATCTCCGTTCATCAGGAGCTATGGCAACTGGTT
GGTATCAGGAAAGTTCGACTTGGTACTATCTAAATGCAAGTAATGGAGAT
ATGAAAACAGGCTGGTTCCAAGTCAATGGTAACTGGTACTATGCCTATGA
TTCAGGTGCTTTAGCTGTTAATACCACAGTAGGTGGTTACTACTTAAACT
ATAATGGTGAATGGGTTAAGTAA (SEQ. ID. NO. 188)
MKLLKKMMQIALATFFFGLLATNTVFADDSEGWQFVQENGRTYYKKGDLK
ETYWRVIDGKYYYFDPLSGEMVVGWQYIPAPHKGVTIGPSPRIEIALRPD
WFYFGQDGVLQEFVGKQVLEAKTATNTNKHHGEEYDSQAEKRVYYFEDQR
SYHTYLHSSGAMATGWYKEGSTWYYLDAENGDMRTGWQNLGNKWYYLRSS
GAMATGWYQESSTWYYLNASNGDMKTGWFQVNGNWYYAYDSGALAVNTTV
GGYYLNYNGEWVKZ

ID306

(SEQ. ID. NO. 201)
TTGGCTGGTAGATATGGTTCTGCTGTTCAGTGTACAGAAGTGACTGCCTC
AAACCTTTCAACAGTTAAAACTAAAGCTACGGTTGTAGAAAAACCACTGA
AAGATTTTAGAGCGTCTACGTCTGATCAGTCTGGTTGGGTGGAATCTAAT
GGTAAATGGTATTTCTATGAGTCTGGTGATGTGAAGACAGGTTGGGTGAA
AACAGATGGTAAATGGTACTATTTGAATGACTTAGGTGTCATGCAGACTG
GATTTGTAAAATTTCTGGTAGCTGGTATTACTTGAGCAATTCAGGTGCT

ATGTTTACAGGCTGGGGAACAGATGGTAGCAGATGGTTCTACTTTGACGG
CTCAGGAGCTATGAAGACAGGCTGGTACAAGGAAAATGGCACTTGGTATT
ACCTTGACGAAGCAGGTATCATGAAGACAGGTTGGTTTAAAGTCGGACCA
CACTGGTACTATGCCTACGGTTCAGGAGCTTTGGCTGTGAGCACAACAAC
ACCAGATGGTTACCGTGTAAATGGTAATGGTGAATGGGTAAACTAG (SEQ. ID. NO. 189)
LAGRYGSAVQCTEVTASNLSTVKTKATVVEKPLKDFRASTSDQSGWVESN
GKWYFYESGDVKTGWVKTDGKWYYLNDLGVMQTGFVKFSGSWYYLSNSGA
MFTGWGTDGSRWFYFDGSGAMKTGWYKENGTWYYLDEAGIMKTGWFKVGP
HWYYAYGSGALAVSTTTPDGYRVNGNGEWVNZ

ID307

(SEQ. ID. NO. 200)
ATGAAAATTTTGAAAAAAACTATGCAAGTTGGACTGACAGTATTTTTCTT
TGGTTTGCTAGGGACCAGTACAGTATTTGCAGATGATTCTGAAGGATGGC
AGTTTGTCCAAGAAACGGAAGAACCTACTACAAAAAGGGGGACCTCAAA
GAAACCTACTGGCGAGTGATTGATGGTAAGTACTATTATTTTGATTCTCT
ATCTGGAGAGATGGTTGTCGGCTGGCAATATATCCCGTTTCCATCTAAAG
GTAGTACAATTGGTCCTTACCCAAATGGTATCAGATTAGAAGGTTTTCCA
AAGTCAGAGTGGTACTACTTCGATAAAAATGGAGTGCTACAAGAGTTTGT
TGGTTGGAAAACATTAGAGATTAAAACTAAAGACAGTGTTGGAAGAAAGT
ACGGGGAAAAACGTGAAGATTCAGAAGATAAAGAAGAGAAGCGTTATTAT
ACGAACTATTACTTTAATCAAAATCATTCTTTAGACACACGTTCGCTTTA
TGATCAGTCTAACTCGTATTATCTAGCTAAGACGGAAATTAATGGAGAAA
ACTACCTTGGTGGTGAAAGACGTGCGGGGTGGATAAACGATGATTCGACT
TGGTACTACCTAGATCCAACAACTGGTATTATGCAAACAGGTTGGCAATA
TCTAGGTAATAAGTGGTACTACCTCCGTTCCTCAGGAGCAATGGCCACTG
GCTGGTATCAGGAAGGTACCACTTGGTATTATTTAGACCACCCAAATGGC
GATATGAAAACAGGTTGGCAAAACCTTGGGAACAAATGGTACTATCTCCG
TTCATCAGGAGCTATGGCAACTGGTTGGTATCAAGATGGTTCAACTTGGT
ACTACCTAAATGCAGGTAATGGAGACATGAAGACAGGTTGGTTCCAGGTC
AATGGCAACTGGTACTATGCTTAT (SEQ. ID. NO. 190)
MKILKKTMQVGLTVFFFGLLGTSTVFADDSEGWQFVQENGRTYYKKGDLK
ETYWRVIDGKYYYFDSLSGEMVVGWQYIPFPSKGSTIGPYPRGIRLEGFP
KSEWYYFDIOGVLQEFVGWKTLEILKTISVGRKYGEKREDSEDKEEKRYY
TNYYFNQNHSLETGWLYDQSNWYYLAKTEINGENYLGGERRAGWINDDST

WYYLDPTTGIMQTGWQYLGNKWYYLRSSGAMATGWYQEGTTWYYLDHPNG
DMKTGWQNLGNKWYYLRSSGAMATGWYQDGSTWYYLNAGNGDMKTGWFQV
NGNWYYAYSSGALAVNTTVDGYSVNYNGEWVRZ

ID308

(SEQ. ID. NO. 203)
ATGAAAAAGAAATTAACTAGTTTAGCACTTGTAGGCGCTTTTTTAGGTTT
GTCATGGTATGGGAATGTTCAGGCTGAAGAAAGTTCAGGAAATAAAATCC
ACTTTATCAATGTTCAAGAAGGTGGCAGTGATGCGATTATTCTTGAAAGC
AATGGACATTTTGCCATGGTGGATACAGGAGAAGATTATGATTTCCCAGA
TGGAAGTGATTCTCGCTATCCATGGAGAGAAGGAATTGAAACGTCTTATA
AGCATGTTCTAACAGACCGTGTCTTTCGTCGTTTGAAGGAATTGGGTGTC
CAAAAACTTGATTTTATTTTGGTGACCCATACCCACAGTGATCATATTGG
AAATGTTGATGAATTACTGTCTACCTATCCAGTTGACCGAGTCTATCTTA
AGAAATATAGTGATAGTCGTATTACTAATTCTGAACGTTATGGGATAAT
CTGTATGGCTATGATAAGGTTTTACAGACTGCTGCAGAAAAAGGTGTTTC
AGTTATTCAAAATATCACACAAGGGGATGCTCATTTTCAGTTTGGGGACA
TGGATATTCAGCTCTATAATTATGAAAATGAAACTGATTCATCGGGTGAA
TTAAAGAAAATTTGGGATGACAATTCCAATTCCTTGATThGCGTGGTGAA
AGTCAATGGCAAGAAAATTTACCTTGGGGGCGATTTAGATAATGTTCATG
GAGCAGAAGACAAGTATGGTCCTCTCATTGGAAAAGTTGATTTGATGAAG
TTTAATCATCACCATGATACCAACAAATCAAATACCAAGGATTTCATTAA
AAATTTGAGTCCGAGTTTGATTGTTCAAACTTCGGATAGTCTACCTTGGA
AAAATGGTGTTTGATAGTGAGTATGTTAATTGGCTCAAAGAACGAGGAAT
TGAGAGAATCACGCAGCCAGCAAAGACTATGATGCAACAGTTTTTGATAT
TCGAAAAGACGGTTTTGTCAATATTTCAACATCCTACAAGCCGATTCCAA
GTTTTCAAGCTGGTTGGCATAAGAGTGCATATGGGAACTGGTGGTATCAA
GCGCCTGATTCTACAGGAGAGTATGCTGTCGGTTGGAATGAAATCGAAGG
TGAATGGTATTACTTTAACCAAACGGGTATCTTGTTACAGAATCAATGGA
AAAAATGGAACAATCATTGGTTCTATITGACAGACTCTGGTGCTTCTGCT
AAAAATTGGAAGAAAATCGCTGGAATCTGGTATTATTTTAACAAAGAAAA
CCAGATGGAAATTGGTTGGATTCAAGATA)*AGAGCAGTGGTATTATTTG
GATGTTGATGGTTCTATGAAGACAGGATGGCTTCAATATATGGGGCAATG
GTATTACTTTGCTCCATCAGGGGAAATGAAAATGGGCTGGGTAAAAGATA
AGGAAACCTGGTACTATATGGATTCTACTGGTGTCATGAAGACAGGTGAG
ATAGAAGTTGCTGGTCAACATTATTATCTGGAAGATTCAGGAGCTATGAA
GCAAGGCTGGCATAAAAAGGCAAATGATTGGTATTTCTACAAGACAGACG
GTTCACGAGCTGTGGGTTGGATCAAGGACAAGGATAAATGGTACTTCTTG
AAAGAAAATGGTCAATTACTTGTGAACGGTAAGACACCAGAAGGTTATAC
TGTGGATTCAAGTGGTGCCTGGTTAGTGGATGTTTCGATCGAGAAATCTG
CTACAATTAAAACTACAAGTCATTCAGAAATAAAAGAATCCAAAGAAGTA

GTGAAAAAGGATCTTGAAAATAAAGAAACGAGTCAACATGAAAGTGTTAC
AAATTTTTCAACTAGTCAAGATTTGACATCCTCAACTTCACAAAGCTCTG
AAACGAGTGTAAACAAATCGGAATCAGAACAGTAG (SEQ. ID. NO. 191)
MKKKLTSLALVGAFLGLSWYGNVQAQESSGNKIHFINVQEGGSDAIILES
NGHFAMVDTGEDYDFPDGSDSRYPWREGIETSYKHVLTDRVFRRLKELGV
QKLDFILVTHTHSDHIGNVDELLSTYPVDRVYLKKYSDSRITNSERLWDN
LYGYDKVLQTAAEKGVSVIQNITQGDAHFQFGDMDIQLYNYENETDSSGE
LKKIWDDNSNSLISVVKVNGKKIYLGGDLDNVHGAEDKYGPLIGKVDLMK
FNHHHDTNKSNTKDFIKNLSPSLIVQTSDSLPWJGVDSRYVNWLKERGIL
ERINAASKDYDATVFDIRKDGFVNISTSYKPIPSFQAGWHKSAYGNWWYQ
APDSTGEYAVGWNEIEGEWYYFNQTGILLQNQWKKWNNHWFYLTDSGASA
KNWKKIAGIWYYFNKENQMEIGWIQDKEQWYYLDVDGSMKTGWLQYMGQW
YYFAPSGEMKMGWVKDKETWYYMDSTGVMKTGEIEVAGQHYYLEDSGAMK
QGWHKKANDWYFYKTDGSRAVGWIKDKDKWYFLKENGQLLVNGKTPEGYT
VDSSGAWLVDVSIEKSATIKTTSHSEIKESKEVVKKDLENKETSQHESVT
MFSTSQDLTSSTSQSSETSVNKSESEQZ

ID309

(SEQ. ID. NO. 204)
ATGGAAATTAATGTGAGTAAATTAAGAACAGATTTGCCTCAAGTCGGCGT
GCAACCATATAGGCAAGTACACGCACACTCAACTGGGAATCCGCATTCAA
CCGTACAGAATGAAGCGGATTATCACTGGCGAAAGACCCAGAATTAGGT
TTTTTCTCGCACATTGTTGGGAACGGTTGCATCATGCAGGTAGGACCTGT
TGATAATGGTGCCTGGGACGTTGGGGGCGGTTGGAATGCTGAGACCTATG
CAGCGGTTGAACTGATTGAAAGCCATTCAACCAAAGAAGAGTTCATGACG
GACTACCGCCTTTATATCGAACTCTTACGCAATCTAGCAGATGAAGCAGG
TTTGCCGAAAACGCTTGATCAGGGAGTTTAGCTGGAATTAAAACGCACG
AGTATTGCACGAATAACCAACCAAACAACCACTCAGACCACGTTGACCCT
TATCCATATCTTGCTAAATGGGGCATTAGCCGTGAGCAGTTTAAGCATGA
TATTGAGAACGGCTTGACGATTGAAACAGGCTGGCAGAAGAATGACACTG
GCTACTGGTACGTACATTCAGACGGCTCTTATCCAAAAGACAAGTTTGAG
AAAATCAATGGCACTTGGTACTACTTTGACAGTTCAGGCTATATGCTTGC
AGACCGCTGGAGGAAGCACACAGACGGCAACTGGTACTGGTTCGACAACT
CAGGCGAAATGGCTACAGGCTGGAAGAAAATCGCTGATAAGTGGTACTAT
TTCAACGAAGAGGTGCCATGAAGACAGGCTGGGTCAAGTACAAGGACAC
TTGGTACTACTTAGACGCTAAAGAAGGCGCCATGGTATCAAATGCCTTTA
TCCAGTCAGCGGACGGAACAGGCTGGTACTACCTCAAACCAGACGGAACA
CTGGCAGACAAGCCAGAATTCACAGTAGAGCCAGATGGCTTGATTACAGT
AAAATAA

TABLE 6-continued (SEQ. ID. NO. 192)
MEINVSKLRTDLPQVGVQPYRQVHAHSTGNPHSTVQNEADYHWRKDPELG
FFSHIVGNGCIMQVGPVDNGAWDVGGGWNAETYAAVELIESHSTKEEFMT
DYRLYIELLRNLADEAGLPKTLDTGSLAGIKTHEYCTNNQPNNHSDHVDP
YPYLAKWGISREQFKHDIENGLTIETGWQKNDTGYWYVHSDGSYPKDKFE
KINGTWYYFDSSGYMLADRWRKHTDGNWYWFDNSGEMATGWKKIADKWYY
FNEEGAMKTGWVKYKDTWYYLDAKEGAMVSNAFIQSADGTGWYYLKPDGT
LADKPEFTVEPDGLITVKZ
ID310

(SEQ. ID. NO. 205)
ATGGGCACAACAGGATTTACAATAATTGACTTAATTATCTTGATTGTTTA
TTTACTTGCGGTGTTGGTTGCAGGTATCTATTTCTCTAAAAAAGAGATGA
AAGGAAAAGAGTTCTTTAAAGGAGATGGTTCGGTTCTTCGGTATGTTACT
TCGGTATCCATTTTTGCCACAATGCTCAGTCCGATTTCCTTCTTGGGACT
CGCTGGTAGCTCTTATGCAGGTAGCTGGATTTATGGTTTGCTCAATTAG
GGATGGTAGTAGCTATTCCACTGACAATTCGTTTTATCTTACCTATCTTT
GCACGGATAGACATCGATACGGCATATGATTACTTGGATAAACGTTTTAA
TTCTAAAGCACTTCGTATTATTTCAGCACTCTTGTTTATTATTTATCAAT
TGGGACGTATGTCTATCATTATGTACCTCCCATCAGCTGGTTTATCAGTA
TTCAGAGGAATTGACATCAATATTTTGATTATTTTGATGGGTGTAGTTGC
AATTGTTTATTCTTATACTGGTGGTCTAAAATCCGTATTATGGACAGACT
TTATTCAAGGTGTGATTCTGATTAGTGGTGTCGTTTTAGCTTTATTTGTA
CTGATTGCTAATATTAAAGGTGGCTTTGGTGCAGTAGCAGAAACATTAGC
AAACGGGAAATTCCTTGCTGCAAATGAAAAACTTTTCGATCCTAACTTGC
TTTCAAACTCCATCTTTTTAATTGTGATGGGTTCAGGCTTTACAATCTTG
TCTTCCTATGCTTCATCTCAAGATTTGGTTCAACGTTTTACTACAACACA
AAATATTAAGAAACTTAATAAGATGTTGTTCACAAAGCCTGTTTTGTCAC
TTGCAACTGCAACAGTCTTTTACTTGATTGGTACAGGCTTGTACGTATTC
TATCAAGTACAAAATGCAGATAGTGCAGCTAGCAATATCCCTCAAGACCA
AATCTTTATGTACTTTATTGCATACCAGTTACCAGTAGGTATCACAGGTT
TGATCTTGGCAGCGATTTATGCAGCATCTCAATCAACTATTTCAACAGGT
TTGAACTCTGRTGCAACTTCATGGACATTGGATATTCAAGATGTCATTTC
TAAAAATATGTCAGACAATCGTCGTACGAAAATTGCACAATTCGTATCTC
TAGCAGTAGGTTTATTCTCAATTGGTGTTTCCATTGTCATGGCTCACTCA
GATATTAAATCTGCATACGAATGGTTCAATAGTTTCATGGGACTTGTACT
TGGTCTACTTGGTGGTGTATTTATTCTTGGATTTGTTTCTAAAAAAGCAA
ATAAACAAGGTGCTTATGCAGCGCTGATTGTATCAACCATCGTCATGGTA
TTTATTAAATACTTCCTTCCTCCAACAGCTGTTAGCTACTGGGCATATTC
ATTGATTTCAATCTCTGTATCAGTAGTTTCAGGTTATATTGTATCTGTTC
TTACTGGAAATAAAGTATCTGCACCTAAATATACAACGATRCATGATATT
ACAGAAATTAAAGCGGATTCAAGTTGGGAAGTTCGTCACTAA (SEQ. ID. NO. 193)
MGTTGFTIIDLIILIVYLLAVLVAGIYFSKKEMKGKEFFKGDGSVPWYVT
SVSIFATMLSPISFLGLAGSSYAGSWILWFAQLGMVVAIPLTIRFILPIF
ARIDIDTAYDYLDKRFNSKALRIISALLFIIYQLGRMSIIMYLPSAGLSV
LTUDINILIILMGVVAIVYSYTGGLKSVLWTDFIQGVILISGVVLALFVL
IANIKGGFGAVAETLANGKFLAANEKLFDPNLLSNSIFLIVMGSGFTILS
SYASSQDLVQRFTTTQNIKKLN14LFTNGVLSLATAIVFYLIGTGLYVFY
QVQNADSAASNIPQDQIFMYFIAYQLPVGITGLILAAIYAASQSTISTGL
NSVATSWTLDIQDVISKNMSDNRRTKIAQFVSLAVGLFSIGVSIVMAHSD
IKSAYEWFNSFMGLVLGLLGGVFILGFVSKKANKQGAYAALIVSTIVMVF
IKYFLPPTAVSYWAYSLISISVSVVSGYIVSVLTGNKVSAPKYTTIHDIT
EIKADSSWEVRHZ
ID311

(SEQ. ID. NO. 206)
ATGAAAATTAATAAAAAATATCTAGCAGGTTCAGTGGCAGTCCTTGCCCT
AAGTGTTTGTTCCTATGAGCTTGGTCGTCACCAAGCTGGTCAGGATAAGA
AAGAGTCTAATCGAGTTGCTTATATAGATGGTGATCAGGCTCGTCAAAAG
GCAGAAAACTTGACACCAGATGAAGTCAGTAAGAGGGAGGGGATCAACGC
CGAACAAATCCTCATCAAGATTACGGATCAAGGTTATGTGACCTCTCATG
GAGACCATTATCATTACTATAATGGCAAGCTCCCTTATGATGCCATCATC
AGTGAAGAGCTCCTCATGAAAGATCCGAATTATCAGTTGAAGGATTCAGA
CATTGTCAATGAAATCAAGGGTGGTTATGTCATCAAGGTAGACGGAAAAT
ACTATGTTThCCTTAAGGATGCAGCTCATGCGGATAATATTCGGACAAAA
GAAGAGATTAAACGTCAGAAGCAGGAACGCAGTCATAATCACGGGTCAGG
AGCTAACGATCATGCAGTAGCTGCAGCCAGAGCCCAAGGACGCTATACAA
CGGATGATGGGTATATCTTCAATGCATCTGATATCATTGAGGACACGGGT
GATGCTTATATCGTTCCTCACGGCGACCATTACCATTACATTCCTAAGAA
TGAGTTATCAGCTAGCGAGTTAGCTGCTGCAGAAOCCTATTGGAATGGGA
AGCAGGGATCTCGTCCTTCTTCAAGTTCTAGTTATAATGCAAATCCAGCT
CAACCAAGATTGTCAGAGAACCACAATCTGACTGTCACTCAAACTTATCA
TCAAAATCAAGGGGAAAACATTCAAGCCTTTTACGTGAATHGTATGCTA
AACCCTTATCAGAACGCCCATTGGAATCTGATGGCCTTATTTTCGACCCA
GCGCAAATCACAAGTCGAACCCCCAGAGGTGTAGCTGTCCCTCATGGTAA
CCATTACCACTTTATCCCTTATGAACAAATCTCTGAATTGGAAAAACGAA
TTGCTCGTATTATTCCCCTTCGTTATCGTTCAAACCATTGGGTACCAGAT
TCAAGACCAGAACAACCAAGTCCACAATCGACTCCGGAACCTAGTCCAAG
TCCGCAACCTGCACCAAATCCTCAACCAGCTCCAAGCAATCCAATTGATG
AGAAATTGGTCAAAGAGCTGTTCGAAAAGTAGGCGATGGTTATGTCTTT
GAGGAGAATGGAGTTTCTCGTTATATCCCAGCCAAGGATCTTTCAGCAGA
AACAGCAGCAGGCATTGATAGCAAACTGGCCAAGCAGGAAAGTTTATCTC
ATAAGCTAGGAGCTAAGAAAACTGACCTCCCATCTAGTGATCGAGAATTT

TABLE 6-continued

TACAATAAGGCTTATGACTTACTAGCAAGAATTCACCAAGATTTACTTGA

TAATAAAGGTCGACAAGTTGATTTGAGGCTTTGGATAACCTGTTGGAAC

GACTCAAGGATGTCCCAAGTGATAAAGTCAAGTTAGTGGATGATATTCTT

GCCTTCTTAGCTCCGATTCGTCATCCAGAACGTTTAGGAAAACCAAATGC

GCAAATTACCTACACTGATGATGAGATTCAAGTAGCCAAGTTGGCAGGCA

AGTACACAACAGAAGACGGTTATATCTTTGATCCTCGTGATATAACCAGT

GATGAGGGGATGCCTATGTAACTCCACATATGACCCATAGCCACTGGAT

TAAAAAGATAGTTTGTCTGAAGCTGAGAGAGCGGCAGCCCAGGCTTATG

CTAAAGAGAAAGGTTTGACCCCTCCTTCGACAGACCATCAGGATTCAGGA

AATACTGAGGCAAAAGGAGCAGAAGCTATCTACAACCGCGTGAAAGCAGC

TAAGAAGGTGCCACTTGATCGTATGCCTTACAATCTTCAATATACTGTAG

AAGTCAAAAACGGTAGTTTAATCATACCTCATTATGACCATTACCATAAC

ATCAAATTTGAGTGGTTTGACGAAGGCCTTTATGAGGCACCTAAGGGGTA

TACTCTTGAGGATCTTTTGGCGACTGTCAAGTACTATGTCGAACATCCAA

ACGAACGTCCGCATTCAGATAATGGTTTTGGTAACGCTAGCGACCATGTT

CAAAGAAACAAAAATGGTCAAGCTGATACCAATCAAACGGAAAAACCAAG

CGAGGAGAAACCTCAGACAGAAAAACCTGAGGAAGAAACCCCTCGAGAAG

AGAAACCGCAAAGCGAGAAACCAGAGTCTCCAAAACCAACAGAGGAACCA

GAAGAATCACCAGAGGAATCAGAAGAACCTCAGGTCGAGACTGAAAAGGT

TGAAGAAAAACTGAGAGAGGCTGAAGATTTACTTGGAAAAATCCAGGATC

CAATTATCAAGTCCAATGCCAAAGAGACTCTCACAGGATTAAAAAATAAT

TTACTATTTGGCACCCAGGACAACAATACATTATGGCAGAAGCTGAAAA

ACTATTGGCTTTATTAAAGGAGAGTAAGTAA (SEQ. ID. NO. 194)
MKINKKYLAGSVAVLALSVCSYELGRHQAGQDKKESNRVAYIDGDQAGQK

AENLTPDEVSKREGINAEQIVIKITDQGYVTSHGDHYHYYNGKVPYDAII

SEELLMKDPNYQLKDSDIVNEIKGGYVIKVDGKYYVYLKDAAHADNIRTK

EEIKRQKQERSHNHGSGANDHAVAAARAQGRYTTDDGYIFNASDIIEDTG

DAYIVPHGDHYHYIPKNELSASELAAAEAYWNGKQGSRPSSSSSYNANPA

QPRLSENWNTTVTPTYHQNQGENISSLLRELYAKPLSERJVESDGLIFDP

AOITSRTARGVAVPHGNHYHFIPYEQMSELEKRIARIIPLRYRSNHWVPD

SRPEQPSPQSTPEPSPSPQPAP4PQPAPSNPIDEKLVKEAVRKVGDGYVF

EENGVSRYIPAKDLSAETAAGIDSKLAKQESLSHKLGAKKTDLPSSDREF

YNKAYDLLARIHQDLLDNKGRQVDFEALDNLLERLKDVPSDKVKLVDDIL

TABLE 6-continued

AFLAPIRHPERLGKPNAQITYTDDEIQVAKLAGKYTTEDGYIFDPRDITS

DEGDAYVTPHMTHSHWIKKDSLSEAERAAAQAYAKEKGLTPPSTDHQDSG

NTEAKGAEAIYNRNKAAKKVPLDRMPYNLQYTVEVKNGSLIIPHYDHYHN

IKFEWFDEGLYEAPKGYTLEDLLATVKYYVEHPNERPHSDNGFGNASDHV

QRNKNGQADTNQTEKPSEEKPQTEKPEEETPREEKPQSEKPESPKPTEEP

EESPEESEEPQVETEKVEEKLREAEDLLGKIQDPIIKSNAKETLTGLKNN

LLFGTQDNNTIMAEAEKLLALLKESKZ

ID312

(SEQ. ID. NO. 307)
ATGGAGGGATTGGTTAGAGTGCATTTATTGCCTGTATTTGGCGATTACAA

GCTATCTAAACTTACTACGCCTATTCTTCAACAGCAAGTAAACAAATGGG

CTGACAAGGCAAATAAAGGCGAAAAGGGGCATTTGCTAACTACTCTTTG

CTCCATAACATGAATAAGCGTATTTTGAAATATGGCGTAGCTATCCAGGT

AATACAATACAACCCAGCTAATGATGTCATCGTTCCACGCAAACAGCAAA

AAGAAAAGGCTGCTGTCAAATACTTAGACAACAAAGAATTAAAACAGTTT

CTTGATTATTTAGATGCTCTGGATCAATCAAATTATGAGAACTTATTTGA

TGTTGTTCTGTATAAGACTTTATTGGCCACTGGTTGCCGTATTAGTGAGG

CTCTGGCTCTTGAATGGTCTGATATTGACCTAGAAAGCGGTGTTATCAGC

ATCAATAAGACACTAAACCGCTATCAGGAATAAACTCACCTAAATCAAG

CGCTGGTTATCGTGATATACCAATAGACAAAGCCACATTACTTTTACTGA

AACAATACAAAAACCGTCAACAAATTCAGTCTTGGAAATTAGGCCGATCT

GAAACAGTTGTATTCTCTGTATTTACGGAGAAATATGCTTATGCTTGTAA

CTTACGCAAACGCCTAAATAAGCATTTTGATGCTGCTGGAGTAACTAACG

TATCATTTCATGGTTTCCGCCATACACATACTACTATGATGCTCTATGCT

CAGGTTAGCCCGAAAGATGTTCAGTATAGATTAGGCCACTCTAATTTAAT

GATCACTGAAAATACTTACTGGCATACTAACCAAGAGAATGCAAAAAAAG

CCGTCTCAAATTATGAAACAGCTATCAACAATTTATAA (SEQ. ID. NO. 195)
MEGLVRVHLLPVFGDYKLSKLTTPILQQQVNKWADKANKGEKGAFANYSL

LHNMNKRILKYGVAIQVIQYNPANDVIVPRKQQKEKAAVKYLDNKELKQF

LDYLDALDQSNYQNLFDVVLYKTLLATGCRISEALALEWSDIDLESGVIS

INKTLNRYQEINSPKSSAGYRDIPIDKATLLLLKQYKNRQQIQSWKLGRS

ETVVFSVFTEKYAYACNLRKRLNKHFDAAGVTNVSFHGFRHTHTTMMLYA

QVSPKDVQYRLGHSNLMITENTYWHTNQENAKKAVSNYETAINNLZ

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08110199B2). An electronic copy of the "Sequence Listing" will also be available from the USPTO upon request and payment of the fee set forth in 37 CFR 1.19(b)(3).

What is claimed is:

1. An isolated *Streptococcus pneumoniae* polypeptide comprising the amino acid sequence of SEQ ID NO: 38 or an amino acid sequence with at least 99% sequence identity to the amino acid sequence of SEQ ID NO: 38.

2. A fusion protein comprising the polypeptide of claim 1.

3. An immunogenic composition comprising the polypeptide of claim 1 and one or more excipients, diluents, or adjuvants.

* * * * *